United States Patent
Cheung et al.

(10) Patent No.: US 11,820,832 B2
(45) Date of Patent: Nov. 21, 2023

(54) BISPECIFIC HER2 AND CD3 BINDING MOLECULES

(71) Applicant: MEMORIAL SLOAN KETTERING CANCER CENTER, New York, NY (US)

(72) Inventors: Nai-Kong V. Cheung, New York, NY (US); Andres Lopez-Albaitero, New York, NY (US); Hong Xu, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 775 days.

(21) Appl. No.: 16/481,446

(22) PCT Filed: Jan. 27, 2017

(86) PCT No.: PCT/US2017/015278
§ 371 (c)(1),
(2) Date: Jul. 26, 2019

(87) PCT Pub. No.: WO2018/140026
PCT Pub. Date: Aug. 2, 2018

(65) Prior Publication Data
US 2019/0359732 A1    Nov. 28, 2019

Related U.S. Application Data

(63) Continuation-in-part of application No. PCT/US2015/041989, filed on Jul. 24, 2015.

(60) Provisional application No. 62/029,342, filed on Jul. 25, 2014.

(51) Int. Cl.
| | |
|---|---|
| *C07K 16/46* | (2006.01) |
| *A61K 39/395* | (2006.01) |
| *C07K 16/28* | (2006.01) |
| *C07K 16/32* | (2006.01) |
| *A61P 35/02* | (2006.01) |
| *A61P 35/04* | (2006.01) |
| *A61K 45/06* | (2006.01) |
| *A61K 35/17* | (2015.01) |
| *A61P 35/00* | (2006.01) |
| *A61K 39/00* | (2006.01) |

(52) U.S. Cl.
CPC ............ *C07K 16/468* (2013.01); *A61K 35/17* (2013.01); *A61K 39/3955* (2013.01); *A61K 39/39558* (2013.01); *A61K 45/06* (2013.01); *A61P 35/00* (2018.01); *A61P 35/02* (2018.01); *A61P 35/04* (2018.01); *C07K 16/2809* (2013.01); *C07K 16/32* (2013.01); *A61K 2039/505* (2013.01); *C07K 2317/31* (2013.01); *C07K 2317/35* (2013.01); *C07K 2317/40* (2013.01); *C07K 2317/622* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,648,176 B2 | 2/2014 | Davis Orcutt et al. | |
| 9,669,107 B2 | 6/2017 | Kim et al. | |
| 2014/0170149 A1 | 6/2014 | Neijssen et al. | |
| 2015/0079088 A1* | 3/2015 | Lowman | C07K 16/2803 435/69.6 |
| 2018/0273623 A1 | 9/2018 | Cheung et al. | |

FOREIGN PATENT DOCUMENTS

| | | |
|---|---|---|
| CA | 2569509 A1 | 12/2005 |
| WO | WO-94/28027 A1 | 12/1994 |
| WO | WO-2008/119567 A2 | 10/2008 |
| WO | WO-2011/160119 A2 | 12/2011 |
| WO | WO-2012/143524 A2 | 10/2012 |
| WO | WO-2012/178137 A1 | 12/2012 |
| WO | WO-2014/079000 A1 | 5/2014 |
| WO | WO-2015/013671 A1 | 1/2015 |
| WO | WO-2015/095418 A1 | 6/2015 |
| WO | WO-2016/014942 A1 | 1/2016 |
| WO | WO-2016/130539 A2 | 8/2016 |
| WO | WO-2018/140026 A1 | 8/2018 |

OTHER PUBLICATIONS

Saenz del Burgo et al (Journal of Drug Targeting, 2015, 23:170-179).*
Dubrot et al (Cancer Immunology Immunotherapy, 2010, 59:1621-1631).*
Haense et al (BMC Cancer, 2016, 16:420, internet pp. 1-10).*
Adair, et al., 1994, "Humanization of the murine anti-human CD3 monoclonal antibody OKT3," Hum Antibodies Hybridomas, 5(1-2):41-47.
Andrade, et al., 2011, "Engraftment of peripheral blood mononuclear cells from systemic lupus erythematosus and antiphospholipid syndrome patient donors into BALB-RAG-2-/- IL-2R?-/- mice: a promising model for studying human disease," Arthritis Rheum, 63(9):2764-73.
Austin, et al., 2004, "Endocytosis and Sorting of ErbB2 and the Site of Action of Cancer Therapeutics Trastuzumab and Geldanamycin," Molecular Biology of the Cell, 15:5268-5282.

(Continued)

*Primary Examiner* — Laura B Goddard
(74) *Attorney, Agent, or Firm* — Foley & Lardner LLP

(57) ABSTRACT

Provided herein are compositions, methods, and uses involving bispecific binding molecules that specifically bind to HER2, a receptor tyrosine kinase, and to $CD_3$, a T cell receptor, and mediate T cell cytotoxicity for managing and treating disorders, such as cancer. Also provided herein are uses and methods for managing and treating HER2-related cancers.

Figure 1A:
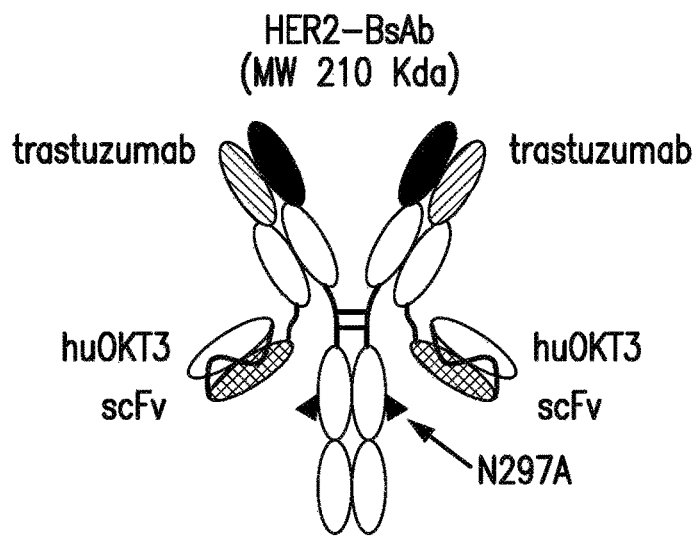

12 Claims, 49 Drawing Sheets
Specification includes a Sequence Listing.

(56) References Cited

OTHER PUBLICATIONS

Baeuerle, et al., 2009, "BiTE: Teaching antibodies to engage T-cells for cancer therapy," Current Opinion in Molecular Therapeutics, 11(1):22-30.
Baselga, et al. 1998, "Recombinant humanized anti-HER2 antibody (Herceptin) enhances the antitumor activity of paclitaxel and doxombicin against HER2/neu overexpressing human breast cancer xenografts," Cancer Res, 58(13): 2825-2831.
Bluemel, et al., 2010, "Epitope distance to the target cell membrane and antigen size determine the potency of T cell-mediated lysis by BiTE antibodies specific for a large melanoma surface antigen," Cancer Immunol Immunother, 49:1197-1209.
Borghaesi, et al., 2007, "Induction of adaptive Anti-HER2/neu immune responses in a Phase 1B/2 trial of 2B1 bispecific murine monoclonal antibody in metastatic breast cancer (E3194): a trial coordinated by the Eastern Cooperative Oncology Group," J Immunother, 30(4):455-467.
Cheadle, 2006, "MT-103 Micromet/MedImmune," Curr Opin Mol Ther, 8(1):62-68.
Cheal, et al., 2014, "Preclinical evaluation of multistep targeting of diasialoganglioside GD2 using an IgG-scFv bispecific antibody with high affinity for GD2 and DOTA metal complex," Mol Cancer Ther, 13(7):1803-1812.
Cheal, et al., 2015, "Theranostic pretargeting of HER2-expressing human carcinoma xenografts in immunocompromised mice with an anti-DOTA(metal) hapten IgG-scFv bispecific antibody," World Molecular Imaging Congress.
Chen, et al., 2012, "MET activation mediates resistance to lapatinib inhibition of HER2-amplified gastric cancer cells," Mol Cancer Ther, 11(3):660-9.
Cheung, et al., 2014, "Characterization of a novel HER2/CD3 Bi-Specific Antibody for the Treatment of Head and Neck Cancer," Meeting Abstracts from the 5th World Congress of IFHNOS and the 2014 Annual Meeting of the AHNS.
Chevalier, et al., 2012, "Trastuzumab for treatment of refractory/relapsed HER2-positive adult B-ALL: results of a phase 2 GRAALL study," Blood, 119(11):2474-7.
Cortes, et al., 2012, "Pertuzumab Monotherapy After Trastuzumab-Based Treatment and Subsequent Reintroduction of Trastuzumab: Activity and Tolerability in Patients With Advanced Human Epidermal Growth Factor Receptor 2-Positive Breast Cancer," Journal of Clinical Oncology, 30(14):1594-1600.
Dean, et al., 2012, "Combination therapies in the context of anti-CD3 antibodies for the treatment of autoimmune diseases," Swiss Med Wkly, 142: w13711.
Diermeier-Daucher, et al., 2012, "Trifunctional antibody ertumaxomab: Non-immunological effects on Her2 receptor activity and downstream signaling," MAbs, 4(5):614-22.
Ebb et al., 2012, "Phase II trial of trastuzumab in combination with cytotoxic chemotherapy for treatment of metastatic osteosarcoma with human epidermal growth factor receptor 2 overexpression: a report from the children's oncology group," J Clin Oncol, 30(20):2545-51.
Franklin, et al., 2004, "Insights into ErbB signaling from the structure of the ErbB2-pertuzumab complex," Cancer Cell, 5(4):317-28.
Fung, et al., 2016, "Serial dynamic and static preclinical PET/CT image-based immunokinetic modeling of 86Y-hapten localization in HER2-expressing SKOV3 xenograft during anti-HER2/antilanthaanide DOTA pretargeted radioimmunotherapy", Journal of Nuclear Medicine, 47, Supplement 2, 365.
Gajria, et al., 2011, "HER2-amplified breast cancer: mechanisms of trastuzumab resistance and novel targeted therapies," Expert Rev Anticancer Ther, 11(2):263-75.
Gorlick, et al., 1999, "Expression of HER2/erbB-2 correlates with survival in osteosarcoma," J Clin Oncol, 17(9):2781-8.

Heiss and Murawa, 2010, "The trifunctional antibody catumaxomab for the treatment of malignant ascites due to epithelial cancer: Results of a prospective randomized phase II/III trial," Int J Cancer, 127(9):2209-21.
Herold, et al., 2009, "Treatment of patients with new onset Type 1 diabetes with a single course of anti-CD3 mAb Teplizumab preserves insulin production for up to 5 years," Clin Immunol, 132(2):166-73.
Higgins, et al., 2011, "A phase I/II study of MM-111, a novel bispecific antibody that targets the ErB2/ErB3 heterodimer, in combination with trastuzumab in advanced refractory HER2-positive breast cancer," J Clin Oncol, 29(Suppl): Abstract TPS119.
Keymeulen, et al., 2010, "Four-year metabolic outcome of a randomised controlled CD3-antibody trial in recent-onset type 1 diabetic patients depends on their age and baseline residual beta cell mass," Diabetologia, 53(4): 614-23.
Kiewe and Thiel, 2008, "Ertumaxomab: a trifunctional antibody for breast cancer treatment," Expert Opin Investig Drugs, 17(10):1553-8.
Kiewe, et al. 2006, "Phase I trial of the trifunctional anti-HER2 × anti-CD3 antibody ertumaxomab in metastatic breast cancer," Clin Cancer Res, 12(10): 3085-91.
Koo, et al., 2009, "Use of humanized severe combined immunodeficient mice for human vaccine development," Expert Rev Vaccines, 8(1):113-20.
Labrijn, et al., 2013, "Efficient generation of stable bispecific IgG1 by controlled Fab-arm exchange," Proceedings of the National Academy of Sciences, 110(13): 5145-50.
Li, et al., 2017, "Membrane-Proximal Epitope Facilitates Efficient T Cell Synapse Formation by Anti-FcRH5/CD3 and Is a Requirement for Myeloma Cell Killing," Cancer Cell, 31(3): 383-395.
Lipton, et al., 2013, "HER3, p95HER2, and HER2 protein expression levels define multiple subtypes of HER2-positive metastatic breast cancer," Breast Cancer Res Treat, 141(1):43-53.
Lum, et al., 2011, "Targeting T Cells with Bispecific Antibodies for Cancer Therapy," BioDrugs, 25(6):365-379.
Lum, et al., 2013, "CD20-targeted T cells after stem cell transplantation for high risk and refractory non-Hodgkin's lymphoma," Biol Blood Marrow Transplant, 19(6):925-33.
Lum, et al., 2015, "Targeted T-cell Therapy in Stage IV Breast Cancer: A Phase I Clinical Trial," Clin Cancer Res 21(10):2305-14.
Nathanson, et al., 2014, "Targeted therapy resistance mediated by dynamic regulation of extrachromosomal mutant EGFR DNA," Science, 343(6166):72-76.
National Center for Biotechnology Information. PubChem, Open Chemistry Database, GD2 Ganglioside, Apr. 29, 2006 (Modified Sep. 2, 2017), https://pubchem.ncbi.nlm.nih.gov/compound/6450346 (last visited Sep. 7, 2017).
Norman, et al., 2000, "Phase I trial of HuM291, a humanized anti-CD3 antibody, in patients receiving renal allografts from living donors," Transplantation, 70(12): 1707-12.
Orcutt, et al., 2011, "Engineering an antibody with picomolar affinity to DOTA chelates of multiple radionuclines for pretargeted radioimmunotherapy and imaging," Nuclear Medicine and Biology, 38:223-233.
Orcutt, et al., 2012, "Effect of Small-Molecule-Binding Affinity on Tumor Uptake in Vivo: A Systematic Study Using a Pre-targeted Bispecific Antibody," Molecular Cancer Therapeutics, 11(6):1365-1172.
Petsch, et al., 2011, "Concentrations of EpCAM ectodomain as found in sera of cancer patients do not significantly impact redirected lysis and T-cell activation by EpCAM/CD3-bispecific BiTE antibody MT110," MAbs, 3(1):31-7.
PhosphoSitePlus?, HER2, https://www.phosphosite.org/proteinAction?id=1580&showAllSites=true (last visited Sep. 7, 2017).
Pollock and Grnadis, 2014, "HER2 as a therapeutic target in head and neck squamous cell carcinoma," Clin Cancer Res, 21(3):526-33.
Portell, et al., 2013, "Clinical and pharmacologic aspects of blinatumomab in the treatment of B-cell acute lymphoblastic leukemia," Clin Pharmacol, 5(Suppl 1):5-11.

(56) References Cited

OTHER PUBLICATIONS

Reusch, et al., 2015, "A tetravalent bispecific TandAb (CD19/CD3), AFM11, efficiently recruits T cells for the potent lysis of CD19() tumor cells," MAbs, 7(3):584-604.
Routledge, et al., 1991, "A humanized monovalent CD3 antibody which can activate homologous complement," Eur J Immunol, 21(11):2717-25.
Sanford, 2015, "Blinatumomab: first global approval," Drugs, 75(3):321-7.
Schwaab, et al., 2001, "Phase I pilot trial of the bispecific antibody MDX11210 (anti-Fc gamma RI X anti-HER-2/neu) in patients whose prostate cancer overexpresses HER-2/neu," J Immunother, 24(1):79-87.
Shalaby, et al., 1995, "Bispecific HER2 × CD3 antibodies enhance T-cell cytotoxicity in vitro and localize to HER2-overexpressing xenografts in nude mice," Clin Immunol Immunopathol, 74(2):185-92.
Silberberg, M.S. "The Components of Matter." Chemistry, The Molecular Nature of Matter and Change (Annotated Instructor's Edition), 5th Edition, Ed. Tamara Good-Hodge, New York: McGraw-Hill Higher Education, 2009. 41-88. Print.
Singh, et al., 2014, "HER2-positive advanced breast cancer: optimizing patient outcomes and opportunities for drug development," Br J Cancer, 111(10):1888-98.
Sondermann, et al., 2000, "The 3.2-A crystal structure of the human IgG1 Fc fragment-Fc gammaRIII complex," Nature, 406(6793):267-73.
Stromnes et al., 2014, "Re-adapting T cells for cancer therapy: from mouse models to clinical trials," Immunol Rev, 257(1):145-64.
Trastuzumab [Highlights of Prescribing Information], South San Francisco, CA: Genentech, Inc.; 2014.
Tumeh, et al., 2014, "PD-1 blockade induces responses by inhibiting adaptive immune resistance," Nature, 515(7528):568-71.
Vaishampayan, et al., 2015, "Phase I Study of Anti-CD3 × Anti-Her2 Bispecific Antibody in Metastatic Castrate Resistant Prostate Cancer Patients," Prostate Cancer, 2015:285193.
Vu and Claret., 2011, "Trastuzumab: updated mechanisms of action and resistance in breast cancer," Front Oncol, 2:62.
Wattenberg, et al., 2014, "Expanding the use of monoclonal antibody therapy of cancer by using ionizing radiation to upregulate antibody targets," British Journal of Cancer, 110: 1472-1480.
Wickham and Futch, 2014, "Abstract P5-18-09: A Phase I Study of MM-302, a HER2-targeted Liposomal Doxorubicin, in Patients with Advanced, HER2—Positive Breast Cancer," Cancer Research, 72(24): Supplement.
Wittrup et al., 2012, "Practical theoretic guidance for the design of tumor-targeting agents," Methods Enzymol, 503:255-68.
Yazaki, et al., 2013, "A series of anti-CEA/anti-DOTA bispecific antibody formats evaluated for pre-targeting: comparison of tumor uptake and blood clearance," Protein Eng Des Sel, 26(3):187-93.
Anthony et al., "Novel roles for the IgG Fc glycan," Ann. N.Y. Acad. Sci., pp. 170-180 (2012) (doi: 10.1111/j.1749-6632.2011.06305.x).
Chan et al., "Therapeutic antibodies for autoimmunity and inflammation," Nature Reviews | Immunology, vol. 10, pp. 301-316 (May 2010).
Moore et al., "A novel bispecific antibody format enables simultaneous bivalent and monovalent coengagement of distinct target antigens," mAbsm 3:6 pp. 546-557 (2011).
International Search Report and Written Opinion, PCT/US2015/041989, Memorial Sloan Kettering Cancer Center (dated Oct. 13, 2015).
International Search Report and Written Opinion, PCT/US2017/015278, Memorial Sloan Kettering Cancer Center (dated Jun. 9, 2017).
Junttila, T.T., et al., "Antitumor efficacy of a bispecific antibody that targets HER2 and activates T cells," Cancer Res., vol. 74, No. 19, pp. 5561-5571 (Oct. 1, 2014).
Lawrence, G., et al., "Targeting T cells with bispecific antibodies for cancer therapy," Biodrugs, vol. 25, No. 6, pp. 365-379 (Dec. 1, 2011).
Lopez-Albaitero, A., et al., "Overcoming resistance to HER2-targeted therapy with a novel HER2/CD3 bispecific antibody," Oncoimmunology, vol. 6, No. 3, p. e1267891 (Mar. 4, 2017).
Lum, L.G., et al., "Phase I/II study of treatment of stage IV breast cancer with OKT3× trashuzumab-armed activated T cells," Clinical Breast Cancer, CIG Media Group, LP, vol. 4, No. 3, pp. 212-217 (Aug. 1, 2003).
Orcutt, K., et al., "A modular IgG-scFv bispecific antibody topology," Protein Engineering, Design and Selection, vol. 23, No. 4, pp. 221-228 (Apr. 1, 2010).
Xu, H., et al., "Retargeting T cells to GD2 pentasaccharide on human tumors using bispecific humanized antibody," Cancer Immunology Research, vol. 3, No. 3, pp. 266-277 (Dec. 26, 2014).
Kontermann et al., "Dual targeting strategies with bispecific antibodies." mAbs4:2, 182-197; Mar./Apr. 2012.

\* cited by examiner

| Tumor Type | Cell Line Name | HER2 Expression (MFI) | EC50 (ng/ml) | EC50 (pM) |
|---|---|---|---|---|
| Breast Carcinoma | AU565 | 1175 | 0.06 | 0.3 |
| Breast Carcinoma | SKBR3 | 760 | 0.2 | 1 |
| Breast Carcinoma | MCF7 | 296 | 0.32 | 1.6 |
| Ovarian Carcinoma | OVCAR3 | 183 | 0.36 | 1.8 |
| Breast Carcinoma | MDA-MB-361 (HTB27) | 777 | 0.5 | 2.5 |
| Melanoma | SKMEL28 | 190 | 0.6 | 3 |
| Osteosarcoma | CRL1427 | 108 | 2 | 10 |
| Ewings | SKEAW | 246 | 2 | 10 |
| Rhabdomyosarcoma | HTB82 | 204 | 2 | 10 |
| Melanoma | HT-144 (HTB63) | 156 | 3 | 15 |
| Neuroblastoma | NB5 | 66 | 3.1 | 15.5 |
| Breast Carcinoma | MDA-MB-231 (HTB26) | 68 | 4 | 20 |
| Osteosarcoma | U2OS | 90 | 4.5 | 22.5 |
| Ewings | SKES-1 | 146 | 10 | 50 |
| Melanoma | M14 | 57 | 26 | 130 |
| Neuroblastoma | NMB7 | 12 | >1000 | >5000 |
| Neuroblastoma | IMR32 | 6 | >1000 | >5000 |
| Small Cell lung Cancer | NCI-H524 | 14 | >1000 | >5000 |
| Neuroblastoma | SKNBE(1)N | 3 | >1000 | >5000 |
| Neuroblastoma | SKNBE(2)C | 8 | >1000 | >5000 |
| Small Cell lung Cancer | NCI-H69 | 10 | >1000 | >5000 |
| Neuroblastoma | SKNBE(2)S | 4 | >1000 | >5000 |
| Small Cell lung Cancer | NCI-H345 | 6 | >1000 | >5000 |
| Breast Carcinoma | MDA-MB-468 (HTB132) | 6 | >1000 | >5000 |

Fig. 4

| SCCHN cell lines | % Max Lysis | Flow HER2 (MFI) | qPCR (relative to MCF7) | Number of Experiments | EC50 ng/mL | EC50 pM |
|---|---|---|---|---|---|---|
| 15B | 47 | 305 | 121 | 2 | 13 | 63 |
| 93VU147T | 45 | 127 | 151 | 3 | 6 | 32 |
| PCI-30 | 53 | 359 | 237 | 3 | 2 | 12 |
| SCC90 | 46 | 274 | 578 | 3 | 1 | 6 |
| UDSCC2 | 42 | 178 | 139 | 5 | 5 | 27 |
| UMSCC47 | 57 | 302 | 49 | 3 | 4 | 20 |

Fig. 8

| Osteosarcoma cell lines | % Max Lysis | Flow HER2 (MFI) | qPCR (relative to MCF7) | Number of Experiments | EC50 ng/mL (average) | EC50 pM |
|---|---|---|---|---|---|---|
| U2OS | 49 | 53 | 713 | 3 | 5 | 25 |
| RG 160 | 62 | 563 | 1881 | 3 | 2 | 11 |
| RG 164 | 68 | 439 | 5510 | 4 | 4 | 18 |
| CRL 1427 | 46 | 81 | 52 | 2 | 3 | 16 |

Fig. 10

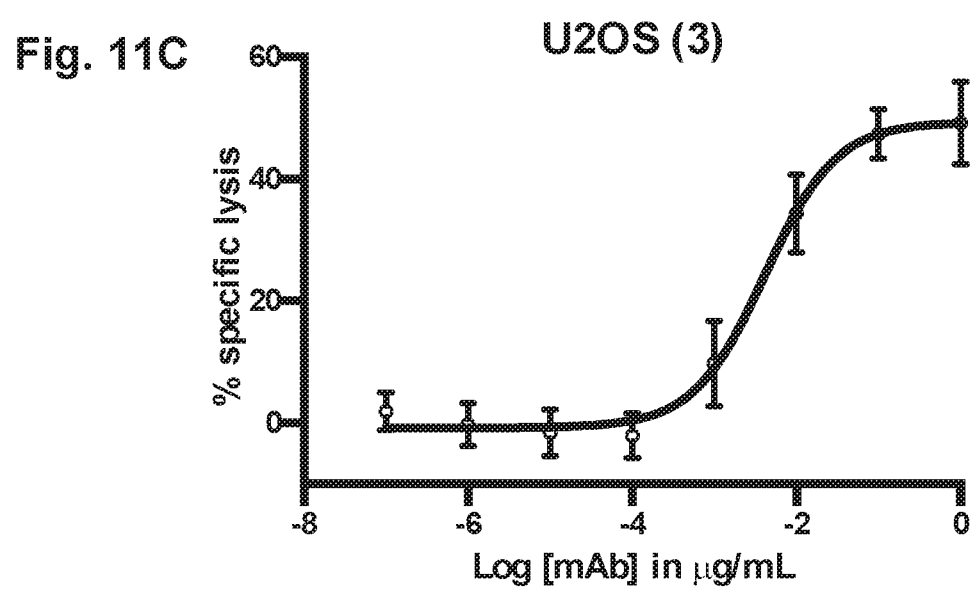

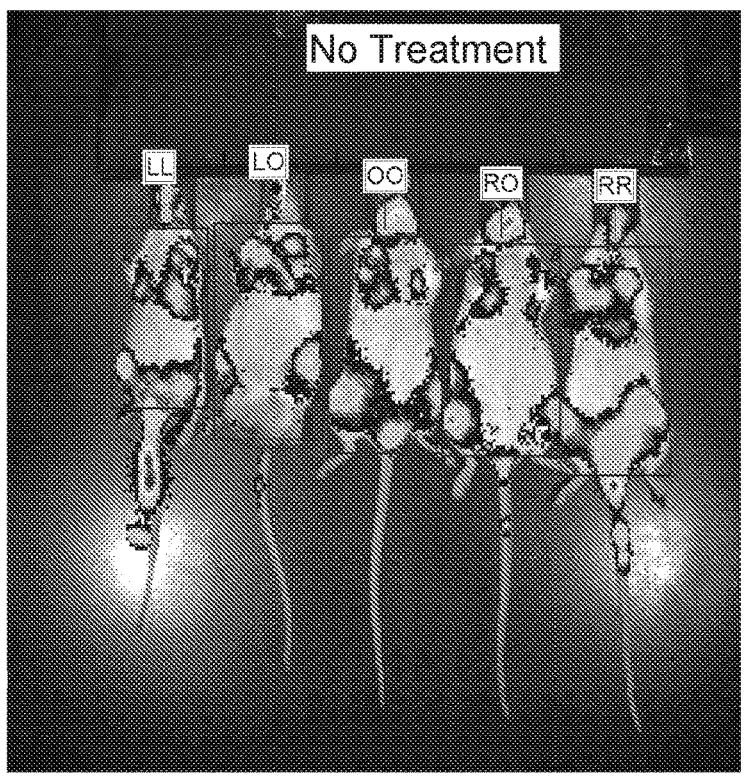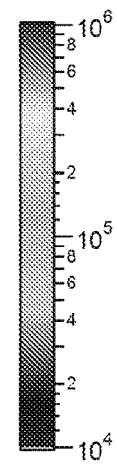
Fig. 16A
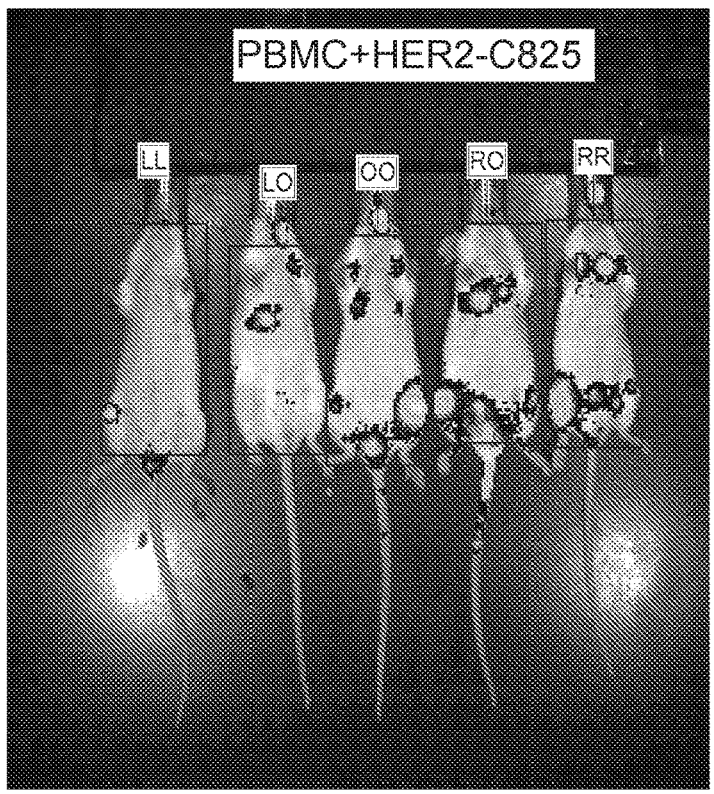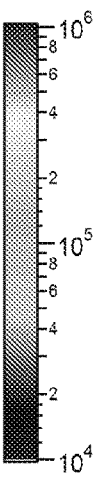
Fig. 16B

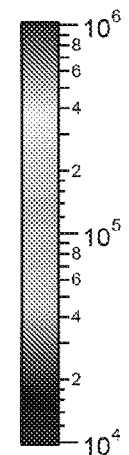
Fig. 16C
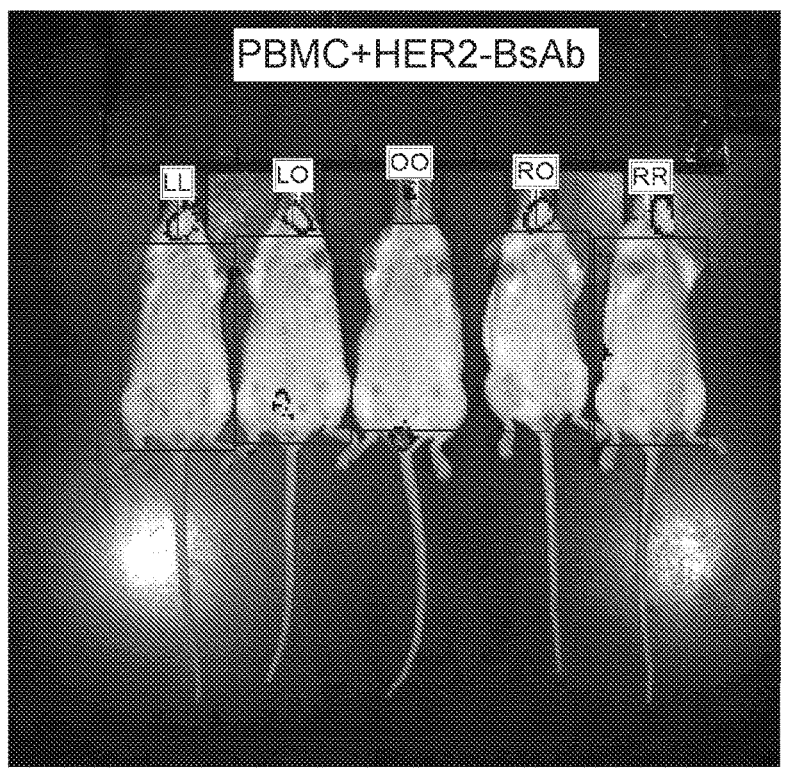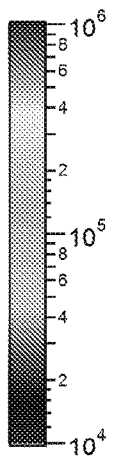
Fig. 16D

| Tumor Type | Cell Line | HER2 Expression (MFI) | EC50 (pM) |
|---|---|---|---|
| Breast Carcinoma | AU565 | 1175 | 0.3 |
| Ovarian Carcinoma | OVCAR3 | 183 | 1.8 |
| Breast Carcinoma | MDA-MB-361 | 777 | 2.5 |
| Ovarian Carcinoma | SKOV3 | 1577 | 2.8 |
| Melanoma | SKMEL28 | 190 | 3 |
| Breast Carcinoma | SKBR3 | 2506 | 4.1 |
| Breast Carcinoma | HCC1954 | 1597 | 5.5 |
| Head and Neck Cancer | SCC90 | 274 | 5.7 |
| Ewings | SKEAW | 246 | 10 |
| Osteosarcoma | CRL1427 | 108 | 10 |
| Rhabdomyosarcoma | HTB82 | 204 | 10 |
| Osteosarcoma | RG 160 | 563 | 11 |
| Head and Neck Cancer | PCI-30 | 359 | 12.2 |
| Melanoma | HT-144 | 156 | 15 |
| Neuroblastoma | NB5 | 66 | 15.5 |
| Osteosarcoma | RG 164 | 439 | 17.7 |
| Head and Neck Cancer | UM SCC47 | 302 | 19.8 |
| Osteosarcoma | U2OS | 90 | 22.5 |
| Head and Neck Cancer | UDSCC2 | 178 | 26.9 |
| Head and Neck Cancer | 93VU147T | 127 | 32.4 |
| Ewings | SKES-1 | 146 | 50 |
| Breast Carcinoma | HTB-26 | 76 | 50.2 |
| Head and Neck Cancer | 15B | 305 | 62.8 |
| Breast Carcinoma | MCF7 | 398 | 64.9 |
| Cervical Cancer | HeLA | 104 | 120.7 |
| Melanoma | M14 | 57 | 130 |
| Breast Carcinoma | MDA-MB-468 | 6 | >5000 |
| Neuroblastoma | NMB7 | 12 | >5000 |
| Neuroblastoma | SKNBE(2)C | 8 | >5000 |
| Neuroblastoma | IMR32 | 6 | >5000 |
| Neuroblastoma | SKNBE(2)S | 4 | >5000 |
| Neuroblastoma | SKNBE(1)N | 3 | >5000 |
| Small Cell lung Cancer | NCI-H524 | 14 | >5000 |
| Small Cell lung Cancer | NCI-H69 | 10 | >5000 |
| Small Cell lung Cancer | NCI-H345 | 6 | >5000 |

Fig. 20

Osteosarcoma Cell Line U2OS

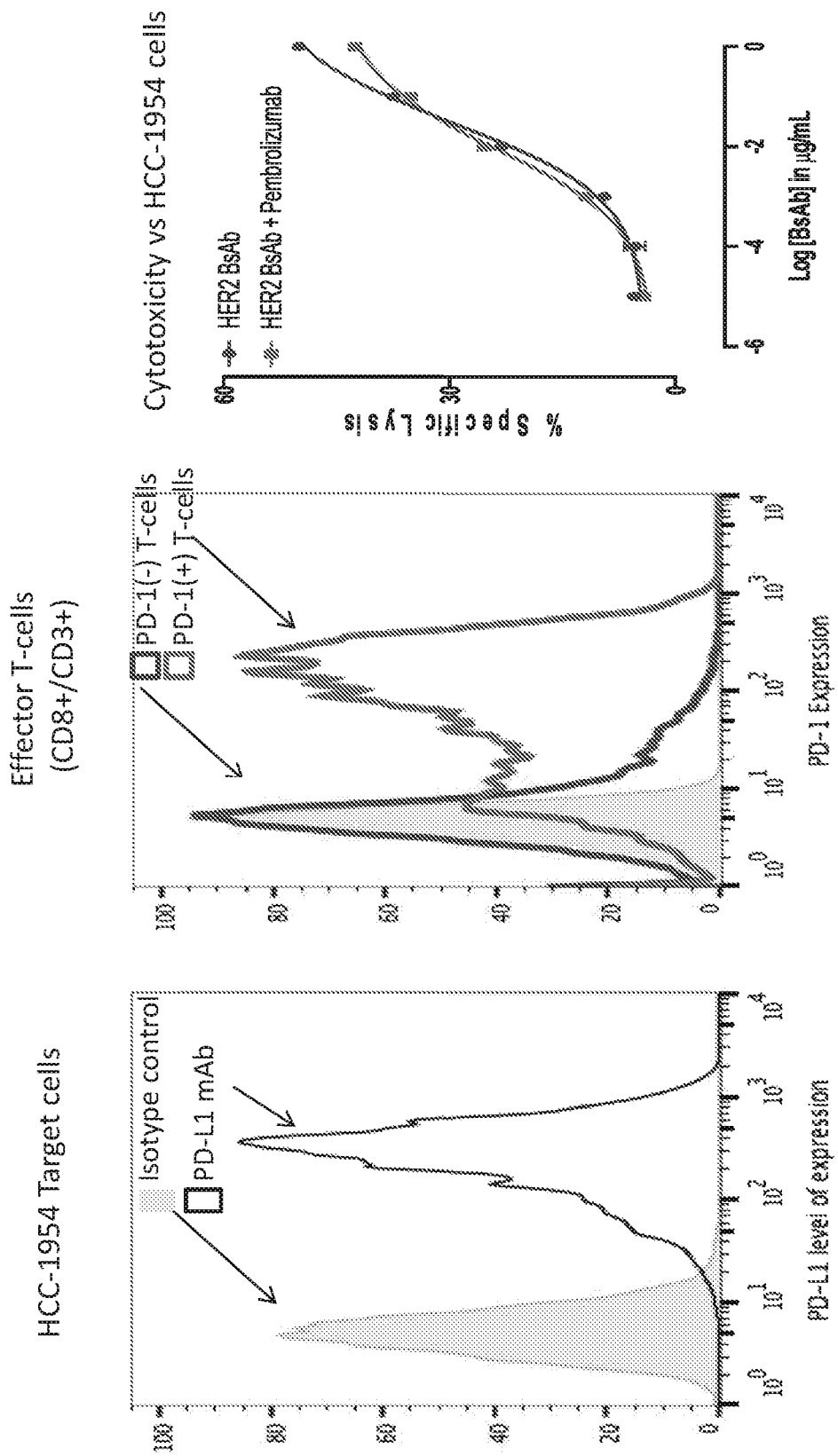

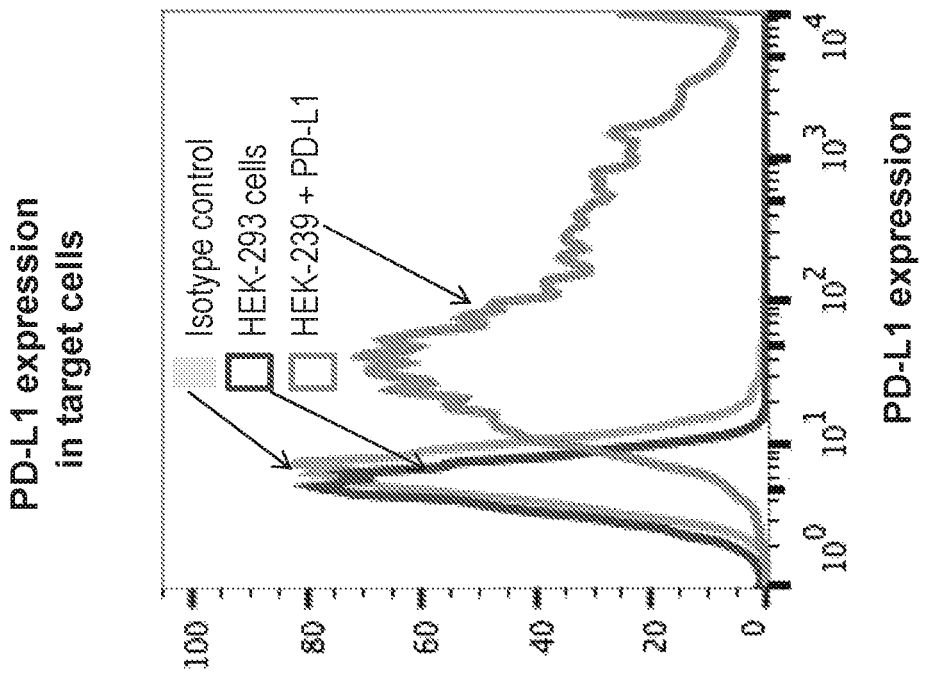
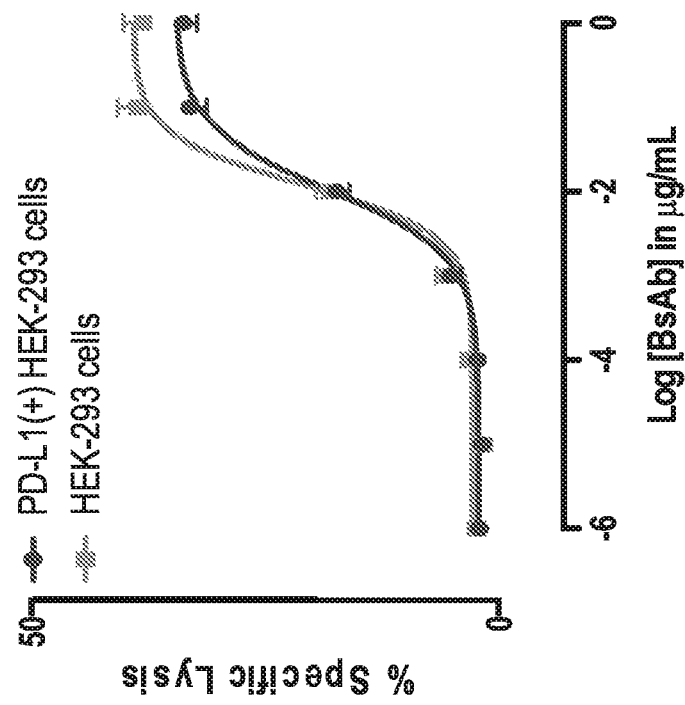
Fig. 24A
Fig. 24B

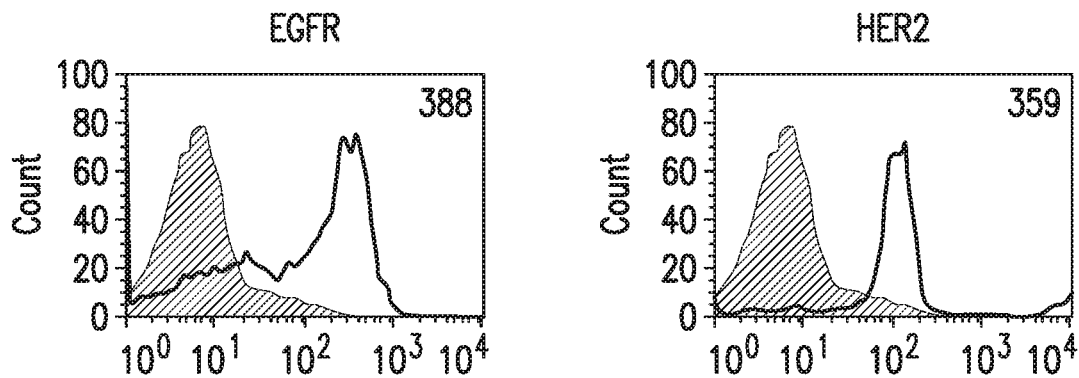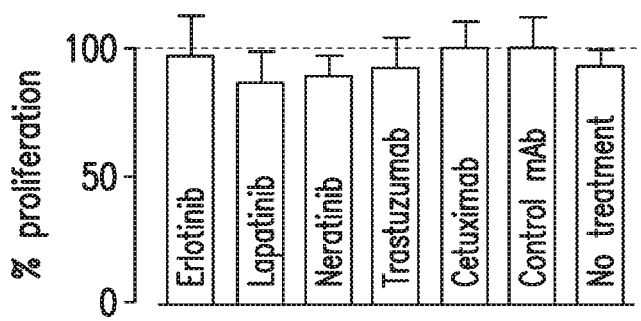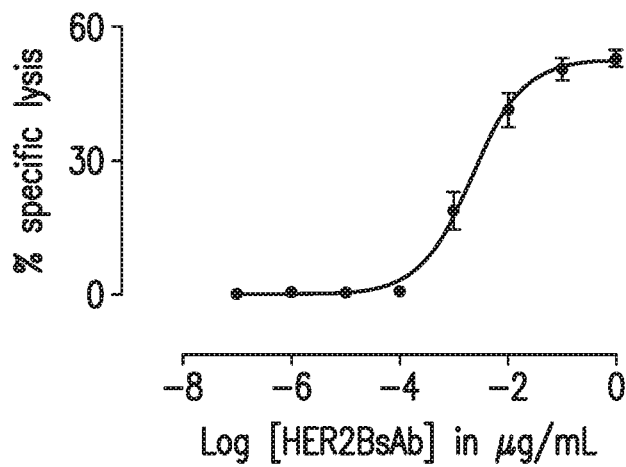
FIG. 28A

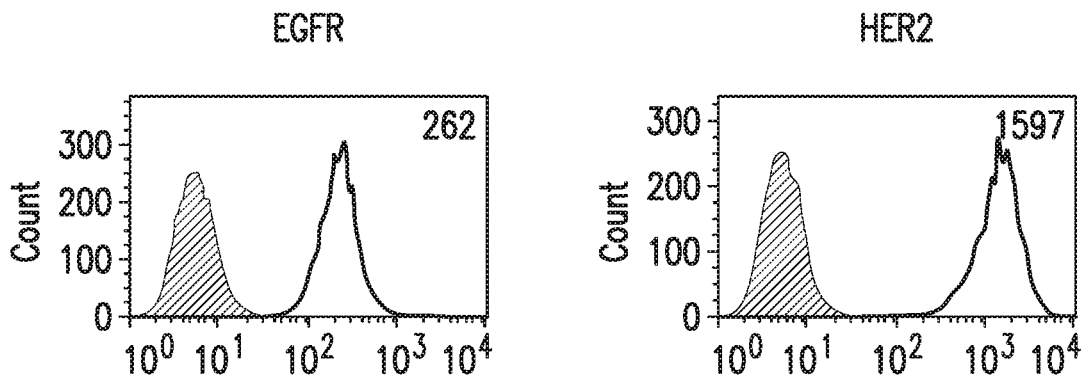
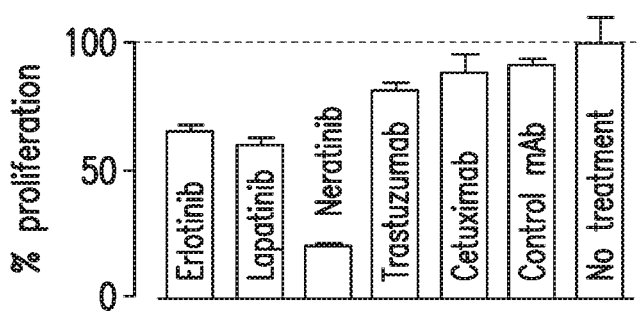
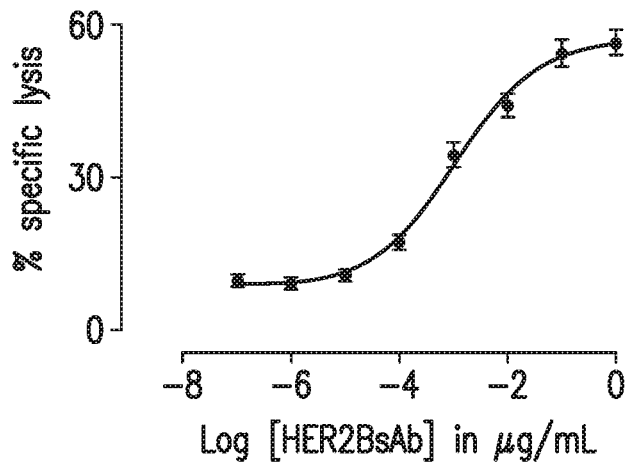
FIG. 28B

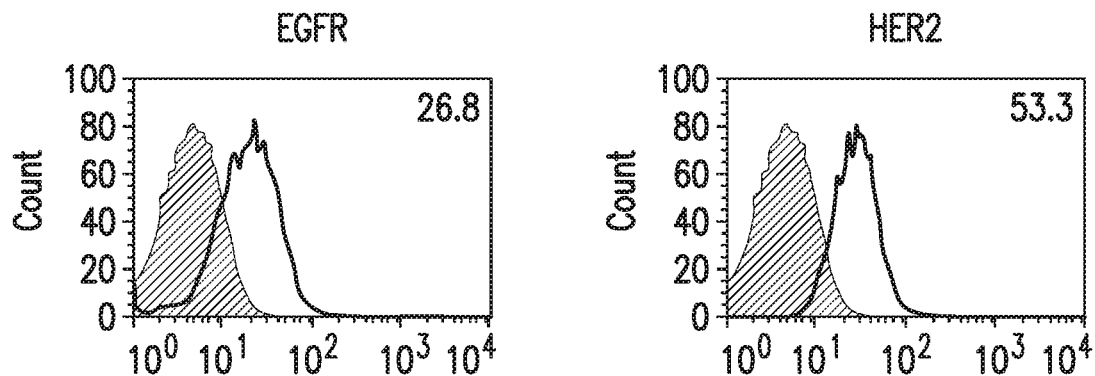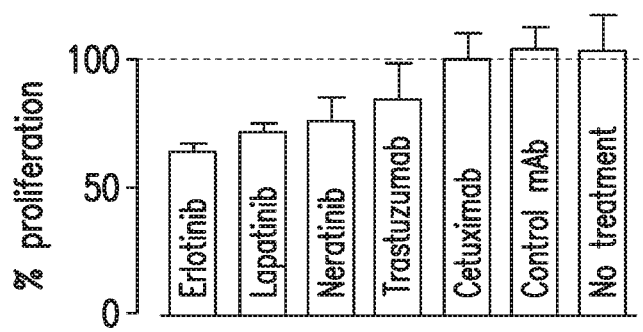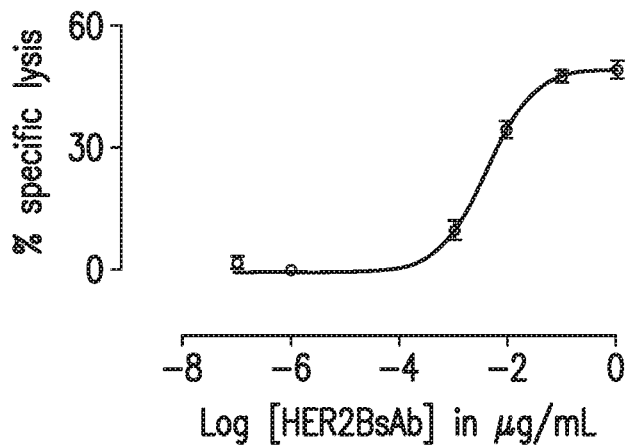
FIG. 28C

BISPECIFIC HER2 AND CD3 BINDING MOLECULES

This application is a National Stage Application of International Application No. PCT/US2017/015278, filed Jan. 27, 2017, which is a continuation-in-part of International Application No. PCT/US2015/041989, filed Jul. 24, 2015, which claims the benefit of and priority to U.S. Provisional Application No. 62/029,342, filed Jul. 25, 2014, each of which is incorporated by reference herein in its entirety.

This application incorporates by reference a Sequence Listing submitted with this application as text file entitled "Sequence_Listing_13542-039-228.txt" created on Jan. 27, 2017 and having a size of 184 kbytes.

1. FIELD

Provided herein are compositions, methods, and uses involving bispecific binding molecules that specifically bind to HER2, a receptor tyrosine kinase, and to CD3, a T cell receptor, and mediate T cell cytotoxicity for managing and treating disorders, such as cancer.

2. BACKGROUND

HER2 is a receptor tyrosine kinase of the epidermal growth factor receptor family. Amplification or overexpression of HER2 has been demonstrated in the development and progression of cancers. Herceptin® (trastuzumab) is an anti-HER2 monoclonal antibody approved for treating HER2-positive metastatic breast cancer and HER2-positive gastric cancer (Trastuzumab [Highlights of Prescribing Information]. South San Francisco, Calif.: Genentech, Inc.; 2014). Ertumaxomab is a tri-specific HER2-CD3 antibody with intact Fc-receptor binding (see, for example, Kiewe et al. 2006, Clin Cancer Res, 12(10): 3085-3091). Ertumaxomab is a rat-mouse antibody; therefore, upon administration to humans, a human anti-mouse antibody response and a human anti-rat antibody response are expected. 2502A, the parental antibody of ertumaxomab, has low affinity for HER2 and low avidity (Diermeier-Daucher et al., MAbs, 2012, 4(5): 614-622). There is a need for therapies capable of mediating T cell cytotoxicity in HER2-positive cancers.

3. SUMMARY

In a specific embodiment, provided herein is a method of treating a HER2-positive cancer in a subject in need thereof, comprising administering to the subject a therapeutically effective amount of a bispecific binding molecule comprising an aglycosylated monoclonal antibody that is an immunoglobulin that binds to HER2, said immunoglobulin comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical, and wherein the cancer expresses a low level of HER2, and preferably wherein the cancer is not a head and neck cancer.

In a specific embodiment, the cancer is deemed to express a low level of HER2 when the cancer expresses a lower level of HER2 than the level of HER2 expressed by cancers that are indicated for treatment with trastuzumab and are of the same tissue type as the HER2-positive cancer.

In a specific embodiment, the cancer is deemed to express a low level of HER2 when the cancer has been determined not to overexpress HER2 based on the following characterization of the cancer: (a) a first determination of a level of HER2 in a test specimen comprising cells of the cancer is reported as negative, or (b) a first determination of a level of HER2 in a test specimen comprising cells of the cancer is reported as equivocal, and a second determination of a level of HER2 in a test specimen comprising cells of the cancer is reported as equivocal or negative. In a specific embodiment, the determination of the level of HER2 in the test specimen is reported as negative when the level of HER2 in the test specimen is characterized as (i) (1) immunohistochemistry (IHC) 1+, wherein the level of HER2 in the test specimen is characterized as IHC 1+ when the test specimen exhibits an incomplete HER2 membrane staining that is faint/barely perceptible and within greater than 10% of the invasive tumor cells, wherein the staining is readily appreciated using a low-power objective; (2) IHC 0, wherein the level of HER2 in the test specimen is characterized as IHC 0 when the test specimen exhibits no HER2 staining observed, wherein the lack of staining is readily appreciated using a low-power objective, or a HER2 membrane staining that is incomplete and is faint/barely perceptible and within less than or equal to 10% of the invasive tumor cells, wherein the staining is readily appreciated using a low-power objective; or (ii) in situ hybridization (ISH) negative, wherein the level of HER2 in the test specimen is characterized as ISH negative when the test specimen exhibits (1) a single-probe average HER2 copy number of less than 4.0 signals per cell; or (2) a dual-probe HER2/CEP17 ratio of less than 2.0 with an average HER2 copy number of less than 4.0 signals per cell. In a specific embodiment, the determination of the level of HER2 in the test specimen is reported as equivocal when the level of HER2 in the test specimen is characterized as: (i) IHC 2+, wherein the level of HER2 in the test specimen is characterized as IHC 2+ when the test specimen exhibits (1) a circumferential HER2 membrane staining that is incomplete and/or weak/moderate and within greater than 10% of invasive tumor cells, wherein the staining is observed in a homogenous and contiguous population, and wherein the staining is readily appreciated using a low-power objective; or (2) a complete and circumferential HER2 membrane staining that is intense and within less than or equal to 10% of invasive tumor cells, wherein the staining is readily appreciated using a low-power objective; or (ii) ISH equivocal, wherein the level of HER2 in the test specimen is characterized as ISH equivocal when the test specimen exhibits (1) a single-probe ISH average HER2 copy number of greater than or equal to 4.0 and less than 6.0 signals/cell, wherein the copy number is determined by counting at least 20 cells within the area and is observed in a homogenous and contiguous population; or (2) a dual-probe HER2/CEP17 ratio of less than 2.0 with an average HER2 copy number of greater than or equal to 4.0 and less than 6.0 signals per cell, wherein the copy number is determined by counting at least 20 cells within the area and is observed in a homogenous and contiguous population.

In a specific embodiment, the cancer is deemed to express a low level of HER2 when a level of HER2 in a test specimen comprising cells of the cancer is characterized as IHC 2+ or less according to applicable American Society of Clinical Oncology/College of American Pathologists guideline recommendations for human epidermal growth factor receptor 2 testing in cancer. In a preferred embodiment, the cancer is deemed to express a low level of HER2 when a level of HER2 in a test specimen comprising cells of the cancer is characterized as IHC 2+ or less according to applicable American Society of Clinical Oncology/College of American Pathologists guideline recommendations for human epidermal growth factor receptor 2 testing in breast cancer. In a specific embodiment, a level of HER2 in a test specimen comprising cells of the cancer is characterized as IHC 2+. In a specific embodiment, the level of HER2 in the test specimen is characterized as IHC 2+ when the test specimen exhibits (1) a circumferential HER2 membrane staining that is incomplete and/or weak/moderate and within greater than 10% of invasive tumor cells, wherein the staining is observed in a homogenous and contiguous population, and wherein the staining is readily appreciated using a low-power objective; or (2) a complete and circumferential HER2 membrane staining that is intense and within less than or equal to 10% of invasive tumor cells, wherein the staining is readily appreciated using a low-power objective. In a specific embodiment, a level of HER2 in a test specimen comprising cells of the cancer is characterized as IHC 1+. In a specific embodiment, the level of HER2 in the test specimen is characterized as IHC 1+ when the test specimen exhibits an incomplete HER2 membrane staining that is faint/barely perceptible and within greater than 10% of the invasive tumor cells, wherein the staining is readily appreciated using a low-power objective. In a specific embodiment, a level of HER2 in a test specimen comprising cells of the cancer is characterized as IHC 0. In a specific embodiment, the level of HER2 in the test specimen is characterized as IHC 0 when the test specimen exhibits no HER2 staining observed, wherein the lack of staining is readily appreciated using a low-power objective, or a HER2 membrane staining that is incomplete and is faint/barely perceptible and within less than or equal to 10% of the invasive tumor cells, wherein the staining is readily appreciated using a low-power objective.

In a specific embodiment, the HER2-positive cancer that expresses a low level of HER2 is a programmed death-ligand 1 (PDL1)-positive cancer. In a specific embodiment, the HER2-positive cancer overexpresses PDL1 relative to expression of PDL1 in analogous noncancerous cells of the same tissue type as the cancer. In a specific embodiment, the HER2-positive cancer is deemed to overexpress PDL1 when a test specimen comprising cells of the cancer expresses a detectable level of PDL1 above background. In a specific embodiment, the cancer is resistant to PDL1 blockade with an anti-PDL1 therapy. In a specific embodiment, the anti-PDL1 therapy is an anti-PDL1 antibody. In a specific embodiment, the anti-PDL1 antibody is atezolizumab. In a specific embodiment, the cancer is resistant to programmed cell death protein 1 (PD1) blockade with an anti-PD1 therapy. In a specific embodiment, the anti-PD1 therapy is an anti-PD1 antibody. In a specific embodiment, the anti-PD1 antibody is pembrolizumab.

In a specific embodiment, the HER2-positive cancer that expresses a low level of HER2 is breast cancer, gastric cancer, an osteosarcoma, desmoplastic small round cell cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, or neuroblastoma. In a specific embodiment, the cancer is gastric cancer or breast cancer. In a specific embodiment of a method described herein, the HER2-positive cancer that expresses a low level of HER2 is a metastatic tumor. In a specific embodiment, the metastatic tumor is a peritoneal metastasis. In a specific embodiment, the cancer is resistant to treatment with trastuzumab, cetuximab, lapatinib, erlotinib, or any other small molecule or antibody that targets the HER family of receptors.

In a specific embodiment, also provided herein is a method of treating a HER2-positive cancer in a subject in need thereof, comprising administering to the subject a therapeutically effective amount of a bispecific binding molecule comprising an aglycosylated monoclonal antibody that is an immunoglobulin that binds to HER2, said immunoglobulin comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical, and wherein the cancer is not indicated for treatment with trastuzumab, and preferably wherein the cancer is not a head and neck cancer. In a specific embodiment, the cancer is determined not to be indicated for treatment with trastuzumab based on the following characterization of the cancer: (a) a first determination of a level of HER2 in a test specimen comprising cells of the cancer is reported as negative, or (b) a first determination of a level of HER2 in a test specimen comprising cells of the cancer is reported as equivocal, and a second determination of a level of HER2 in a test specimen comprising cells of the cancer is reported as equivocal or negative. In a specific embodiment, the determination of the level of HER2 in the test specimen is reported as negative when the level of HER2 in the test specimen is characterized as (i) (1) immunohistochemistry (IHC) 1+, wherein the level of HER2 in the test specimen is characterized as IHC 1+ when the test specimen exhibits an incomplete HER2 membrane staining that is faint/barely perceptible and within greater than 10% of the invasive tumor cells, wherein the staining is readily appreciated using a low-power objective; (2) IHC 0, wherein the level of HER2 in the test specimen is characterized as IHC 0 when the test specimen exhibits no HER2 staining observed, wherein the lack of staining is readily appreciated using a low-power objective, or a HER2 membrane staining that is incomplete and is faint/barely perceptible and within less than or equal to 10% of the invasive tumor cells, wherein the staining is readily appreciated using a low-power objective; or (ii) in situ hybridization (ISH) negative, wherein the level of HER2 in the test specimen is characterized as ISH negative when the test specimen exhibits (1) a single-probe average HER2 copy number of less than 4.0 signals per cell; or (2) a dual-probe HER2/CEP17 ratio of less than 2.0 with an average HER2 copy number of less than 4.0 signals per cell. In a specific embodiment, the determination of the level of HER2 in the test specimen is reported as equivocal when the level of HER2 in the test specimen is characterized as: (i) IHC 2+, wherein the level of HER2 in the test specimen is characterized as IHC 2+ when the test specimen exhibits (1) a circumferential HER2 membrane staining that is incomplete and/or weak/moderate and within greater than 10% of invasive tumor cells, wherein the staining is observed in a homogenous and contiguous population, and wherein the staining is readily appreciated using a low-power objective; or (2) a complete and circumferential HER2 membrane staining that is intense and within less than or equal to 10% of invasive tumor cells, wherein the staining is readily appreciated using a low-power objective; or (ii) ISH equivocal, wherein the level of HER2 in the test specimen is characterized as ISH equivocal when the test specimen exhibits (1) a single-probe ISH average HER2 copy number of greater than or equal to 4.0 and less than 6.0 signals/cell, wherein the copy number is determined by counting at least 20 cells within the area and is observed in a homogenous and contiguous population; or (2) a dual-probe HER2/CEP17 ratio of less than 2.0 with an average HER2 copy number of greater than or equal to 4.0 and less than 6.0 signals per cell, wherein the copy number is determined by counting at least 20 cells within the area and is observed in a homogenous and contiguous population. In a specific embodiment, the HER2-positive cancer is a programmed death-ligand 1 (PDL1)-positive cancer. In a specific embodiment, the HER2-positive cancer overexpresses PDL1 relative to expression of PDL1 in analogous noncancerous cells of the same tissue type as the cancer. In a specific embodiment, the HER2-positive cancer is deemed to overexpress PDL1 when a test specimen comprising cells of the cancer expresses a detectable level of PDL1 above background. In a specific embodiment, the cancer is resistant to PDL1 blockade with an anti-PDL1 therapy. In a specific embodiment, the anti-PDL1 therapy is an anti-PDL1 antibody. In a specific embodiment, the anti-PDL1 antibody is atezolizumab. In a specific embodiment, the cancer is resistant to programmed cell death protein 1 (PD1) blockade with an anti-PD1 therapy. In a specific embodiment, the anti-PD1 therapy is an anti-PD1 antibody. In a specific embodiment, the anti-PD1 antibody is pembrolizumab. In a specific embodiment, the HER2-positive that is not indicated for treatment with trastuzumab is breast cancer, gastric cancer, an osteosarcoma, desmoplastic small round cell cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, or neuroblastoma. In a specific embodiment, the HER2-positive that is not indicated for treatment with trastuzumab is gastric cancer or breast cancer. In a specific embodiment, the HER2-positive that is not indicated for treatment with trastuzumab is a metastatic tumor. In a specific embodiment, the metastatic tumor is a peritoneal metastasis. In a specific embodiment, the cancer is resistant to treatment with trastuzumab, cetuximab, lapatinib, erlotinib, or any other small molecule or antibody that targets the HER family of receptors.

Also provided herein is a method of treating a HER2-positive, PDL1-positive cancer in a subject in need thereof, comprising administering to the subject a therapeutically effective amount of a bispecific binding molecule comprising an aglycosylated monoclonal antibody that is an immunoglobulin that binds to HER2, said immunoglobulin comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical, wherein the cancer is resistant to PDL1 blockade with an anti-PDL1 therapy and/or is resistant to PD1 blockade with an anti-PD1 therapy. In a specific embodiment, the HER2-positive cancer overexpresses PDL1 relative to expression of PDL1 in analogous noncancerous cells of the same tissue type as the cancer. In a specific embodiment, the HER2-positive cancer is deemed to overexpress PDL1 when a test specimen comprising cells of the cancer expresses a detectable level of PDL1 above background. In a specific embodiment, the anti-PDL1 therapy is an anti-PDL1 antibody. In a specific embodiment, the anti-PDL1 antibody is atezolizumab. In a specific embodiment, the anti-PD1 therapy is an anti-PD1 antibody. In a specific embodiment, the anti-PD1 antibody is pembrolizumab. In a specific embodiment, the HER2-positive cancer is breast cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, or neuroblastoma. In a specific embodiment, the HER2-positive cancer is a metastatic tumor. In a specific embodiment, the metastatic tumor is a peritoneal metastasis. In a specific embodiment, the cancer is resistant to treatment with trastuzumab, cetuximab, lapatinib, erlotinib, or any other small molecule or antibody that targets the HER family of receptors.

In a specific embodiment of a method described herein, the sequence of each heavy chain is any of SEQ ID NOs: 23, 27, 62 or 63. In a specific embodiment, the sequence of each light chain is SEQ ID NO: 25. In a specific embodiment, the sequence of the peptide linker is any of SEQ ID NOs: 14 or 35-41. In a specific embodiment, the sequence of a $V_H$ domain in the first scFv is any of SEQ ID NOs: 15, 17 or 64. In a specific embodiment, the sequence of an intra-scFv peptide linker between a $V_H$ domain and a $V_L$ domain in the first scFv is any of SEQ ID NOs: 14 or 35-41. In a specific embodiment, the sequence of a $V_L$ domain in the first scFv is any of SEQ ID NOs: 16 or 65. In a specific embodiment, the sequence of the scFv is any of SEQ ID NOs: 19 or 48-59. In a specific embodiment, the sequence of the first light chain fusion polypeptide is any of SEQ ID NOs: 29, 34, 42-47, or 60. In a specific embodiment, the sequence of each heavy chain is SEQ ID NO: 27 and the sequence of each light chain is SEQ ID NO: 25. In a specific embodiment, the sequence of the scFv is SEQ ID NO: 19. In a specific embodiment, the peptide linker is 5-30, 5-25, 5-15, 10-30, 10-20, 10-15, 15-30, or 15-25 amino acids in length. In a specific embodiment, the sequence of the peptide linker is SEQ ID NO: 14. In a specific embodiment, the sequence of the first light chain fusion polypeptide is SEQ ID NO: 60. In a specific embodiment, the sequence of the heavy chain is SEQ ID NO: 62 and the sequence of each light chain fusion polypeptide is SEQ ID NO: 60. In a specific embodiment, the sequence of the first light chain fusion polypeptide is SEQ ID NO: 47. In a specific embodiment, the sequence of the heavy chain is SEQ ID NO: 27 and the sequence of each light chain fusion polypeptide is SEQ ID NO: 47. In a specific embodiment, the sequence of the first light chain fusion polypeptide is SEQ ID NO: 29. In a specific embodiment, the sequence of the heavy chain is SEQ ID NO: 27 and the sequence of each light chain fusion polypeptide is SEQ ID NO: 29. In a specific embodiment, the $K_D$ of the bispecific binding molecule is between 70 nM and 1 µM for CD3. In a specific embodiment, the bispecific binding molecule does not bind an Fc receptor in its soluble or cell-bound form. In a specific embodiment, the heavy chain has been mutated to destroy an N-linked glycosylation site. In a specific embodiment, the heavy chain has an amino acid substitution to replace an asparagine that is an N-linked glycosylation site, with an amino acid that does not function as a glycosylation site. In a specific embodiment, the heavy chain has been mutated to destroy a C1q binding site. In a specific embodiment, the bispecific binding molecule does not activate complement. In a specific embodiment, the scFv is disulfide stabilized.

In a specific embodiment of a method described herein, the administering is intravenous. In a specific embodiment of a method described herein, the administering is intraperitoneal, intrathecal, intraventricular in the brain, or intraparenchymal in the brain. In a specific embodiment of a method described herein, the administering is performed in combination with multi-modality anthracycline-based therapy.

In a specific embodiment of a method described herein, the method further comprises administering to the subject doxorubicin, cyclophosphamide, paclitaxel, docetaxel, and/or carboplatin. In a specific embodiment of a method described herein, the method further comprises administering to the subject radiotherapy. In a specific embodiment of a method described herein, the method further comprises administering to the subject an agent that increases cellular HER2 expression.

In a specific embodiment of a method described herein, the bispecific binding molecule is not bound to a T cell during said administering step.

In a specific embodiment of a method described herein, the method further comprises administering T cells to the subject. In a specific embodiment, the T cells are bound to molecules identical to said bispecific binding molecule.

In a specific embodiment of a method described herein, the subject is a human. In a specific embodiment, the subject is a canine.

In a specific embodiment of a method described herein, the bispecific binding molecule is contained in a pharmaceutical composition, which pharmaceutical composition further comprises a pharmaceutically acceptable carrier.

Also provided herein is a method of treating a HER2-positive cancer in a subject in need thereof, comprising administering to the subject a therapeutically effective amount of a cell expressing a bispecific binding molecule of the invention, wherein the cancer expresses a low level of HER2, and preferably wherein the cancer is not a head and neck cancer. In a specific embodiment, the sequence of the heavy chain of the bispecific binding molecule is SEQ ID NO: 27. In a specific embodiment, the nucleotide sequence encoding the heavy chain of the bispecific binding molecule is SEQ ID NO: 26.

Also provided herein is a method of treating a HER2-positive cancer in a subject in need thereof, comprising administering to the subject (a) a therapeutically effective amount of an ex vivo cell comprising a vector comprising (i) a first polynucleotide comprising nucleotide sequences encoding a light chain fusion polypeptide comprising an immunoglobulin light chain fused to a scFv, via a peptide linker, operably linked to a first promoter, and (ii) a a second polynucleotide encoding an immunoglobulin heavy chain that binds to HER2 operably linked to a second promoter, wherein the light chain binds to HER2 and wherein the scFv binds to CD3, or (b) a therapeutically effective amount of an ex vivo cell comprising a mixture of polynucleotides comprising (i) a first polynucleotide comprising nucleotide sequences encoding a light chain fusion polypeptide comprising an immunoglobulin light chain fused to a scFv, via a peptide linker, operably linked to a first promoter, and (ii) a second polynucleotide encoding an immunoglobulin heavy chain that binds to HER2 operably linked to a second promoter; and wherein the cancer expresses a low level of HER2, and wherein the cancer is not a head and neck cancer. In a specific embodiment, the sequence of the heavy chain is SEQ ID NO: 27. In a specific embodiment, the nucleotide sequence encoding the heavy chain is SEQ ID NO: 26.

Also provided herein is a method of treating a HER2-positive cancer in a subject in need thereof, comprising administering to the subject a therapeutically effective amount of a cell expressing a bispecific binding molecule of the invention, wherein the cancer is not indicated for treatment with trastuzumab, and preferably wherein the cancer is not a head and neck cancer. In a specific embodiment, the sequence of the heavy chain of the bispecific binding molecule is SEQ ID NO: 27. In a specific embodiment, the nucleotide sequence encoding the heavy chain of the bispecific binding molecule is SEQ ID NO: 26.

Also provided herein is a method of treating a HER2-positive cancer in a subject in need thereof, comprising administering to the subject (a) a therapeutically effective amount of an ex vivo cell comprising a vector comprising (i) a first polynucleotide comprising nucleotide sequences encoding a light chain fusion polypeptide comprising an immunoglobulin light chain fused to a scFv, via a peptide linker, operably linked to a first promoter, and (ii) a a second polynucleotide encoding an immunoglobulin heavy chain that binds to HER2 operably linked to a second promoter, wherein the light chain binds to HER2 and wherein the scFv binds to CD3, or (b) a therapeutically effective amount of an ex vivo cell comprising a mixture of polynucleotides comprising (i) a first polynucleotide comprising nucleotide sequences encoding a light chain fusion polypeptide comprising an immunoglobulin light chain fused to a scFv, via a peptide linker, operably linked to a first promoter, and (ii) a second polynucleotide encoding an immunoglobulin heavy chain that binds to HER2 operably linked to a second promoter; and wherein the cancer is not indicated for treatment with trastuzumab, and wherein the cancer is not a head and neck cancer.

In certain embodiments, provided herein is a bispecific binding molecule comprising an aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical.

In certain embodiments of the bispecific binding molecule, the sequence of each heavy chain is any of SEQ ID NOs: 23 or 27. In certain embodiments of the bispecific binding molecule, the sequence of each light chain is SEQ ID NO: 25. In certain embodiments of the bispecific binding molecule, the sequence of the peptide linker is SEQ ID NO: 14. In certain embodiments of the bispecific binding molecule, the sequence of a $V_H$ domain in the first scFv is any of SEQ ID NOs: 15 or 17. In certain embodiments of the bispecific binding molecule, the sequence of an intra-scFv peptide linker between a $V_H$ domain and a $V_L$ domain in the first scFv is of SEQ ID NO: 14. In certain embodiments of the bispecific binding molecule, the sequence of a $V_L$ domain in the first scFv is of SEQ ID NO: 16. In certain embodiments of the bispecific binding molecule, the sequence of the scFv is SEQ ID NO: 19. In certain embodiments of the bispecific binding molecule, the sequence of the first light chain fusion polypeptide is SEQ ID NO: 29.

In certain embodiments of the bispecific binding molecule, the sequence of each heavy chain is any of SEQ ID NOs: 23, 27, 62 or 63. In certain embodiments of the bispecific binding molecule, the sequence of each light chain is SEQ ID NO: 25. In certain embodiments of the bispecific binding molecule, the sequence of the peptide linker is any of SEQ ID NOs: 14 or 35-41. In certain embodiments of the bispecific binding molecule, the sequence of a $V_H$ domain in the first scFv is any of SEQ ID NOs: 15, 17 or 64. In certain embodiments of the bispecific binding molecule, the sequence of an intra-scFv peptide linker between a $V_H$ domain and a $V_L$ domain in the first scFv is any of SEQ ID NOs: 14 or 35-41. In certain embodiments of the bispecific binding molecule, the sequence of a $V_L$ domain in the first scFv is any of SEQ ID NOs: 16 or 65. In certain embodiments of the bispecific binding molecule, the sequence of the scFv is any of SEQ ID NOs: 19 or 48-59. In certain embodiments of the bispecific binding molecule, the sequence of the first light chain fusion polypeptide is any of SEQ ID NOs: 29, 34, 42-47, or 60.

In certain embodiments of the bispecific binding molecule, the sequence of each heavy chain is SEQ ID NO: 27 and the sequence of each light chain is SEQ ID NO: 25. In certain embodiments of the bispecific binding molecule, the sequence of the scFv is SEQ ID NO: 19. In certain embodiments of the bispecific binding molecule, the sequence of the heavy chain is SEQ ID NO: 27, the sequence of each light chain is SEQ ID NO: 25 and the sequence of the scFv is SEQ ID NO: 19. In certain embodiments of the bispecific binding molecule, the peptide linker is 5-30, 5-25, 5-15, 10-30, 10-20, 10-15, 15-30, or 15-25 amino acids in length. In certain embodiments, the sequence of the peptide linker is SEQ ID NO: 14.

In certain embodiments, the sequence of the first light chain fusion polypeptide is SEQ ID NO: 60. In certain embodiments, the sequence of the heavy chain is SEQ ID NO: 62 and the sequence of each light chain fusion polypeptide is SEQ ID NO: 60.

In certain embodiments, the sequence of the first light chain fusion polypeptide is SEQ ID NO: 47. In certain embodiments, the sequence of the heavy chain is SEQ ID NO: 27 and the sequence of each light chain fusion polypeptide is SEQ ID NO: 47.

In certain embodiments, the sequence of the first light chain fusion polypeptide is SEQ ID NO: 29. In certain embodiments, the sequence of the heavy chain is SEQ ID NO: 27 and the sequence of each light chain fusion polypeptide is SEQ ID NO: 29.

In certain embodiments of the bispecific binding molecule, the $K_D$ is between 70 nM and 1 µM for CD3.

In certain embodiments of the bispecific binding molecule, the scFv of the bispecific binding molecule comprises one or more mutations to stabilize disulfide binding. In certain embodiments of the bispecific binding molecule, the stabilization of disulfide binding prevents aggregation of the bispecific binding molecule. In certain embodiments of the bispecific binding molecule, the stabilization of disulfide binding reduces aggregation of the bispecific binding molecule as compared to aggregation of the bispecific binding molecule without the stabilization of disulfide binding. In certain embodiments of the bispecific binding molecule, the one or more mutations to stabilize disulfide binding comprise a $V_H$ G44C mutation and a $V_L$ Q100C mutation (e.g., as present in SEQ ID NOS: 54-59). In certain embodiments of the bispecific binding molecule, the one or more mutations to stabilize disulfide binding are the replacement of the amino acid residue at $V_H$44 (according to the Kabat numbering system) with a cysteine and the replacement of the amino acid residue at $V_L$100 (according to the Kabat numbering system) with a cysteine so as to introduce a disulfide bond between $V_H$44 and $V_L$100 (e.g., as present in SEQ ID NOS: 54-59).

In certain embodiments of the bispecific binding molecule, the bispecific binding molecule does not bind an Fc receptor in its soluble or cell-bound form. In certain embodiments of the bispecific binding molecule, the heavy chain has been mutated to destroy an N-linked glycosylation site. In certain embodiments of the bispecific binding molecule, the heavy chain has an amino acid substitution to replace an asparagine that is an N-linked glycosylation site, with an amino acid that does not function as a glycosylation site. In certain embodiments of the bispecific binding molecule, the heavy chain has been mutated to destroy a C1q binding site. In certain embodiments, the bispecific binding molecule does not activate complement.

In certain embodiments, provided herein is a bispecific binding molecule comprising an aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, wherein the first and second light chain fusion polypeptides are identical, and wherein (a) the sequence of each heavy chain is SEQ ID NO: 62; and (b) the sequence of each light chain fusion polypeptide is SEQ ID NO: 60.

In certain embodiments, provided herein is a bispecific binding molecule comprising an aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, wherein the first and second light chain fusion polypeptides are identical, and wherein (a) the sequence of each heavy chain is SEQ ID NO: 27; and (b) the sequence of each light chain fusion polypeptide is SEQ ID NO: 47.

In certain embodiments, provided herein is a bispecific binding molecule comprising an aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, wherein the first and second light chain fusion polypeptides are identical, and wherein (a)

the sequence of each heavy chain is SEQ ID NO: 27; and (b) the sequence of each light chain fusion polypeptide is SEQ ID NO: 29.

In certain embodiments, provided herein is a polynucleotide comprising nucleotide sequences encoding a light chain fusion polypeptide comprising an immunoglobulin light chain fused to a scFv, via a peptide linker, wherein the light chain binds to HER2 and wherein the scFv binds to CD3. In certain embodiments of the polynucleotide, the sequence of the light chain is SEQ ID NO: 25. In certain embodiments of the polynucleotide, the nucleotide sequence encoding the light chain is SEQ ID NO: 24. In certain embodiments of the polynucleotide, the sequence of the scFv is SEQ ID NO: 19. In certain embodiments of the polynucleotide, the nucleotide sequence encoding the scFv is SEQ ID NO: 18. In certain embodiments of the polynucleotide, the sequence of the light chain is SEQ ID NO: 25 and the sequence of the scFv is SEQ ID NO: 19. In certain embodiments of the polynucleotide, the nucleotide sequence encoding the light chain is SEQ ID NO: 24 and the nucleotide sequence encoding the scFv is SEQ ID NO: 18. In certain embodiments of the polynucleotide, the peptide linker is 5-30, 5-25, 5-15, 10-30, 10-20, 10-15, 15-30, or 15-25 amino acids in length. In certain embodiments of the polynucleotide, the sequence of the peptide linker is SEQ ID NO: 14. In certain embodiments of the polynucleotide, the nucleotide sequence encoding the peptide linker is SEQ ID NO: 13.

In certain embodiments, provided herein is a vector comprising a polynucleotide encoding nucleotide sequences encoding a light chain fusion polypeptide comprising an immunoglobulin light chain fused to a scFv, via a peptide linker, wherein the light chain binds to HER2 and wherein the scFv binds to CD3, operably linked to a promoter. In certain embodiments, provided herein is an ex vivo cell comprising the polynucleotide provided herein operably linked to a promoter. In certain embodiments, provided herein is an ex vivo cell comprising the vector.

In certain embodiments, provided herein is a vector comprising (i) a first polynucleotide comprising nucleotide sequences encoding a light chain fusion polypeptide comprising an immunoglobulin light chain fused to a scFv, via a peptide linker, wherein the light chain binds to HER2 and wherein the scFv binds to CD3 operably linked to a first promoter, and (ii) a second polynucleotide encoding an immunoglobulin heavy chain that binds to HER2 operably linked to a second promoter. In certain embodiments, provided herein is an ex vivo cell comprising the vector.

In certain embodiments, provided herein is a method of producing a bispecific binding molecule comprising (a) culturing the cell comprising the vector comprising (i) a first polynucleotide comprising nucleotide sequences encoding a light chain fusion polypeptide comprising an immunoglobulin light chain fused to a scFv, via a peptide linker, wherein the light chain binds to HER2 and wherein the scFv binds to CD3 operably linked to a first promoter, and (ii) a second polynucleotide encoding an immunoglobulin heavy chain that binds to HER2 operably linked to a second promoter, to express the first and second polynucleotides such that a bispecific binding molecule comprising said light chain fusion polypeptide and said immunoglobulin heavy chain is expressed, and (b) recovering the bispecific binding molecule.

In certain embodiments, provided herein is a pharmaceutical composition comprising a therapeutically effective amount of (i) the first polynucleotide operably linked to the first promoter, and (ii) the second polynucleotide encoding an immunoglobulin heavy chain that binds to HER2 operably linked to the second promoter. In certain embodiments, provided herein is a pharmaceutical composition comprising a therapeutically effective amount of a vector comprising (i) the first polynucleotide operably linked to the first promoter, and (ii) the second polynucleotide encoding an immunoglobulin heavy chain that binds to HER2 operably linked to the second promoter. In certain embodiments, the vector is a viral vector.

In certain embodiments, provided herein is a mixture of polynucleotides comprising (i) a polynucleotide comprising nucleotide sequences encoding a light chain fusion polypeptide comprising an immunoglobulin light chain fused to a scFv, via a peptide linker, wherein the light chain binds to HER2 and wherein the scFv binds to CD3 operably linked to a first promoter, and (ii) a second polynucleotide encoding an immunoglobulin heavy chain that binds to HER2 operably linked to a second promoter. In certain embodiments of the mixture of polypeptides, the sequence of the heavy chain is SEQ ID NO: 27. In certain embodiments of the mixture of polypeptides, the nucleotide sequence encoding the heavy chain is SEQ ID NO: 26. In certain embodiments, provided herein is an ex vivo cell comprising the mixture of polynucleotides provided herein.

In certain embodiments, provided herein is a method of producing a bispecific binding molecule, comprising (i) culturing the cell comprising the mixture of polynucleotides to express the first and second polynucleotides such that a bispecific binding molecule comprising said light chain fusion polypeptide and said immunoglobulin heavy chain is produced, and (ii) recovering the bispecific binding molecule.

In certain embodiments, provided herein is a method of producing a bispecific binding molecule, comprising (i) expressing the mixture of polynucleotides such that a bispecific binding molecule comprising said first light chain fusion polypeptide and said immunoglobulin heavy chain is produced, and (ii) recovering the bispecific binding molecule.

In certain embodiments, provided herein is a method of making a therapeutic T cell comprising binding a bispecific binding molecule described herein to a T cell. In certain embodiments, the T cell is a human T cell. In certain embodiments, the binding is noncovalently.

In certain embodiments, provided herein is a pharmaceutical composition comprising a therapeutically effective amount of the bispecific binding molecule and a pharmaceutically acceptable carrier.

In certain embodiments, provided herein is a pharmaceutical composition comprising a therapeutically effective amount of the bispecific binding molecule, a pharmaceutically acceptable carrier, and T cells. In certain embodiments, the T cells are bound to the bispecific binding molecule. In certain embodiments, the binding of the T cells to the bispecific binding molecule is noncovalently. In certain embodiments, the T cells are administered to a subject for treatment of a HER2-positive cancer in the subject. In certain embodiments, the T cells are autologous to the subject to whom they are administered. In certain embodiments, the T cells are allogeneic to the subject to whom they are administered. In certain embodiments, the T cells are human T cells.

In certain embodiments, provided herein is a method of treating a HER2-positive cancer in a subject in need thereof comprising administering a pharmaceutical composition provided herein. In certain embodiments, provided herein is a method of treating a HER2-positive cancer in a subject in need thereof comprising administering a therapeutically effective amount of a bispecific binding molecule provided herein. In certain embodiments, the HER2-positive cancer is breast cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhamdomyosarcoma, neuroblastoma, small cell lung cancer, or any other neoplastic tissue that expresses the HER2 receptor. In certain embodiments, the HER2-positive cancer is a primary tumor or a metastatic tumor, e.g., a brain or peritoneal metastases.

In certain embodiments of the method of treating, the administering is intravenous. In certain embodiments of the method of treating, the administering is intraperitoneal, intrathecal, intraventricular, or intraparenchymal. In certain embodiments of the method of treating, the method further comprises administering to the subject doxorubicin, cyclophosphamide, paclitaxel, docetaxel, and/or carboplatin. In certain embodiments of the method of treating, the method further comprises administering to the subject radiotherapy. In certain embodiments of the method of treating, the administering is performed in combination with multi-modality anthracycline-based therapy. In certain embodiments of the method of treating, the administering is performed in combination with cytoreductive chemotherapy. In a specific embodiment, the administering is performed after treating the subject with cytoreductive chemotherapy. In certain embodiments of the method of treating, the bispecific binding molecule is not bound to a T cell. In certain embodiments of the method of treating, the bispecific binding molecule is bound to a T cell. In certain embodiments of the method of treating, the binding of the bispecific binding molecule to the T cell is non-covalently. In certain embodiments of the method of treating, the administering is performed in combination with T cell infusion. In a specific embodiment, the administering is performed after treating the patient with T cell infusion. In certain embodiments, the T cell infusion is performed with T cells that are autologous to the patient to whom the T cells are administered. In certain embodiments, the T cell infusion is performed with T cells that are allogeneic to the patient to whom the T cells are administered. In certain embodiments, the T cells can be bound to molecules identical to a bispecific binding molecule as described herein. In certain embodiments, the binding of the T cells to the molecules identical to a bispecific binding molecule is noncovalently. In certain embodiments, the T cells are human T cells.

In certain embodiments of the method of treating, the method further comprises administering to the subject an agent that increases cellular HER2 expression. In certain embodiments of the method of treating, the HER2-positive cancer is resistant to treatment with trastuzumab, cetuximab, lapatinib, erlotinib, or any other small molecule or antibody that targets the HER family of receptors. In certain embodiments, the subject is a human. In certain embodiments of the method of treating, the subject is a canine.

4. BRIEF DESCRIPTION OF THE DRAWINGS

Figure 1B:
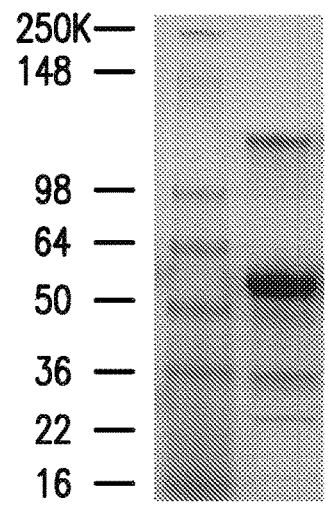
Figure 1C:
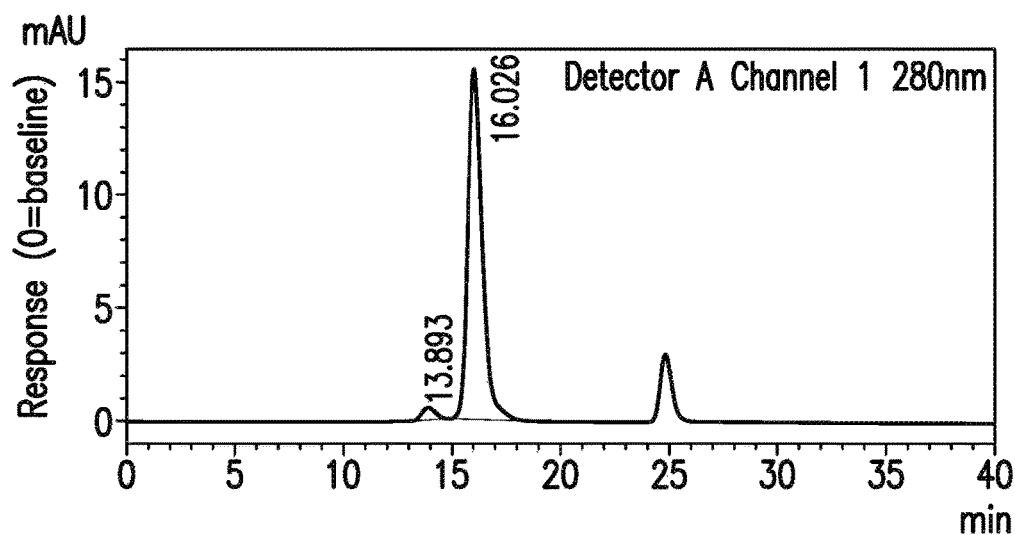
Figure 1D:
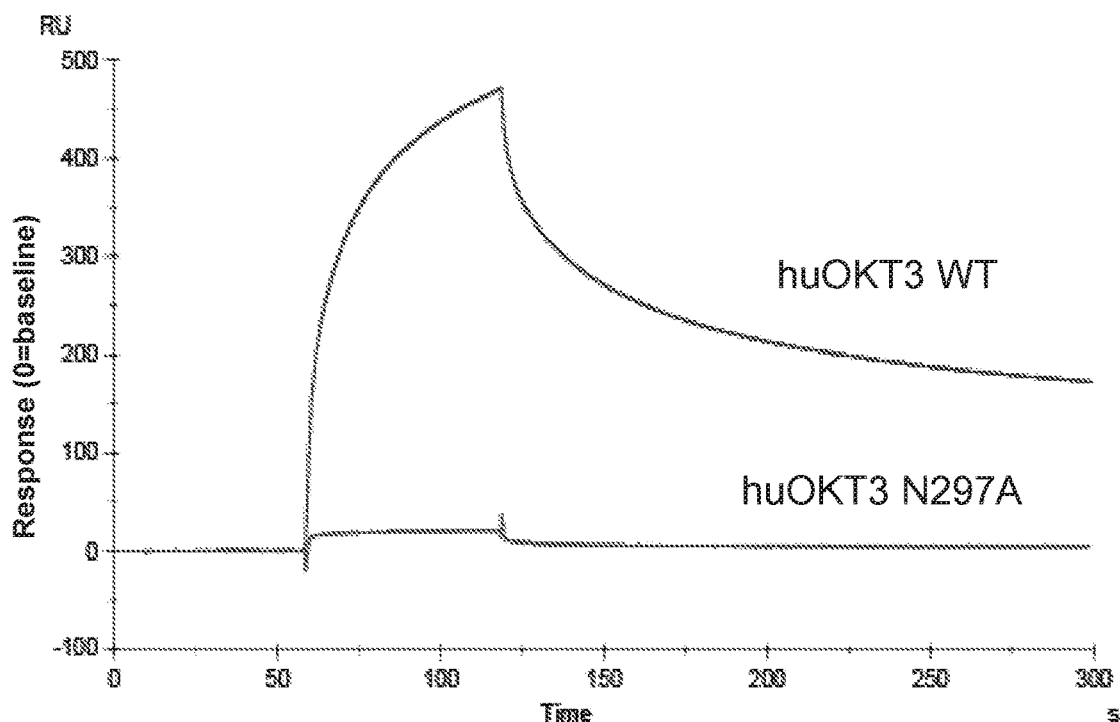
Figure 1E:
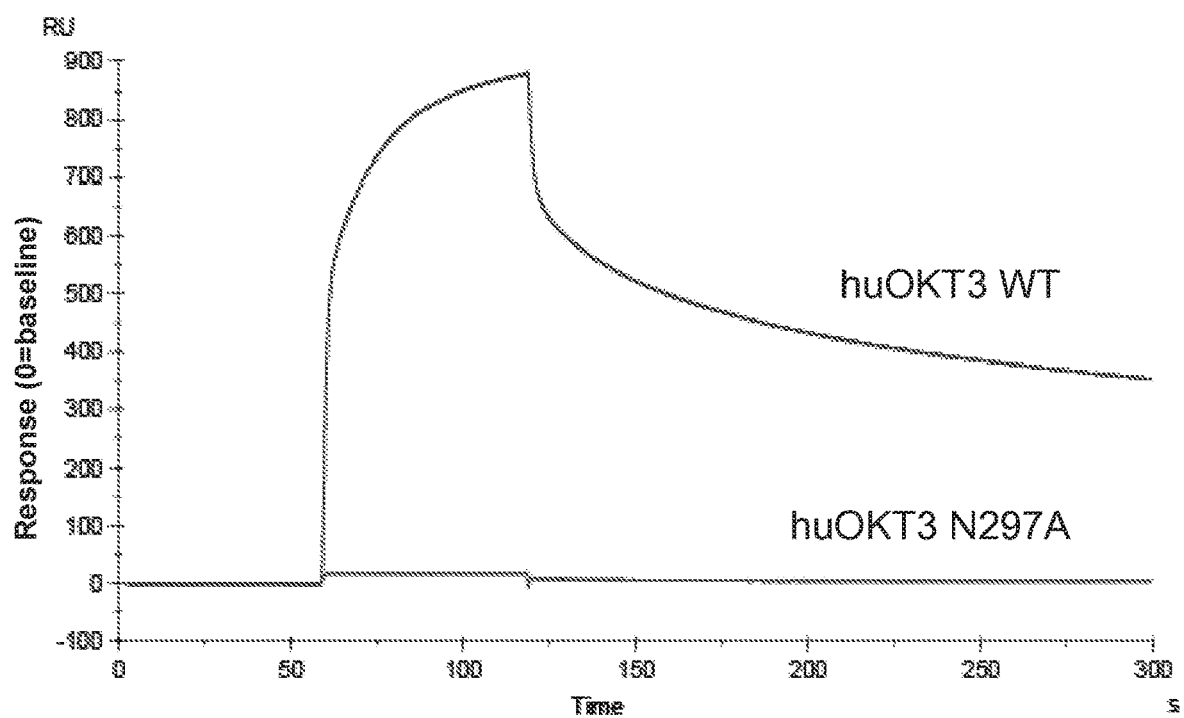

FIG. 1A, FIG. 1B, FIG. 1C, FIG. 1D, and FIG. 1E describe HER2-BsAb. FIG. 1A depicts a schematic of the HER2-BsAb. The arrow points to the N297A mutation introduced into the heavy chain to remove glycosylation. FIG. 1B depicts the purity of HER2-BsAb as demonstrated under reducing SDS-PAGE conditions. FIG. 1C depicts the purity of HER2-BsAb as demonstrated by SEC-HPLC. FIG. 1D demonstrates that the N297A mutation in the human IgG1-Fc inhibits binding to the CD16A Fc receptor. FIG. 1E demonstrates that the N297A mutation in the human IgG1-Fc inhibits binding to the CD32A Fc receptor.

Figure 2A:
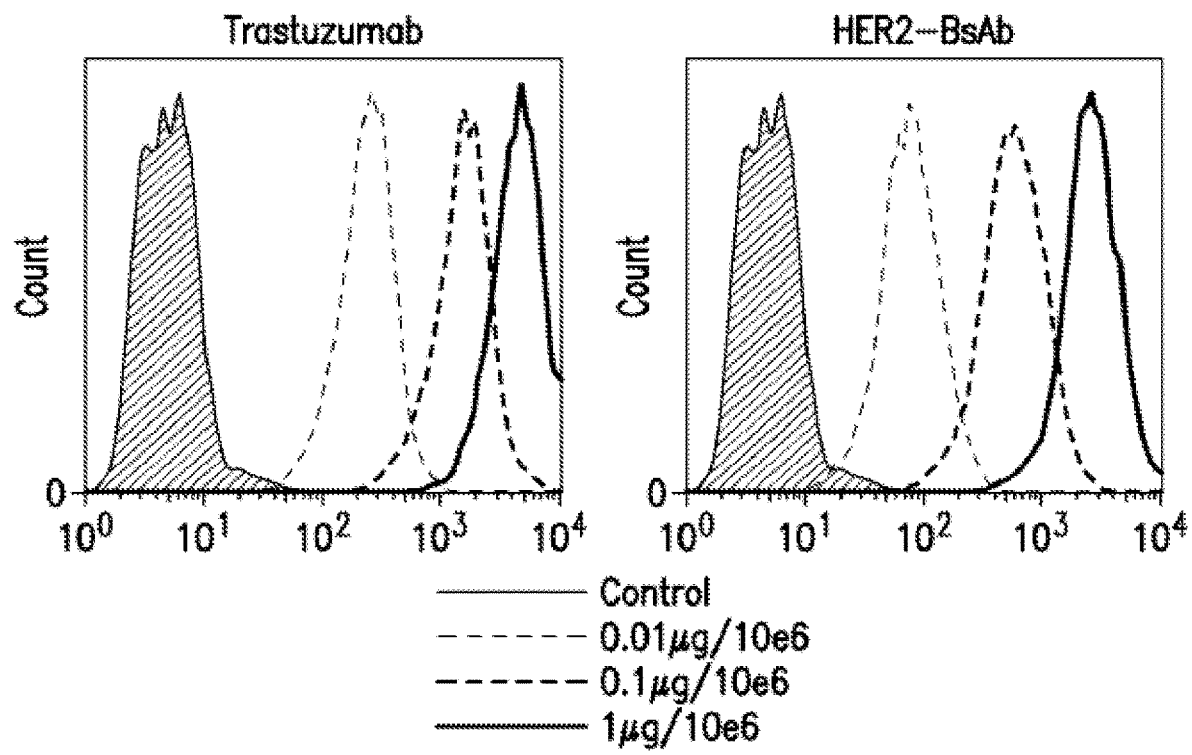
Figure 2B:
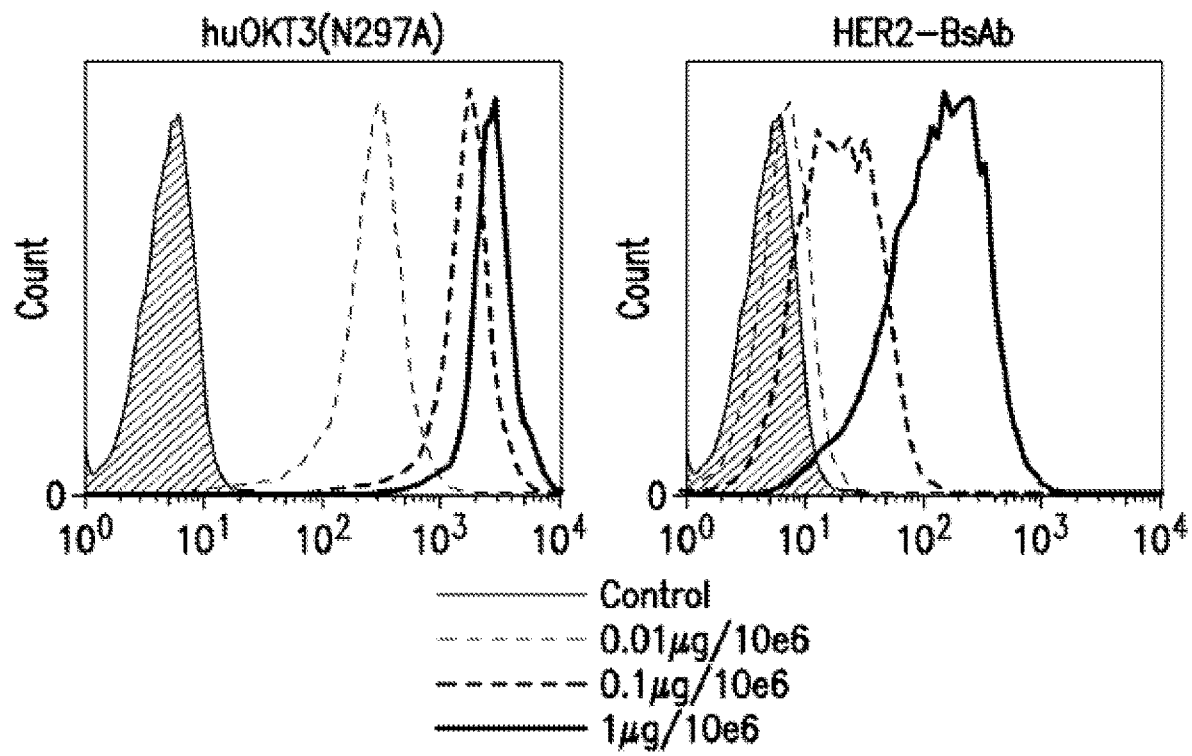

FIG. 2A and FIG. 2B demonstrate that HER2-BsAb binds to a breast cancer cell line and to T cells. FIG. 2A depicts the staining of AU565 breast cancer cells with trastuzumab (left) or with HER2-BsAb (right). FIG. 2B depicts the staining of CD3+ T cells with huOKT3 (left) or with HER2-BsAb (right).

Figure 3:
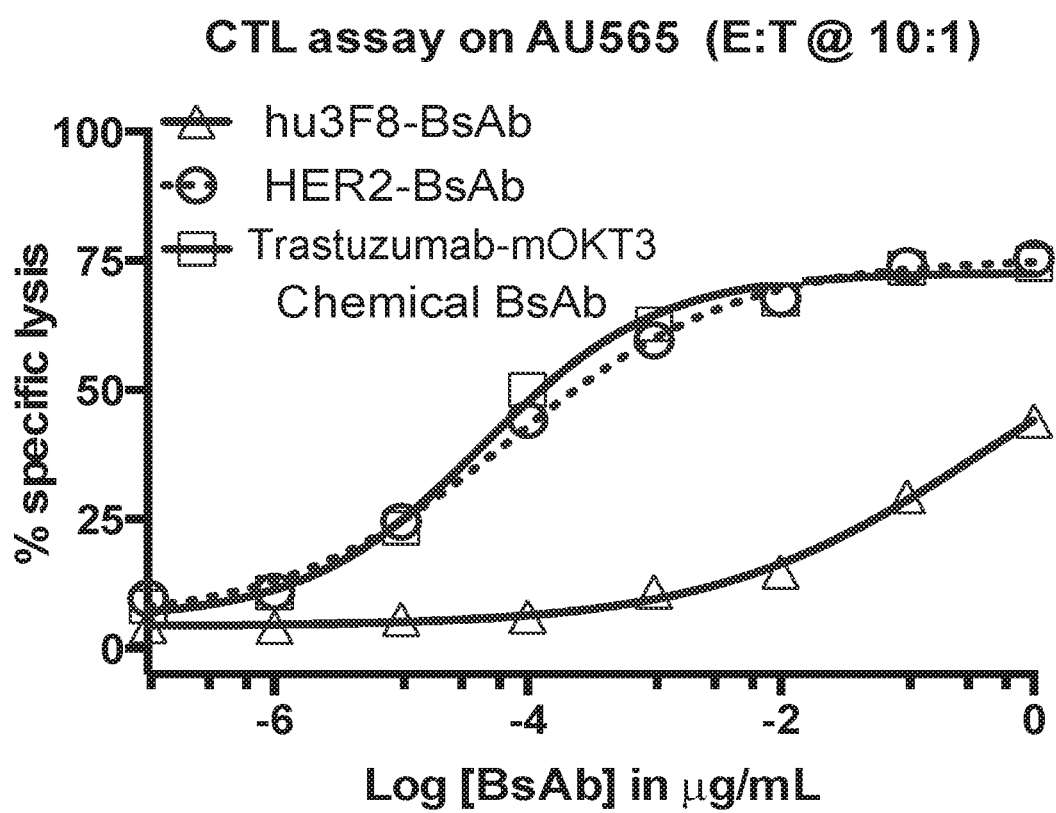

FIG. 3 demonstrates that HER2-BsAb displays potent cytotoxic T lymphocyte activity in a 4 hour $^{51}$Cr release assay. For a description of trastuzumab-mOKT3, see, Thakur et al., 2010, Curr Opin Mol Ther, 12: 340.

FIG. 4 compares the HER2 expression against HER2-BsAb T cell cytotoxicity in a panel of cancer cell lines.

Figure 5A:
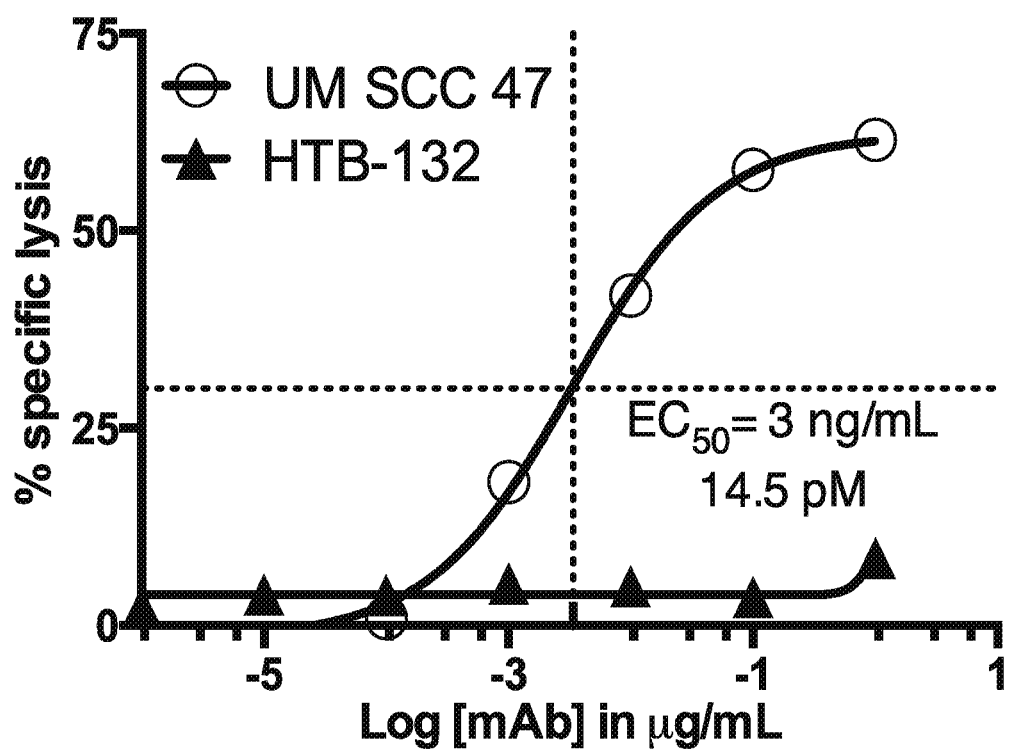
Figure 5B:
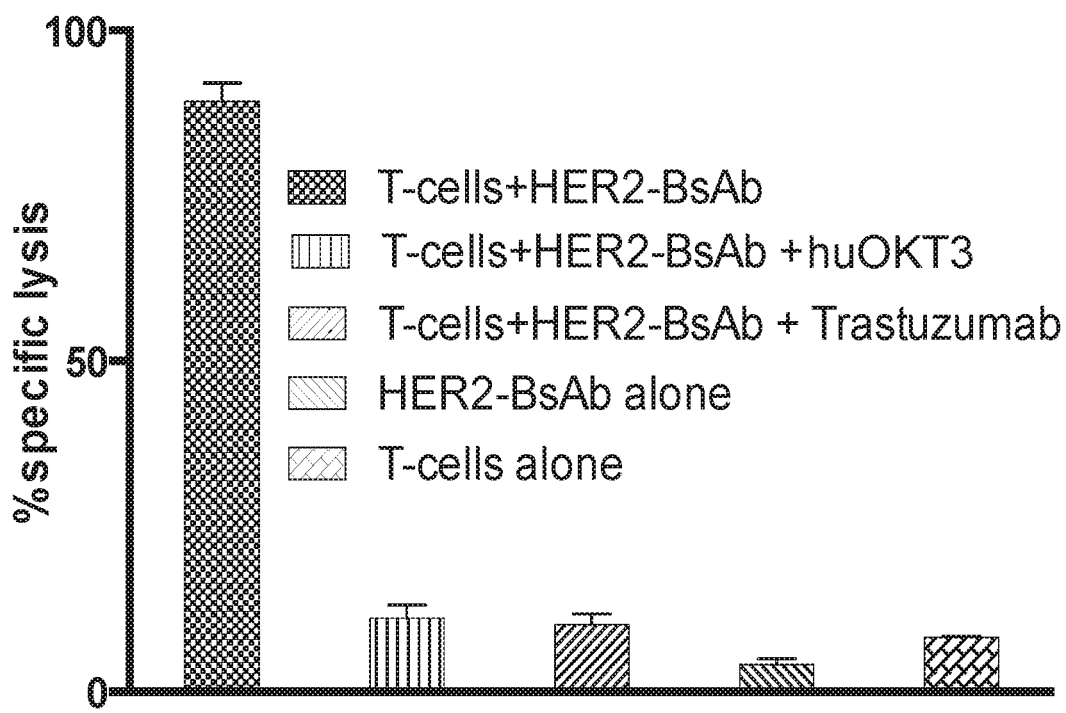

FIG. 5A and FIG. 5B demonstrate that HER2-BsAb-redirected T cell cytotoxicity is antigen specific. FIG. 5A demonstrates that HER2-BsAb mediates T cell cytotoxicity against the HER2-positive cell line, UM SCC 47, but not the HER2-negative cell line HTB-132. FIG. 5B demonstrates that huOKT3 and trastuzumab can block the ability of HER2-BsAb to mediate T cell cytotoxicity.

Figure 6:
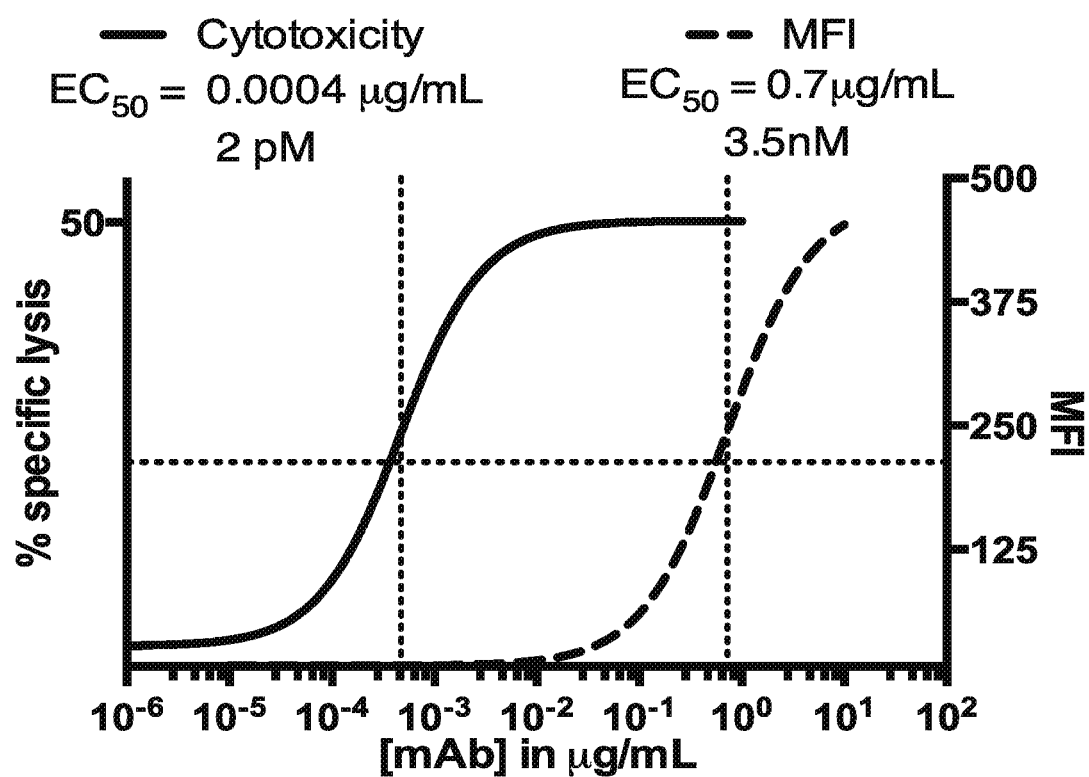

FIG. 6 demonstrates that HER2-BsAb detects low levels of HER2 by comparing the HER2-BsAb mediated T cell cytotoxicity to the HER2 threshold of detection by flow cytometry.

Figure 7A:
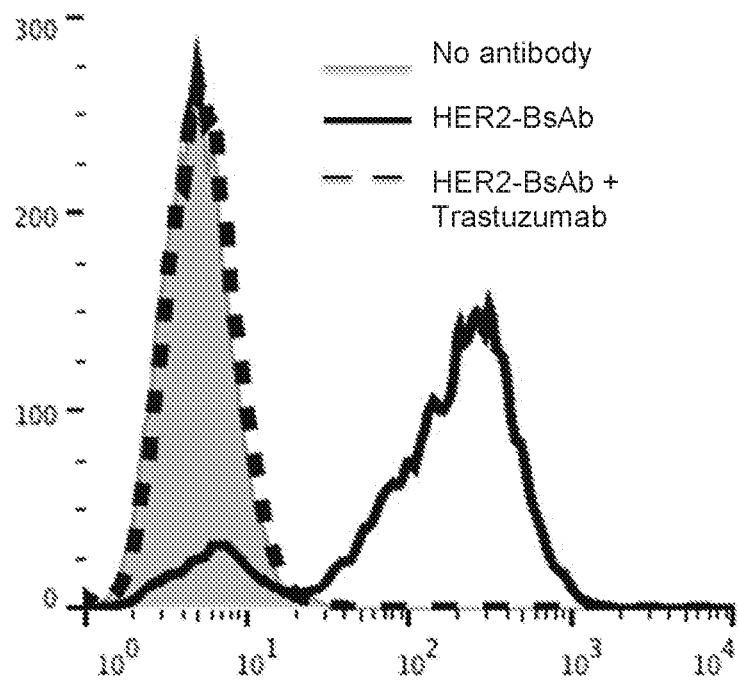
Figure 7B:
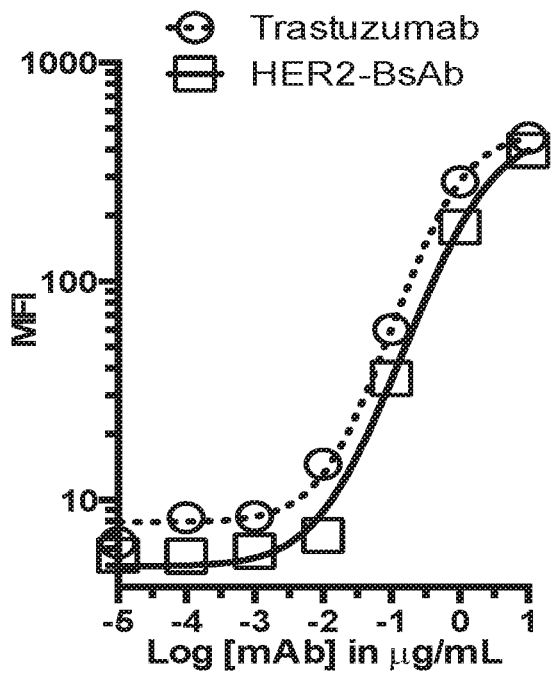
Figure 7C:
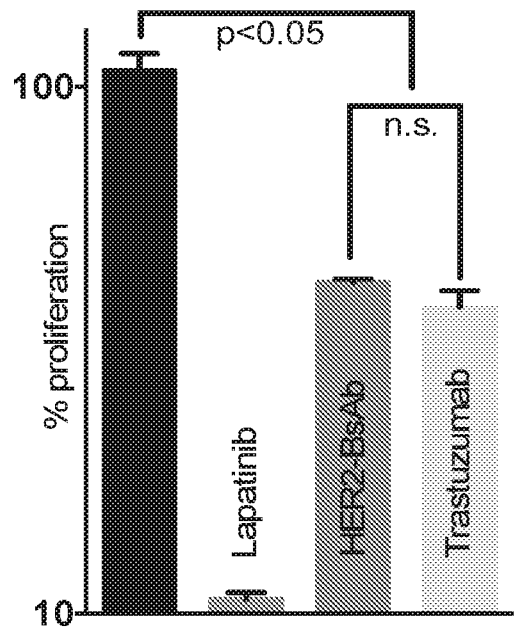

FIG. 7A, FIG. 7B, and FIG. 7C provide the specificity, affinity, and antiproliferative action of HER2-BsAb. FIG. 7A demonstrates that pre-incubation of the HER2-positive SKOV3 ovarian carcinoma cell line blocks binding of HER2-BsAb. FIG. 7B demonstrates that SKOV3 cells labeled with dilutions of trastuzumab or with HER2-BsAb display similar curves when mean fluorescence intensity (MFI) is plotted against antibody concentration. FIG. 7C demonstrates the antiproliferative action of HER2-BsAb compared against trastuzumab in the trastuzumab sensitive breast cancer cell line SKBR3.

FIG. 8 demonstrates that HER2-BsAb is effective against squamous cell carcinoma of the head and neck (SCCHN) cell lines. A panel of SCCHN cells were analyzed for HER2-BsAb-mediated cytotoxicity and EC50 and compared to the expression level of HER2 in each cell line as determined by flow cytometry and by qRT-PCR.

Figure 9A:
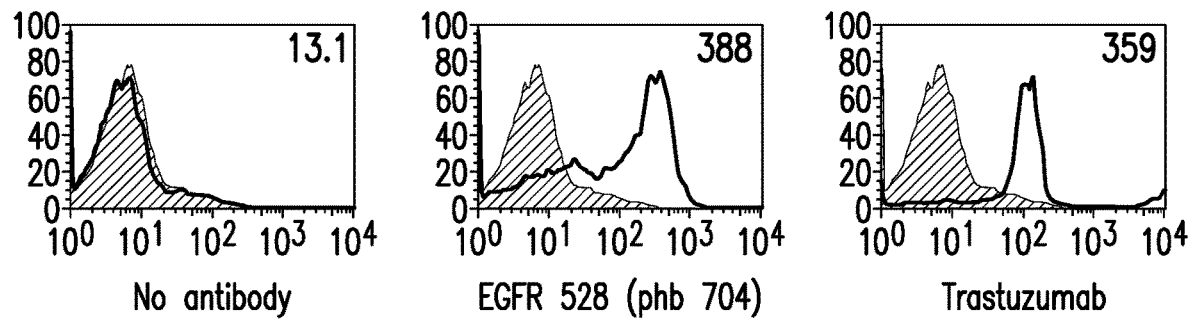
Figure 9B:
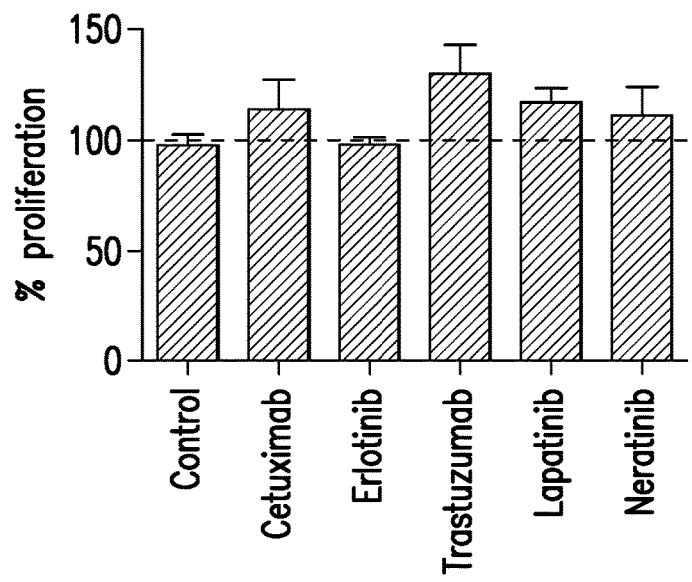
Figure 9C:
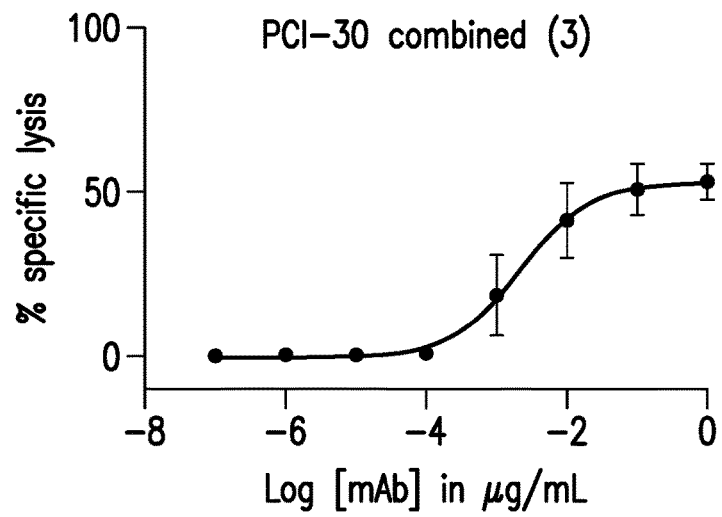

FIG. 9A, FIG. 9B, and FIG. 9C. HER2-BsAb mediates T cell cytotoxicity against SCCHN resistant to other HER targeted therapies. FIG. 9A demonstrates that the SCCHN cell line PCI-30 expresses EGFR and HER2. FIG. 9B demonstrates that PCI-30 cells are resistant to HER-targeted therapies lapatinib, erlotinib, neratinib, trastuzumab, and cetuximab. FIG. 9C demonstrates that PCI-30 cells are sensitive to T cells in the presence of HER2-BsAb. Data represents the average of three different cytotoxicity assays.

Figure 11A:
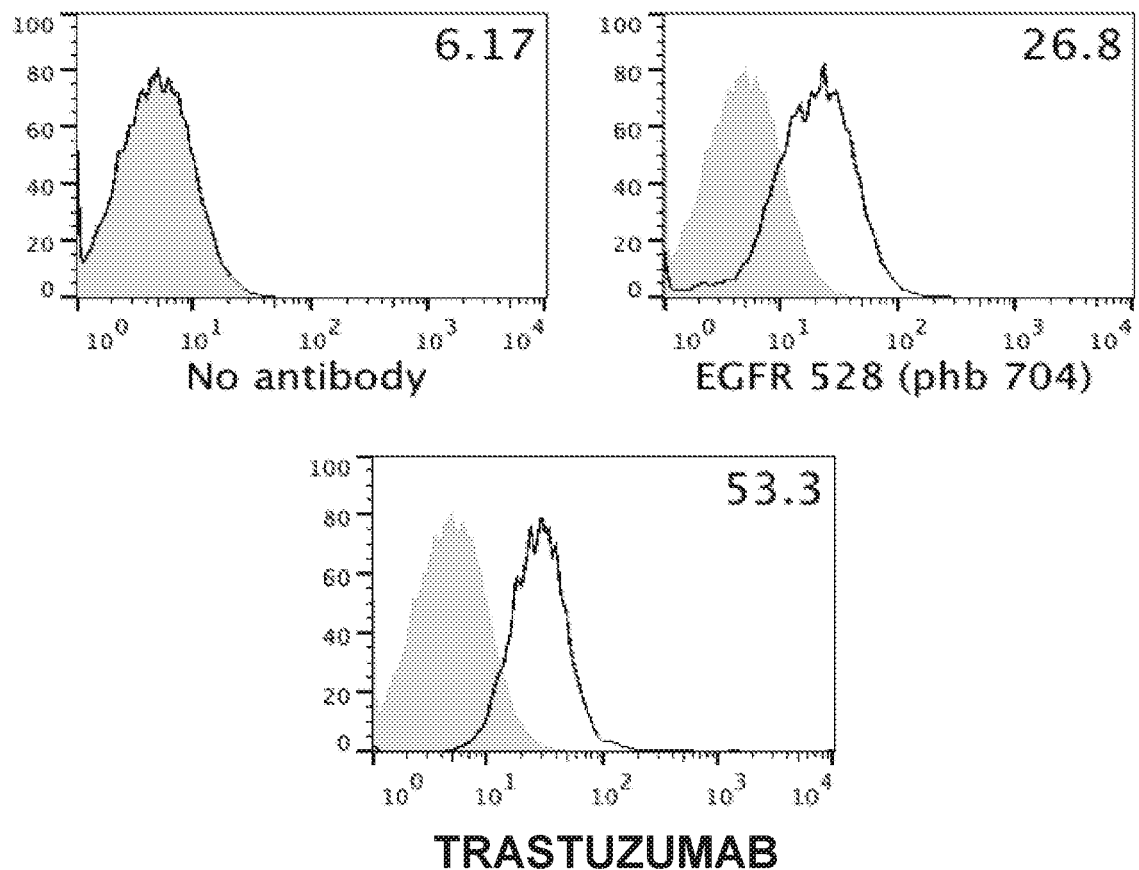
Figure 11B:
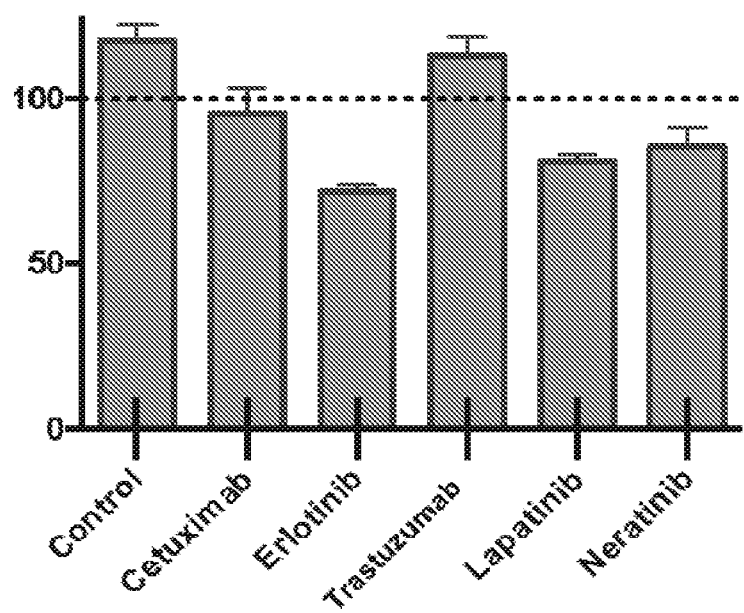

FIG. 10 demonstrates that HER2-BsAb is effective against osteosarcoma cell lines. A panel of osteosarcoma cell lines were analyzed for HER2-BsAb-mediated cytotoxicity and EC50 and compared to the expression level of HER2 in each cell line as determined by flow cytometry and by qRT-PCR FIG. 11A, FIG. 11B, and FIG. 11C demonstrate that HER2-BsAb is effective against osteosarcoma cell lines resistant to other targeted therapies. FIG. 11A demonstrates that the osteosarcoma cell line U2OS expresses EGFR and HER2. FIG. 11B demonstrates that USOS cells are resistant to HER-targeted therapies lapatinib, erlotinib, neratinib, trastuzumab, and cetuximab. FIG. 11C demonstrates that U5OS cells are sensitive to T cells in the presence of HER2-BsAb. Data represents the average of three different cytotoxicity assays.

Figure 12A:
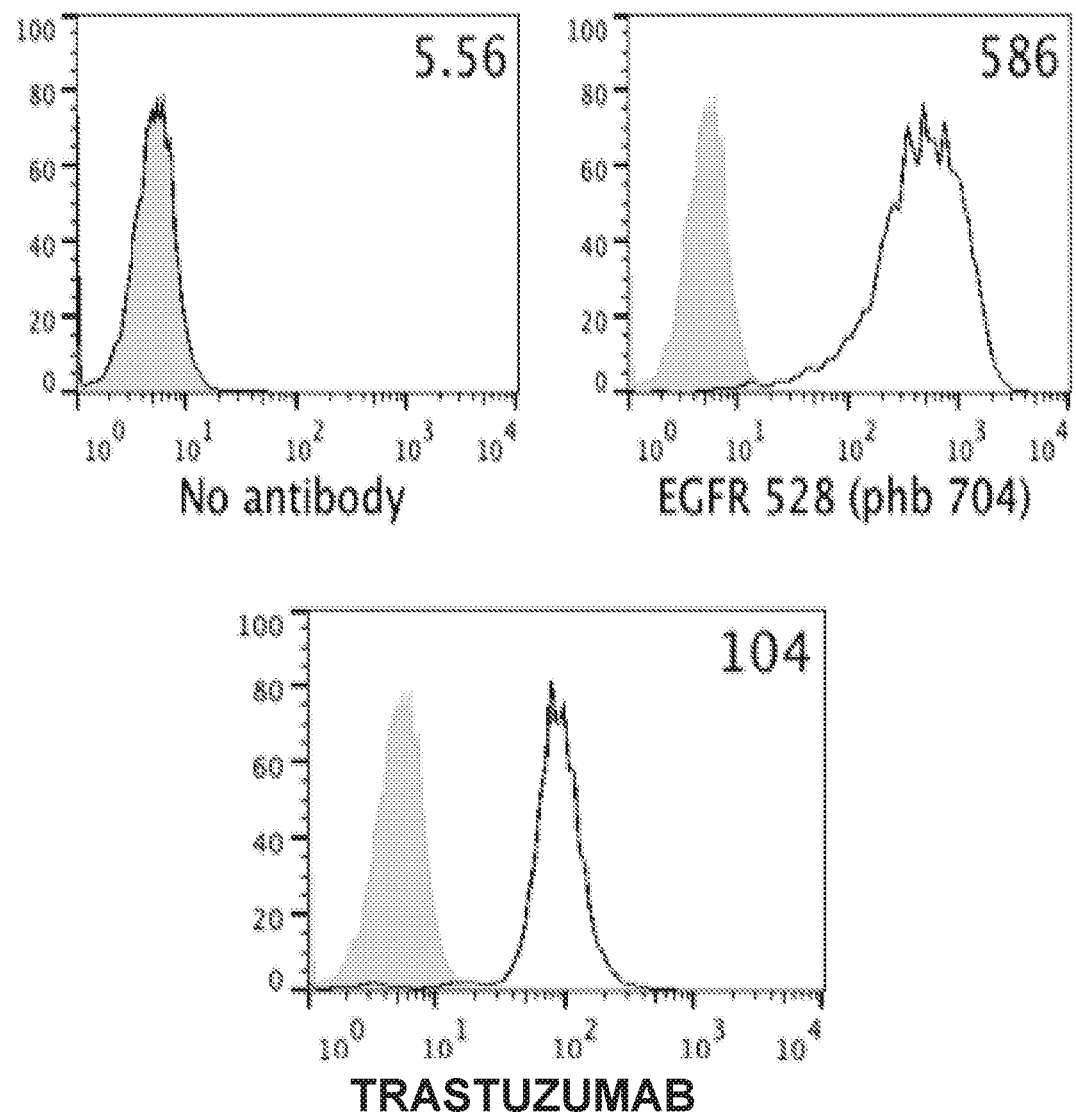
Figure 12B:
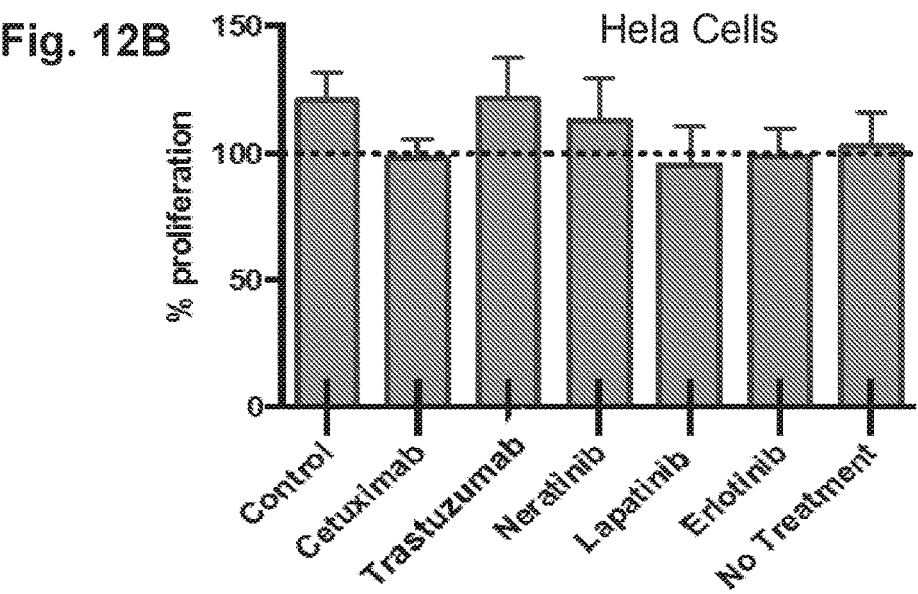
Figure 12C:
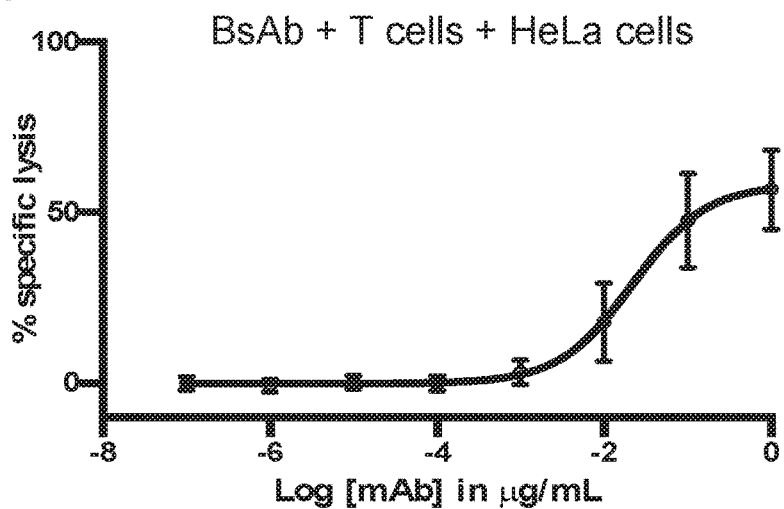
Figure 12D:
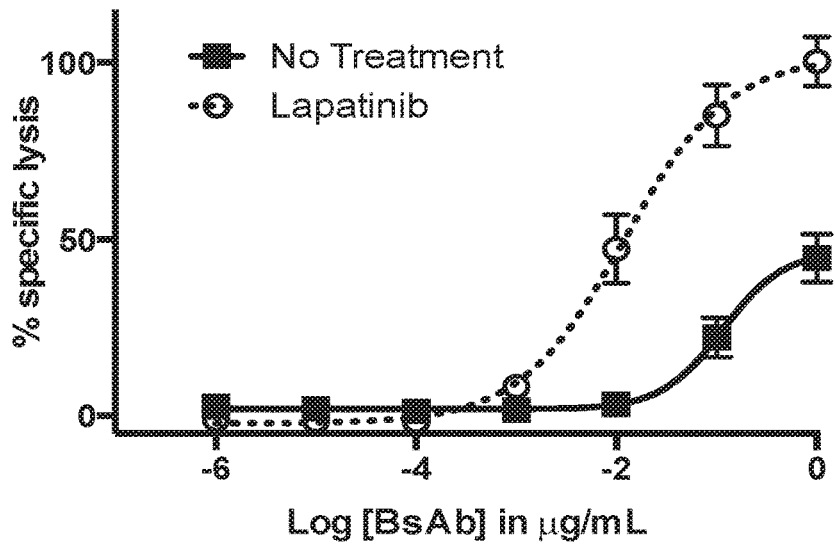

FIG. 12A, FIG. 12B, FIG. 12C and FIG. 12D demonstrate that HER2-BsAb is effective against the HeLa cervical carcinoma cell line resistant to other targeted therapies. FIG. 12A demonstrates that HeLa cells express EGFR and HER2. FIG. 12B demonstrates that HeLa cells are resistant to HER-targeted therapies lapatinib, erlotinib, neratinib, trastuzumab, and cetuximab. FIG. 12C demonstrates that HeLa cells are sensitive to T cells in the presence of HER2-BsAb. Data represents the average of three different cytotoxicity assays. FIG. 12D demonstrates that pre-treatment with lapatinib enhances HeLa sensitivity to HER2-BsAb.

Figure 13:
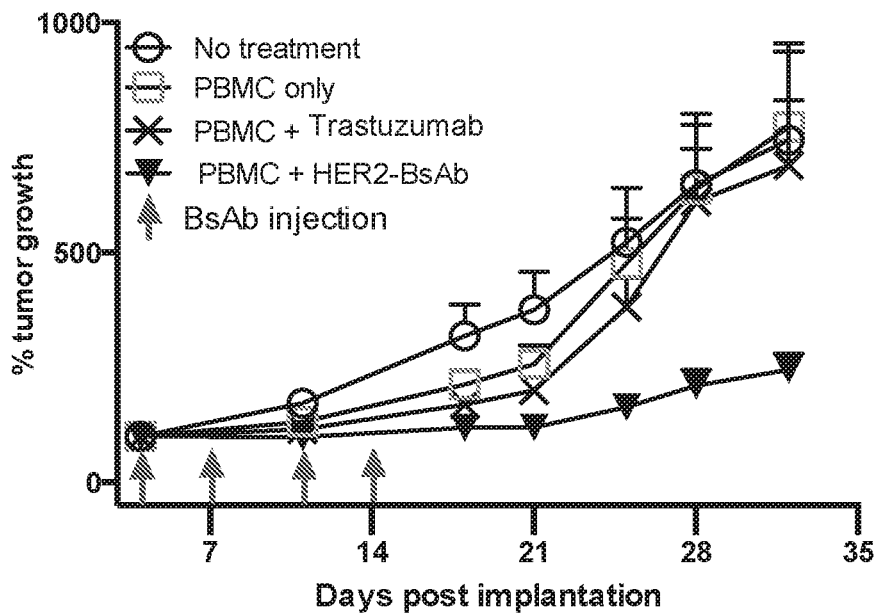

FIG. 13 demonstrates that HER2-BsAb reduces tumor growth in vivo. FIG. 13 demonstrates that HER2-BsAb protects against tumor progression in implanted MCF7 breast cancer cells mixed with PBMCs.

Figure 14:
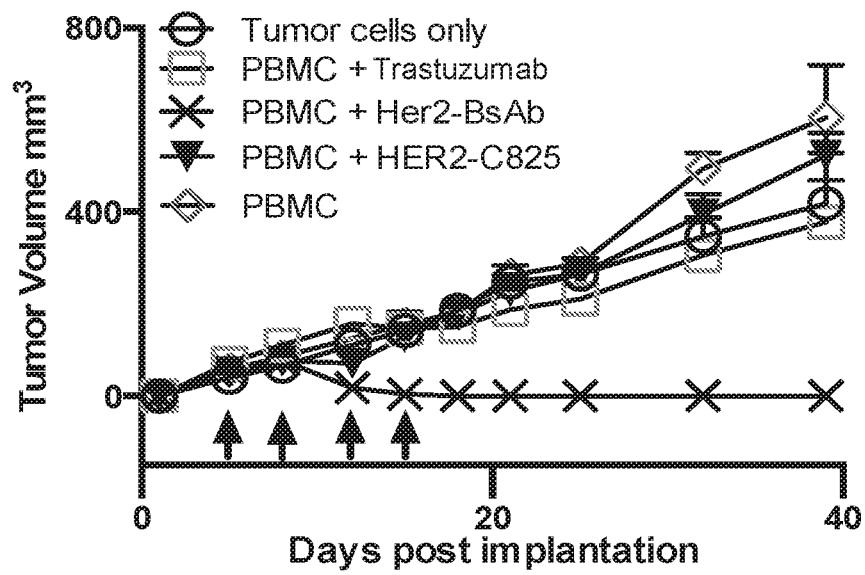

FIG. 14 demonstrates that HER2-BsAb protects against tumor progression in implanted HCC1954 breast cancer mixed with peripheral blood mononuclear cells (PBMC) in vivo.

Figure 15:
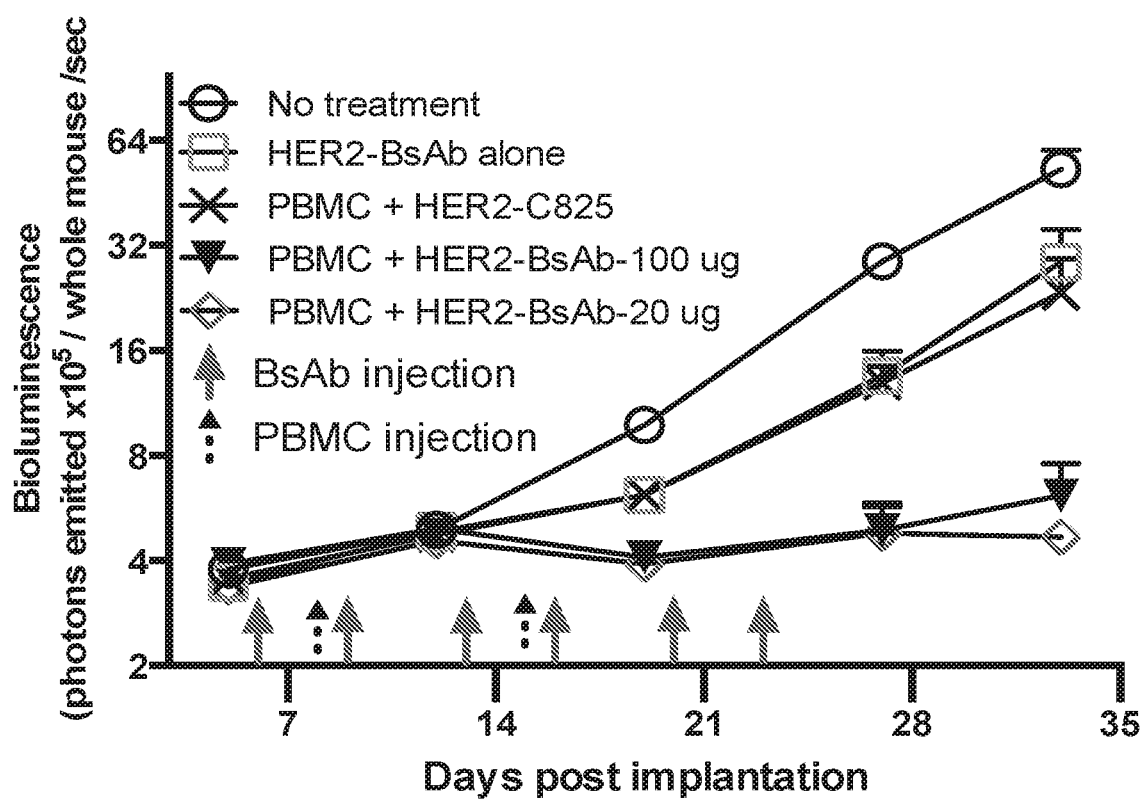

FIG. 15 demonstrates that HER2-BsAb protects against a metastatic model of tumor progression induced by intravenous introduction of luciferase-tagged MCF7 cells in vivo.

FIG. 16A, FIG. 16B, FIG. 16C, and FIG. 16D demonstrate that HER2-BsAb blocks the metastatic tumor growth of luciferase-tagged MCF7 cells in vivo. FIG. 16A represents mice without treatment. FIG. 16B represents mice treated with PBMC and HER2-C825. FIG. 16C represents mice treated with HER2-BsAb. FIG. 16D represents mice treated with PBMC and HER2-BsAb.

Figures 17A, 17B:
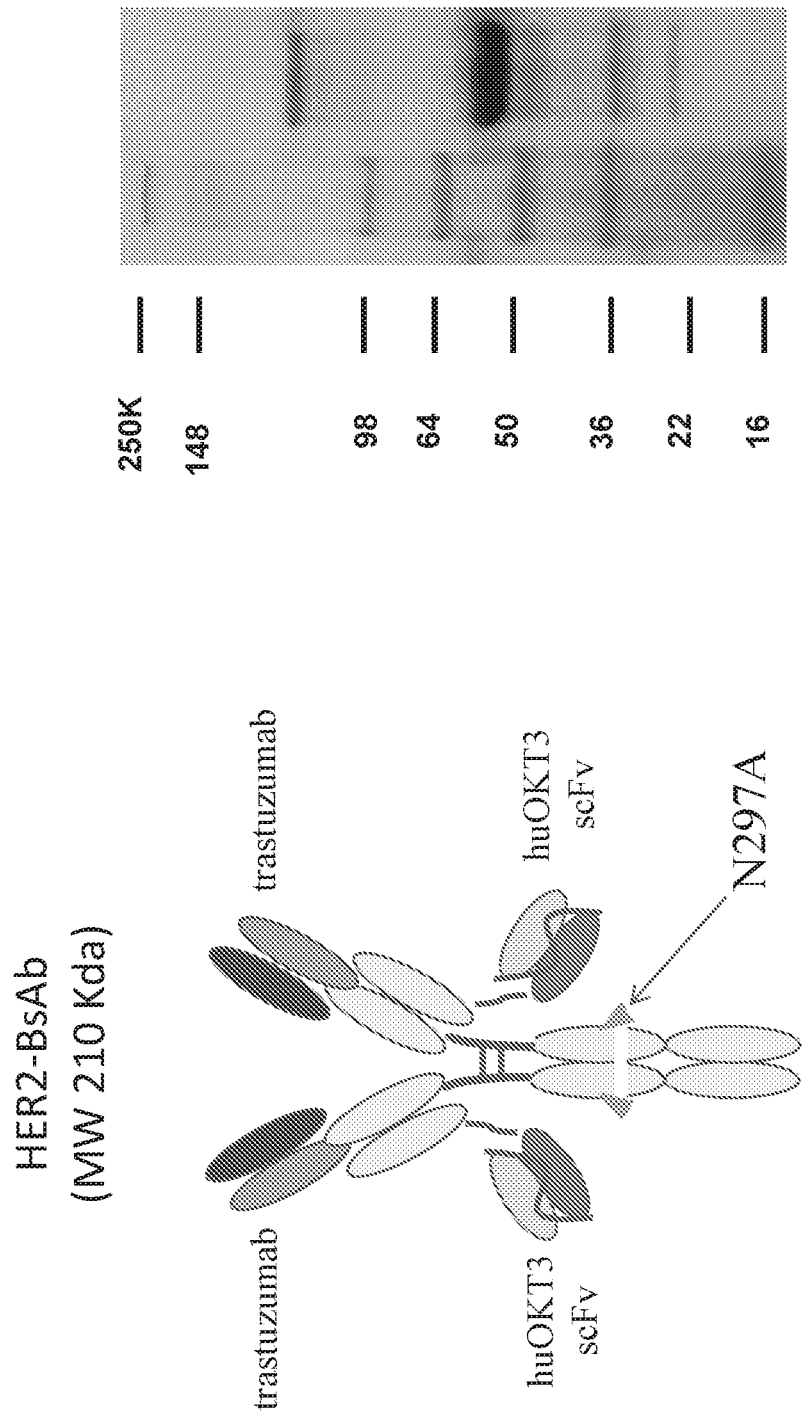
Figure 17C:
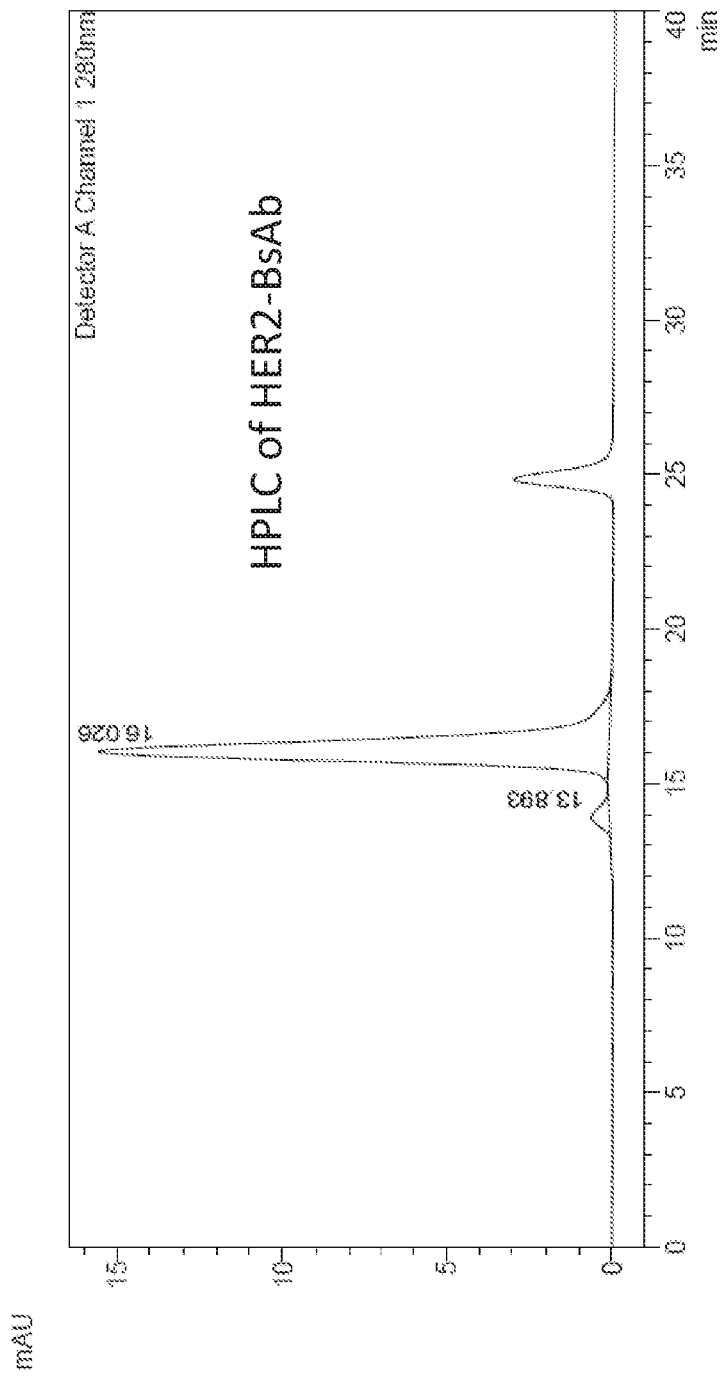

FIG. 17A, FIG. 17B, and FIG. 17C describe HER2-BsAb. FIG. 17A depicts a schematic of the HER2-BsAb. The arrow points to the N297A mutation introduced into the heavy chain to remove glycosylation. FIG. 17B depicts the purity of HER2-BsAb as demonstrated under reducing SDS-PAGE conditions. FIG. 17C depicts the purity of HER2-BsAb as demonstrated by size exclusion chromatography high performance liquid chromatography (SEC-HPLC).

Figures 18A, 18B, 18C:
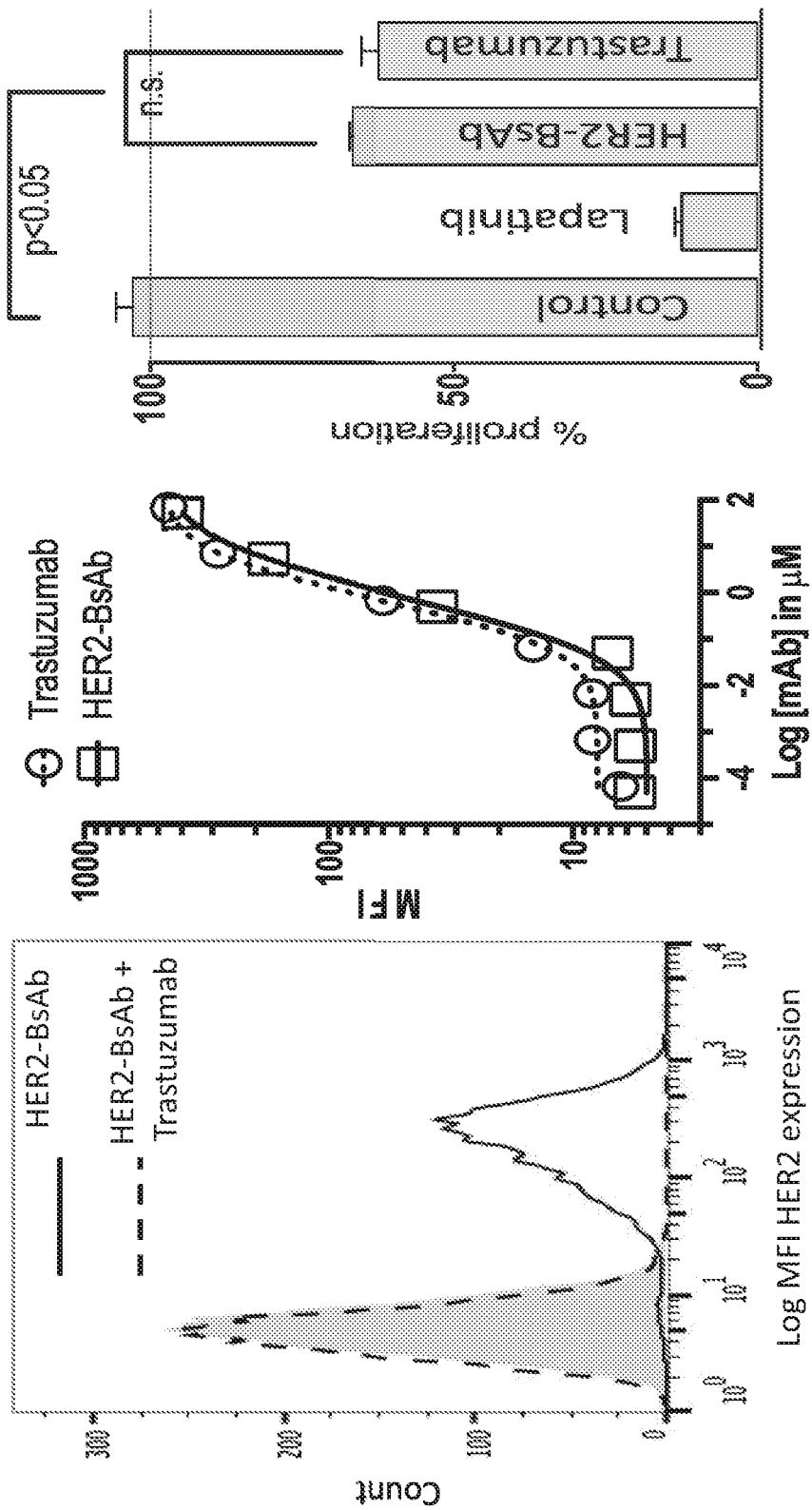

FIG. 18A, FIG. 18B, and FIG. 18C demonstrate that HER2-BsAb has the same specificity, similar affinity, and antiproliferative effects as trastuzumab.

Figures 19A, 19B:
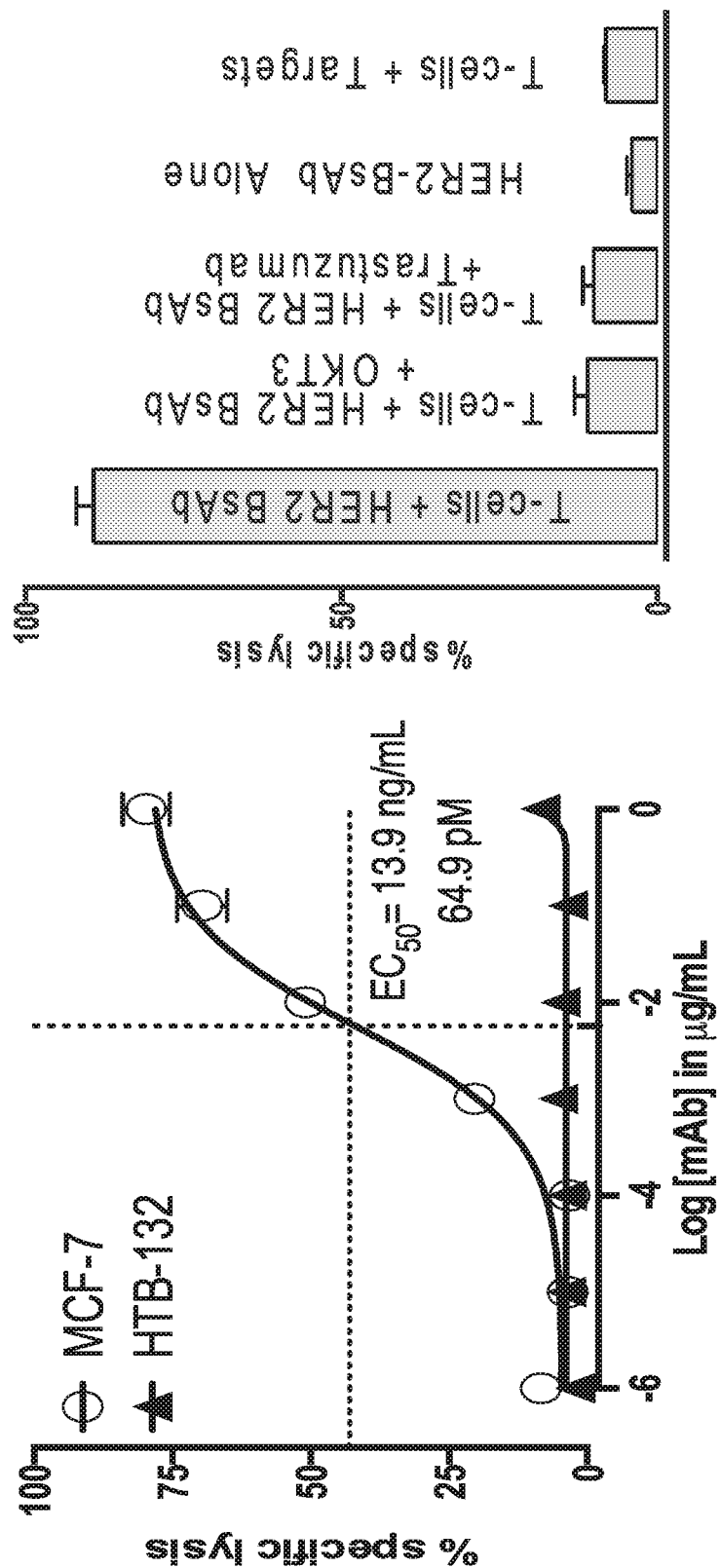
Figure 21A:
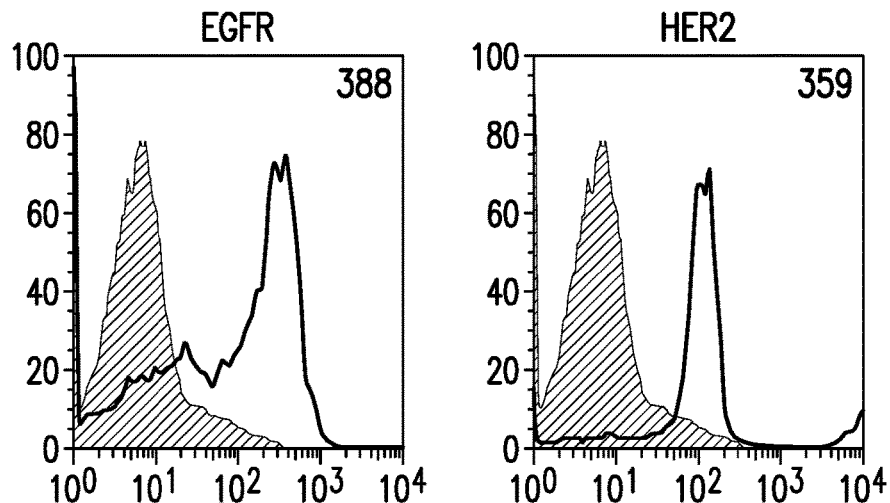
Figure 21B:
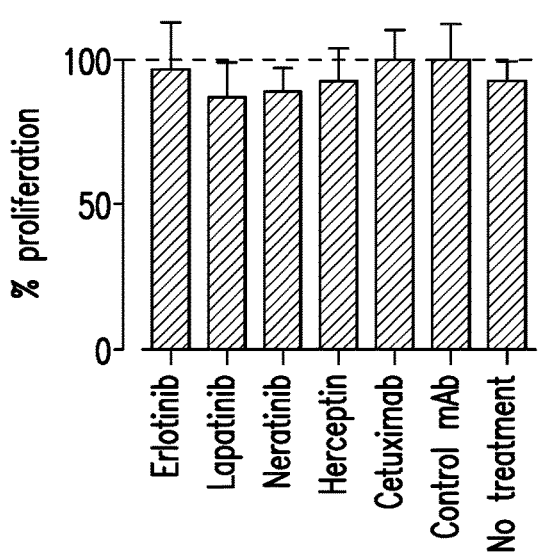
Figure 21C:
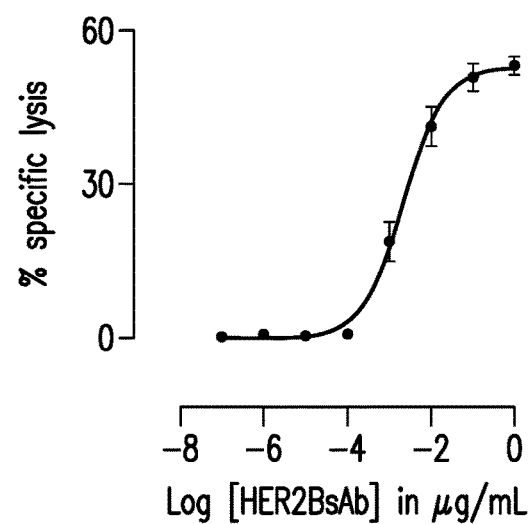
Figure 21D:
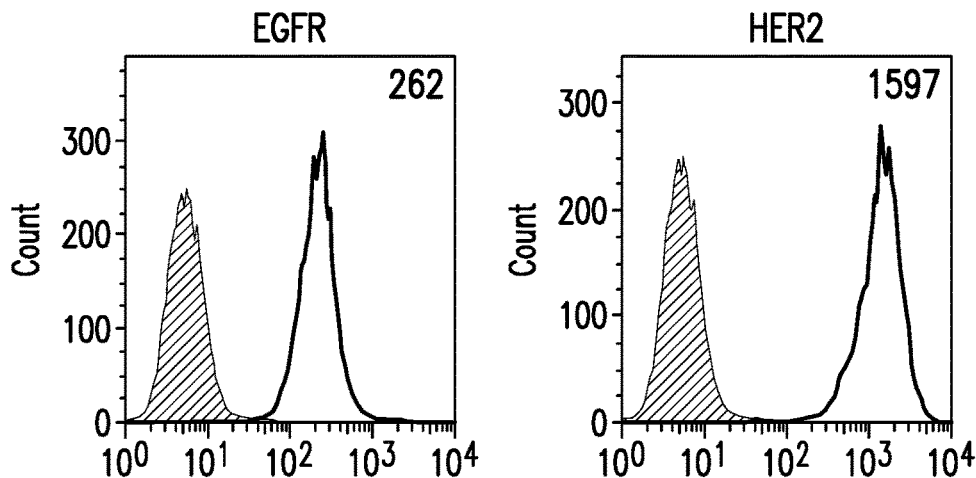
Figure 21E:
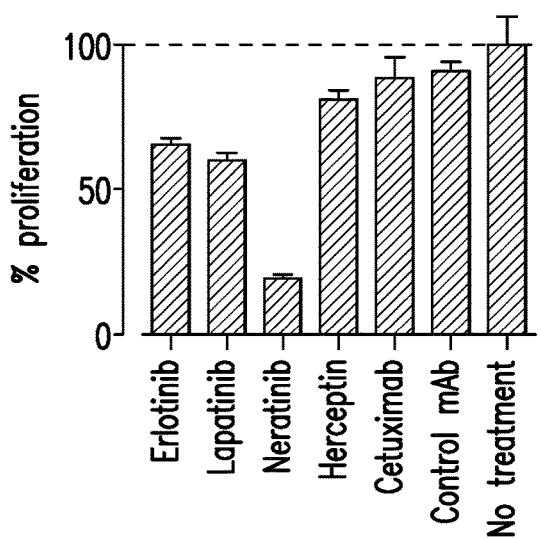
Figure 21F:
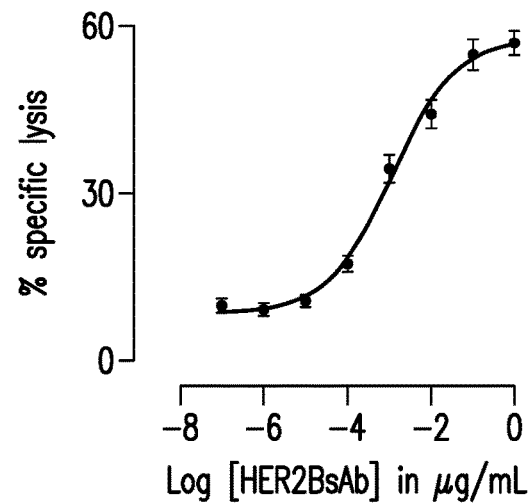
Figure 21G:
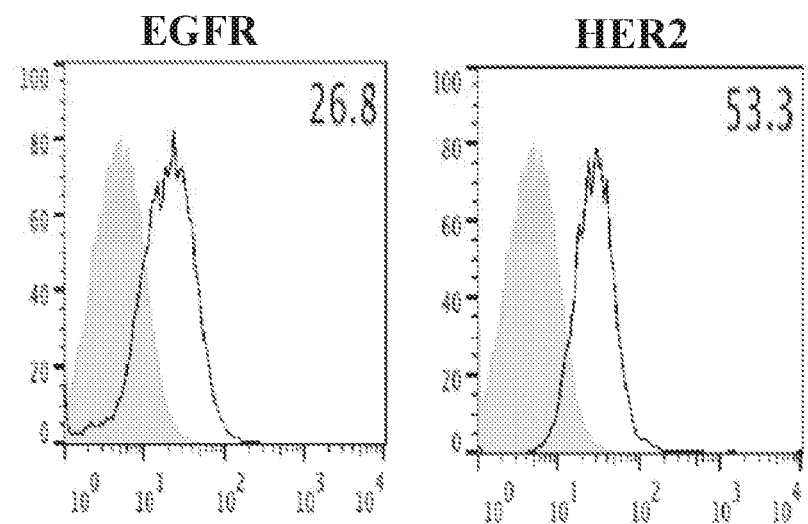
Figure 21H:
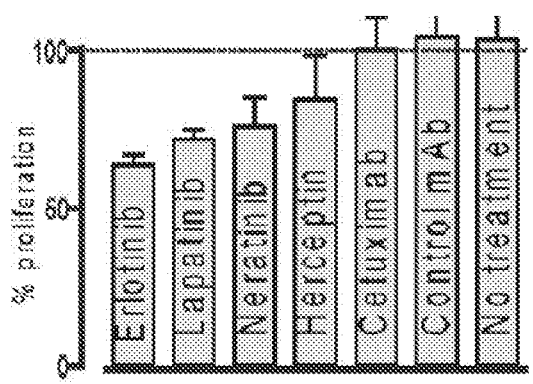
Figure 21I:
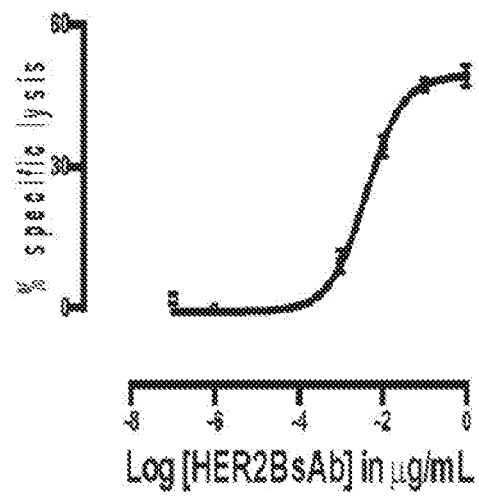

FIG. 19A and FIG. 19B demonstrate that HER2-BsAb redirected T cell cytotoxicity is HER2-specific and dependent on CD3.

FIG. 20 depicts HER2 expression and half maximal effective concentration (EC50) in the presence of ATC and HER2-BsAb in 35 different cell lines from different tumor systems.

FIG. 21A, FIG. 21B, FIG. 21C, FIG. 21D, FIG. 21E, FIG. 21F, FIG. 21G, FIG. 21H, and FIG. 21I demonstrate that HER2-BsAb mediates cytotoxic responses against carcinoma cell lines resistant to other HER-targeted therapies.

Figure 22:
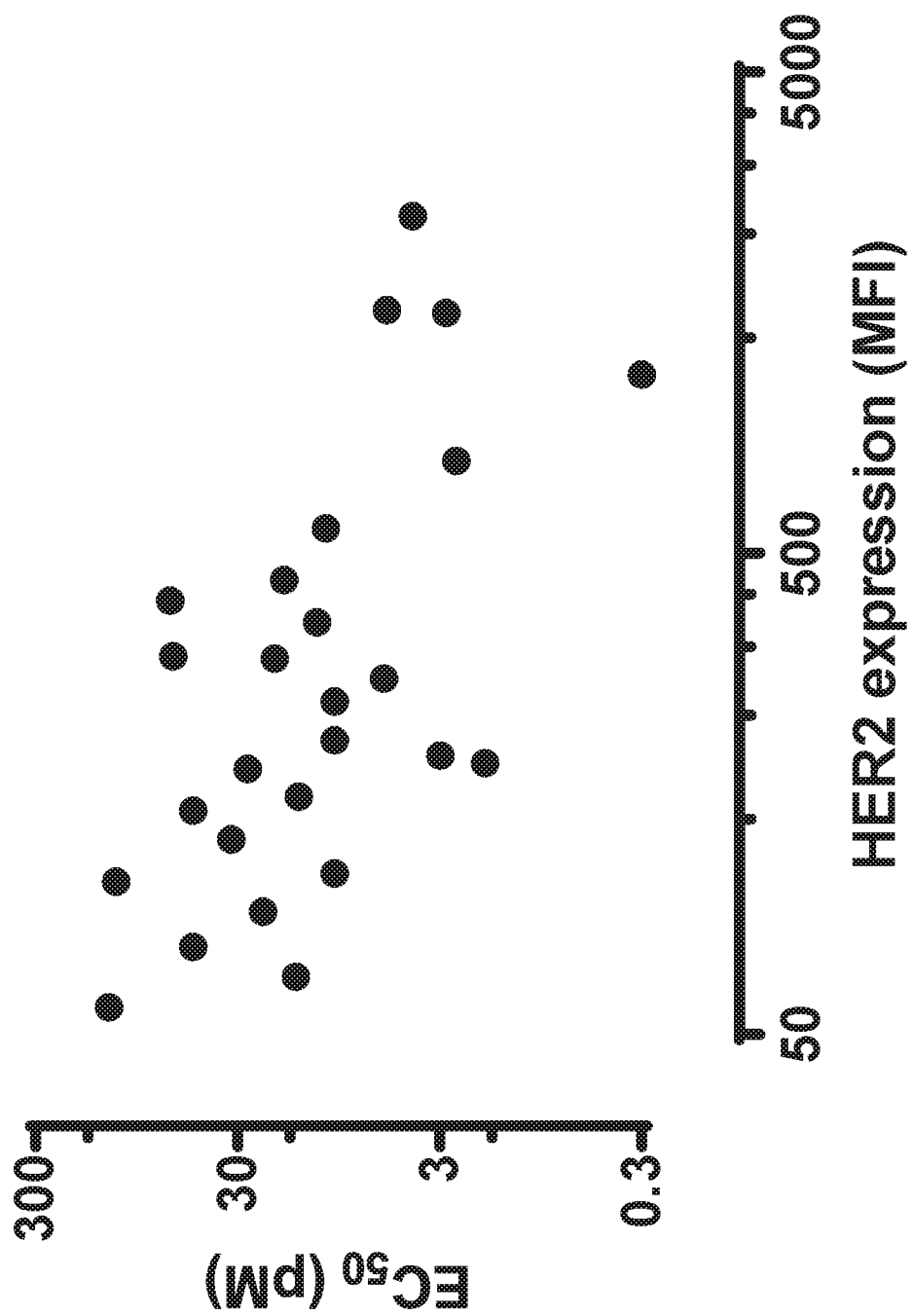

FIG. 22 demonstrates that the EC50 of HER2-BsAb correlates with the HER2 level of expression determined by flow-cytometry. pM=picomolar; MFI=mean fluorescence intensity.

FIG. 23A, FIG. 23B, and FIG. 23C demonstrates that HER2-BsAb mediates T cell cytotoxicity against PD-L1-positive HCC1954 targets in a manner that is relatively insensitive to PD-1 blockade by pembrolizumab, even with PD-1 expression on effector T cells.

FIG. 24A and FIG. 24B demonstrates that HER2-BsAb mediates T cell cytotoxicity against PD-L1-positive HEK-293 targets in a manner that is relatively insensitive to PD-1 expression on effector T cells. The cytotoxicity is an average of 6 experiments.

FIG. 25A, FIG. 25B, FIG. 25C, and FIG. 25D demonstrate that HER2-BsAb is effective against HER2-positive xenografts.

Figure 26A:
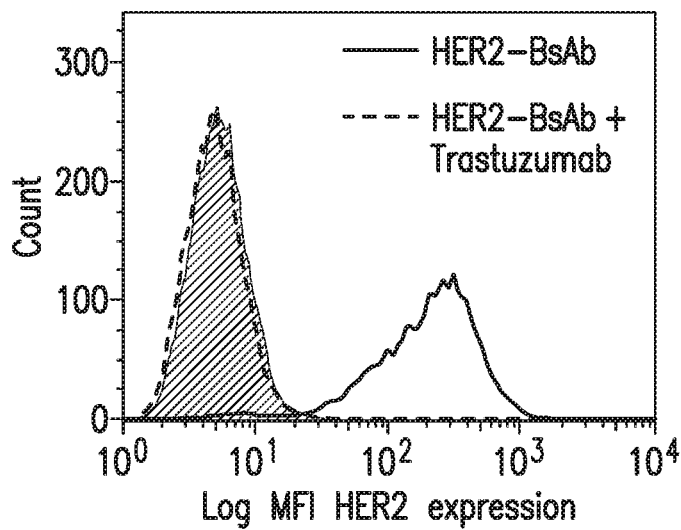
Figure 26B:
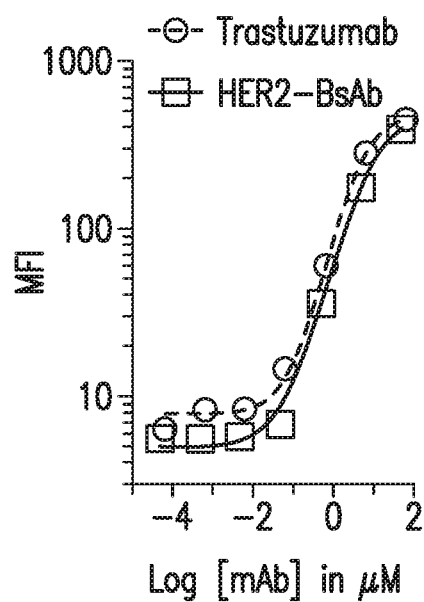
Figure 26C:
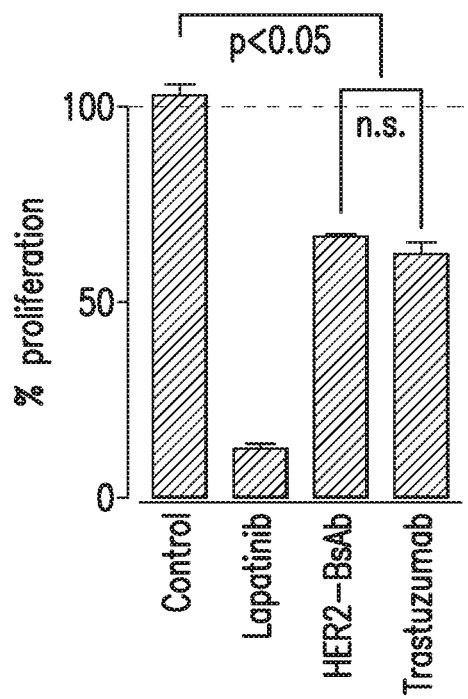
Figure 26D:
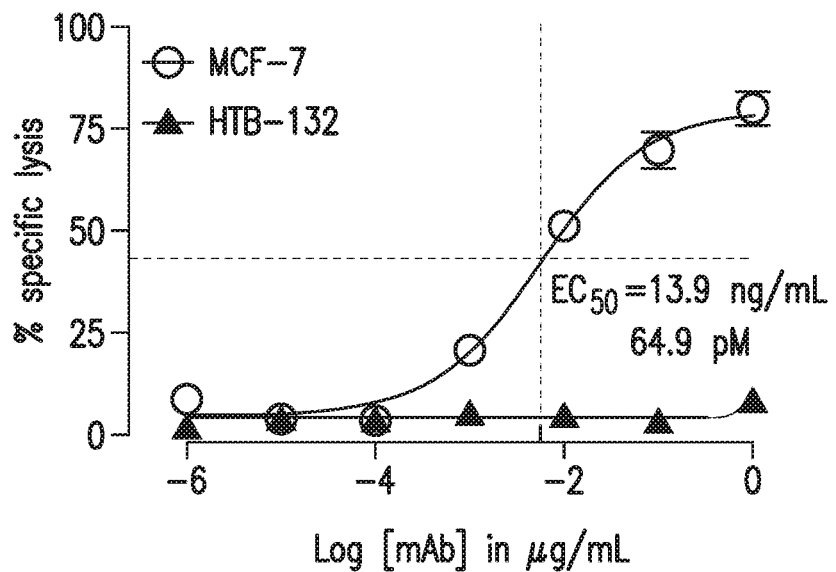
Figure 26E:
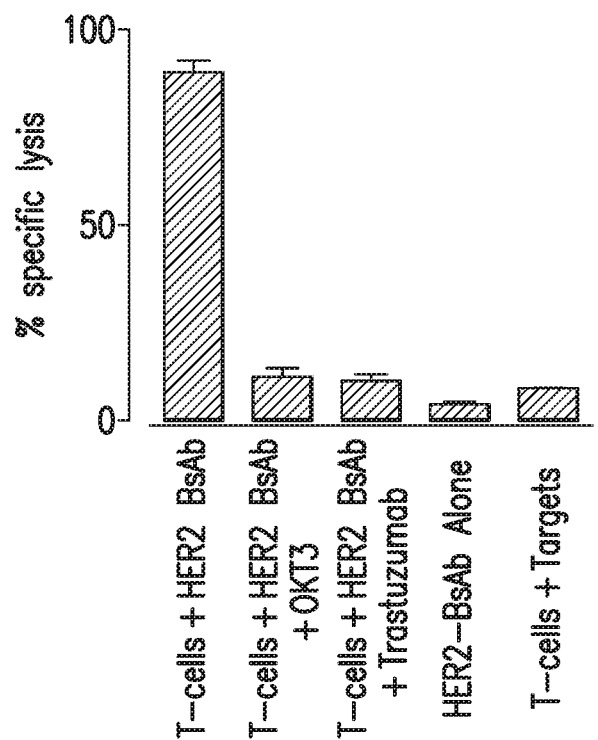

FIG. 26A, FIG. 26B, FIG. 26C, FIG. 26D, and FIG. 26E demonstrate in vitro characterization of HER2-BsAB. FIG. 26A: HER2-BsAb has the same specificity as trastuzumab. Pre-Incubation of the HER2(+)high SKOV3 cells with trastuzumab prevents HER2-BsAb binding. FIG. 26B: HER2-BsAb and trastuzumab have similar avidity for SKOV3 cells. Mean fluorescence intensity ("MFI") was plotted against the antibody concentration. FIG. 26C: HER2-BsAb maintained same anti-proliferative effects as trastuzumab against the trastuzumab-sensitive SKBR3 cells. FIG. 26D: HER2-BsAb mediates T-cell cytotoxicity against the HER2(+) MCF-7 cells but not the HER2(−) HTB-132 cells. FIG. 26E: Blocking of HER2 or CD3 by trastuzumab or huOKT3, abrogates HER2-BsAb T-cell cytotoxicity. HER2(+) SCCHN PCI-13 cells were used in the cytotoxicity assay. For this experiment 0.1 µg/mL of HER2-BsAb with 10 µg/mL of the blocking antibodies were used.

Figure 27A:
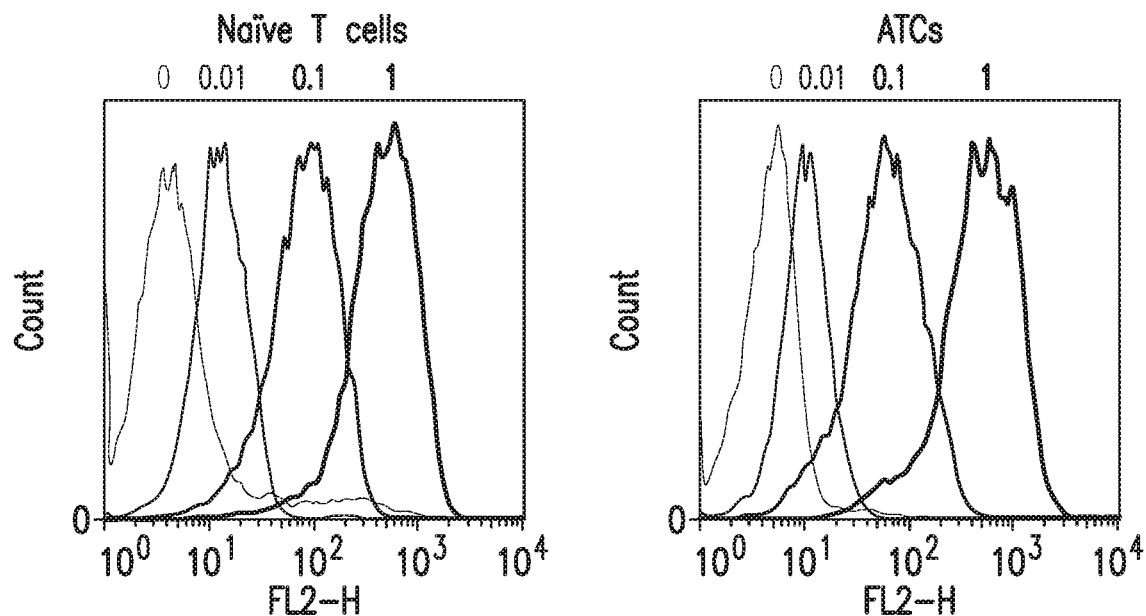
Figure 27B:
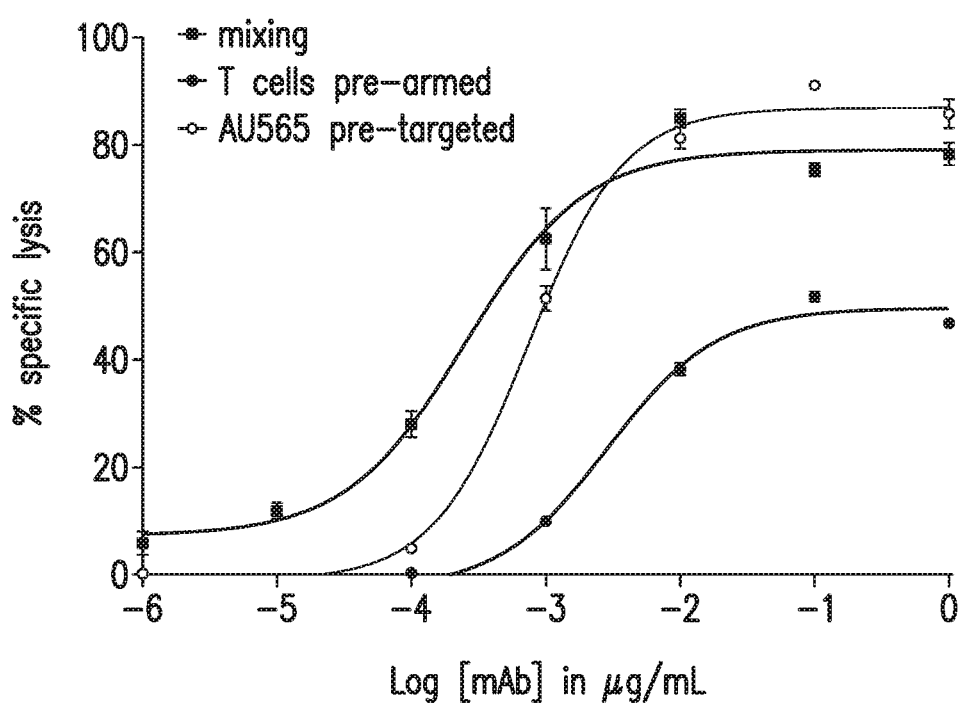

FIG. 27A and FIG. 27B demonstrate HER2-BsAb binding to T cells and redirecting T-cell killing. FIG. 27A: FACS histograms of HER2-BsAb binding to naïve T cells purified from fresh PBMC (left panel) or ATCs (right panel). Concentrations of BsAbs (m/$10^6$ cells) were recorded on the top of the left histogram, and Rituxan was used as negative control (mean fluorescence intensity set at 5). FIG. 27B: HER2-BsAb redirected T-cell killing of HER2(+) AU565 breast cancer cells by 4-hour $^{51}$Cr release assay. BsAb was either mixed directly with T cells and AU565 together (mixing), or pre-incubated with T cells/target first (T cells pre-armed or AU565 pre-targeted), and unbound BsAb washed off before adding the other cells. ATC-to-target ratio was 10:1. Data points are shown as Mean±SEM.

Figure 28D:
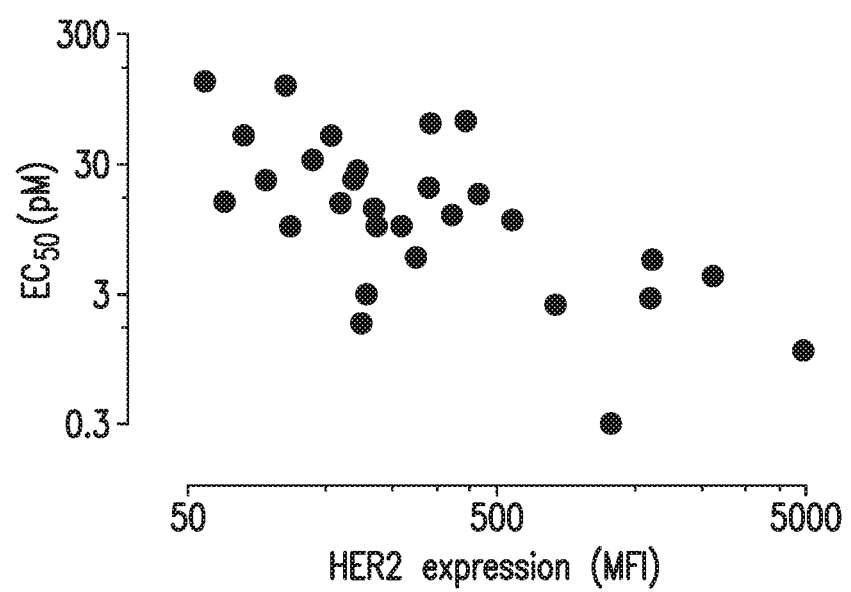

FIG. 28A, FIG. 28B, FIG. 28C, and FIG. 28D demonstrate that HER2-BsAb mediates cytotoxic responses against carcinoma cell lines resistant to other HER targeted therapies. FIG. 28A, FIG. 28B, and FIG. 28C: Three representative cell lines were used for FACS assay (upper panel), proliferation assay (middle panel), and HER2-BsAb mediated CTL assay (lower panel): (FIG. 28A) SCCHN PCI-30, (FIG. 28B) breast carcinoma HCC-1954, and (FIG. 28C) osteosarcoma U2OS. FIG. 28D: HER2-BsAb EC50 inversely correlates with level of HER2 expression. Each of the cell lines used in a cytotoxicity assay (Table 9) was assayed at least twice. The EC50 was determined each time and averaged. These values (except those beyond assay limit 5 nM) were compared to HER2 expression (MFI).

Figure 29A:
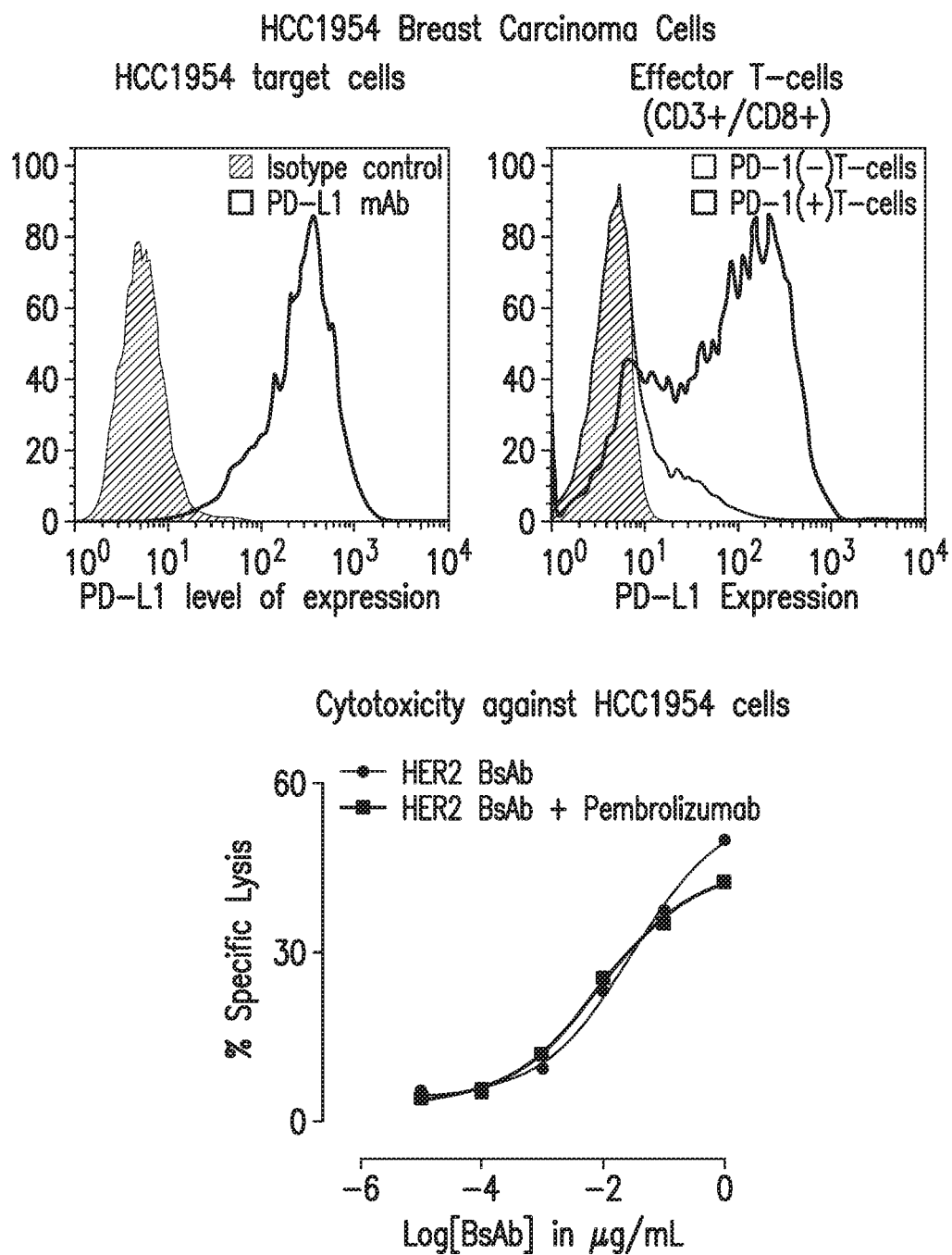
Figure 29B:
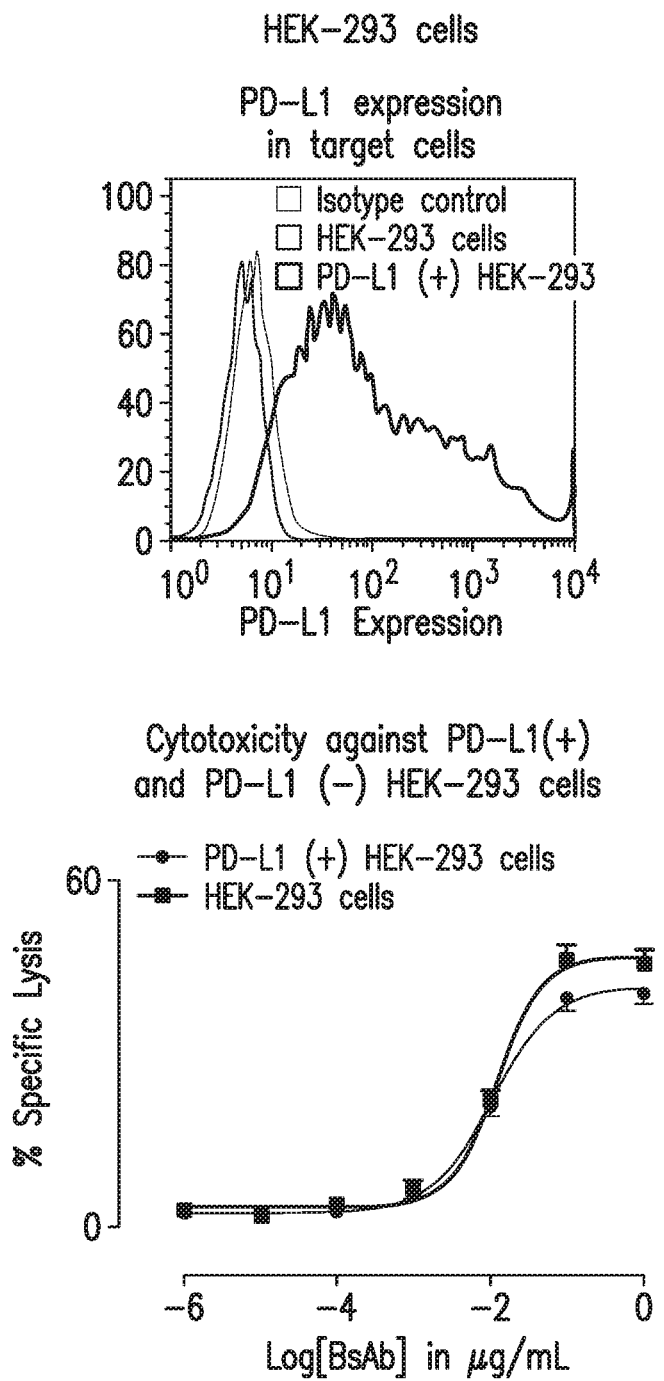

FIG. 29A and FIG. 29B demonstrate that HER2-BsAb-mediated in vitro T-cell cytotoxicity was relatively insensitive to PD-L1 expression on the tumor targets or PD-1 expression on T cells. FIG. 29A: FACS analysis of PD-L1 expression in HCC1954 cells (left panel), of induced PD-1 expression in ATCs (middle panel), and HER2-BsAb-mediated cytotoxicity (right panel). FIG. 29B: FACS analysis of PD-L1 expression in HEK-293 cells (left panel), and HER2-BsAb mediated cytotoxicity using the ATCs as in FIG. 29A (middle panel). Mean+SEM (n=6).

Figure 30A:
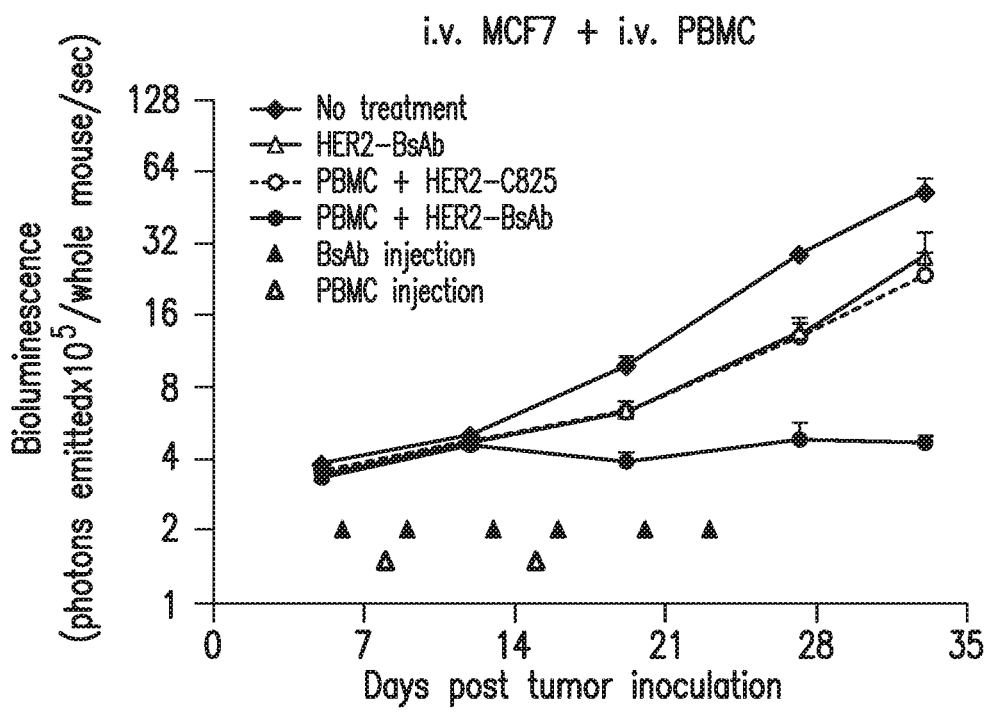
Figure 30B:
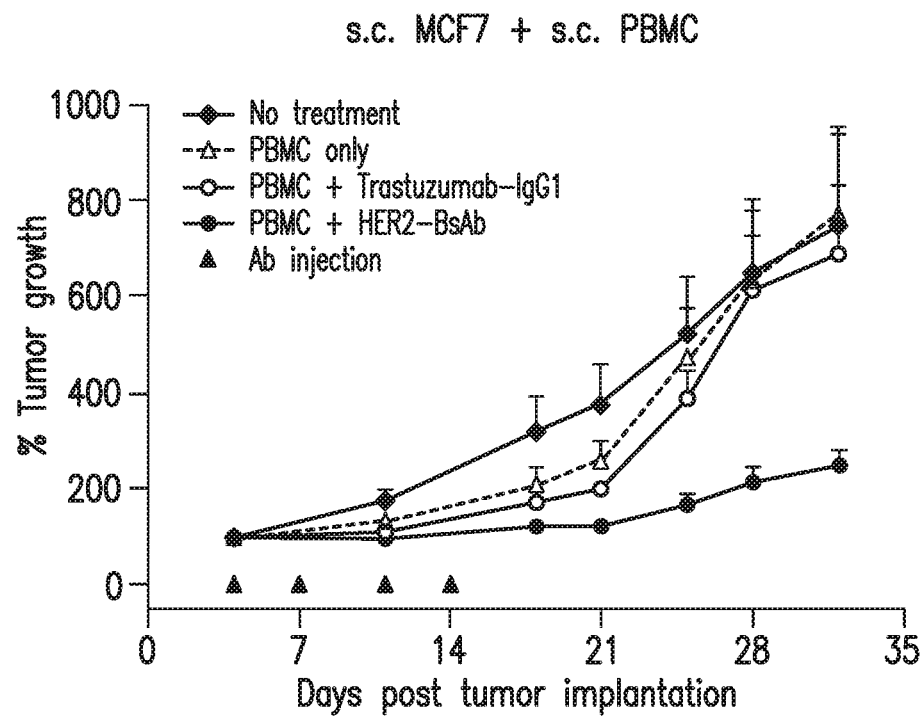
Figure 30C:
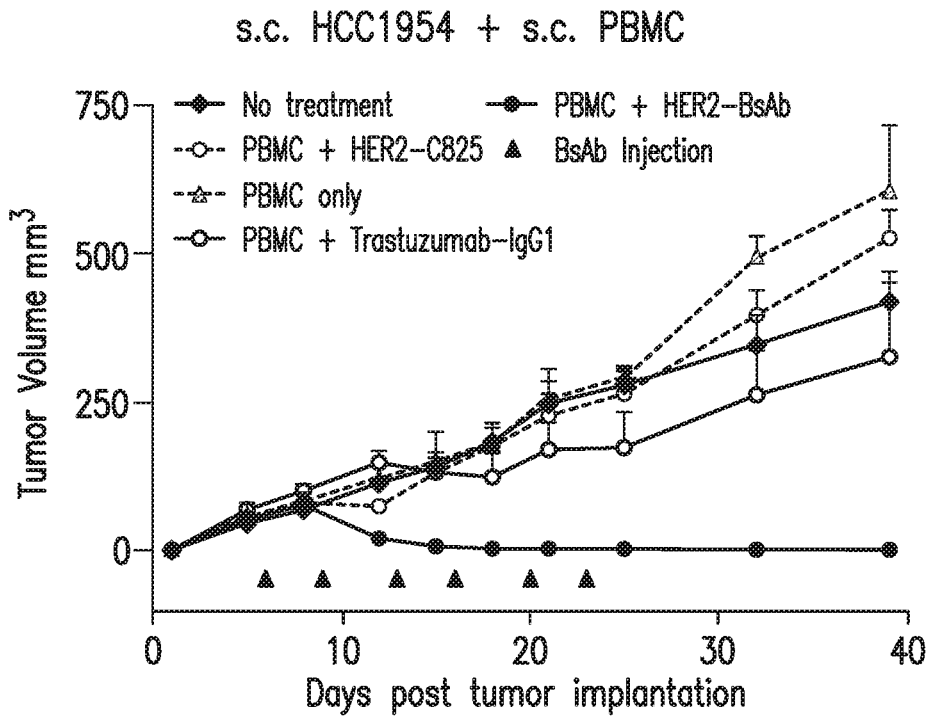
Figure 30D:
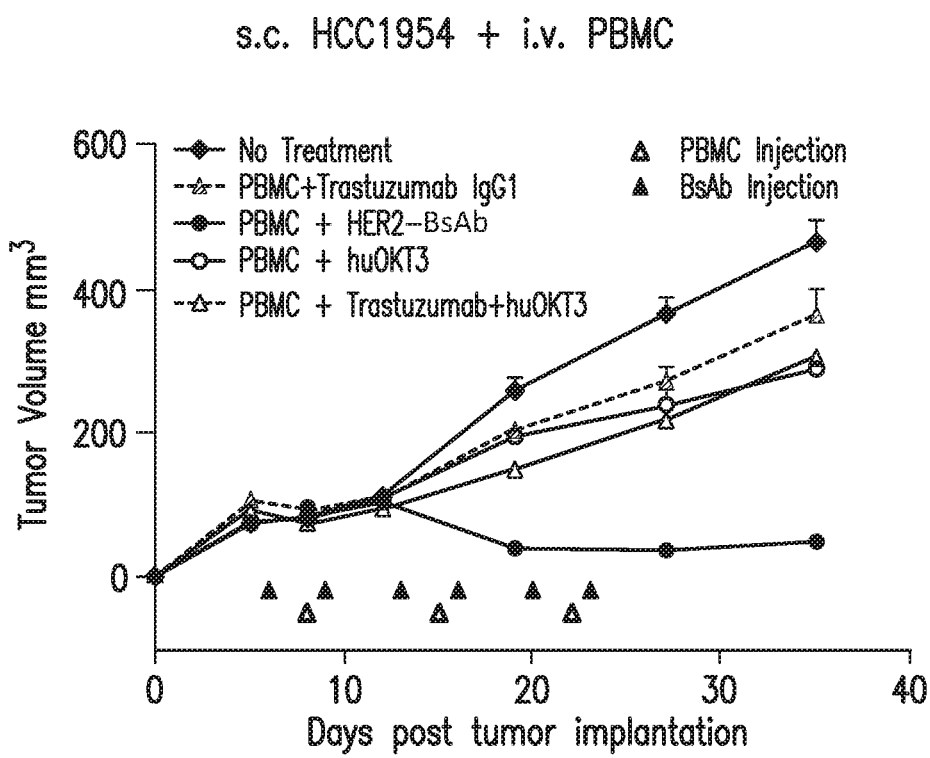
Figure 30E:
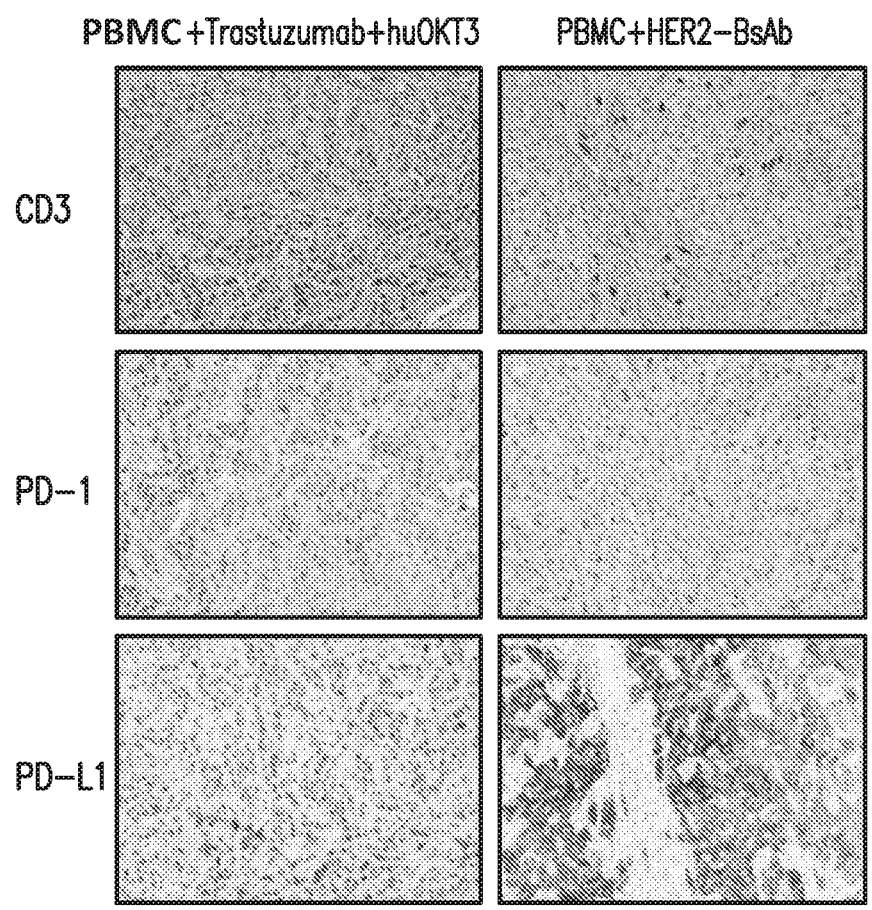

FIG. 30A, FIG. 30B, FIG. 30C, FIG. 30D, and FIG. 30E demonstrate that HER2-BsAb is effective against HER2(+) breast cancer cell line xenografts. Treatment schedules were marked on the figures, and doses of BsAbs and effector cells were detailed in the Results of Section 6.3.3. Data shown as mean+SEM (n=5). FIG. 30A: intravenous ("i.v.") tumor plus i.v. effector cells model: Bioluminescence changes of MCF7 breast cancers during treatment. FIG. 30B and FIG. 30C: subcutaneous ("s.c." tumor plus s.c. effector cells (mixing) model: % tumor growth of MCF7 (FIG. 30B), and tumor volume changes of HCC1954 (FIG. 30C). FIG. 30D: s.c. tumor plus i.v. effector cells model: tumor volume changes of HCC1954. FIG. 30E: HCC1954 s.c. tumor model as in (FIG. 30D), with treatments of one dose of PBMC ($2 \times 10^7$ cells i.v.) at day 14, and two doses of BsAbs (100 μg i.v.) at day 12 and 15. Representative images (200× magnifications) of IHC staining of tumor sections collected 5 days after i.v. PBMC were shown.

Figure 31A:
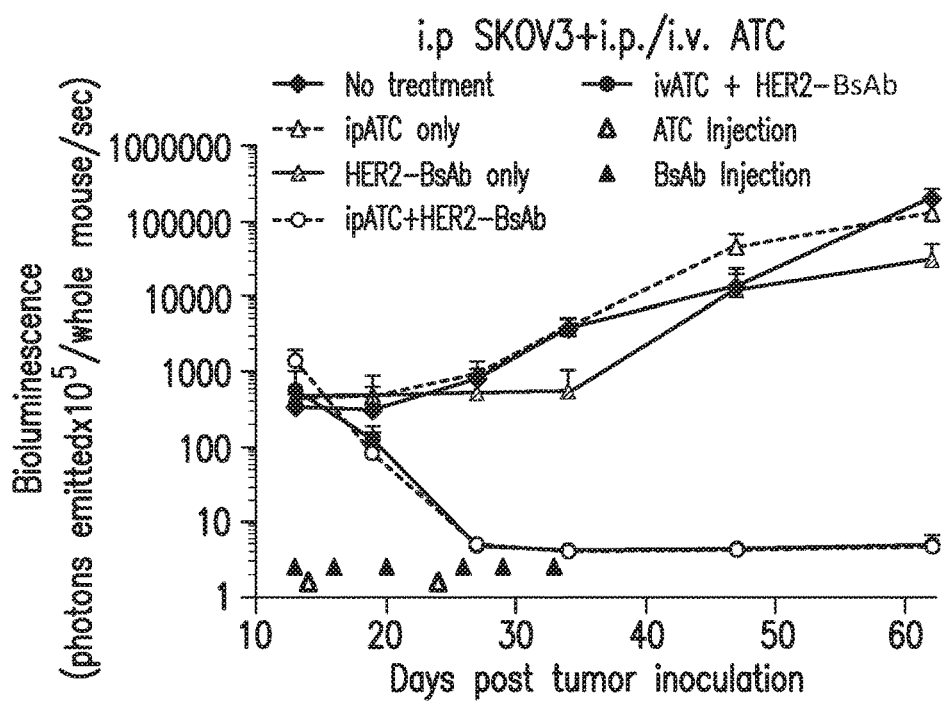
Figure 31B:
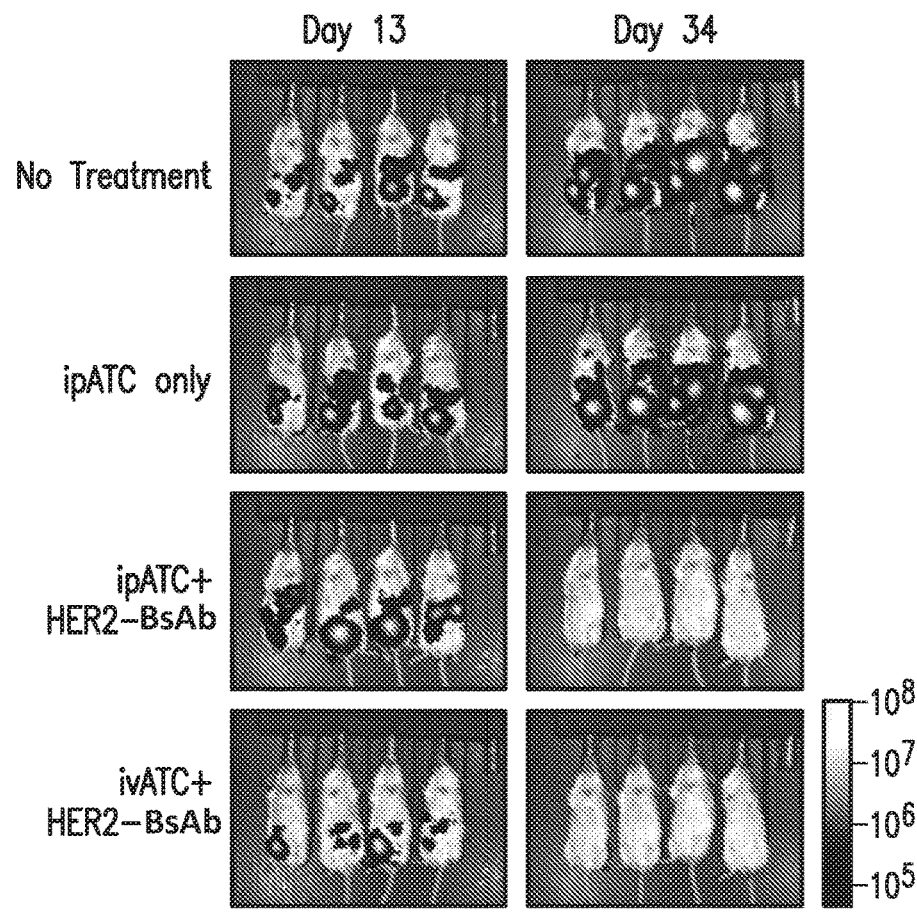

FIG. 31A and FIG. 31B demonstrate that HER2-BsAb is effective against HER2(+) ovarian cancer cell line xenografts. Treatment schedules were marked on the figures, and doses of BsAbs and effector cells were detailed in the Results of Section 6.3.3. Data shown as mean+SEM (n=4). FIG. 31A: intraperitoneal ("i.p.") tumor plus i.p./i.v. effector cells model: Bioluminescence changes of SKOV3-luc ovarian cancers during treatment. FIG. 31B: Representative bioluminescence images at the beginning (Day 13) and ending (Day 34) of the treatment were shown.

Figure 32A:
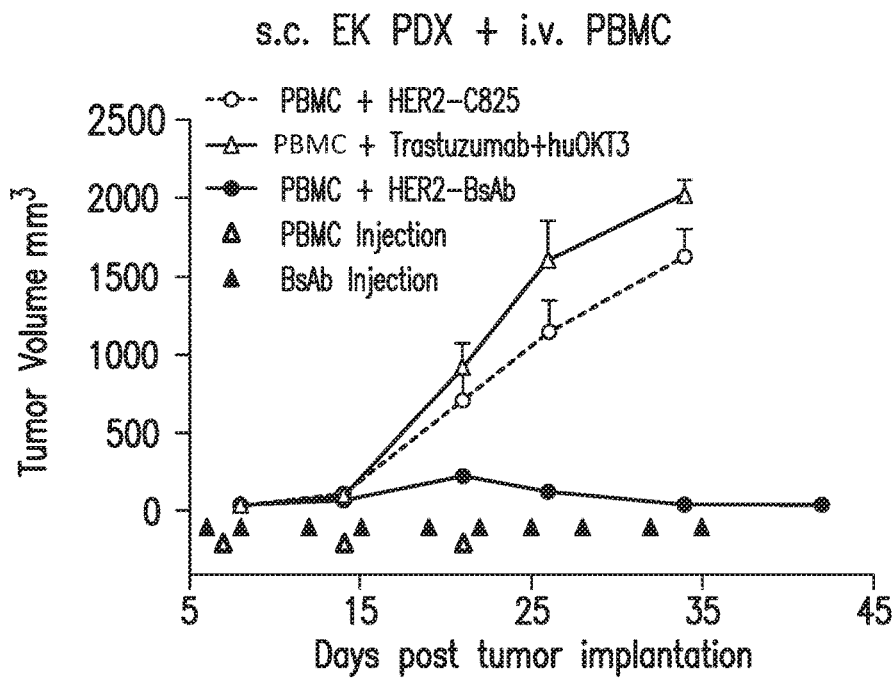
Figure 32B:
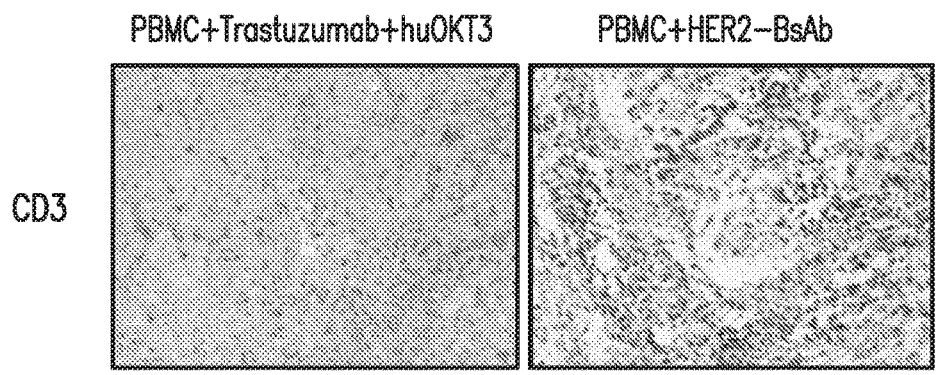
Figure 32C:
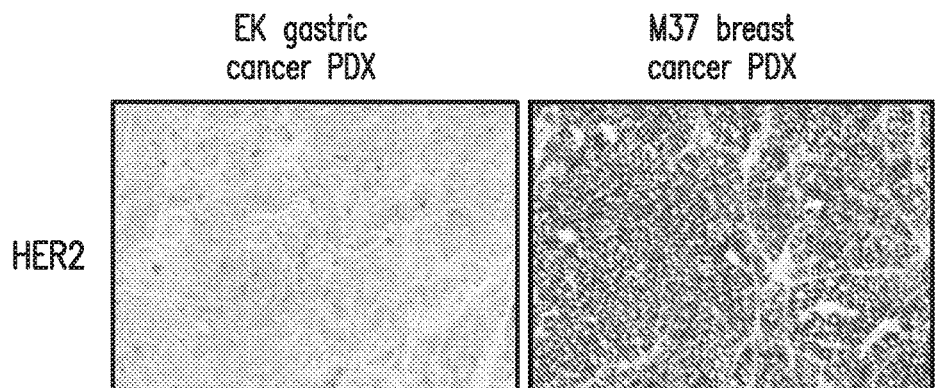
Figure 32D:
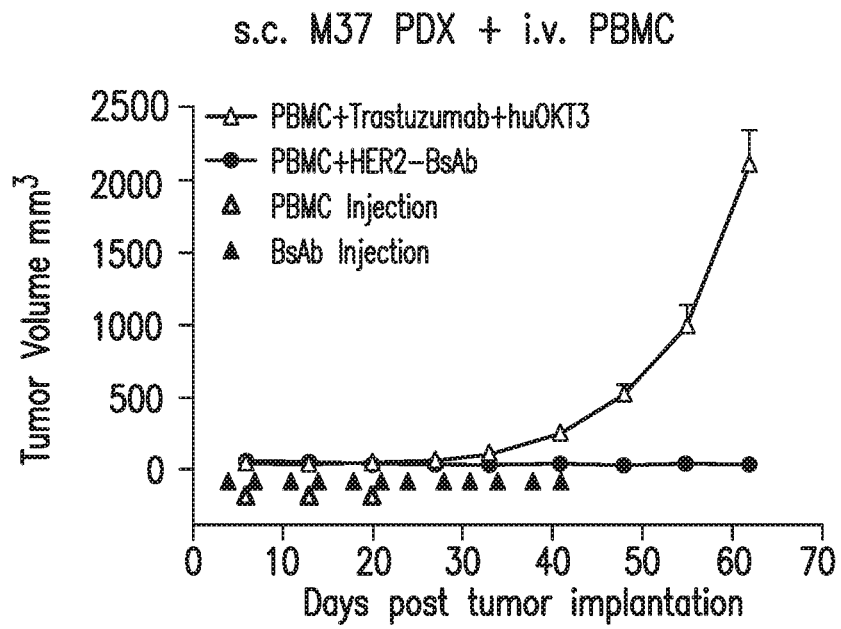
Figure 32E:
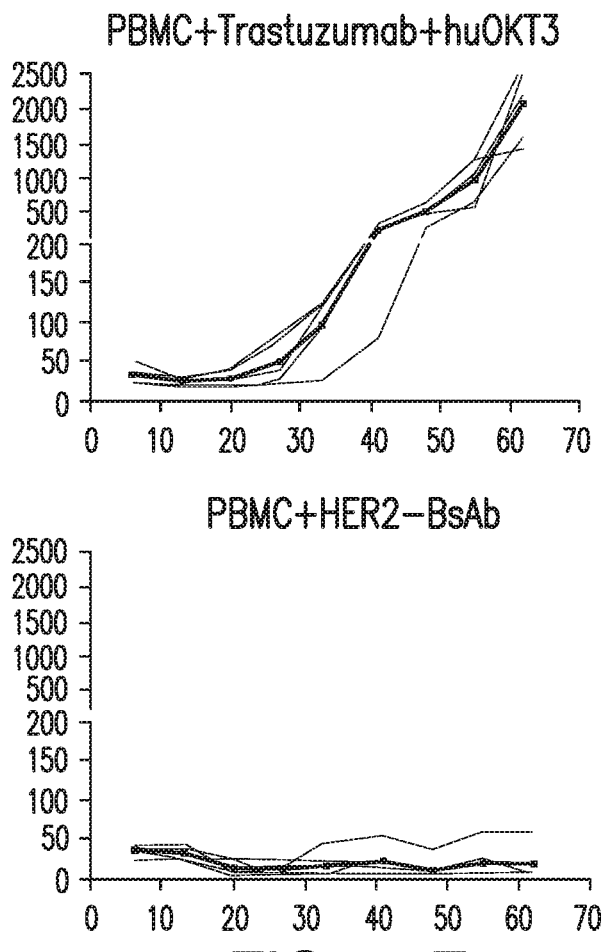

FIG. 32A, FIG. 32B, FIG. 32C, FIG. 32D, and FIG. 32E demonstrate that HER2-BsAb is effective against HER2(+) PDXs. s.c. tumor plus i.v. effector cells model was used for PDXs. Treatment schedules were marked on the figures, and doses of BsAbs and effector cells were detailed in the Results of Section 6.3.3. Data shown as mean+SEM (n=5). FIG. 32A: Tumor volume changes of EK gastric cancer PDX. FIG. 32B: IHC images of CD3 staining from another experiment with similar setting as in FIG. 32A. Representative images (200× magnifications) of IHC staining of tumor sections collected 36 days after i.v. PBMC were shown. FIG. 32C: IHC images (200× magnifications) of HER2 staining of control treated tumor sections. FIG. 32D and FIG. 32E: Average tumor volume changes of M37 breast cancer PDX (FIG. 32D), and tumor growth of 5 individual mouse (black thin line) and averages (black thick line) in each group (FIG. 32E).

Figure 33A:
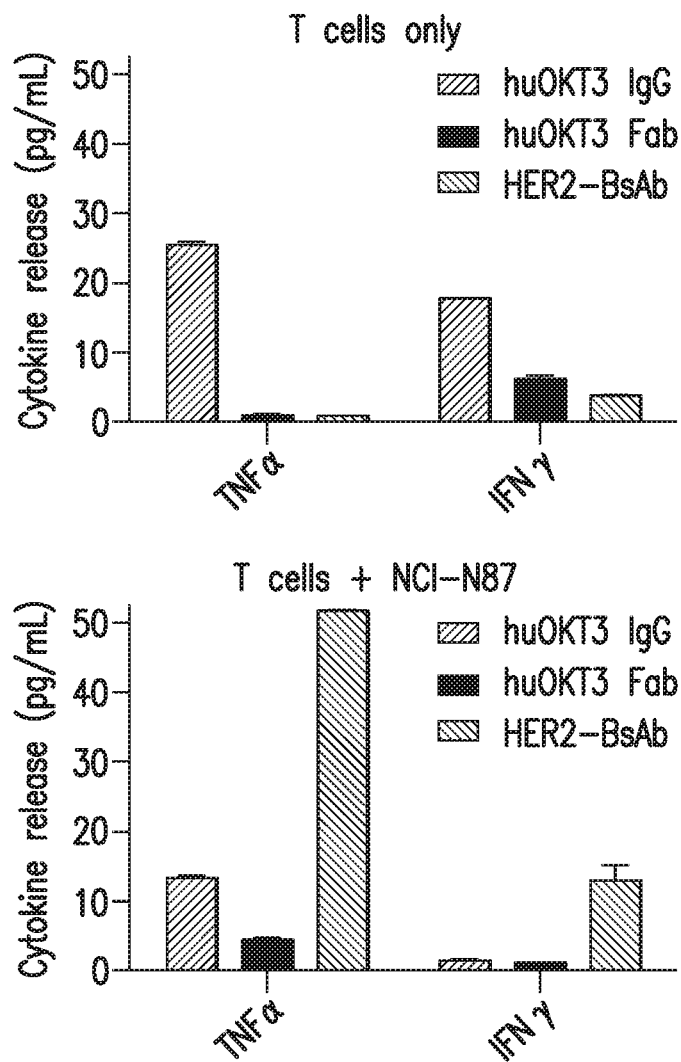
Figure 33B:
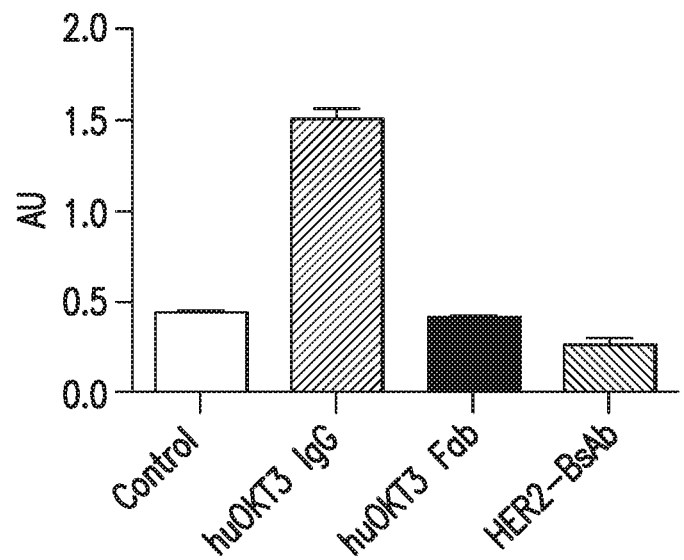

FIG. 33A and FIG. 33B demonstrate that HER2-BsAb binding to CD3 on T cells was functionally monovalent. FIG. 33A: Cytokine release from naïve T cells induced by 16.7 nM HER2-BsAb when compared to bivalent huOKT3 IgG and monovalent huOKT3 Fab, in the absence (left panel) or presence (right panel) of HER2(+) NCI-N87 gastric tumor cells. Cytokine release level below detection level was assigned as 1 pg/ml. FIG. 33B: T cell proliferation stimulated by 67 nM of the related antibodies, in the absence of tumor targets. T cells only (Control) as the negative control. OD reading at 450 nm (AU) was shown. All data points are shown as Mean+SD.

Figure 34:
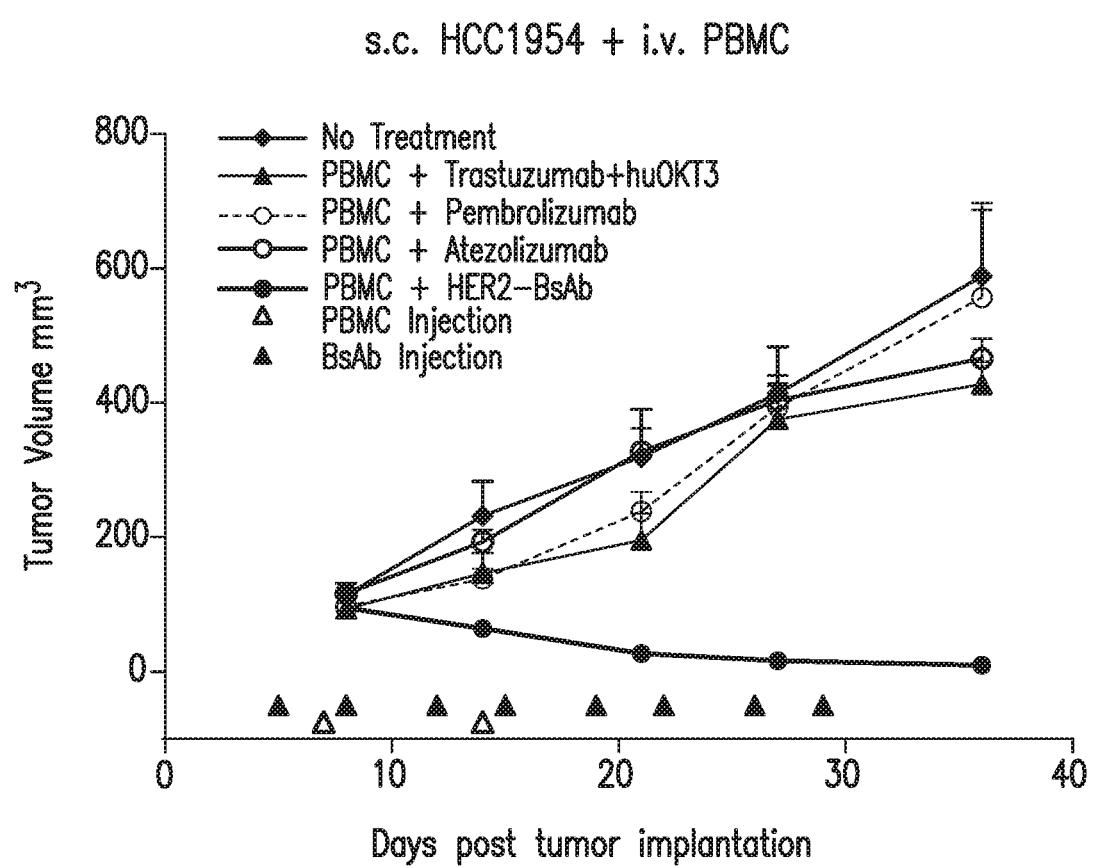

FIG. 34 demonstrates that HER2-BsAb is effective against HER2(+) breast cancer cell line xenografts that express PDL1 but are resistant to PD1 or PDL1 treatment. s.c. tumor plus i.v. effector cell model: tumor volume changes of HCC1954. Data shown as mean+SEM (n=5). Treatment schedules are marked on the figures. s.c. $5 \times 10^6$ HCC1954 xenografts were treated with i.v. PBMC ($7.5 \times 10^6$, once per week for 2 weeks), and i.v. HER2-BsAb, anti-PD1 Pembrolizumab, or anti-PDL1 Atezolizumab (100 ug each, twice per week for 4 weeks). Tumors were completely eradicated with HER2-BsAb treatment, in contrast to no effect for treatment with PD1/PDL1 blockade (i.e., treatment with anti-PD1 Pembrolizumab or anti-PDL1 Atezolizumab).

5. DETAILED DESCRIPTION

Provided herein are bispecific binding molecules that bind to both HER2 and CD3. Also provided herein are isolated nucleic acids (polynucleotides), such as complementary DNA (cDNA), encoding such bispecific binding molecules or fragments thereof. Further provided are vectors (e.g., expression vectors) and cells (e.g., ex vivo cells) comprising nucleic acids (polynucleotides) or vectors (e.g., expression vectors) encoding such bispecific binding molecules or fragments thereof. Also provided herein are methods of making such bispecific binding molecules, cells, and vectors. Also provided herein are T cells bound to bispecific binding molecules provided herein. Also provided herein are methods of binding such bispecific binding molecules to T cells. In other embodiments, provided herein are methods and uses for treating HER2-positive cancers using the bispecific binding molecules, nucleic acids, vectors, and/or T cells described herein. Additionally, related compositions (e.g., pharmaceutical compositions), kits, and diagnostic methods are also provided herein.

In certain embodiments, provided herein are bispecific binding molecules that specifically bind to HER2 and to CD3, and invoke T cell cytotoxicity for treating cancer. Without being bound by any theory, it is believed that the bispecific binding molecules described herein not only bind tumors to T cells, they also cross-link CD3 on T cells and initiate the activation cascade, and, this way, T cell receptor (TCR)-based cytotoxicity is redirected to desired tumor targets, bypassing major histocompatibility complex (MHC) restrictions.

5.1 Bispecific Binding Molecules

Provided herein are bispecific binding molecules that bind to HER2 and CD3. A binding molecule, which can be used within the methods provided herein, is a bispecific binding molecule comprising an aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first fusion polypeptide, and wherein the second light chain is fused to a second scFv, via a peptide linker, to create a second fusion polypeptide, wherein the first and second scFv (i) are identical, and (ii) bind to CD3, and wherein the first and second fusion polypeptides are identical.

HER2 is a member of the epidermal growth factor receptor (EGFR) family of receptor tyrosine kinases. In a specific embodiment, HER2 is human HER2. GenBank™ accession number NM_004448.3 (SEQ ID NO: 1) provides an exemplary human HER2 nucleic acid sequence. GenBank™ accession number NP_004439.2 (SEQ ID NO: 2) provides an exemplary human HER2 amino acid sequence. In another specific embodiment, HER2 is canine HER2. GenBank™ accession number NM_001003217.1 (SEQ ID NO: 3) provides an exemplary canine HER2 nucleic acid sequence. GenBank™ accession number NP_001003217.1 (SEQ ID NO: 4) provides an exemplary canine HER2 amino acid sequence.

CD3 is a T cell co-receptor comprised of a gamma chain, a delta chain, and two epsilon chains. In a specific embodiment, CD3 is a human CD3. GenBank™ accession number NM_000073.2 (SEQ ID NO: 5) provides an exemplary human CD3 gamma nucleic acid sequence. GenBank™ accession number NP_000064.1 (SEQ ID NO: 6) provides an exemplary human CD3 gamma amino acid sequence. GenBank™ accession number NM_000732.4 (SEQ ID NO: 7) provides an exemplary human CD3 delta nucleic acid sequence. GenBank™ accession number NP_000723.1 (SEQ ID NO: 8) provides an exemplary human CD3 delta amino acid sequence. GenBank™ accession number NM_000733.3 (SEQ ID NO: 9) provides an exemplary human CD3 epsilon nucleic acid sequence. GenBank™ accession number NP_000724.1 (SEQ ID NO: 10) provides an exemplary human CD3 epsilon amino acid sequence. In another specific embodiment, CD3 is a canine CD3. GenBank™ accession number NM_001003379.1 (SEQ ID NO: 11) provides an exemplary canine CD3 epsilon nucleic acid sequence. GenBank™ accession number NP_001003379.1 (SEQ ID NO: 12) provides an exemplary canine CD3 epsilon amino acid sequence.

The immunoglobulin in the bispecific binding molecules of the invention can be, as non-limiting examples, a monoclonal antibody, a naked antibody, a chimeric antibody, a humanized antibody, or a human antibody. As used herein, the term "immunoglobulin" is used consistent with its well known meaning in the art, and comprises two heavy chains and two light chains. Methods for making antibodies are described in Section 5.3.

A chimeric antibody is a recombinant protein that contains the variable domains including the complementarity-determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as, for example, horse, monkey, cow, pig, cat, or dog.

A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Similarly, forward mutations may be made to revert back to murine sequence for a desired reason, e.g., stability or affinity to antigen. Without being bound by any theory, humanized antibodies generally are less likely to elicit an immune response in humans as compared to chimeric human antibodies because the former contain considerably fewer non-human components.

The term "epitope" is art-recognized and is generally understood by those of skill in the art to refer to the region of an antigen that interacts with an antibody. An epitope of a protein antigen can be linear or conformational, or can be formed by contiguous or noncontiguous amino acid sequences of the antigen.

A scFv is an art-recognized term. An scFv comprises a fusion protein of the variable regions of the heavy ($V_H$) and light ($V_L$) chains of an immunoglobulin, wherein the fusion protein retains the same antigen specificity as the whole immunoglobulin. The $V_H$ is fused to the $V_L$ via a peptide linker (such a peptide linker is sometimes referred to herein as an "intra-scFv peptide linker").

In certain embodiments of the invention, the scFv has a peptide linker that is between 5-30, 5-25, 5-15, 10-30, 10-20, 10-15, 15-30, or 15-25 amino acid residues in length. In certain embodiments, the scFv peptide linker displays one or more characteristics suitable for a peptide linker known to one of ordinary skill in the art. In certain embodiments, the scFv peptide linker comprises amino acids that allow for scFv peptide linker solubility, such as, for example, serine and threonine. In certain embodiments, the scFv peptide linker comprises amino acids that allow for scFv peptide linker flexibility, such as, for example, glycine. In certain embodiments, the scFv peptide linker connects the N-terminus of the $V_H$ to the C-terminus of the $V_L$. In certain embodiments, the scFv peptide linker can connect the C-terminus of the $V_H$ to the N-terminus of the $V_L$. In certain embodiments, the scFv peptide linker is a linker as described in Table 1, below (e.g., any one of SEQ ID NOs: 14, or 35-41). In a preferred embodiment, the peptide linker is SEQ ID NO: 14.

In certain embodiments of the bispecific binding molecules of the invention, the scFv that binds to CD3 comprises the $V_H$ and the $V_L$ of a CD3-specific antibody known in the art, such as, for example, huOKT3 (see, for example, Adair et al., 1994, Hum Antibodies Hybridomas 5:41-47), YTH12.5 (see, for example Routledge et al., 1991, Eur J Immunol, 21: 2717-2725), HUM291 (see, for example, Norman et al., 2000, Clinical Transplantation, 70(12): 1707-1712), teplizumab (see, for example, Herold et al., 2009, Clin Immunol, 132: 166-173), huCLB-T3/4 (see, for example, Labrijn et al., 2013, Proceedings of the National Academy of Sciences, 110(13): 5145-5150), otelixizumab (see, for example, Keymeulen et al., 2010, Diabetologia, 53: 614-623), blinatumomab (see, for example, Cheadle, 2006, Curr Opin Mol Ther, 8(1): 62-68), MT110 (see, for example, Silke and Gires, 2011, MAbs, 3(1): 31-37), catumaxomab (see, for example, Heiss and Murawa, 2010, Int J Cancer, 127(9): 2209-2221), 28F11 (see, for example, Canadian Patent Application CA 2569509 A1), 27H5 (see, for example, Canadian Patent Application CA 2569509 A1), 23F10 (see, for example, Canadian Patent Application CA 2569509 A1), 15C3 (see, for example, Canadian Patent Application CA 2569509 A1), visilizumab (see, for example, Dean et al., 2012, Swiss Med Wkly, 142: w13711), and Hum291 (see, for example, Dean et al., 2012, Swiss Med Wkly, 142: w13711).

In certain embodiments, the scFv in a bispecific binding molecule of the invention binds to the same epitope as a CD3-specific antibody known in the art. In a specific embodiment, the scFv in a bispecific binding molecule of the invention binds to the same epitope as the CD3-specific antibody huOKT3. Binding to the same epitope can be determined by assays known to one skilled in the art, such as, for example, mutational analyses or crystallographic studies. In certain embodiments, the scFv competes for binding to CD3 with an antibody known in the art. In a specific embodiment, the scFv in a bispecific binding molecule of the invention competes for binding to CD3 with the CD3-specific antibody huOKT3. Competition for binding to CD3 can be determined by assays known to one skilled in the art, such as, for example, flow cytometry. See, for example, Section 6.1.2.4. In certain embodiments, the scFv comprises a $V_H$ with at least 85%, 90%, 95%, 98%, or at least 99% similarity to the $V_H$ of a CD3-specific antibody known in the art. In certain embodiments, the scFv comprises the $V_H$ of a CD3-specific antibody known in the art, comprising between 1 and 5 conservative amino acid substitutions. In certain embodiments, the scFv comprises a $V_L$ with at least 85%, 90%, 95%, 98%, or at least 99% similarity to the $V_L$ of a CD3-specific antibody known in the art. In certain embodiments, the scFv comprises the $V_L$ of a CD3-specific antibody known in the art, comprising between 1 and 5 conservative amino acid substitutions.

Conservative amino acid substitutions are amino acid substitutions that occur within a family of amino acids, wherein the amino acids are related in their side chains. Generally, genetically encoded amino acids are divided into families: (1) acidic, comprising aspartate and glutamate; (2) basic, comprising arginine, lysine, and histidine; (3) non-polar, comprising isoleucine, alanine, valine, proline, methionine, leucine, phenylalanine, tryptophan; and (4) uncharged polar, comprising cysteine, threonine, glutamine, glycine, asparagine, serine, and tyrosine. In addition, an aliphatic-hydroxy family comprises serine and threonine. In addition, an amide-containing family comprises asparagine and glutamine. In addition, an aliphatic family comprises alanine, valine, leucine and isoleucine. In addition, an aromatic family comprises phenylalanine, tryptophan, and tyrosine. Finally, a sulfur-containing side chain family comprises cysteine and methionine. As an example, one skilled in the art would reasonably expect an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups include: lysine-arginine, alanine-valine, phenylalanine-tyrosine, glutamic acid-aspartic acid, valine-leucine-isoleucine, cysteine-methionine, and asparagine-glutamine.

In a preferred embodiment, the scFv is derived from the huOKT3 antibody, and thus contains the $V_H$ and $V_L$ of huOKT3 monoclonal antibody (SEQ ID NOS: 15 and 16, respectively). See, for example, Van Wauwe et al., 1991, nature, 349: 293-299. In specific embodiments of the bispecific binding molecule, the scFv is derived from the huOKT3 monoclonal antibody and has no more than 5 amino acid mutations relative to native huOKT3 $V_H$ and $V_L$ sequences. In certain embodiments of the bispecific binding molecule, the scFv is derived from the huOKT3 monoclonal antibody and comprises one or more mutations, relative to native huOKT3 $V_H$ and $V_L$ sequences, to stabilize disulfide binding. In certain embodiments of the bispecific binding molecule, the stabilization of disulfide binding prevents aggregation of the bispecific binding molecule. In certain embodiments of the bispecific binding molecule, the stabilization of disulfide binding reduces aggregation of the bispecific binding molecule as compared to aggregation of the bispecific binding molecule without the stabilization of disulfide binding. In certain embodiments of the bispecific binding molecule, the one or more mutations to stabilize disulfide binding comprise a $V_H$ G44C mutation and a $V_L$ Q100C mutation (e.g., as present in SEQ ID NOS: 54-59). In certain embodiments of the bispecific binding molecule, the one or more mutations to stabilize disulfide binding are the replacement of the amino acid residue at $V_H44$ (according to the Kabat numbering system) with a cysteine and the replacement of the amino acid residue at $V_L100$ (according to the Kabat numbering system) with a cysteine so as to introduce a disulfide bond between $V_H44$ and $V_L100$ (e.g., as present in SEQ ID NOS: 54-59). In an especially preferred embodiment, the scFv comprises the $V_H$ of huOKT3 comprising the amino acid substitution at numbered position 105, wherein the cysteine is substituted with a serine (SEQ ID NO: 17). In certain embodiments, the sequence of the $V_H$ of the scFv is as described in Table 4, below (e.g., any one of SEQ ID NOs: 15, 17, or 64). In certain embodiments, the sequence of the $V_L$ of the scFv is as described in Table 5, below (e.g., any one of SEQ ID NOs: 16 or 65). In certain embodiments, the sequence of the scFv is as described in Table 6, below (e.g., any one of SEQ ID NOs: 19 or 48-59). In a preferred embodiment, the sequence of the scFv is SEQ ID NO: 19. In a specific embodiment, the scFv comprises a variant of the $V_H$ of huOKT3 that has no more than 5 amino acid mutations relative to the native sequence of huOKT3 $V_H$. In a specific embodiment, the scFv comprises a variant of the $V_L$ of huOKT3 that has no more than 5 amino acid mutations relative to the native sequence of huOKT3 $V_L$.

The sequences of the variable regions of an anti-CD3 scFv may be modified by insertions, substitutions and deletions to the extent that the resulting scFv maintains the ability to bind to CD3, as determined by, for example, ELISA, flow cytometry, and BiaCore™. The ordinarily skilled artisan can ascertain the maintenance of this activity by performing the functional assays as described herein below, such as, for example, binding analyses and cytotoxicity analyses.

In certain embodiments, the peptide linker conjugating the immunoglobulin light chain and the scFv is between 5-30, 5-25, 5-15, 10-30, 10-20, 10-15, 15-30, or 15-25 amino acids in length. In certain embodiments, the peptide linker displays one or more characteristics suitable for a peptide linker known to one of ordinary skill in the art. In certain embodiments, the peptide linker comprises amino acids that allow for peptide linker solubility, such as, for example, serine and threonine. In certain embodiments, the peptide linker comprises amino acids that allow for peptide linker flexibility, such as, for example, glycine. In certain embodiments, the sequence of the peptide linker conjugating the immunoglobulin light chain and the scFv is as described in Table 1, below (e.g., any one of SEQ ID NOs: 14 or 35-41). In preferred embodiments, the peptide linker is SEQ ID NO: 14.

In certain embodiments of the bispecific binding molecules of the invention, the immunoglobulin that binds to HER2 comprises the heavy chain and/or the light chain of a HER2-specific antibody known in the art, such as, for example, trastuzumab (see, for example, Baselga et al. 1998, Cancer Res 58(13): 2825-2831), M-111 (see, for example, Higgins et al., 2011, J Clin Oncol, 29(Suppl): Abstract TPS119), pertuzumab (see, for example, Franklin et al., 2004, Cancer Cell, 5: 317-328), ertumaxomab (see, for example, Kiewe and Thiel, 2008, Expert Opin Investig Drugs, 17(10): 1553-1558), MDXH210 (see, for example, Schwaab et al., 2001, Journal of Immunotherapy, 24(1): 79-87), 2B1 (see, for example, Borghaei et al., 2007, J Immunother, 30: 455-467), and MM-302 (see, for example, Wickham and Futch, 2012, Cancer Research, 72(24): Supplement 3). In certain embodiments of the bispecific binding molecules of the invention, the immunoglobulin that binds to HER2 comprises the heavy chain of trastuzumab. In certain embodiments of the bispecific binding molecules of the invention, the immunoglobulin that binds to HER2 comprises the sequence as set forth in SEQ ID NO: 23. In certain embodiments of the bispecific binding molecules of the invention, the immunoglobulin that binds to HER2 comprises a variant of the heavy chain of trastuzumab (see, e.g., Table 2, below). In a specific embodiment of the bispecific binding molecules of the invention, the immunoglobulin that binds to HER2 comprises a variant of the light chain of trastuzumab that has no more than 5 amino acid mutations relative to the native sequence of trastuzumab. In certain embodiments of the bispecific binding molecules of the invention, the immunoglobulin that binds to HER2 comprises the light chain of trastuzumab (SEQ ID NO: 25). In certain embodiments of the bispecific binding molecules of the invention, the immunoglobulin that binds to HER2 comprises a variant of the light chain of trastuzumab. In a specific embodiment of the bispecific binding molecules of the invention, the immunoglobulin that binds to HER2 comprises a variant of the light chain of trastuzumab that has no more than 5 amino acid mutations relative to the native sequence of trastuzumab.

In certain embodiments of the bispecific binding molecules of the invention, the immunoglobulin that binds to HER2 binds to the same epitope as a HER2-specific antibody known in the art. In a specific embodiment, the immunoglobulin in a bispecific binding molecule of the invention binds to the same epitope as trastuzumab. Binding to the same epitope can be determined by assays known to one skilled in the art, such as, for example, mutational analyses or crystallographic studies. In certain embodiments, the immunoglobulin that binds to HER2 competes for binding to HER2 with an antibody known in the art. In a specific embodiment, the immunoglobulin in a bispecific binding molecule of the invention competes for binding to HER2 with trastuzumab. Competition for binding to HER2 can be determined by assays known to one skilled in the art, such as, for example, flow cytometry. See, for example, Section 6.1.2.4. In certain embodiments, the immunoglobulin comprises a $V_H$ with at least 85%, 90%, 95%, 98%, or at least 99% similarity to the $V_H$ of a HER2-specific antibody known in the art. In certain embodiments, the immunoglobulin comprises the $V_H$ of a HER2-specific antibody known in the art, comprising between 1 and 5 conservative amino acid substitutions. In certain embodiments, the immunoglobulin comprises a $V_L$ with at least 85%, 90%, 95%, 98%, or at least 99% similarity to the $V_L$ of a HER2-specific antibody known in the art. In certain embodiments, the immunoglobulin comprises the $V_L$ of a HER2-specific antibody known in the art, comprising between 1 and 5 conservative amino acid substitutions. In certain embodiments, the immunoglobulin comprises a $V_H$ of a heavy chain described in Table 2, below (e.g., the $V_H$ of any one of SEQ ID NOs: 23, 27, 62, or 63). In certain embodiments, the immunoglobulin comprises a $V_L$ of a light chain described in Table 3, below (e.g., the $V_L$ of SEQ ID NO: 25).

The sequences of the variable regions of an anti-HER2 antibody may be modified by insertions, substitutions and deletions to the extent that the resulting antibody maintains the ability to bind to HER2, as determined by, for example, ELISA, flow cytometry, and BiaCore™ The ordinarily skilled artisan can ascertain the maintenance of this activity by performing the functional assays as described herein below, such as, for example, binding analyses and cytotoxicity analyses.

In certain embodiments of the bispecific binding molecules of the invention, the immunoglobulin that binds to HER2 is an IgG1 immunoglobulin.

Methods of producing human antibodies are known to one skilled in the art, such as, for example, phage display methods described above using antibody libraries derived from human immunoglobulin sequences. See also, U.S. Pat. Nos. 4,444,887 and 4,716,111; and PCT publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

In certain embodiments, human antibodies are produced using transgenic mice, which are incapable of expressing functional endogenous mouse immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, for example, all or a portion of a polypeptide provided herein. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, for example, PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Human monoclonal antibodies can also be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, for example, a mouse antibody, is used to guide the selection of a completely human antibody recognizing the same epitope. See, for example, Jespers et al., Bio/technology 12:899-903 (1988). Human antibodies may also be generated by in vitro activated B cells. See U.S. Pat. Nos. 5,567,610 and 5,229,275, which are incorporated in their entirety by reference.

Methods for making humanized antibodies are known to one skilled in the art. See, for example, Winter EP 0 239 400;

Jones et al., Nature 321:522-525 (1986); Riechmann et al., Nature 332:323-327 (1988); Verhoeyen et al., Science 239:1534-1536 (1988); Queen et al., Proc. Nat. Acad. ScL USA 86:10029 (1989); U.S. Pat. No. 6,180,370; and Orlandi et al., Proc. Natl. Acad. Sd. USA 86:3833 (1989); the disclosures of all of which are incorporated by reference herein in their entireties. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs, encoding the CDRs are inserted into the corresponding regions of a human antibody heavy or light chain variable domain coding sequences, attached to human constant region gene segments of a desired isotype (e.g., gamma-1 for CH and K for $C_L$), are gene synthesized. The humanized heavy and light chain genes are co-expressed in mammalian host cells (e.g., CHO or NSO cells) to produce soluble humanized antibody. To facilitate large scale production of antibodies, it is often desirable select for high expressor using a DHFR gene or GS gene in the producer line. These producer cell lines are cultured in bioreactors, or hollow fiber culture system, or WAVE technology, to produce bulk cultures of soluble antibody, or to produce transgenic mammals (e.g., goats, cows, or sheep) that express the antibody in milk (see, e.g., U.S. Pat. No. 5,827,690).

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a $F(ab')_2$ heavy chain portion can be designed to include DNA sequences encoding the CH, domain and/or hinge region of the heavy chain. The various portions of antibodies can be joined together chemically by conventional techniques, or can be prepared as a contiguous protein using genetic engineering techniques. In certain embodiments, elements of a human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See, for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993).

Antibody humanization can also be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

Antibody humanization can be used to evolve mouse or other non-human antibodies into "fully human" antibodies. The resulting antibody contains only human sequence and no mouse or non-human antibody sequence, while maintaining similar binding affinity and specificity as the starting antibody.

For full length antibody molecules, the immunoglobulin genes can be obtained from genomic DNA or mRNA of hybridoma cell lines. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A), or the like, or heteromylomas, fusion products thereof, or any cell or fusion cell derived therefrom, or any other suitable cell line as known in the art. See, for example, the ATCC or LifeTech website, and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, avian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, for example, Ausubel, supra, and Colligan, Immunology, supra, chapter 2, entirely incorporated herein by reference. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

In a preferred specific embodiment, the bispecific binding molecule comprises a variant Fc region, wherein said variant Fc region comprises at least one amino acid modification relative to a wild-type Fc region, such that said molecule does not bind or has reduced binding to an Fc receptor (FcR), in soluble form or cell-bound form (including on immune-effector cells, such as, for example, NK cells, monocytes, and neutrophils). These FcRs include, but are not limited to, FcR1 (CD64), FcRII (CD32), and FcRIII (CD16). The affinity to FcR(n), the neonatal Fc receptor, is not affected, and thus maintained in the bispecific binding molecule. For example, if the immunoglobulin is an IgG, preferably, the IgG has reduced or no affinity for an Fc gamma receptor. In certain embodiments, one or more positions within the Fc region that makes a direct contact with Fc gamma receptor, such as, for example, amino acids 234-239 (hinge region), amino acids 265-269 (B/C loop), amino acids 297-299 (C'/E loop), and amino acids 327-332 (F/G) loop, are mutated such that the bispecific binding molecule has a decreased or no affinity for an Fc gamma receptor. See, for example, Sondermann et al., 2000, Nature, 406: 267-273, which is incorporated herein by reference in its entirety. Preferably, for an IgG, the mutation N297A is made to destroy Fc receptor binding. In certain embodiments, affinity of the bispecific binding molecule or fragment thereof for an Fc gamma receptor is determined by, for example, BiaCore™ assay, as described, for example, in Okazaki et al., 2004. J Mol Biol, 336(5):1239-49. See also, Section 6. In certain embodiments, the bispecific binding molecule comprising such a variant Fc region binds an Fc receptor on a FcR-bearing immune-effector cell with less than 25%, 20%, 15%, 10%, or 5% binding as compared to a reference Fc region. Without being bound by any particular theory, a bispecific binding molecule comprising such a variant Fc region will have a decreased ability to induce a cytokine storm. In preferred embodiments, the bispecific binding molecule comprising such a variant Fc region does not bind an Fc receptor in soluble form or as a cell-bound form.

In certain embodiments, the bispecific binding molecule comprises a variant Fc region, such as, for example, an Fc region with additions, deletions, and/or substitutions to one or more amino acids in the Fc region of an antibody provided herein in order to alter effector function, or enhance or diminish affinity of antibody to FcR. In a preferred embodiment, the affinity of the antibody to FcR is diminished. Reduction or elimination of effector function is desirable in certain cases, such as, for example, in the case of antibodies whose mechanism of action involves blocking or antagonism but not killing of the cells bearing a target antigen. In certain embodiments, the Fc variants provided herein may be combined with other Fc modifications, including but not limited to modifications that alter effector function. In certain embodiments, such modifications provide additive, synergistic, or novel properties in antibodies or Fc fusions. Preferably, the Fc variants provided herein enhance the phenotype of the modification with which they are combined.

In preferred embodiments, the bispecific binding molecule of the invention is aglycosylated. Preferably, this is achieved by mutating the anti-HER2 immunoglobulin portion of the bispecific binding molecule in its Fc receptor to destroy a glycosylation site, preferably an N-linked glycosylation site. In another specific embodiment, an immunoglobulin is mutated to destroy an N-linked glycosylation site. In certain preferred embodiments, the bispecific binding molecule has been mutated to destroy an N-linked glycosylation site. In certain embodiments, the heavy chain of the bispecific binding molecule has an amino acid substitution to replace an asparagine that is an N-linked glycosylation site, with an amino acid that does not function as a glycosylation site. In a preferred embodiment, the method encompasses deleting the glycosylation site of the Fc region of a bispecific binding molecule, by modifying position 297 from asparagine to alanine (N297A). For example, in certain embodiments, the bispecific binding molecule comprises a heavy chain with the sequence of SEQ ID NO: 20. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. Methods for modifying the glycosylation content of antibodies are well known in the art, see, for example, U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In another embodiment, aglycosylation of the bispecific binding molecules of the invention can be achieved by recombinantly producing the bispecific binding molecule in a cell or expression system incapable of glycosylation, such as, for example, bacteria. In another embodiment, aglycosylation of the bispecific binding molecules of the invention can be achieved by enzymatically removing the carbohydrate moieties of the glycosylation site.

In preferred embodiments, the bispecific binding molecule of the invention does not bind or has reduced binding affinity (relative to a reference or wild type immunoglobulin) to the complement component C1q. Preferably, this is achieved by mutating the anti-HER2 immunoglobulin portion of the bispecific binding molecule to destroy a C1q binding site. In certain preferred embodiments, the method encompasses deleting the C1q binding site of the Fc region of an antibody, by modifying position 322 from lysine to alanine (K322A). For example, in certain embodiments, the bispecific binding molecule comprises a heavy chain with the sequence of SEQ ID NO: 21. In certain embodiments, affinity of the bispecific binding molecule or fragment thereof for the complement component C1q is determined by, for example, BiaCore™ assay, as described, for example, in Okazaki et al., 2004. J Mol Biol, 336(5):1239-49. See also, Section 6. In certain embodiments, the bispecific binding comprising an anti-HER2-immunoglobulin comprising a destroyed C1q binding site binds the complement component C1q with less than 25%, 20%, 15%, 10%, or 5% binding compared to a reference or wild type immunoglobulin. In certain embodiments, the bispecific binding molecule does not activate complement.

In preferred embodiments, the bispecific binding molecule of the invention comprises an immunoglobulin, wherein the immunoglobulin (i) comprises at least one amino acid modification relative to a wild-type Fc region, such that said molecule does not bind or has reduced binding to an Fc receptor in soluble form or as cell-bound form; (ii) comprises one or more mutations in the Fc region to destroy an N-linked glycosylation site; and (iii) does not or has reduced binding to the complement component C1q. For example, in certain embodiments, the bispecific binding molecule comprises an IgG comprising a first mutation, N297A, in the Fc region to (i) abolish or reduce binding to an Fc receptor in soluble form or as cell-bound form; and (ii) destroy an N-linked glycosylation site in the Fc region; and a second mutation, K322A, in the Fc region to (iii) abolish or reduce binding to the complement component C1q. See, for example, SEQ ID NO: 27.

In a preferred embodiment, the immunoglobulin that binds to HER2 comprises the variable regions of trastuzumab (see, e.g., Tables 2 and 3), and preferably a human IgG1 constant region. In a preferred embodiment, the immunoglobulin that binds to HER2 comprises the variable regions of trastuzumab wherein the sequence of the heavy chain is SEQ ID NO: 27 and wherein the sequence of the light chain is SEQ ID NO: 25. In a preferred embodiment, the immunoglobulin that binds to HER2 is a variant of trastuzumab, wherein the heavy chain does not bind or has reduced binding to an Fc receptor in soluble form or as cell-bound form. In a preferred embodiment, the heavy chain that does not bind an Fc receptor in soluble form or as a cell-bound form comprises a mutation in the Fc region to destroy an N-linked glycosylation site. In a preferred embodiment, the heavy chain has an amino acid substitution to replace an asparagine that is an N-linked glycosylation site, with an amino acid that does not function as a glycosylation site. In a preferred embodiment, the mutation to destroy an N-linked glycosylation site is N297A in the Fc region (SEQ ID NO: 20). In a preferred embodiment, the immunoglobulin that binds to HER2 comprises the variable regions of trastuzumab, wherein the sequence of the heavy chain comprises a mutation in the Fc region to destroy a C1q binding site. In a preferred embodiment, the immunoglobulin does not activate complement. In a preferred embodiment, the mutation to destroy a C1q binding site is K322A in the Fc region (SEQ ID NO: 21). In an especially preferred embodiment, the immunoglobulin that binds to HER2 comprises the variable regions of trastuzumab, wherein the immunoglobulin heavy chain comprises a mutation in the Fc region to destroy an N-linked glycosylation site and a mutation in the Fc region to destroy a C1q binding site (see, for example, SEQ ID NO: 27). In an especially preferred embodiment, the immunoglobulin that binds to HER2 comprises the variable regions of trastuzumab wherein the sequence of the heavy chain of the immunoglobulin has been mutated in the Fc region and is SEQ ID NO: 27 and wherein the sequence of the light chain is SEQ ID NO: 25. In an especially preferred embodiment, the sequence of the light chain fusion polypeptide is SEQ ID NO: 29. In certain embodiments, the heavy chain comprises the constant region of trastuzumab. In certain embodiments, the heavy chain comprises the constant region of a heavy chain described in Table 2, below (e.g., the constant region of any one of SEQ ID NOs: 23, 27, 62, or 63). In certain embodiments, the sequence of the heavy chain is as described in Table 2, below (e.g., any one of SEQ ID NOs: 23, 27, 62, or 63). In certain embodiments, the light chain comprises the constant region of a light chain described in Table 3, below (e.g., the constant region of SEQ ID NO: 25). In certain embodiments, the sequence of the light chain is as described in Table 3, below (e.g., SEQ ID NO: 25).

In certain embodiments, the bispecific binding molecule has a trastuzumab-derived sequence that contains one or more of the modifications in the trastuzumab immunoglobulin, and has a huOKT3-derived sequence that contains one or more of the modifications in the huOKT3 $V_H$ and $V_L$ sequences, as described in Table 8, below. Bispecific binding molecules having other immunoglobulin or scFv sequences can contain analogous mutations at corresponding positions in these other immunoglobulin or scFv sequences. In certain embodiments, the bispecific binding molecule is (a) derived from trastuzumab and huOKT3; and (b) contains one or more of the modifications as described in Table 8, below. In certain embodiments, the sequence of the peptide linker conjugating the immunoglobulin light chain and the scFv is as described in Table 1, below (e.g., any one of SEQ ID NOs: 14 or 35-41). In certain embodiments, the sequence of the heavy chain is as described in Table 2, below (e.g., any one of SEQ ID NOs: 23, 27, 62, or 63). In certain embodiments, the sequence of the light chain is as described in Table 3, below (e.g., SEQ ID NO: 25). In certain embodiments, the sequence of the $V_H$ of the scFv is as described in Table 4, below (e.g., any one of SEQ ID NOs: 15, 17, or 64). In certain embodiments, the sequence of the $V_L$ of the scFv is as described in Table 5, below (e.g., any one of SEQ ID NOs: 16 or 65). In certain embodiments, the sequence of the scFv peptide linker is as described in Table 1, below (e.g., any one of SEQ ID NOs: 14 or 35-41). In certain embodiments, the sequence of the scFv is as described in Table 6, below (e.g., any one of SEQ ID NOs: 19 48-59, or 66). In certain embodiments, the sequence of the light chain fusion polypeptide is as described in Table 7, below (e.g., any one of SEQ ID NOs: 29, 34, 42-47, or 60).

In certain embodiments, the bispecific binding molecule comprises a glycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, wherein the first and second light chain fusion polypeptides are identical, wherein the sequence of each heavy chain is SEQ ID NO: 62, and wherein the sequence of each light chain fusion polypeptide is SEQ ID NO: 60.

In certain embodiments, the bispecific binding molecule comprises a glycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, wherein the first and second light chain fusion polypeptides are identical, wherein the sequence of each heavy chain is SEQ ID NO: 27, and wherein the sequence of each light chain fusion polypeptide is SEQ ID NO: 47.

In certain embodiments, the bispecific binding molecule comprises a glycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, wherein the first and second light chain fusion polypeptides are identical, wherein the sequence of each heavy chain is SEQ ID NO: 27, and wherein the sequence of each light chain fusion polypeptide is SEQ ID NO: 29.

In certain embodiments, the bispecific binding molecule has low immunogenicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (Elliott et al., Lancet 344:1125-1127 (1994), entirely incorporated herein by reference).

The bispecific binding molecules provided herein can bind HER2 and CD3 with a wide range of affinities. The affinity or avidity of an antibody for an antigen can be determined experimentally using any suitable method. See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein. The measured affinity of a particular antibody-antigen interaction can vary if measured under different conditions (e.g., salt concentration, pH). Thus, measurements of affinity and other antigen-binding parameters are preferably made with standardized solutions of antibody and antigen, and a standardized buffer, such as the buffer described herein. The affinity, $K_D$ is a ratio of $k_{on}/k_{off}$. Generally, a $K_D$ in the micromolar range is considered low affinity. Generally, a $K_D$ in the picomolar range is considered high affinity. In another specific embodiment, the bispecific binding molecule has high affinity for HER2 and low affinity for CD3. In another specific embodiment, the bispecific binding molecule has high affinity for HER2 and average affinity for CD3. In a specific embodiment, the bispecific binding molecule has a $K_D$ of between 70 nM and 1 µM for CD3. In a specific embodiment, the bispecific binding molecule has a $K_D$ of between 70 nM and 500 nM for CD3. In a specific embodiment, the bispecific binding molecule has a $K_D$ of between 500 nM and 1 µM for CD3.

In certain embodiments, the bispecific binding molecule binds to one or more HER2-positive carcinoma cell lines, as determined by assays known to one skilled in the art, such as, for example, ELISA, BiaCore™, and flow cytometry. In certain embodiments, the carcinoma cell line is a breast carcinoma cell line, such as, for example, MDA-MB-361, MDA-MB-468, AU565, SKBR3, HTB27, HTB26, HCC1954, and/or MCF7. In certain embodiments, the carcinoma cell line is an ovarian carcinoma cell line, such as, for example, OVCAR3 and/or SKOV3. In certain embodiments, the carcinoma cell line is a gastric carcinoma cell line, such as, for example, NCI-N87, KATO III, AGS, and/or SNU-16. In certain embodiments, the carcinoma cell line is a melanoma cell line, such as, for example, HT144, SKMEL28, M14, and/or HTB63. In certain embodiments, the carcinoma cell line is an osteosarcoma cell line, such as, for example, RG160, RG164, CRL1427, and/or U2OS. In certain embodiments, the carcinoma cell line is a Ewings sarcoma cell line, such as, for example, SKEAW and/or SKES-1. In certain embodiments, the carcinoma cell line is a rhabdomyosarcoma cell line, such as, for example, HTB82. In certain embodiments, the carcinoma cell line is a neuroblastoma cell line, such as, for example, NMB7, SKNBE(2)C, IMR32, SKNBE(2)S, SKNBE(1)N, and/or NBS. In certain embodiments, the carcinoma cell line is a squamous cell carcinoma head and neck (SCCHN) cell lines, such as, for example, 15B, 93-VU-147T, PCI-30, UD-SCC2, PCI-15B, SCC90, and/or UMSCC47. In certain embodiments, the carcinoma cell line is a cervical cancer cell line, such as, for example, HeLa. In certain embodiments, the carcinoma cell line is a small cell lung cancer cell line, such as, for example, NCI-H524, NCI-H69, and/or NCI-H345. In certain embodiments, the bispecific binding molecule binds to the HER2-positive carcinoma cell line with an EC50 in the picomolar range. See, for example, Section 6.1.3.4 and Section 6.1.3.6.

In certain embodiments, the bispecific binding molecule binds to CD3+ T cells, as determined by assays known to one skilled in the art, such as, for example, ELISA, BiaCore™ and flow cytometry. In certain preferred embodiments, the bispecific binding molecule binds to CD3+ T cells with greater than 15-fold less binding than huOKT3 binding to CD3+ T cells. See, for example, Section 6.1.3.1. In certain embodiments, the CD3+ T cells are human T cells.

In certain embodiments, the bispecific binding molecule the bispecific binding molecule mediates T cell cytotoxicity against HER2-positive cells, as determined by assays known to one skilled in the art, such as, for example, cytotoxicity assays. In preferred embodiments, the bispecific binding molecule mediates T cell cytotoxicity against HER2-positive cell lines with an EC50 in the picomolar range. In certain embodiments, the HER2-positive cells are breast carcinoma cell lines, such as, for example, MDA-MB-361, MDA-MB-468, AU565, SKBR3, HTB27, HTB26, and/or MCF7. In certain embodiments, the HER2-positive cells are of an ovarian carcinoma cell line, such as, for example, OVCAR3 and/or SKOV3. In certain embodiments, the HER-2 positive cells are of a gastric carcinoma cell line, such as, for example, NCI-N87, KATO III, AGS, and/or SNU-16. In certain embodiments, the HER2-positive cells are of a melanoma cell line, such as, for example, HT144, SKMEL28, M14, and/or HTB63. In certain embodiments, the HER2-positive cells are of an osteosarcoma cell line, such as, for example, RG160, RG164, CRL1427, and/or U205. In certain embodiments, the HER2-positive cells are of an Ewings sarcoma cell line, such as, for example, SKEAW and/or SKES-1. In certain embodiments, the HER2-positive cells are of a rhabdomyosarcoma cell line, such as, for example, HTB82. In certain embodiments, the HER2-positive cells are of a neuroblastoma cell line, such as, for example, NMB7, SKNBE(2)C, IMR32, SKNBE(2)S, SKNBE(1)N, and/or NBS. In certain embodiments, the HER2-positive cells are of a squamous cell carcinoma head and neck (SCCHN) cell line, such as, for example, 15B, 93-VU-147T, PCI-30, UD-SCC2, PCI-15B, SCC90, and/or UMSCC47. In certain embodiments, the HER2-positive cells are of a cervical cancer cell line, such as, for example, HeLa. In certain embodiments, the HER2-positive cells are of a small cell lung cancer cell line, such as, for example, NCI-H524, NCI-H69, and/or NCI-H345. See, for example, Section 6.1.3.4 and Section 6.1.3.6.

In certain embodiments, preincubation of HER2-positive cells with huOKT3 blocks the ability of the bispecific binding molecule to induce T cell cytotoxicity. In certain embodiments, preincubation of HER2-positive cells with trastuzumab blocks the ability of the bispecific binding molecule to induce T cell cytotoxicity. See, for example, Section 6.1.3.3.

In certain embodiments, the bispecific binding molecule mediates T cell cytotoxicity against HER2-positive cells, wherein the level of HER2-expression in said cells is below the threshold of detection by flow cytometry performed with the bispecific binding molecule. See, for example, Section 6.1.3.4.

In certain embodiments, the bispecific binding molecule mediates T cell cytotoxicity against HER2-positive cells resistant to other HER-targeted therapies, such as, for example, trastuzumab, cetuximab, lapatinib, erlotinib, neratinib, or any other small molecule or antibody that targets the HER family of receptors. In a specific embodiment, the tumor that is resistant to HER-targeted therapies, such as, for example, trastuzumab, cetuximab, lapatinib, erlotinib, neratinib, or any other small molecule or antibody that targets the HER family of receptors is responsive to treatment with a bispecific binding molecule to the invention. See, for example, Section 6.1.3.7, Section 6.1.3.8, Section 6.1.3.9, and Section 6.1.3.10.

In certain embodiments, the bispecific binding molecule reduces HER2-positive tumor progression, metastasis, and/or tumor size. See, for example, Section 6.1.3.11.

In certain embodiments, the bispecific binding molecule is bound to a T cell. In certain embodiments, the binding of the bispecific binding molecule to a T cell is noncovalently. In certain embodiments, the T cell is administered to a subject. In certain embodiments, the T cell is autologous to the subject to whom the T cell is to be administered. In certain embodiments, the T cell is allogeneic to the subject to whom the T cell is to be administered. In certain embodiments, the T cell is a human T cell.

In certain embodiments, the bispecific binding molecule is not bound to a T cell.

In certain embodiments, the bispecific binding molecule is conjugated to an organic moiety, a detectable marker, and/or isotope as described in Section 5.2.

In certain embodiments, the bispecific binding molecule or fragment thereof is produced as described in Section 5.3. In certain embodiments, the bispecific binding molecule or fragment thereof is encoded by a polynucleotide as described in Section 5.3.1. In certain embodiments, the bispecific binding molecule or fragment thereof is encoded by a vector (e.g., expression vector) as described in Section 5.3.2. In certain embodiments, the bispecific binding molecule or fragment thereof is produced from a cell as described in Section 5.3.2.

In certain embodiments, the bispecific binding molecule is a component of a composition (e.g., pharmaceutical composition) and/or as part of a kit as described in Section 5.5.

In certain embodiments, the bispecific binding molecule is used according to the methods provided in Section 5.6. In certain embodiments, the bispecific binding molecule is used as a diagnostic tool according to the methods provided in Section 5.6.2. In certain embodiments, the bispecific binding molecule is used as a therapeutic according to the methods provided in Section 5.6.1. In certain embodiments, the bispecific binding molecule is administered to a subject, such as a subject described in Section 5.7, for use according to the methods provided in Section 5.6. In certain embodiments, the bispecific binding molecule is administered to a subject as part of a combination therapy as described in Section 5.9, for use according to the methods provided in Section 5.6.

TABLE 1

Linker Sequence

| DESCRIPTION | SEQUENCE (SEQ ID NO:) |
|---|---|
| $(G_4S)_3$ | GGGGSGGGGSGGGGS (SEQ ID NO: 14) |
| $TS(G_4S)_3$ Linker | TSGGGGSGGGGSGGGGS (SEQ ID NO: 35) |
| $G_4S$ Linker | GGGGS (SEQ ID NO: 36) |
| $(G_4S)_2$ Linker | GGGGSGGGGS (SEQ ID NO: 37) |
| $(G_4S)_3$ Linker | GGGGSGGGGSGGGGS (SEQ ID NO: 38) |
| $(G_4S)_4$ Linker | GGGGSGGGGSGGGGSGGGGS (SEQ ID NO: 39) |
| $(G_4S)_5$ Linker | GGGGSGGGGSGGGGSGGGGSGGGGS (SEQ ID NO: 40) |
| $(G_4S)_6$ Linker | GGGGSGGGGSGGGGSGGGGSGGGGSGGGGS (SEQ ID NO: 41) |

TABLE 2

Heavy Chain Sequence. The non-italicized, non-underlined sequence represents the $V_H$ domain. The italicized sequence represents the constant region. The underlined, italicized, and bold sequences represent the mutations described in the "DESCRIPTION" column.

| DESCRIPTION | SEQUENCE (SEQ ID NO:) |
|---|---|
| Trastuzumab $V_H$ domain with human IgG1 constant region | EVQLVESGGGLVQPGGSLRLSCAASGFNIKDTYIHWVRQAPGKG LEWVARIYPTNGYTRYADSVKGRFTISADTSKNTAYLQMNSLRA EDTAVYYCSRWGGDGFYAMIDYWGQGTLVTVSS*ASTKGPSVFPL APSSKSTSGGTAALGCLVKDYFPEPVTVSWNSGALTSGVHTFPAVLQS SGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEV KFNWYVDGVEVHNAKTKPREEQYNSTYRVVSVLTVLHQDWLNGKEY KCKVSNKALPAPIEKTISKAKGQPREPQVYTLPPSRDELTKNQVSLTC LVKGFYPSDIAVEWESNGQPENNYKTTPPVLDSDGSFFLYSKLTVDKS RWQQGNVFSCSVMHEALHNHYTQKSLSLSPGK* (SEQ ID NO: 23) |

TABLE 2-continued

Heavy Chain Sequence. The non-italicized, non-underlined sequence represents the $V_H$ domain. The italicized sequence represents the constant region. The underlined, italicized, and bold sequences represent the mutations described in the "DESCRIPTION" column.

| DESCRIPTION | SEQUENCE (SEQ ID NO:) |
| --- | --- |
| Trastuzumab $V_H$ domain with human IgG1 constant region; N297A; K322A | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSS*ASTKGPSVFPL*<br>*APSSKSTSGGTAALGCLVKDYFPEPVTVSWNSGALTSGVHTFPAVLQS*<br>*SGLYSLSSVVTVPSSSLGTQTYICNVNHKPSNTKVDKRVEPKSCDKTHT*<br>*CPPCPAPELLGGPSVFLFPPKPKDTLMISRTPEVTCVVVDVSHEDPEV*<br>*KFNWYVDGVEVHNAKTKPREEQYASTYRVVSVLTVLHQDWLNGKEY*<br>*KCAVSNKALPAPIEKTISKAKGQPREPQVYTLPPSRDELTKNQVSLTC*<br>*LVKGFYPSDIAVEWESNGQPENNYKTTPPVLDSDGSFFLYSKLTVDKS*<br>*RWQQGNVFSCSVMHEALHNHYTQKSLSLSPG* (SEQ ID NO: 27) |
| Trastuzumab $V_H$ domain with human IgG1 constant region; N297A | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSS*ASTKGPSVFPL*<br>*APSSKSTSGGTAALGCLVKDYFPEPVTVSWNSGALTSGVHTFPAVLQS*<br>*SGLYSLSSVVTVPSSSLGTQTYICNVNHKPSNTKVDKRVEPKSCDKTHT*<br>*CPPCPAPELLGGPSVFLFPPKPKDTLMISRTPEVTCVVVDVSHEDPEV*<br>*KFNWYVDGVEVHNAKTKPREEQYASTYRVVSVLTVLHQDWLNGKEY*<br>*KCKVSNKALPAPIEKTISKAKGQPREPQVYTLPPSRDELTKNQVSLTC*<br>*LVKGFYPSDIAVEWESNGQPENNYKTTPPVLDSDGSFFLYSKLTVDKS*<br>*RWQQGNVFSCSVMHEALHNHYTQKSLSLSPGK* (SEQ ID NO: 62) |
| Trastuzumab $V_H$ domain with human IgG1 constant region; K322A | EVQLVESGGGLVQPGGSLRLSCAASGFNIKDTYIHWVRQAPGKG<br>LEWVARIYPTNGYTRYADSVKGRFTISADTSKNTAYLQMNSLRA<br>EDTAVYYCSRWGGDGFYAMDYWGQGTLVTVSS*ASTKGPSVFPL*<br>*APSSKSTSGGTAALGCLVKDYFPEPVTVSWNSGALTSGVHTFPAVLQS*<br>*SGLYSLSSVVTVPSSSLGTQTYICNVNHKPSNTKVDKRVEPKSCDKTHT*<br>*CPPCPAPELLGGPSVFLFPPKPKDTLMISRTPEVTCVVVDVSHEDPEV*<br>*KFNWYVDGVEVHNAKTKPREEQYNSTYRVVSVLTVLHQDWLNGKEY*<br>*KCAVSNKALPAPIEKTISKAKGQPREPQVYTLPPSRDELTKNQVSLTC*<br>*LVKGFYPSDIAVEWESNGQPENNYKTTPPVLDSDGSFFLYSKLTVDKS*<br>*RWQQGNVFSCSVMHEALHNHYTQKSLSLSPGK* (SEQ ID NO: 63) |

TABLE 3

Light Chain Sequence. The non-italicized sequence represents the $V_L$ domain. The italicized sequence represents the constant region.

| DESCRIPTION | SEQUENCE (SEQ ID NO:) |
| --- | --- |
| Trastuzumab light chain | DIQMTQSPSSLSASVGDRVTITCRASQDVNTAVAWYQQKPGKAP<br>KLLIYSASFLYSGVPSRFSGSRSGTDFTLTISSLQPEDFATYYCQQH<br>YTTPPTFGQGTKVEIKR*TVAAPSVFIFPPSDEQLKSGTASVVCLLNNF*<br>*YPREAKVQWKVDNALQSGNSQESVTEQDSKDSTYSLSSTLTLSKADYE*<br>*KHKVYACEVTHQGLSSPVTKSFNRGECTS* (SEQ ID NO: 25) |

TABLE 4 scFv $V_H$ Sequence. The underlined, italicized, and bold sequences represent the mutations described in the "DESCRIPTION" column.

| DESCRIPTION | SEQUENCE (SEQ ID NO:) |
| --- | --- |
| huOKT3 $V_H$ | QVQLVQSGGGVVQPGRSLRLSCKASGYTFTRYTMHWVRQAPGK<br>GLEWIGYINPSRGYTNYNQKFKDRFTISRDNSKNTAFLQMDSLRP<br>EDTGVYFCARYYDDHYCLDYWGQGTPVTVSS (SEQ ID NO: 15) |
| huOKT3 $V_H$; C105S | QVQLVQSGGGVVQPGRSLRLSCKASGYTFTRYTMHWVRQAPGK<br>GLEWIGYINPSRGYTNYNQKFKDRFTISRDNSKNTAFLQMDSLRP<br>EDTGVYFCARYYDDHYSLDYWGQGTPVTVSS (SEQ ID NO: 17) |

TABLE 4-continued scFv V$_H$ Sequence. The underlined, italicized, and bold sequences represent the mutations described in the "DESCRIPTION" column.

| DESCRIPTION | SEQUENCE (SEQ ID NO:) |
|---|---|
| huOKT3 V$_H$; C105S + V$_H$-G44C | QVQLVQSGGGVVQPGRSLRLSCKASGYTFTRYTMHWVRQAPGK CLEWIGYINPSRGYTNYNQKFKDRFTISRDNSKNTAFLQMDSLRP EDTGVYFCARYYDDHY*S*LDYWGQGTPVTVSS (SEQ ID NO: 64) |

TABLE 5 scFv V$_L$ Sequence. The underlined, italicized, and bold sequence represent the mutations described in the "DESCRIPTION" column.

| DESCRIPTION | SEQUENCE (SEQ ID NO:) |
|---|---|
| huOKT3 V$_L$ | DIQMTQSPSSLSASVGDRVTITCSASSSVSYMNWYQQTPGKAPKR WIYDTSKLASGVPSRFSGSGSGTDYTFTISSLQPEDIATYYCQQWS SNPFTFGQGTKLQITR (SEQ ID NO: 16) |
| huOKT3 V$_L$; V$_L$-Q100C | DIQMTQSPSSLSASVGDRVTITCSASSSVSYMNWYQQTPGKAPKR WIYDTSKLASGVPSRFSGSGSGTDYTFTISSLQPEDIATYYCQQWS SNPFTFG*C*GTKLQITR (SEQ ID NO: 65) |

TABLE 6 scFv Sequence. The uppercase, non-italicized, non-bold, non-underlined sequence represents the V$_H$ domain. The uppercase, italicized sequence represents the V$_L$ domain. The uppercase, underlined, italicized, and bold sequences represent the mutations described in the "DESCRIPTION" column. The lowercase bold sequences represent the intra-scFv linker.

| DESCRIPTION | SEQUENCE (SEQ ID NO:) |
|---|---|
| huOKT3 scFv C105S; 15 amino acid intra-scFv linker | QVQLVQSGGGVVQPGRSLRLSCKASGYTFTRYTMHWVRQAPGK GLEWIGYINPSRGYTNYNQKFKDRFTISRDNSKNTAFLQMDSLRP EDTGVYFCARYYDDHY*S*LDYWGQGTPVTVSSggggsggggsggggs*DI QMTQSPSSLSASVGDRVTITCSASSSVSYMNWYQQTPGKAPKRWIYDT SKLASGVPSRFSGSGSGTDYTFTISSLQPEDIATYYCQQWSSNPFTFGQ GTKLQITR* (SEQ ID NO: 19) |
| huOKT3 scFv C105S; 5 amino acid intra-scFv linker | QVQLVQSGGGVVQPGRSLRLSCKASGYTFTRYTMHWVRQAPGK GLEWIGYINPSRGYTNYNQKFKDRFTISRDNSKNTAFLQMDSLRP EDTGVYFCARYYDDHY*S*LDYWGQGTPVTVSSggggs*DIQMTQSPSS LSASVGDRVTITCSASSSVSYMNWYQQTPGKAPKRWIYDTSKLASGVPS RFSGSGSGTDYTFTISSLQPEDIATYYCQQWSSNPFTFGQGTKLQITR* (SEQ ID NO: 48) |
| huOKT3 scFv C105S; 10 amino acid intra-scFv linker | QVQLVQ SGGGVVQPGRSLRLSCKASGYTFTRYTMHWVRQAPGK GLEWIGYINPSRGYTNYNQKFKDRFTISRDNSKNTAFLQMDSLRP EDTGVYFCARYYDDHY*S*LDYWGQGTPVTVSSggggsggggs*DIQMT QSPSSLSASVGDRVTITCSASSSVSYMNWYQQTPGKAPKRWIYDTSKLA SGVPSRFSGSGSGTDYTFTISSLQPEDIATYYCQQWSSNPFTFGQGTKL QITR* (SEQ ID NO: 49) |
| huOKT3 scFv C105S; 20 amino acid intra-scFv linker | QVQLVQSGGGVVQPGRSLRLSCKASGYTFTRYTIVIEIWVRQAPGK GLEWIGYINPSRGYTNYNQKFKDRFTISRDNSKNTAFLQMDSLRP EDTGVYFCARYYDDHY*S*LDYWGQGTPVTVSSggggsggggsggggsgg ggs*DIQMTQSPSSLSASVGDRVTITCSASSSVSYMNWYQQTPGKAPKRW IYDTSKLASGVPSRFSGSGSGTDYTFTISSLQPEDIATYYCQQWSSNPFT FGQGTKLQITR* (SEQ ID NO: 50) |
| huOKT3 scFv C105S; 25 amino acid intra-scFv linker | QVQLVQSGGGVVQPGRSLRLSCKASGYTFTRYTIVIEIWVRQAPGK GLEWIGYINPSRGYTNYNQKFKDRFTISRDNSKNTAFLQMDSLRP EDTGVYFCARYYDDHY*S*LDYWGQGTPVTVSSggggsggggsggggsgg ggsggggs*DIQMTQSPSSLSASVGDRVTITCSASSSVSYMNWYQQTPGKA PKRWIYDTSKLASGVPSRFSGSGSGTDYTFTISSLQPEDIATYYCQQWS SNPFTFGQGTKLQITR* (SEQ ID NO: 51) |

TABLE 6-continued scFv Sequence. The uppercase, non-italicized, non-bold, non-underlined sequence represents the $V_H$ domain. The uppercase, italicized sequence represents the $V_L$ domain. The uppercase, underlined, italicized, and bold sequences represent the mutations described in the "DESCRIPTION" column. The lowercase bold sequences represent the intra-scFv linker.

| DESCRIPTION | SEQUENCE (SEQ ID NO:) |
| --- | --- |
| huOKT3 scFv C105S; 30 amino acid intra-scFv linker | QVQLVQSGGGVVQPGRSLRLSCKASGYTFTRYTIVIEIWVRQAPGK GLEWIGYINPSRGYTNYNQKFKDRFTISRDNSKNTAFLQMDSLRP EDTGVYFCARYYDDHY_S_LDYWGQGTPVTVSSggggsggggsggggsgg ggsggggsggggs_DIQMTQSPSSLSASVGDRVTITCSASSSVSYMNWYQQTP GKAPKRWIYDTSKLASGVPSRFSGSGSGTDYTFTISSLQPEDIATYYCQ QWSSNPFTFGQGTKLQITR_ (SEQ ID NO: 52) |
| huOKT3 scFv C105S; $V_L$-Q100C; $V_H$-G44C; 5 amino acid intra-scFv linker | QVQLVQSGGGVVQPGRSLRLSCKASGYTFTRYTIVIEIWVRQAPGK _C__LEWIGYINPSRGYTNYNQKFKDRFTISRDNSKNTAFLQMDSLRP_ EDTGVYFCARYYDDHY_S_LDYWGQGTPVTVSSggggs_DIQMTQSPSS LSASVGDRVTITCSASSSVSYMNWYQQTPGKAPKRWIYDTSKLASGVPS RFSGSGSGTDYTFTISSLQPEDIATYYCQQWSSNPFTFGCGTKLQITR_ (SEQ ID NO: 53) |
| huOKT3 scFv C105S; $V_L$-Q100C; $V_H$-G44C; 10 amino acid intra-scFv linker | QVQLVQSGGGVVQPGRSLRLSCKASGYTFTRYTIVIEIWVRQAPGK _C__LEWIGYINPSRGYTNYNQKFKDRFTISRDNSKNTAFLQMDSLRP_ EDTGVYFCARYYDDHY_S_LDYWGQGTPVTVSSggggsggggs_DIQMT QSPSSLSASVGDRVTITCSASSSVSYMNWYQQTPGKAPKRWIYDTSKLA SGVPSRFSGSGSGTDYTFTISSLQPEDIATYYCQQWSSNPFTFGCGTKL QITR_ (SEQ ID NO: 54) |
| huOKT3 scFv C105S; $V_L$-Q100C; $V_H$-G44C; 15 amino acid intra-scFv linker | QVQLVQSGGGVVQPGRSLRLSCKASGYTFTRYTIVIEIWVRQAPGK _C__LEWIGYINPSRGYTNYNQKFKDRFTISRDNSKNTAFLQMDSLRP_ EDTGVYFCARYYDDHY_S_LDYWGQGTPVTVSSggggsggggsggggs_DI QMTQSPSSLSASVGDRVTITCSASSSVSYMNWYQQTPGKAPKRWIYDT SKLASGVPSRFSGSGSGTDYTFTISSLQPEDIATYYCQQWSSNPFTFGC GTKLQITR_ (SEQ ID NO: 55) |
| huOKT3 scFv C105S; $V_L$-Q100C; $V_H$-G44C; 20 amino acid intra-scFv linker | QVQLVQSGGGVVQPGRSLRLSCKASGYTFTRYTIVIEIWVRQAPGK _C__LEWIGYINPSRGYTNYNQKFKDRFTISRDNSKNTAFLQMDSLRP_ EDTGVYFCARYYDDHY_S_LDYWGQGTPVTVSSggggsggggsggggsgg ggs_DIQMTQSPSSLSASVGDRVTITCSASSSVSYMNWYQQTPGKAPKRW IYDTSKLASGVPSRFSGSGSGTDYTFTISSLQPEDIATYYCQQWSSNPFT FGCGTKLQITR_ (SEQ ID NO: 56) |
| huOKT3 scFv C105S; $V_L$-Q100C; $V_H$-G44C; 25 amino acid intra-scFv linker | QVQLVQSGGGVVQPGRSLRLSCKASGYTFTRYTIVIEIWVRQAPGK _C__LEWIGYINPSRGYTNYNQKFKDRFTISRDNSKNTAFLQMDSLRP_ EDTGVYFCARYYDDHY_S_LDYWGQGTPVTVSSggggsggggsggggsgg ggsggggs_DIQMTQSPSSLSASVGDRVTITCSASSSVSYMNWYQQTPGKA PKRWIYDTSKLASGVPSRFSGSGSGTDYTFTISSLQPEDIATYYCQQWS SNPFTFGCGTKLQITR_ (SEQ ID NO: 57) |
| huOKT3 scFv C105S; $V_L$-Q100C; $V_H$-G44C; 30 amino acid intra-scFv linker | QVQLVQSGGGVVQPGRSLRLSCKASGYTFTRYTMHWVRQAPGK _C__LEWIGYINPSRGYTNYNQKFKDRFTISRDNSKNTAFLQMDSLRP_ EDTGVYFCARYYDDHY_S_LDYWGQGTPVTVSSggggsggggsggggsgg ggsggggsggggs_DIQMTQSPSSLSASVGDRVTITCSASSSVSYMNWYQQTP GKAPKRWIYDTSKLASGVPSRFSGSGSGTDYTFTISSLQPEDIATYYCQ QWSSNPFTFGCGTKLQITR_ (SEQ ID NO: 58) |
| huOKT3; 15 amino acid intra-scFv linker | QVQLVQSGGGVVQPGRSLRLSCKASGYTFTRYTMHWVRQAPGK GLEWIGYINPSRGYTNYNQKFKDRFTISRDNSKNTAFLQMDSLRP EDTGVYFCARYYDDHYCLDYWGQGTPVTVSSggggsggggsggggs_DI QMTQSPSSLSASVGDRVTITCSASSSVSYMNWYQQTPGKAPKRWIYDT SKLASGVPSRFSGSGSGTDYTFTISSLQPEDIATYYCQQWSSNPFTFGQ GTKLQITR_ (SEQ ID NO: 59) |

TABLE 7

Light Chain Fusion Polypeptide Sequence. The uppercase, non-italicized, non-bold, non-underlined sequence represents the V_L domain of the trastuzumab light chain. The uppercase, italicized sequence represents the constant region of the trastuzumab light chain. The lowercase, non-italicized, non-bold, non-underlined sequence represents the linker conjugating the light chain to the scFv. The uppercase, underlined sequence represents the V_H domain of the scFv. The uppercase, bold sequence represents the V_L domain of the scFv. The uppercase, underlined, italicized, and bold sequences represent the mutations described in the "DESCRIPTION" column. The lowercase bold sequences represent the intra-scFv linker.

| DESCRIPTION | SEQUENCE (SEQ ID NO:) |
| --- | --- |
| Trastuzumab light chain; C105S; 17 amino acid linker conjugating the light chain to the scFv; 15 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMEIWVRQAPGKGLEWIGY INPSRGYTNYNQKFKDRFTISRDNSKNTAFLQMDSLRPEDTGVYF CARYYDDHY*S*LDYWGQGTPVTVSSggggsggggsggggsDIQMTQSP SSLSASVGDRVTITCSASSSVSYMNWYQQTPGKAPKRWIYDTS KLASGVPSRFSGSGSGTDYTFTISSLQPEDIATYYCQQWSSNPF TFGQGTKLQITR (SEQ ID NO: 29) |
| Trastuzumab light chain; C105S; 17 amino acid linker conjugating the light chain to the scFv; 5 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMHWVRQAPGKGLEWIGY INPSRGYTNYNQKFKDRFTISRDNSKNTAFLQMDSLRPEDTGVYF CARYYDDHY*S*LDYWGQGTPVTVSSggggsDIQMTQSPSSLSASVG DRVTITCSASSSVSYMNWYQQTPGKAPKRWIYDTSKLASGVP SRFSGSGSGTDYTFTISSLQPEDIATYYCQQWSSNPFTFGQGTK LQITR (SEQ ID NO: 30) |
| Trastuzumab light chain; C105S; 17 amino acid linker conjugating the light chain to the scFv; 10 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMHWVRQAPGKGLEWIGY INPSRGYTNYNQKFKDRFTISRDNSKNTAFLQMDSLRPEDTGVYF CARYYDDHY*S*LDYWGQGTPVTVSSggggsggggsDIQMTQSPSSLS ASVGDRVTITCSASSSVSYMNWYQQTPGKAPKRWIYDTSKLA SGVPSRFSGSGSGTDYTFTISSLQPEDIATYYCQQWSSNPFTFG QGTKLQITR (SEQ ID NO: 31) |
| Trastuzumab light chain; C105S; 17 amino acid linker conjugating the light chain to the scFv; 20 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMHWVRQAPGKGLEWIGY INPSRGYTNYNQKFKDRFTISRDNSKNTAFLQMDSLRPEDTGVYF CARYYDDHY*S*LDYWGQGTPVTVSSggggsggggsggggsggggsDIQMT QSPSSLSASVGDRVTITCSASSSVSYMNWYQQTPGKAPKRWIY DTSKLASGVPSRFSGSGSGTDYTFTISSLQPEDIATYYCQQWSS NPFTFGQGTKLQITR (SEQ ID NO: 32) |
| Trastuzumab light chain; C105S; 17 amino acid linker conjugating the light chain to the scFv; 25 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMHWVRQAPGKGLEWIGY INPSRGYTNYNQKFKDRFTISRDNSKNTAFLQMDSLRPEDTGVYF CARYYDDHY*S*LDYWGQGTPVTVSSggggsggggsggggsggggsggggsDI QMTQSPSSLSASVGDRVTITCSASSSVSYMNWYQQTPGKAPK RWIYDTSKLASGVPSRFSGSGSGTDYTFTISSLQPEDIATYYCQ QWSSNPFTFGQGTKLQITR (SEQ ID NO: 33) |
| Trastuzumab light chain; C105S; 17 amino acid linker conjugating the light chain to the scFv; 30 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMHWVRQAPGKGLEWIGY INPSRGYTNYNQKFKDRFTISRDNSKNTAFLQMDSLRPEDTGVYF CARYYDDHY*S*LDYWGQGTPVTVSSggggsggggsggggsggggsggggsgg |

TABLE 7-continued

Light Chain Fusion Polypeptide Sequence. The uppercase, non-italicized, non-bold, non-underlined sequence represents the V_L domain of the trastuzumab light chain. The uppercase, italicized sequence represents the constant region of the trastuzumab light chain. The lowercase, non-italicized, non-bold, non-underlined sequence represents the linker conjugating the light chain to the scFv. The uppercase, underlined sequence represents the V_H domain of the scFv. The uppercase, bold sequence represents the V_L domain of the scFv. The uppercase, underlined, italicized, and bold sequences represent the mutations described in the "DESCRIPTION" column. The lowercase bold sequences represent the intra-scFv linker.

| DESCRIPTION | SEQUENCE (SEQ ID NO:) |
|---|---|
| | ggsDIQMTQSPSSLSASVGDRVTITCSASSSVSYMNWYQQTPGK APKRWIYDTSKLASGVPSRFSGSGSGTDYTFTISSLQPEDIATY YCQQWSSNPFTFGQGTKLQITR (SEQ ID NO: 34) |
| Trastuzumab light chain; C105S; 17 amino acid linker conjugating the light chain to the huOKT3 scFv; 5 amino acid intra-scFv peptide linker; V_L-Q100C; V_H-G44C | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSLSSTLTLSKADYE KHKVYACEVTHQGLSSPVTKSFNRGE*Ct sggggsggggsggggsQVQLVQS GGGVVQPGRSLRLSCKASGYTFTRYTMHWVRQAPGK*C*LEWIGYI NPSRGYTNYNQKFKDRFTISRDNSKNTAFLQMDSLRPEDTGVYF CARYYDDHY*S*LDYWGQGTPVTVSSggggsDIQMTQSPSSLSASVG DRVTITCSASSSVSYMNWYQQTPGKAPKRWIYDTSKLASGVP SRFSGSGSGTDYTFTISSLQPEDIATYYCQQWSSNPFTFGCGTK LQITR (SEQ ID NO: 42) |
| Trastuzumab light chain; C105S; 17 amino acid linker conjugating the light chain to the huOKT3 scFv; 10 amino acid intra-scFv peptide linker; V_L-Q100C; V_H-G44C | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGE*Ct sggggsggggsggggsQVQLVQS GGGVVQPGRSLRLSCKASGYTFTRYTMHWVRQAPGK*C*LEWIGYI NPSRGYTNYNQKFKDRFTISRDNSKNTAFLQMDSLRPEDTGVYF CARYYDDHY*S*LDYWGQGTPVTVSSggggsggggsDIQMTQSPSSLS ASVGDRVTITCSASSSVSYMNWYQQTPGKAPKRWIYDTSKLA SGVPSRFSGSGSGTDYTFTISSLQPEDIATYYCQQWSSNPFTFG CGTKLQITR (SEQ ID NO: 43) |
| Trastuzumab light chain; C105S; 17 amino acid linker conjugating the light chain to the huOKT3 scFv; 15 amino acid intra-scFv peptide linker; V_L-Q100C; V_H-G44C | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGE*Ct sggggsggggsggggsQVQLVQS GGGVVQPGRSLRLSCKASGYTFTRYTMHWVRQAPGK*C*LEWIGYI NPSRGYTNYNQKFKDRFTISRDNSKNTAFLQMDSLRPEDTGVYF CARYYDDHY*S*LDYWGQGTPVTVSSggggsggggsggggsDIQMTQSP SSLSASVGDRVTITCSASSSVSYMNWYQQTPGKAPKRWIYDTS KLASGVPSRFSGSGSGTDYTFTISSLQPEDIATYYCQQWSSNPF TFGCGTKLQITR (SEQ ID NO: 44) |
| Trastuzumab light chain; C105S; 17 amino acid linker conjugating the light chain to the huOKT3 scFv; 20 amino acid intra-scFv peptide linker; V_L-Q100C; V_H-G44C | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGE*Ct sggggsggggsggggsQVQLVQS GGGVVQPGRSLRLSCKASGYTFTRYTMHWVRQAPGK*C*LEWIGYI NPSRGYTNYNQKFKDRFTISRDNSKNTAFLQMDSLRPEDTGVYF CARYYDDHY*S*LDYWGQGTPVTVSSggggsggggsggggsggggsDIQMT QSPSSLSASVGDRVTITCSASSSVSYMNWYQQTPGKAPKRWIY DTSKLASGVPSRFSGSGSGTDYTFTISSLQPEDIATYYCQQWSS NPFTFGCGTKLQITR (SEQ ID NO: 45) |
| Trastuzumab light chain; C105S; 17 amino acid linker conjugating the light chain to the huOKT3 scFv; 25 amino acid intra-scFv peptide linker; V_L-Q100C; V_H-G44C | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGE*Ct sggggsggggsggggsQVQLVQS GGGVVQPGRSLRLSCKASGYTFTRYTMEIWRQAPGK*C*LEWIGYI NPSRGYTNYNQKFKDRFTISRDNSKNTAFLQMDSLRPEDTGVYF CARYYDDHY*S*LDYWGQGTPVTVSSggggsggggsggggsggggsggggsDI QMTQSPSSLSASVGDRVTITCSASSSVSYMNWYQQTPGKAPK RWIYDTSKLASGVPSRFSGSGSGTDYTFTISSLQPEDIATYYCQ QWSSNPFTFGQCGTKLQITR (SEQ ID NO: 46) |

TABLE 7-continued

Light Chain Fusion Polypeptide Sequence. The uppercase, non-italicized, non-bold, non-underlined sequence represents the $V_L$ domain of the trastuzumab light chain. The uppercase, italicized sequence represents the constant region of the trastuzumab light chain. The lowercase, non-italicized, non-bold, non-underlined sequence represents the linker conjugating the light chain to the scFv. The uppercase, underlined sequence represents the $V_H$ domain of the scFv. The uppercase, bold sequence represents the $V_L$ domain of the scFv. The uppercase, underlined, italicized, and bold sequences represent the mutations described in the "DESCRIPTION" column. The lowercase bold sequences represent the intra-scFv linker.

| DESCRIPTION | SEQUENCE (SEQ ID NO:) |
|---|---|
| Trastuzumab light chain; C105S; 17 amino acid linker conjugating the light chain to the huOKT3 scFv; 30 amino acid intra-scFv peptide linker; $V_L$-Q100C; $V_H$-G44C | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMEIWVRQAPGKCLEWIGYI NPSRGYTNYNQKFKDRFTISRDNSKNTAFLQMDSLRPEDTGVYF CARYYDDHYSLDYWGQGTPVTVSSggggsggggsggggsggggsggggsgg ggsDIQMTQSPSSLSASVGDRVTITCSASSSVSYMNWYQQTPGK APKRWIYDTSKLASGVPSRFSGSGSGTDYTFTISSLQPEDIATY YCQQWSSNPFTFGCGTKLQITR (SEQ ID NO: 47) |
| Trastuzumab light chain; 17 amino acid linker conjugating the light chain to the scFv; 15 amino acid intra-scFv peptide linker | DIQMTQSPSSLSASVGDRVTITCRASQDVNTAVAWYQQKPGKAP KLLIYSASFLYSGVPSRFSGSRSGTDFTLTISSLQPEDFATYYCQQH YTTPPTFGQGTKVEIKR*TVAAPSVFIFPPSDEQLKSGTASVVCLLNNF YPREAKVQWKVDNALQSGNSQESVTEQDSKDSTYSTSSTLTLSKADYE KHKVYACEVTHQGLSSPVTKSFNRGEC*tsggggsggggsggggsQVQLVQS GGGVVQPGRSLRLSCKASGYTFTRYTMEIWVRQAPGKGLEWIGY INPSRGYTNYNQKFKDRFTISRDNSKNTAFLQMDSLRPEDTGVYF CARYYDDHYSLDYWGQGTPVTVSSggggsggggsggggsDIQMTQSP SSLSASVGDRVTITCSASSSVSYMNWYQQTPGKAPKRWIYDTS KLASGVPSRFSGSGSGTDYTFTISSLQPEDIATYYCQQWSSNPF TFGQGTKLQITR (SEQ ID NO: 60) |

TABLE 8

Modifications to bispecific binding molecules

| LOCATION OF MODIFICATION | DESCRIPTION |
|---|---|
| Heavy chain | Mutation to reduce binding to the Fc receptor (as an example, N297A mutation) Mutation to destroy a glycosylation site (as an example, N297A mutation) Mutation to reduce C1q binding (as an example, K322A mutation) |
| Linker conjugating the light chain to the huOKT3 scFv | Increase or decrease the length of the linker |
| huOKT3 scFv $V_H$ | Mutation to increase stabilization and/or reduce aggregation (as an example, introduce disulfide binding between $V_H$40 and $V_L$100 (according to Kabat numbering), as an example, $V_H$ G44C and $V_L$ Q100C) Reduce aggregation (as an example, C105S mutation) |
| huOKT3 scFv $V_L$ | Mutation to increase stabilization and/or reduce aggregation (as an example,, introduce disulfide binding between $V_H$40 and $V_L$100 (according to Kabat numbering), as an example, $V_H$ G44C and $V_L$ Q100C) |
| huOKT3 intra-scFv linker | Increase or decrease the length of the linker |

5.2 Bispecific Binding Molecule Conjugates

In preferred embodiments, a bispecific binding molecule provided herein is not conjugated to any other molecule, such as an organic moiety, a detectable label, or an isotope. In alternative embodiments, a bispecific binding molecule provided herein is conjugated to one or more organic moieties. In alternative embodiments, a bispecific binding molecule provided herein is conjugated to one or more detectable labels. In alternative embodiments, a bispecific binding molecule provided herein is conjugated to one or more isotopes.

5.2.1 Detectable Labels and Isotopes

In certain embodiments, a bispecific binding molecule provided herein is conjugated to one or more detectable labels or isotopes, e.g., for imaging purposes. In certain embodiments, a bispecific binding molecule is detectably labeled by covalent or non-covalent attachment of a chromogenic, enzymatic, radioisotopic, isotopic, fluorescent, toxic, chemiluminescent, nuclear magnetic resonance contrast agent or other label.

Non-limiting examples of suitable chromogenic labels include diaminobenzidine and 4-hydroxyazo-benzene-2-carboxylic acid.

Non-limiting examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Non-limiting examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{223}$Ra, $^{223}$Ra, $^{89}$Zr, $^{177}$Lu, and $^{109}$Pd. In certain embodiments, $^{111}$In is a preferred isotope for in vivo imaging as it avoids the problem of dehalogenation of $^{125}$I or $^{131}$I-labeled bispecific binding molecules in the liver. In addition, $^{111}$In has a more favorable gamma emission energy for imaging (Perkins et al., Eur. J. Nucl. Med. 70:296-301 (1985); Carasquillo et ah, J. Nucl. Med. 25:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Non-limiting examples of suitable non-radioactive isotopic labels include $^{157}$Gd, $^{55}$Mn, $^{162}$Dy, $^{52}$Tr, and $^{56}$Fe.

Non-limiting examples of suitable fluorescent labels include a $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Non-limiting examples of chemiluminescent labels include a luminol label, an isoluminol label, an aromatic acridinium ester label, an imidazole label, an acridinium salt label, an oxalate ester label, a luciferin label, a luciferase label, and an aequorin label.

Non-limiting examples of nuclear magnetic resonance contrasting agents include heavy metal nuclei such as Gd, Mn, and iron.

Techniques known to one of ordinary skill in the art for binding the above-described labels to a bispecific binding molecule provided herein are described in, for example, Kennedy et at., Clin. CMm. Acta 70:1-31 (1976), and Schurs et al., Clin. CMm. Acta 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

In certain embodiments, the bispecific binding molecule is conjugated to a diagnostic agent. A diagnostic agent is an agent useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MM technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, for example, ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MM, when used along bispecific binding molecules provided herein. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed herein.

5.2.2 Organic Conjugates

In certain embodiments, the bispecific binding molecules provided herein comprise one or more organic moieties that are covalently bonded, directly or indirectly, to the bispecific binding molecule. Such modification can produce an antibody or antigen-binding fragment with improved pharmacokinetic properties (e.g., increased in vivo serum half-life). The organic moiety can be a hydrophilic polymeric group, fatty acid group, or fatty acid ester group. As used herein, the term "fatty acid" encompasses mono-carboxylic acids and di-carboxylic acids. As used herein, a "hydrophilic polymeric group" refers to an organic polymer that is more soluble in water than in octane, e.g., polylysine. Hydrophilic polymers suitable for modifying a bispecific binding molecule provided herein can be linear or branched and include, for example, polyalkane glycols (e.g., polyethylene glycol, (PEG), monomethoxy-polyethylene glycol, and polypropylene glycol), carbohydrates (e.g., dextran, cellulose, oligosaccharides, and polysaccharides), polymers of hydrophilic amino acids (e.g., polylysine, polyarginine, and polyaspartate), polyalkane oxides (e.g., polyethylene oxide and polypropylene oxide) and polyvinyl pyrolidone. In certain embodiments, the hydrophilic polymer that modifies a bispecific binding molecule provided herein has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying bispecific binding molecules provided herein can be saturated or can contain one or more units of unsaturation. Fatty acids that are suitable for modifying bispecific binding molecules provided herein include, for example, n-dodecanoate, n-tetradecanoate, n-octadecanoate, n-eicosanoate, n-docosanoate, n-triacontanoate, n-tetracontanoate, cis-delta-9-octadecanoate, all cis-delta-5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The bispecific binding molecule conjugates provided herein can be prepared using suitable methods, such as by reaction with one or more modifying agents. As used herein, an "activating group" is a chemical moiety or functional group that can, under appropriate conditions, react with a second chemical group thereby forming a covalent bond between the modifying agent and the second chemical group. For example, amine-reactive activating groups include electrophilic groups such as, for example, tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see, for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group, wherein one or more carbon atoms can be replaced by a heteroatom such as oxygen, nitrogen or sulfur. Suitable linker moieties include, for example, tetraethylene glycol, $(CH_2)_3$, and NH. Modifying agents that comprise a linker moiety can be produced, for example, by reacting a mono-Boc-alkyldiamine (e.g., mono-Boc-ethylenediamine or mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

As used herein, a "modifying agent" refers to a suitable organic group (e.g., hydrophilic polymer, a fatty acid, and a fatty acid ester) that comprises an activating group. For example, the organic moieties can be bonded to the bispecific binding molecule in a non-site specific manner by employing an amine-reactive modifying agent, for example, an N-hydroxysuccinimide ester of PEG. Modified bispecific binding molecules can also be prepared by reducing disulfide bonds (e.g., intra-chain disulfide bonds) of bispecific binding molecule. The reduced bispecific binding molecule can then be reacted with a thiol-reactive modifying agent to produce the modified bispecific binding molecule provided herein. Modified bispecific binding molecules comprising an organic moiety that is bonded to specific sites of a bispecific binding molecule provided herein can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

5.3 Bispecific Binding Molecule Production

Provided herein are methods for producing bispecific binding molecules as described in Section 5.1 and Section 5.2. In certain embodiments, provided herein are methods for producing a bispecific binding molecule comprising an aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFV), via a peptide linker, to create a first fusion polypeptide, and wherein the second light chain is fused to a second scFv, via a peptide linker, to create a second fusion polypeptide, wherein the first and second scFv (i) are identical, and (ii) bind to CD3, and wherein the first and second fusion polypeptides are identical.

Methods to produce bispecific binding molecules described herein are known to one of ordinary skill in the art, for example, by chemical synthesis, by purification from biological sources, or by recombinant expression techniques, including, for example, from mammalian cell or transgenic preparations. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, for example, Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

A variety of methods exist in the art for the production of bispecific binding molecules. For example, the bispecific binding molecule may be made by recombinant DNA methods, such as those described in U.S. Pat. No. 4,816,567. The one or more DNAs encoding a bispecific binding molecule provided herein can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NSO cells, Simian COS cells, Chinese hamster ovary (CHO) cells, yeast cells, algae cells, eggs, or myeloma cells that do not otherwise produce immunoglobulin protein, to obtain the synthesis of the bispecific binding molecules in the recombinant host cells. The DNA also may be modified, for example, by substituting the coding sequence for human heavy and light chain constant domains of a desired species in place of the homologous human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of a bispecific binding molecule provided herein. In certain embodiments, the DNA is as described in Section 5.3.1.

Bispecific binding molecules provided herein can also be prepared using at least one bispecific binding molecule-encoding polynucleotide to provide transgenic animals or mammals, such as goats, cows, horses, sheep, and the like, that produce such antibodies in their milk. Such animals can be provided using known methods. See, for example, but not limited to, U.S. Pat. Nos. 5,827,690; 5,849,992; 4,873,316; 5,849,992; 5,994,616, 5,565,362; 5,304,489, and the like, each of which is entirely incorporated herein by reference.

In certain embodiments, bispecific binding molecules provided herein can additionally be prepared using at least one bispecific binding molecule-encoding polynucleotide provided herein to provide transgenic plants and cultured plant cells (for example, but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, for example, using an inducible promoter. See, for example, Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, for example, Hood et al., Adv. Exp. Med. Biol. 464:127-147 (1999) and references cited therein. Antibodies have also been produced in large amounts from transgenic plant seeds including antibody fragments, such as scFvs, including tobacco seeds and potato tubers. See, for example, Conrad et al., Plant Mol. Biol. 38:101-109 (1998) and references cited therein. Thus, bispecific binding molecules can also be produced using transgenic plants, according to known methods. See also, for example, Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

In certain embodiments, bispecific binding molecules provided herein can be prepared using at least one bispecific binding molecule-encoding polynucleotide provided herein to provide bacteria that produce such bispecific binding molecules. As a non-limiting example, E. coli expressing recombinant proteins has been successfully used to provide large amounts of recombinant proteins. See, for example, Verma et al., 1998, 216(1-2): 165-181 and references cited therein.

See, also, Section 6.1.2.1 for a detailed example for the design and production of a bispecific binding molecule described herein.

In certain embodiments, the bispecific binding molecules can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, for example, Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

In certain embodiments, the bispecific binding molecules provided herein include naturally purified products, products of chemical synthetic procedures, and products produced by recombinant techniques from a eukaryotic host, including, for example, yeast, higher plant, insect and mammalian cells. In preferred embodiments, the bispecific binding molecule is generated in a host such that the bispecific binding molecule is aglycosylated. In another preferred embodiment, the bispecific binding molecule is generated in a bacterial cell such that the bispecific binding molecule is aglycosylated. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified antibodies can be characterized by, for example, ELISA, ELISPOT, flow cytometry, immunocytology, Biacore™ analysis, Sapidyne KinExA™ kinetic exclusion assay, SDS-PAGE and Western blot, or by HPLC analysis as well as by a number of other functional assays disclosed herein.

5.3.1 Polynucleotides

In certain embodiments, provided herein are polynucleotides comprising a nucleotide sequence encoding a bispecific binding molecule described herein or a fragment thereof (e.g., a heavy chain and/or a light chain fusion polypeptide) that immunospecifically binds to HER2 and CD3, as described in Section 5.1 and Section 5.2. Also provided herein are vectors comprising such polynucleotides. See, Section 5.3.2. Also provided herein are polynucleotides encoding antigens of the bispecific binding molecules provided herein. Also provided herein are polynucleotides that hybridize under stringent or lower stringency hybridization conditions to polynucleotides that encode a bispecific binding molecule or fragment thereof provided herein.

The language "purified" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding a bispecific binding molecule described herein is isolated or purified.

Nucleic acid molecules provided herein can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

In certain embodiments, provided herein is a polynucleotide comprising nucleotide sequences encoding a bispecific binding molecule or fragment thereof as described in Section 5.1 and Section 5.2, wherein the bispecific binding molecule comprises an aglycosylated monoclonal antibody that is an immunoglobulin that binds to HER2, comprising two identical heavy chains and two identical light chains, said light chains being a first light chain and a second light chain, wherein the first light chain is fused to a first scFv, via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical.

For a detailed example for the generation of a bispecific binding molecule as described herein, see, Section 6.1.2.1 for a detailed example for the design and production of a bispecific binding molecule described herein.

In certain embodiments, provided herein is a polynucleotide comprising nucleotide sequences encoding a light chain fusion polypeptide comprising a light chain fused to a scFv, via a peptide linker, wherein the light chain binds to HER2 and wherein the scFv binds to CD3. In certain embodiments, the light chain is the light chain of a HER2-specific antibody known in the art, such as, for example, trastuzumab, M-111, pertuzumab, ertumaxomab, MDXH210, 2B1, and MM-302. In certain embodiments, the scFv comprises the $V_H$ and $V_L$ of an anti-CD3 antibody known in the art, such as, for example, huOKT3, YTH12.5, HUM291, teplizumab, huCLB-T3/4, otelixizumab, blinatumomab, MT110, catumaxomab, 28F11, 27H5, 23F10, 15C3, visilizumab, and Hum291. In a preferred embodiment, the anti-CD3 antibody is huOKT3. In an especially preferred embodiment, the scFv comprises the VH of huOKT3, further comprising the amino acid substitution at numbered position 105, wherein the cysteine is substituted with a serine. See, for example, Kipriyanov et al. 1997, Protein Eng. 445-453. In certain embodiments, the scFv is derived from the huOKT3 monoclonal antibody and comprises one or more mutations, relative to the native huOKT3 $V_H$ and $V_L$, to stabilize disulfide binding. In certain embodiments, the stabilization of disulfide binding prevents aggregation of the bispecific binding molecule. In certain embodiments, the stabilization of disulfide binding reduces aggregation of the bispecific binding molecule as compared to aggregation of the bispecific binding molecule without the stabilization of disulfide binding. In certain embodiments of the bispecific binding molecule, the one or more mutations to stabilize disulfide binding comprise a $V_H$ G44C mutation and a $V_L$ Q100C mutation (e.g., as present in SEQ ID NOS: 54-59). In certain embodiments of the bispecific binding molecule, the one or more mutations to stabilize disulfide binding are the replacement of the amino acid residue at $V_H44$ (according to the Kabat numbering system) with a cysteine and the replacement of the amino acid residue at $V_L100$ (according to the Kabat numbering system) with a cysteine so as to introduce a disulfide bond between $V_H44$ and $V_L100$ (e.g., as present in SEQ ID NOS: 54-59). In certain embodiments, the peptide linker is between 5-30, 5-25, 5-15, 10-30, 10-20, 10-15, 15-30, or 15-25 amino acid residues in length. In certain embodiments, the sequence of the peptide linker is as described in Table 1, above (e.g., any one of SEQ ID NOs: 14 or 35-41). In a particularly preferred embodiment, the sequence of the peptide linker is SEQ ID NO: 14. In certain embodiments, the sequence to the scFv comprises one or more modifications as described in Table 8, above.

In particular aspects, provided herein are polynucleotides comprising nucleotide sequences encoding bispecific binding molecules or fragments thereof, which specifically bind to HER2 and CD3, and comprise an amino acid sequence as described herein, as well as antibodies which compete with such bispecific binding molecules for binding to HER2 and/or CD3, or which binds to the same epitope as that of such antibodies.

In a preferred embodiment, the sequence of the light chain is SEQ ID NO: 25. In a preferred embodiment, the nucleotide sequence encoding the light chain is SEQ ID NO: 24. In a preferred embodiment, the sequence of the scFv SEQ ID NO: 19. In a preferred embodiment, the nucleotide sequence encoding the scFv SEQ ID NO: 18. In a preferred embodiment, the sequence of the light chain is SEQ ID NO: 25 and the sequence of the scFv is SEQ ID NO: 19. In a preferred embodiment, the nucleotide sequence encoding the light chain is SEQ ID NO: 24 and the nucleotide sequence encoding the scFv is SEQ ID NO: 18. In a preferred embodiment, the sequence of the light chain fusion polypeptide is SEQ ID NO: 29. In a preferred embodiment, the nucleotide sequence encoding the light chain fusion polypeptide is SEQ ID NO: 28.

In certain embodiments, the bispecific binding molecule has a trastuzumab-derived sequence that contains one or more of the modifications in the trastuzumab immunoglobulin, and has a huOKT3-derived sequence that contains one or more of the modifications in the huOKT3 $V_H$ and $V_L$ sequences, as described in Table 8, below. Bispecific binding molecules having other immunoglobulin or scFv sequences can contain analogous mutations at corresponding positions in these other immunoglobulin or scFv sequences. In certain embodiments, the bispecific binding molecule is (a) derived from trastuzumab and huOKT3; and (b) contains one or more of the modifications as described in Table 8, above. In certain embodiments, the sequence of the peptide linker conjugating the immunoglobulin light chain and the scFv is as described in Table 1, above (e.g., any one of SEQ ID NOs: 14 or 35-41). In certain embodiments, the sequence of the heavy chain is as described in Table 2, above (e.g., any one of SEQ ID NOs: 23, 27, 62, or 63). In certain embodiments, the sequence of the light chain is as described in Table 3, above (e.g., SEQ ID NO: 25). In certain embodiments, the sequence of the $V_H$ of the scFv is as described in Table 4, above (e.g., any one of SEQ ID NOs: 15, 17, or 64). In certain embodiments, the sequence of the $V_L$ of the scFv is as described in Table 5, above (e.g., any one of SEQ ID NOs: 16 or 65). In certain embodiments, the sequence of the scFv peptide linker is as described in Table 1, above (e.g., any one of SEQ ID NOs: 14 or 35-41). In certain embodiments, the sequence of the scFv is as described in Table 6, above (e.g., any one of SEQ ID NOs: 19 or 48-59). In certain embodiments, the sequence of the light chain fusion polypeptide is as described in Table 7, above (e.g., any one of SEQ ID NOs: 29, 34, 42-47, or 60).

In certain embodiments, provided herein is a polynucleotide comprising nucleotide sequences encoding the heavy chain of a HER2-specific antibody described in Section 5.2. In certain embodiments, the heavy chain is the heavy chain a HER2-specific antibody known in the art, such as, for example, trastuzumab, M-111, pertuzumab, ertumaxomab, MDXH210, 2B1, and MM-302. In a preferred embodiment, the antibody comprises the $V_H$ of trastuzumab, wherein the sequence of the heavy chain is SEQ ID NO: 27. In a preferred embodiment, the antibody comprises the $V_H$ of trastuzumab, wherein the nucleotide sequence encoding the heavy chain is SEQ ID NO: 26. In a preferred embodiment, the sequence of the heavy chain is comprises the $V_H$ of trastuzumab and comprises the amino acid substitution N297A in the Fc region (SEQ ID NO: 26). In a preferred embodiment, the nucleotide sequence encoding the heavy chain comprises the nucleotide sequence encoding the trastuzumab $V_H$ and comprises the amino acid substitution N297A in the Fc region (SEQ ID NO: 26). In preferred embodiment, the sequence of the heavy chain comprises the sequence of the trastuzumab $V_H$ and comprises the amino acid substitution K322A in the Fc region (SEQ ID NO: 27). In a preferred embodiment, the nucleotide sequence encoding the heavy chain comprises the nucleotide sequence encoding the trastuzumab $V_H$ and comprises the amino acid substitution K322A in the Fc region (SEQ ID NO: 26). In an especially preferred embodiment, the sequence of the heavy chain comprises the sequence of the trastuzumab $V_H$ and comprises the amino acid substitutions N297A and K322A in the Fc region (SEQ ID NO: 27). In an especially preferred embodiment, the nucleotide sequence encoding the heavy chain comprises the nucleotide sequence encoding the trastuzumab $V_H$ and comprises the amino acid substitutions N297A and K322A in the Fc region (SEQ ID NO: 26).

The polynucleotides provided herein can be obtained by any method known in the art. For example, if the nucleotide sequence encoding a bispecific binding molecule or fragment thereof described herein is known, a polynucleotide encoding the bispecific binding molecule or fragment thereof can be may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding a bispecific binding molecule or fragment thereof may be generated from nucleic acid from a suitable source. If a clone containing a nucleic acid encoding a particular bispecific binding molecule or fragment thereof is not available, but the sequence of the bispecific binding molecule or fragment thereof is known, a nucleic acid encoding the bispecific binding molecule or fragment thereof may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody provided herein) by PCR amplification using synthetic primers that hybridize to the 3' and 5' ends of the sequence or by cloning using an oligonucleotide probe specific for the particular gene sequence to identify, for example, a cDNA clone from a cDNA library that encodes the antibody. Amplified nucleic acids generated by PCR may then be cloned into replicable cloning vectors using any method well known in the art. See, for example, Section 5.3.2.

In certain embodiments, the amino acid sequence of the antibody of the bispecific binding molecule is known in the art. In such embodiments, a polypeptide encoding such an antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate bispecific binding molecules having a different amino acid sequence, for example, to create amino acid substitutions, deletions, and/or insertions. For example, such manipulations can be performed to render the encoded amino acid aglycosylated, or to destroy the antibody's ability to bind to C1q, Fc receptor, or to activate the complement system.

Isolated nucleic acid molecules provided herein can include nucleic acid molecules comprising an open reading frame (ORF), optionally with one or more introns, for example, but not limited to, at least one specified portion of at least one complementarity determining region (CDR), as CDR1, CDR2 and/or CDR3 of at least one heavy chain or light chain; nucleic acid molecules comprising the coding sequence for an anti-HER2 antibody or variable region, an anti-CD3 scFv, or a single chain fusion polypeptide; and nucleic acid molecules which comprise a nucleotide sequence substantially different from those described above but which, due to the degeneracy of the genetic code, still encode at least one bispecific binding molecule as described herein and/or as known in the art.

Also provided herein are isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides provided herein can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

The nucleic acids can conveniently comprise sequences in addition to a polynucleotide provided herein. For example, a multi-cloning site comprising one or more endonuclease restriction sites can be inserted into the nucleic acid to aid in isolation of the polynucleotide. In addition, translatable sequences can be inserted to aid in the isolation of the translated polynucleotide provided herein. For example, a hexa-histidine marker sequence provides a convenient means to purify the polypeptides provided herein. The nucleic acid provided herein—excluding the coding sequence—is optionally a vector, adapter, or linker for cloning and/or expression of a polynucleotide provided herein.

Additional sequences can also be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

In a specific embodiment, using routine recombinant DNA techniques, one or more of the CDRs of an antibody described herein may be inserted within framework regions. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds HER2. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are provided herein and within the skill of the art.

In certain embodiments, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, for example, Gateway™ (Invitrogen)). See, also, U.S. Pat. No. 5,314,995.

In certain embodiments, a polynucleotide provided herein is in the form of a vector (e.g., expression vector) as described in Section 5.3.2.

5.3.2 Cells and Vectors

In certain embodiments, provided herein are cells (e.g., ex vivo cells) expressing (e.g., recombinantly) bispecific binding molecules as described herein. Also provided herein are vectors (e.g., expression vectors) comprising nucleotide sequences (see, for example, Section 5.3.1) encoding a bispecific binding molecule or fragment thereof described herein for recombinant expression in host cells, preferably in mammalian cells. Also provided herein are cells (e.g., ex vivo cells) comprising such vectors or nucleotide sequences for recombinantly expressing a bispecific binding molecule described here. Also provided herein are methods for producing a bispecific binding molecule described herein, comprising expressing such bispecific binding molecule from a cell (e.g., ex vivo cell). In a preferred embodiment, the cell is an ex vivo cell.

A vector (e.g., expression vector) is a DNA molecule comprising a gene that is expressed in a cell (e.g., ex vivo cell). Typically, gene expression is placed under the control of certain regulatory elements, including constitutive or inducible promoters, tissue-specific regulatory elements and enhancers. Such a gene is said to be "operably linked to" the regulatory elements, e.g., a promoter. A recombinant host may be any prokaryotic or eukaryotic cell that contains either a cloning vector or expression vector. This term also includes those prokaryotic or eukaryotic cells, as well as a transgenic animal, that have been genetically engineered to contain the cloned gene(s) in the chromosome or genome of the host cell or cells of the host cells (e.g., ex vivo cells).

In a preferred embodiment, the promoter is the CMV promoter.

In certain embodiments, provided herein is a vector comprising one or more polynucleotide as described in Section 5.3.1.

In certain embodiments, a polynucleotide as described in Section 5.3.1 can be cloned into a suitable vector and can be used to transform or transfect any suitable host. Vectors and methods to construct such vectors are known to one of ordinary skill in the art and are described in general technical references (see, in general, "Recombinant DNA Part D," Methods in Enzymology, Vol. 153, Wu and Grossman, eds., Academic Press (1987)). In certain embodiments, the vector comprises regulatory sequences, such as transcription and translation initiation and termination codons, which are specific to the type of host (e.g., bacterium, fungus, plant, insect, or mammal) into which the vector is to be introduced, as appropriate and taking into consideration whether the vector is DNA or RNA. In certain embodiments, the vector comprises regulatory sequences that are specific to the genus of the host. In certain embodiments, the vector comprises regulatory sequences that are specific to the species of the host.

In certain embodiments, the vector comprises one or more marker genes, which allow for selection of transformed or transfected hosts. Non-limiting examples of marker genes include biocide resistance, e.g., resistance to antibiotics, heavy metals, etc., complementation in an auxotrophic host to provide prototrophy, and the like. In a preferred embodiment, the vector comprises ampicillin and hygromycin selectable markers.

In certain embodiments, an expression vector can comprise a native or normative promoter operably linked to a polynucleotide as described in Section 5.3.1. The selection of promoters, for example, strong, weak, inducible, tissue-specific and developmental-specific, is within the skill in the art. Similarly, the combining of a nucleic acid molecule, or fragment thereof, as described above with a promoter is also within the skill in the art.

Non-limiting examples of suitable vectors include those designed for propagation and expansion or for expression or both. For example, a cloning vector can be selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as lamda-GT10, lamda-GT11, lamda-ZapII (Stratagene), lamda-EMBL4, and lamda-NM1149, can also be used. Non-limiting examples of plant expression vectors include pBI110, pBI101.2, pBI101.3, pBI121 and pBIN19 (Clontech). Non-limiting examples of animal expression vectors include pEUK-C1, pMAM and pMAMneo (Clontech). The TOPO cloning system (Invitrogen, Carlsbad, Calif.) can also be used in accordance with the manufacturer's recommendations.

In certain embodiments, the vector is a mammalian vector. In certain embodiments, the mammalian vector contains at least one promoter element, which mediates the initiation of transcription of mRNA, the bispecific binding molecule coding sequence, and signals required for the termination of transcription and polyadenylation of the transcript. In certain embodiments, the mammalian vector contains additional elements, such as, for example, enhancers, Kozak sequences and intervening sequences flanked by donor and acceptor sites for RNA splicing. In certain embodiments, highly efficient transcription can be achieved with, for example, the early and late promoters from SV40, the long terminal repeats (LTRS) from retroviruses, for example, RSV, HTLVI, HIVI and the early promoter of the cytomegalovirus (CMV). However, cellular elements can also be used (e.g., the human actin promoter). Non-limiting examples of mammalian expression vectors include, vectors such as pIRESIneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Non-limiting example of mammalian host cells that can be used in combination with such mammalian vectors include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

In certain embodiments, the vector is a viral vector, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. In certain embodiments, the viral vector is manipulated to render the virus replication deficient. In certain embodiments, the viral vector is manipulated to eliminate toxicity to the host. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

In certain embodiments, a vector or polynucleotide described herein can be transferred to a cell (e.g., an ex vivo cell) by conventional techniques and the resulting cell can be cultured by conventional techniques to produce a bispecific binding molecule described herein. Accordingly, provided herein are cells comprising a polynucleotide encoding a bispecific binding molecule or fragment thereof, a heavy or light chain thereof, or a light chain fusion polypeptide thereof, operably linked to a promoter for expression of such sequences in the host cell. In certain embodiments, a vector encoding the heavy chain operably linked to a promoter and a vector encoding the light chain fusion polypeptide operably linked to a promoter can be co-expressed in the cell for expression of the entire bispecific binding molecule, as described below. In certain embodiments, a cell comprises a vector comprising a polynucleotide encoding both the heavy chain and the light chain fusion polypeptide of a bispecific binding molecule described herein operably linked to a promoter. In certain embodiments, a cell comprises two different vectors, a first vector comprising a polynucleotide encoding a heavy chain operably linked to a promoter, and a second vector comprising a polynucleotide encoding a light chain fusion polypeptide operably linked to a promoter. In certain embodiments, a first cell comprises a first vector comprising a polynucleotide encoding a heavy chain of a bispecific binding molecule described herein, and a second cell comprises a second vector comprising a polynucleotide encoding a light chain fusion polypeptide of a bispecific binding molecule described herein. In certain embodiments, provided herein is a mixture of cells comprising such first cell and such second cell. In a preferred embodiment, the cell expresses the vector or vectors such that the oligonucleotide is both transcribed and translated efficiently by the cell.

In embodiment, the cell expresses the vector, such that the oligonucleotide, or fragment thereof, is both transcribed and translated efficiently by the cell.

In certain embodiments, the cell is present in a host, which can be an animal, such as a mammal. Examples of cells include, but are not limited to, a human cell, a human cell line, *E. coli* (e.g., *E. coli* TB-1, TG-2, DH5a, XL-Blue MRF' (Stratagene), SA2821 and Y1090), *B. subtilis, P. aerugenosa, S. cerevisiae, N. crassa*, insect cells (e.g., Sf9, Ea4) and others set forth herein below. In a preferred embodiment, the cell is a CHO cell. In an especially preferred embodiment, the cell is a CHO-S cell.

In certain embodiments, a polynucleotide described herein can be expressed in a stable cell line that comprises the polynucleotide integrated into a chromosome by introducing the polynucleotide into the cell. In certain embodiments, the polynucleotide is introduced into the cell by, for example, electroporation. In certain embodiments, the polynucleotide is introduced into the cell by, for example, transfection of a vector comprising the polynucleotide into the cell. In certain embodiments, the vector is co-transfected with a selectable marker such as DHFR, GPT, neomycin, or hygromycin to allow for the identification and isolation of the transfected cells. In certain embodiments, the transfected polynucleotide can also be amplified to express large amounts of the encoded bispecific binding molecule. For example, the DHFR (dihydrofolate reductase) marker can be utilized to develop cell lines that carry several hundred or even several thousand copies of the polynucleotide of interest. Another example of a selection marker is the enzyme glutamine synthase (GS) (Murphy, et al., Biochem. J. 227: 277-279 (1991); Bebbington, et al., Bio/Technology 10:169-175 (1992)). Using these markers, the cells are grown in selective medium and the cells with the highest resistance are selected. These cell lines contain the amplified gene(s) integrated into a chromosome. Chinese hamster ovary (CHO) and NSO cells are often used for the production of bispecific binding molecules.

In a preferred embodiment, the vector comprises (i) a first polynucleotide sequence encoding a light chain fusion polypeptide comprising an immunoglobulin light chain fused to a scFv, via a peptide linker, wherein the light chain binds to HER2 and wherein the scFv binds to CD3, operably linked to a first promoter and (ii) a second polynucleotide encoding an immunoglobulin heavy chain that binds to HER2 operably linked to a second promoter. In certain embodiments, the vector is a viral vector.

5.4 T Cells Bound to Bispecific Binding Molecules

Without being bound by any theory, it is believed that when the bispecific binding molecules provided herein are bound to T cells, by, for example, procedures such as those described herein, an anti-CD3 scFv of the bispecific binding molecule binds to CD3 on the surface of the T cell. Without being bound by any theory, it is believed that binding of the bispecific binding molecule to the T cell (i.e., binding of an anti-CD3 scFv to CD3 expressed on the T cell) activates the T cell, and consequently, allows for the T cell receptor-based cytotoxicity to be redirected to desired tumor targets, bypassing MHC restrictions.

Thus, the invention also provides T cells which are bound to a bispecific binding molecule of the invention (e.g., as described in Section 5.1 and Section 5.2). In specific embodiments, the T cells are bound to the bispecific binding molecule noncovalently. In specific embodiments, the T cells are autologous to a subject to whom the T cells are to be administered. In specific embodiments, the T cells are allogeneic to a subject to whom the T cells are to be administered. In specific embodiments, the T cells are human T cells.

In specific embodiments, the T cells which are bound to bispecific binding molecules of the invention are used in accordance with the methods described in Section 5.6. In specific embodiments, the T cells which are bound to bispecific binding molecules of the invention are used as part of a combination therapy as described in Section 5.9.

5.5 Pharmaceutical Compositions and Kits

In certain embodiments, provided herein are compositions (e.g., pharmaceutical compositions) and kits comprising a pharmaceutically effective amount of one or more bispecific binding molecule as described in Section 5.1 or Section 5.2. Compositions may be used in the preparation of individual, single unit dosage forms. Compositions provided herein can be formulated for parenteral, subcutaneous, intramuscular, intravenous, intrarticular, intrabronchial, intraabdominal, intracapsular, intracartilaginous, intracavitary, intracelial, intracerebellar, intracerebroventricular, intra-Ommaya, intraocular, intravitreous, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, intrathecal, intraventricular in the brain, intraparenchymal in the brain, or transdermal administration. In a preferred embodiment, the composition is formulated for parenteral administration. In an especially preferred embodiment, the composition is formulated for intravenous administration. In a preferred embodiment, the composition is formulated for intraperitoneal administration. In a specific embodiment, the composition is formulated for intraperitoneal administration to treat peritoneal metastases. In a preferred embodiment, the composition is formulated for intrathecal administration. In a specific embodiment, the composition is formulated for intrathecal administration to treat brain metastases. See, for example, Kramer et al., 2010, 97: 409-418. In a preferred embodiment, the composition is formulated for intraventricular administration in the brain. In a specific embodiment, the composition is formulated for intraventricular administration to treat brain metastases. See, for example, Kramer et al., 2010, 97: 409-418. In a preferred embodiment, the composition is formulated for intraparenchymal administration in the brain. In a specific embodiment, the composition is formulated for intraparenchymal administration to treat a brain tumor or brain tumor metastases. See, for example, Luther et al., 2014, Neuro Oncol, 16: 800-806, and Clinical Trial ID NO NCT01502917.

In a specific embodiment, the composition is formulated for intraperitoneal administration for peritoneal metastases.

In certain embodiments, provided herein is a composition comprising one or more polynucleotide comprising nucleotide sequences encoding a bispecific binding molecule as described herein. In certain embodiments, provided herein is a composition comprising a cell, wherein the cell comprises one or more polynucleotide comprising nucleotide sequences encoding a bispecific binding molecule as described herein. In certain embodiments, provided herein is a composition comprising a vector, wherein the vector comprises one or more polynucleotide comprising nucleotide sequences encoding a bispecific binding molecule as described herein. In certain embodiments, provided herein is a composition comprising a cell, wherein the cell comprises a vector, wherein the vector comprises one or more polynucleotide comprising nucleotide sequences encoding a bispecific binding molecule as described herein.

In certain embodiments, a composition described herein is a stable or preserved formulation. In certain embodiments, the stable formulation comprises a phosphate buffer with saline or a chosen salt. In certain embodiments, a composition described is a multi-use preserved formulation, suitable for pharmaceutical or veterinary use. In certain embodiments, a composition described herein comprises a preservative. Preservatives are known to one of ordinary skill in the art. Non-limiting examples of preservatives include phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, and sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

It can be sometimes desirable to deliver the compositions provided herein to a subject over prolonged periods of time, for example, for periods of one week to one year or more from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g., a zinc tannate salt. Additionally, a composition provided herein, preferably, a relatively insoluble salt such as those just described, can be formulated in a gel, for example, an aluminum monostearate gel with, e.g., sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer, for example, as described in U.S. Pat. No. 3,773,919. The compounds or, preferably, relatively insoluble salts such as those described above can also be formulated in cholesterol matrix silastic pellets, particularly for use in animals. Additional slow release, depot or implant compositions, e.g., gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

The range of at least one bispecific binding molecule composition provided herein includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

In certain embodiments, compositions provided herein comprise at least one of any suitable auxiliary, such as, but not limited to, diluent, binder, stabilizer, buffers, salts, lipophilic solvents, preservative, adjuvant or the like. In certain embodiments, pharmaceutically acceptable auxiliaries are preferred. Non-limiting examples of, and methods of preparing such sterile solutions are well known in the art, such as, but not limited to, Gennaro, Ed., Remington's Pharmaceutical Sciences, 18$^{th}$ Edition, Mack Publishing Co. (Easton, Pa.) 1990. Pharmaceutically acceptable carriers can be routinely selected that are suitable for the mode of administration, solubility and/or stability of the bispecific binding molecule as described herein.

In certain embodiments, compositions provided herein contain one or more pharmaceutical excipient and/or additive. Non-limiting examples of pharmaceutical excipients and additives are proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Non-limiting examples of protein excipients include serum albumin such as human serum albumin (HSA), recombinant human albumin (rHA), gelatin, casein, and the like. Non-limiting examples of amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. In certain embodiments, the amino acid is glycine. Non-limiting examples of carbohydrate excipients include monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. In certain embodiments, the carbohydrate excipient is mannitol, trehalose, or raffinose.

In certain embodiments, a composition provided herein includes one or more buffer or a pH adjusting agent; typically, the buffer is a salt prepared from an organic acid or base. Non-limiting examples of buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In certain embodiments, the buffer is an organic acid salts such as citrate. Other excipients, e.g., isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The compositions can cover a wide range of pHs, such as from about pH 4 to about pH 10, and preferred ranges from about pH 5 to about pH 9, and a most preferred range of about 6.0 to about 8.0. Preferably, the compositions provided herein have pH between about 6.8 and about 7.8. Preferred buffers include phosphate buffers, most preferably sodium phosphate, particularly phosphate buffered saline (PBS).

In certain embodiments, a composition provided herein includes one or more polymeric excipient/additive such as, for example, polyvinylpyrrolidones, ficolls (a polymeric sugar), dextrates (e.g., cyclodextrins, such as 2-hydroxypropyl-.beta.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and/or chelating agents (e.g., EDTA).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block copolymers, and chelators such as EDTA and EGTA can optionally be added to the compositions to reduce aggregation. These additives are particularly useful if a pump or plastic container is used to administer the composition. The presence of pharmaceutically acceptable surfactant mitigates the propensity for the protein to aggregate.

Additional pharmaceutical excipients and/or additives suitable for use in a composition provided herein are known to one of skill in the art and are referenced in, for example, "Remington: The Science & Practice of Pharmacy", 19.sup.th ed., Williams & Williams, (1995), and in the "Physician's Desk Reference", 52$^{nd}$ ed., Medical Economics, Montvale, N.J. (1998), which are entirely incorporated herein by reference. In certain preferred embodiments, the carrier or excipient materials are carbohydrates (e.g., saccharides and alditols) and buffers (e.g., citrate) or polymeric agents.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the composition is a concentration sufficient to yield an anti-microbial effect. Such concentrations are dependent on the preservative selected and are readily determined by the skilled artisan.

The compositions provided herein can be prepared by a process which comprises mixing at least one bispecific binding molecule as described herein and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one bispecific binding molecule and preservative in an aqueous diluent is carried out using conventional dissolution and mixing procedures. To prepare a suitable composition, for example, a measured amount of at least one bispecific binding molecule in buffered solution is combined with the desired preservative in a buffered solution in quantities sufficient to provide the bispecific binding molecule and preservative at the desired concentrations. The compositions provided herein can be prepared by a process that comprises mixing at least one bispecific binding molecule as described herein and a selected buffer, preferably a phosphate buffer containing saline or a chosen salt. Mixing the at least one bispecific binding molecule and buffer in an aqueous diluent is carried out using conventional dissolution and mixing procedures. To prepare a suitable composition, for example, a measured amount of at least one bispecific binding molecule in water or buffer is combined with the desired buffering agent in water in quantities sufficient to provide the protein and buffer at the desired concentrations. Variations of these processes would be recognized by one of ordinary skill in the art. For example, the order the components are added, whether additional additives are used, the temperature and pH at which the composition is prepared, are all factors that can be optimized for the concentration and means of administration used.

In specific embodiments involving combination therapy with infusion of T cells, provided herein is a pharmaceutical composition comprising (a) a bispecific binding molecule described herein (see, e.g., Section 5.1 or 5.2); (b) T cells; and/or (c) a pharmaceutically effective carrier. In specific embodiments, the T cells are autologous to the subject to whom the T cells are administered. In certain embodiments, the T cells are allogeneic to the subject to whom the T cells are administered. In specific embodiments, the T cells are bound to the bispecific binding molecule. In specific embodiments, the binding of the T cells to the bispecific binding molecule is noncovalently. In specific embodiments, the T cells are human T cells. Methods that can be used to bind bispecific binding molecules to T cells are known in the art. See, e.g., Lum et al., 2013, Biol Blood Marrow Transplant, 19:925-33, Janeway et al., Immunobiology: The Immune System in Health and Disease, 5$^{th}$ edition, New York: Garland Science; Vaishampayan et al., 2015, Prostate Cancer, 2015:285193, and Stromnes et al., 2014, Immunol Rev. 257(1):145-164. See, also, Vaishampayan et al., 2015, Prostate Cancer, 2015:285193, which describes the following exemplary, non-limiting method for binding bispecific binding molecules to T cells:

Peripheral blood mononuclear cells (PBMCs) are collected to obtain lymphocytes for activated T cell expansion from 1 or 2 leukopheresis. PBMCs are activated with, for example, 20 ng/mL of OKT3 and expanded in 100 IU/mL of IL-2 to generate 40-320 billion activated T cells during a maximum of 14 days of culture under cGMP conditions as described in Ueda et al., 1993, Transplantation, 56(2):351-356 and Uberti et al., 1994, Clinical Immunology and Immunopathology, 70(3): 234-240. Cells are grown in breathable flasks (FEP Bag Type 750-C1, American Fluoroseal Corporation, Gaithersburg, Md.) in RPMI 1640 medium (Lonza) supplemented with 2% pooled heat inactivated human serum. Activated T cells are split approximately every 2-3 days based on cell counts. After 14 days, activated T cells are cultured with 50 ng of a bispecific binding molecule described herein per $10^6$ activated T cells. The mixture is then washed and cryopreserved.

In certain embodiments, a pharmaceutical composition described herein is to be used in accordance with the methods provided herein (see, e.g., Section 5.6).

5.5.1 Parenteral Formulations

In certain embodiments, a composition provided herein is formulated for parenteral injectable administration. As used herein, the term "parenteral" includes intravenous, intravascular, intramuscular, intradermal, subcutaneous, and intraocular. For parenteral administration, the composition can be formulated as a solution, suspension, emulsion or lyophilized powder in association, or separately provided, with a pharmaceutically acceptable parenteral vehicle. Non-limiting examples of such vehicles are water, saline, Ringer's solution, dextrose solution, glycerol, ethanol, and 1-10% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

5.5.2 Pulmonary Formulations

In certain embodiments, a composition comprising a bispecific binding molecule described herein is formulated for pulmonary administration. For pulmonary administration, the composition is delivered in a particle size effective for reaching the lower airways of the lung or sinuses. Compositions for pulmonary administration can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of bispecific binding molecules described herein are also known in the art. All such devices use formulations suitable for the administration for the dispensing of a bispecific binding molecule described herein in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler®. (Glaxo), Diskus® (Glaxo), devices marketed by Inhale Therapeutics, to name a few, use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. Such examples of commercially available inhalation devices are non-limiting examples are not intended to be limiting in scope.

In certain embodiments, a spray comprising a bispecific binding molecule as described herein can be produced by forcing a suspension or solution of at least one bispecific binding molecule as described herein through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of a composition comprising at least one bispecific binding molecule described herein delivered by a sprayer have a particle size less than about 10 um, preferably in the range of about 1 um to about 5 um, and most preferably about 2 um to about 3 um.

Formulations of a composition comprising at least one bispecific binding molecule described herein suitable for use with a sprayer typically include the at least one bispecific binding molecule in an aqueous solution at a concentration of about 0.1 mg to about 100 mg per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the bispecific binding molecule composition, such as a buffer, a reducing agent, a bulk protein, or a carbohydrate. Bulk proteins useful in formulating such a composition include albumin, protamine, or the like. Typical carbohydrates useful in formulating antibody composition proteins include sucrose, mannitol, lactose, trehalose, glucose, or the like. The composition can also include a surfactant, which can reduce or prevent surface-induced aggregation of the composition caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Preferred surfactants are polyoxyethylene sorbitan monooleate, polysorbate 80, polysorbate 20, or the like.

In certain embodiments, the composition is administered via a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 um, preferably in the range of about 1 um to about 5 um, and most preferably about 2 um to about 3 um.

In certain embodiments, the composition is administered via a metered dose inhaler (MDI), wherein a propellant, at least one bispecific binding molecule described herein, and any excipients or other additives are contained in a canister as a mixture including a liquefied compressed gas. Actuation of the metering valve releases die mixture as an aerosol, preferably containing particles in the size range of less than about 10 um, preferably about 1 um to about 5 um, and most preferably about 2 um to about 3 um. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of a bispecific binding molecule described herein for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one bispecific binding molecule as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

5.5.3 Oral Formulations

In certain embodiments, a composition provided herein is formulated for oral administration. In certain embodiments, for oral administration, compositions and methods of administering at least one bispecific binding molecule described herein rely on the co-administration of adjuvants such as, for example, resorcinols and nonionic surfactants such as polyoxyethylene oleyl ether and n-hexadecylpolyethylene ether, to artificially increase the permeability of the intestinal walls, as well as the co-administration of enzymatic inhibitors such as, for example, pancreatic trypsin inhibitors, diisopropylfluorophosphate (DFF) and trasylol, to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, such as, for example, inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

In certain embodiments, tablets and pills for oral administration can be further processed into enteric-coated preparations. In certain embodiments, liquid preparations for oral administration include, for example, emulsion, syrup, elixir, suspension and solution preparations allowable for medical use. These preparations can contain inactive diluting agents ordinarily used in said field, for example, water. Liposome preparations can be utilized for oral administration preparations, for example, as described for insulin and heparin (U.S. Pat. No. 4,239,754). Additionally, microspheres of artificial polymers of mixed amino acids (proteinoids) can be utilized to in oral administration of pharmaceuticals, for example, as described in U.S. Pat. No. 4,925,673. Furthermore, carrier compounds, such as those described in U.S. Pat. Nos. 5,879,681 and 5,871,753, are used in oral administration of biologically active agents.

5.5.4 Mucosal Formulations

In certain embodiments, a composition provided herein is formulated for absorption through mucosal surfaces. In certain embodiments, for absorption through mucosal surfaces, compositions and methods of administering at least one bispecific binding molecule described herein include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions provided herein can include, for example, corneal, conjunctival, buccal, sublingual, nasal, vaginal, pulmonary, stomachic, intestinal, and rectal routes of administration. Formulations for vaginal or rectal administration, for example, suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include, for example, sugars, calcium stearate, magnesium stearate, pregelinatined starch, and the like (U.S. Pat. No. 5,849,695).

5.5.5 Transdermal Formulations

In certain embodiments, a composition provided herein is formulated for transdermal administration. In certain embodiments, for transdermal administration, the composition comprises at least one bispecific binding molecule described herein encapsulated in a delivery device such as, for example, a liposome or polymeric nanoparticles, microparticle, microcapsule, or microspheres (referred to collectively as microparticles unless otherwise stated). A number of suitable devices are known for transdermal administration, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

5.5.6 Kits

Provided herein are kits comprising one or more bispecific binding molecule as described herein, or one or more composition as described herein. In certain embodiments, the kit comprises packaging material and at least one vial comprising a composition comprising a bispecific binding molecule or composition described herein. In certain embodiments, the vial comprises a solution of at least one bispecific binding molecule or composition as described herein with the prescribed buffers and/or preservatives, optionally in an aqueous diluents. In certain embodiments, the packaging material comprises a label that indicates that such solution can be held over a period of 1, 2, 3, 4, 5, 6, 9, 12, 18, 20, 24, 30, 36, 40, 48, 54, 60, 66, 72 hours or greater. In certain embodiments, the kit comprises two vials. In certain embodiments, the first vial comprises at least one lyophilized bispecific binding molecule or composition as described herein and the second vial comprises aqueous diluents of prescribed buffer or preservative. In certain embodiments, the packaging material comprises a label that instructs a subject to reconstitute the at least one lyophilized bispecific binding molecule in the aqueous diluents to form a solution that can be held over a period of twenty-four hours or greater. In certain embodiments, the packaging material comprises a label that indicates that such solution can be held over a period of 1, 2, 3, 4, 5, 6, 9, 12, 18, 20, 24, 30, 36, 40, 48, 54, 60, 66, 72 hours or greater.

In certain embodiments, the compositions provided herein can be provided to a subject as solutions or as dual vials comprising a vial of lyophilized at least one bispecific binding molecule or composition that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of subject treatment and thus can provide a more convenient treatment regimen than currently available.

In certain embodiments, a kit comprising a bispecific binding molecule or composition described herein is useful for administration over a period of immediately to twenty-four hours or greater. Accordingly, the kit offers significant advantages to the patient. In certain embodiments, a kit comprising a bispecific binding molecule or composition described herein can optionally be safely stored at temperatures of from about 2° C. to about 40° C. and retain the biologically activity of the protein for extended periods of time, thus, allowing a package label indicating that the solution can be held and/or used over a period of 6, 12, 18, 24, 36, 48, 72, or 96 hours or greater. In certain embodiments, the kit comprises a If preserved diluent is used, such label can include use up to 1-12 months, one-half, one and a half, and/or two years.

The kits can be provided indirectly to a subject, such as a subject as described in Section 5.7, by providing to pharmacies, clinics, or other such institutions and facilities, solutions or dual vials comprising a vial of lyophilized at least one bispecific binding molecule or composition that is reconstituted with a second vial containing the aqueous diluent. The solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, e.g., as made or developed by Becton Dickensen (Franklin Lakes, N.J.,), Disetronic (Burgdorf, Switzerland; Bioject, Portland, Oreg.; National Medical Products, Weston Medical (Peterborough, UK), Medi-Ject Corp (Minneapolis, Minn.). Recognized devices comprising a dual vial system include those pen-injector systems for reconstituting a lyophilized drug in a cartridge for delivery of the reconstituted solution such as the HumatroPen®.

In certain embodiments, the kits comprise packaging material. In certain embodiments, the packaging material provides, in addition to the information required by a regulatory agencies, the conditions under which the product can be used. In certain embodiments, the packaging material provides instructions to the subject to reconstitute the at least one bispecific binding molecule in the aqueous diluent to form a solution and to use the solution over a period of 2-24 hours or greater for the two vial, wet/dry, product. For the single vial, solution product, the label indicates that such solution can be used over a period of 2-24 hours or greater. In a preferred embodiment, the kit is useful for human pharmaceutical product use. In certain embodiments, the kit is useful for veterinarian pharmaceutical use. In a preferred embodiment, the kit is useful for canine pharmaceutical product use. In a preferred embodiment, the kit is useful for intravenous administration. In another preferred embodiment, the kit is useful for intraperitoneal, intrathecal, intraventricular in the brain, or intraparenchymal in the brain administration.

5.6 Uses and Methods 5.6.1 Therapeutic Uses

In certain embodiments, provided herein are methods for treating a HER2-positive cancer in a subject comprising administering to the subject in need thereof a therapeutically effective amount of a bispecific binding molecule as described in Section 5.1 or in Section 5.2, a therapeutically effective amount of a cell, polynucleotide, or vector encoding such a bispecific binding molecule as described in Section 5.3, or a therapeutically effective amount of a pharmaceutical composition as described in Section 5.5, or a therapeutically effective amount of T cells bound to a bispecific binding molecule as described in Section 5.4. In a specific embodiment, the subject is a subject as described in Section 5.7. In a specific embodiment, the bispecific binding molecule is administered at a dose as described in Section 5.8. In a specific embodiment, the bispecific binding molecule is administered according to the methods as described in Section 5.5. In a preferred embodiment, the bispecific binding molecule is administered intravenously. In another preferred embodiment, the bispecific binding molecule is administered intrathecally, intraventricularly in the brain, intraparenchymally in the brain, or intraperitoneally. In a specific embodiment, the bispecific binding molecule is administered in combination with one or more additional pharmaceutically active agents as described in Section 5.9.

In certain embodiments, provided herein are methods for treating a HER2-positive cancer in a subject comprising administering to the subject in need thereof a pharmaceutical composition as described in Section 5.1 or in Section 5.2. In a specific embodiment, the pharmaceutical composition is a composition as described in Section 5.5. In a specific embodiment, the subject is a subject as described in Section 5.7. In a specific embodiment, the pharmaceutical composition is administered at a dose as described in Section 5.8. In a specific embodiment, the pharmaceutical composition is administered according to the methods as described in Section 5.5. In a preferred embodiment, the pharmaceutical composition is administered intravenously. In another preferred embodiment, the bispecific binding molecule is administered intrathecally, intraventricularly in the brain, intraparenchymally in the brain, or intraperitoneally. In a specific embodiment, the pharmaceutical composition is administered in combination with one or more additional pharmaceutically active agents as described in Section 5.9.

For use of a bispecific binding molecule in a subject of a particular species, a bispecific binding molecule is used that binds to the HER2 and the CD3 of that particular species. For example, to treat a human, the bispecific binding molecule comprises an aglycosylated monoclonal antibody that is an immunoglobulin that binds to human HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to human CD3, and wherein the first and second light chain fusion polypeptides are identical. In another example, to treat a canine, the bispecific binding molecule comprises an aglycosylated monoclonal antibody that is an immunoglobulin that binds to canine HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to canine CD3, and wherein the first and second light chain fusion polypeptides are identical. Bispecific binding molecules that are cross-reactive with HER2 and/or CD3 of various species can be used to treat subjects in those species. For example, trastuzumab is expected to bind both human and canine HER2 due to the relative conservation of the epitope in HER2 recognized by trastuzumab. See, also, for example, Singer et al., 2012, Mol Immunol, 50: 200-209.

In addition, for use of a bispecific binding molecule in a subject of a particular species, the bispecific binding molecule, preferably, the constant region of the immunoglobulin portion, is derived from that particular species. For example, to treat a human, the bispecific binding molecule can comprise an aglycosylated monoclonal antibody that is an immunoglobulin, wherein the immunoglobulin comprises a human constant region. In another example, to treat a canine, the bispecific binding molecule can comprise an aglycosylated monoclonal antibody that is an immunoglobulin, wherein the immunoglobulin comprises a canine constant region. In a specific embodiment, when treating a human, the immunoglobulin is humanized. In a specific embodiment, the subject is a human. In a specific embodiment, the subject is a canine.

In a specific embodiment, the HER2-positive cancer is breast cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, neuroblastoma, or any other neoplastic tissue that expresses the HER2 receptor.

In a specific embodiment, the HER2-positive cancer is resistant to treatment with trastuzumab, cetuximab, lapatinib, erlotinib, or any other small molecule or antibody that targets the HER family of receptors. In a specific embodiment, the tumor that is resistant to treatment with trastuzumab, cetuximab, lapatinib, erlotinib, or any other small molecule or antibody that targets the HER family of receptors is responsive to treatment with a bispecific binding molecule of the invention. In a specific embodiment, the HER2-positive cancer is resistant to treatment with necitumumab, pantitumumab, pertuzumab, or ado-trastuzumab emtansine. In a specific embodiment, the HER2-positive cancer that is resistant to treatment with necitumumab, pantitumumab, pertuzumab, or ado-trastuzumab emtansine is responsive to treatment with a bispecific binding molecule of the invention.

In a specific embodiment, the HER2-positive cancer is a cancer that expresses programmed death-ligand 1 ("PDL1" or "PDL-1") (i.e., a HER2-positive, PDL1-positive cancer). Thus, in a specific embodiment, provided herein is a method of treating a HER2-positive, PDL1-positive cancer in a subject in need thereof, comprising administering to the subject a therapeutically effective amount of a bispecific binding molecule as described in Section 5.1 or in Section 5.2, a therapeutically effective amount of a cell, polynucleotide, or vector encoding such a bispecific binding molecule as described in Section 5.3, or a therapeutically effective amount of a pharmaceutical composition as described in Section 5.5, or a therapeutically effective amount of T cells bound to a bispecific binding molecule as described in Section 5.4. In a specific embodiment, the HER2-positive, PDL1-positive cancer overexpresses PDL1. In a specific embodiment, the HER2-positive, PDL1-positive cancer overexpresses PDL1 in cancerous cells relative to expression of PDL1 in analogous noncancerous cells of the same tissue type as the HER2-positive, PDL1-positive cancer. The noncancerous cells are analogous to the cancerous cells by virtue of the fact that they, for example, are from the same tissue or organ type or are otherwise suitable for comparison of PDL1 expression. The level of PDL1 expression in analogous noncancerous cells can be a known, standard level for a population or for particular individual(s) or for the subject having cancer, or can be newly measured. The overexpression can be shown, for example, by detecting increased PDL1 expression in a test specimen comprising cancerous cells relative to expression in a control specimen comprising analogous noncancerous cells. In contrast to the test specimen, the control specimen does not contain a significant amount of cancerous cells. In a specific embodiment, a HER2-positive, PDL1-positive cancer is deemed to overexpress PDL1 when the test specimen expresses a detectable level of PDL1 above background (i.e., experimental noise), preferably as measured by immunohistochemistry ("IHC") since most normal tissue should be PDL1-negative. In a specific embodiment, the detectable level of PDL1 above background is 1% to 5%, or is at least 1%, at least 2%, at least 3%, at least 4%, or at least 5% above background. In a specific embodiment in which the HER2-positive, PDL1-positive cancer is a melanoma, in a particular embodiment, the melanoma is deemed to overexpress PDL1 when the test specimen expresses a detectable level of PDL1 that is at least 5% above background. In a specific embodiment in which the HER2-positive, PDL1-positive cancer is a non-small cell lung carcinoma, in a particular embodiment, the non-small cell lung carcinoma is deemed to overexpress PDL1 if the test specimen expresses a detectable level of PDL1 that is at least 5% above background. In a specific embodiment where binding to an anti-PDL1 antibody is used to measure the level of PDL1 expression in the test specimen and the control specimen, in a particular embodiment, the background level is measured by measuring nonspecific signal, for example, arising from binding to an antibody that recognizes an antigen known not to be expressed by the test or control specimen, e.g., an anti-IgG antibody. In a specific embodiment, PDL1 expression is measured by measuring PDL1 protein levels. In a specific embodiment, PDL1 expression is measured by measuring PDL1 nucleic acid levels (e.g., cDNA or RNA encoding PDL1). In a specific embodiment, PDL1 protein level is measured according to any assay known in the art, such as, e.g., IHC, western blot, enzyme-linked immunosorbent assay, or fluorescence-activated cell sorting. In a specific embodiment, PDL1 nucleic acid level is measured according to any assay known in the art, such as, e.g., in situ hybridization ("ISH"), southern blot, northern blot, quantitative reverse transcriptase polymerase chain reaction, or deep sequencing. The test specimen comprises cancer cells from the subject having cancer, and may be in the form of various biological specimens known in the art, e.g., from a biopsy or surgical resection. In a specific embodiment, a test specimen comprises cancerous cells from a primary tumor from the subject having cancer. In a specific embodiment, the test specimen comprises cancerous cells from a metastatic tumor from the subject having cancer. In a specific embodiment, the control specimen comprising analogous noncancerous cells (analogous to the cancerous cells in the test specimen) is a specimen obtained or derived from the subject who has cancer. Alternatively, a control specimen may be a specimen obtained or derived from a healthy subject or a subject who does not have cancer. In a specific embodiment, the control specimen does not comprise cancerous cells. In a specific embodiment, the test specimen and control specimen are from the same subject. In a specific embodiment, the test specimen and the control specimen are from different subjects. In a specific embodiment, the test specimen contains cancerous cells from breast tissue and the control specimen contains noncancerous cells from breast tissue.

Nonlimiting examples of HER2-positive cancers that express PDL1 and thus can be treated according to the methods described herein include breast cancer, gastric cancer, an osteosarcoma, desmoplastic small round cell cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, or neuroblastoma. In a specific embodiment, the HER2-positive, PDL1-positive cancer is not a head and neck cancer.

In a specific embodiment, a HER2-positive, PDL1-positive cancer treated according to the methods described herein is resistant to PDL1 blockade with an anti-PDL1 therapy. In a specific embodiment, the HER2-positive, PDL1-positive cancer is resistant to programmed cell death 1 ("PD1" or "PD-1") blockade with an anti-PD1 therapy. In a specific embodiment, the HER2-positive, PDL1-positive cancer is resistant to (i) PDL1 blockade with an anti-PDL1 therapy, and (ii) PD1 blockade with an anti-PD1 therapy.

In a specific embodiment, PDL1 blockade refers to (i) inhibition of PDL1-dependent PD1 activation, or (ii) blocking of PDL1 binding to PD1. In a specific embodiment, the inhibition or blocking is partial. In another specific embodiment, the inhibition or blocking is complete. In a specific embodiment, PDL1 blockade refers to least 5%, 10%, 15%, 20%, 25%, 30%, 35%, 40%, 45%, 50%, 55%, 60%, 65%, 70%, 75%, 80%, 85%, 90%, 95%, 98%, or 99% inhibition of PDL1-dependent PD1 activation as assessed by any method known to one of skill in the art, such as, e.g., a phosphorylation assay, as compared to PDL1-dependent PD1 activation in the presence of a negative control therapy (e.g., an anti-IgG antibody). For example, in a specific embodiment, PDL1 blockade that is inhibition of activation is assessed by (a) contacting a PDL1-expressing cell and a PD1-expressing activated T cell with an anti-PDL1 therapy (e.g., an anti-PDL1 antibody) or a negative control therapy (e.g., an anti-IgG antibody), and (b) measuring the phosphorylation of PD1 or dephosphorylation of a downstream signaling molecule, such as, e.g., Lck or Zap-70, as assessed by, for e.g., ELISA or western blot, in the presence of the anti-PDL1 therapy as compared to the phosphorylation of PD1 or dephosphorylation of a downstream signaling molecule, such as, e.g., Lck or Zap-70, as assessed by, for e.g., ELISA or western blot, in the presence of the negative control therapy. In a specific embodiment, PDL1 blockade that is blocking of PDL1 binding to PD1 is assessed by (a) contacting a PDL1-expressing cell and a PD1-expressing activated T cell with an anti-PDL1 therapy (e.g., an anti-PDL1 antibody) or a negative control therapy (e.g., an anti-IgG antibody), and (b) measuring the interaction between PDL1 and PD1 by, for example, co-localization (as assessed by, e.g., immunohistochemistry) or co-immunoprecipitation (as assessed by, e.g., western blot) of PDL1 and PD1, in the presence of the anti-PDL1 therapy as compared to the interaction between PDL1 and PD1 by, for example, co-localization (as assessed by, e.g., immunohistochemistry) or co-immunoprecipitation (as assessed by, e.g., western blot), in the presence of the negative control therapy.

In a specific embodiment, PD1 blockade refers to (i) inhibition of ligand-dependent PD1 activation, or (ii) blocking of ligand binding to PD1. In a specific embodiment, the inhibition or blocking is partial. In another specific embodiment, the inhibition or blocking is complete. In a specific embodiment, PD1 blockade refers to least 5%, 10%, 15%, 20%, 25%, 30%, 35%, 40%, 45%, 50%, 55%, 60%, 65%, 70%, 75%, 80%, 85%, 90%, 95%, 98%, or 99% inhibition of ligand-dependent PD1 activation as assessed by any method known to one of skill in the art, such as, e.g., a phosphorylation assay, as compared to ligand-dependent PD1 activation in the presence of a negative control therapy (e.g., an anti-IgG antibody). For example, in a specific embodiment, PD1 blockade that is inhibition of activation is assessed by (a) contacting a PD1 ligand-expressing cell and a PD1-expressing activated T cell with an anti-PD1 therapy (e.g., an anti-PD1 antibody) or a negative control therapy (e.g., an anti-IgG antibody), and (b) measuring the phosphorylation of PD1 or dephosphorylation of a downstream signaling molecule, such as, e.g., Lck or Zap-70, as assessed by, for e.g., ELISA or western blot, in the presence of the anti-PD1 therapy as compared to the phosphorylation of PD1 or dephosphorylation of a downstream signaling molecule, such as, e.g., Lck or Zap-70, as assessed by, for e.g., ELISA or western blot, in the presence of the negative control therapy. In a specific embodiment, PD1 blockade that is blocking of ligand binding to PD1 is assessed by (a) contacting a ligand-expressing cell and a PD1-expressing activated T cell with an anti-PD1 therapy (e.g., an anti-PD1 antibody) or a negative control therapy (e.g., an anti-IgG antibody), and (b) measuring the interaction between ligand and PD1 by, for example, co-localization (as assessed by, e.g., immunohistochemistry) or co-immunoprecipitation (as assessed by, e.g., western blot) of ligand and PD1, in the presence of the anti-PD1 therapy as compared to the interaction between ligand and PD1 by, for example, co-localization (as assessed by, e.g., immunohistochemistry) or co-immunoprecipitation (as assessed by, e.g., western blot), in the presence of the negative control therapy.

In a specific embodiment, an anti-PDL1 therapy is a PDL1-targeted therapy that is effective in the treatment of one or more cancers expressing PDL1. In a specific embodiment, the anti-PDL1 therapy comprises an antibody or antigen-binding fragment thereof (e.g., a Fab fragment, a F(ab')2 fragment, or a disulfide-linked Fv) or antigen-binding derivative thereof (e.g., a bispecific antibody, an scFv, an intrabody, or a camelized antibody), a polypeptide, a RNAi-inducing nucleic acid (e.g., an antisense oligonucleotide, a small interfering RNA, a microRNA, or a short hairpin RNA), or a small molecule that targets PDL1. Nonlimiting examples of an anti-PDL1 therapy include mpd13280A (see, e.g., Herbst et al., J Clin Oncol. 2013; 31(suppl):abstr 3000), durvalumab (e.g., for bladder cancer) (also referred to as "medi-4736"; see, e.g., Lutzky et al., J Clin Oncol. 2014; 32(suppl 5S):abstr 3001), avelumab (e.g., for Merkel cell carcinoma) (also referred to as "MSB0010718C"; see, e.g., Heery et al. J Clin Oncol. 2014; 32(suppl 5S):abstr 3064), and bms-936559 (see, e.g., Brahmer et al. N. Engl. J. Med. 2012; 366, 2455-2465), and atezolizumab (see, e.g., McDermott et al., J Clin Oncol. 2016; 34(8):833-842). In a preferred embodiment, the anti-PDL1 therapy is an anti-PDL1 antibody. In a preferred embodiment, the anti-PDL1 antibody is atezolizumab. In a specific embodiment, the anti-PDL1 therapy is a therapy approved by the U.S. Food and Drug Administration ("FDA") for treatment of one or more cancers. A nonlimiting example of an anti-PDL1 therapy approved by the U.S. Food and Drug Administration for treatment of cancer is atezolizumab. In a specific embodiment, the anti-PDL1 therapy is a PDL1-targeted therapy approved by the European Medicines Agency ("EMA") for treatment of one or more cancers. A nonlimiting example of an anti-PDL1 therapy approved by the EMA for treatment of a PDL1-expressing cancer is atezolizumab.

In a specific embodiment, an anti-PD1 therapy is a PD1-targeted therapy that is effective in the treatment of one or more cancers expressing PDL1. In a specific embodiment, the anti-PD1 therapy comprises an antibody or antigen-binding fragment thereof (e.g., a Fab fragment, a F(ab')2 fragment, or a disulfide-linked Fv) or antigen-binding derivative thereof (e.g., a bispecific antibody, an scFv, an intrabody, or a camelized antibody), a polypeptide, a RNAi-inducing nucleic acid (e.g., an antisense oligonucleotide, a small interfering RNA, a microRNA, or a short hairpin RNA), or a small molecule that targets PD1. Nonlimiting examples of an anti-PD1 therapy include nivolumab (see, e.g., Topalian et al., N Engl J Med. 2012; 366:2443-54), pidilizumab (see, e.g., Atkins et al., J Clin Oncol. 2014; 32(suppl 5S):abstr 9001), AMP-224 (see, e.g., Infante et al., J Clin Oncol. 2013; 31(suppl):abstr 3044), MEDI0680 (also referred to as "AMP-514"; see, e.g., Hamid et al., Ann Oncol. 2016; 27(suppl 6):1050PD), and pembrolizumab (see, e.g., Hamid et al., N Engl J Med. 2013; 369:134-44). In a preferred embodiment, the anti-PD1 therapy is an anti-PD1 antibody. In a preferred embodiment, the anti-PD1 antibody is pembrolizumab. In a specific embodiment, the anti-PD1 therapy is a therapy approved by the U.S. FDA for treatment of one or more cancers. Nonlimiting examples of an anti-PD1 therapy approved by the U.S. FDA for treatment of cancer include pembrolizumab and nivolumab. In a specific embodiment, the anti-PD1 therapy is a therapy approved by the EMA for treatment of one or more cancers. Nonlimiting examples of an anti-PD1 therapy approved by the EMA for treatment of cancer include pembrolizumab and nivolumab.

In contrast to trastuzumab (which is indicated for treatment of HER2-overexpressing breast cancer, metastatic gastric cancer, and gastroesophageal junction adenocarcinoma (see Trastuzumab [Highlights of Prescribing Information], South San Francisco, Calif.: Genentech, Inc.; 2014)), the bispecific binding molecules described herein are therapeutically effective against HER2-positive cancers that express low levels of HER2. See, e.g., the working example of Section 6.3, in particular, FIG. 32, which demonstrates that tumor growth was completely suppressed in a gastric cancer patient-derived xenograft model with low HER2 expression when treated with a bispecific binding molecule described herein; in contrast, treatment of the gastric cancer patient-derived xenograft model with trastuzumab did not suppress tumor growth. Thus, also provided herein is a method of treating a HER2-positive cancer in a subject in need thereof, comprising administering to the subject a therapeutically effective amount of a bispecific binding molecule as described in Section 5.1 or in Section 5.2, a therapeutically effective amount of a cell, polynucleotide, or vector encoding such a bispecific binding molecule as described in Section 5.3, or a therapeutically effective amount of a pharmaceutical composition as described in Section 5.5, or a therapeutically effective amount of T cells bound to a bispecific binding molecule as described in Section 5.4, wherein the cancer is not indicated for treatment with trastuzumab, and wherein the cancer is not a head and neck cancer. In a specific embodiment, the cancer is breast cancer. In a specific embodiment, the cancer is gastric cancer. In a specific embodiment, the cancer is gastroesophageal junction adenocarcinoma.

In a specific embodiment, the HER2-positive cancer is determined not to be indicated for treatment with trastuzumab according to applicable American Society of Clinical Oncology/College of American Pathologists ("ASCO/CAP") guideline recommendations for HER2 testing in cancer ("ASCO HER2 Testing Guidelines") (see, e.g., Wolff et al., Journal of Clinical Oncology, 2013, 31(31): 3997-4013 and Bartley et al., Journal of Clinical Oncology, 2016, 146(6):647-669). The applicable ASCO HER2 Testing Guideline will be known to one of skill in the art. In a specific embodiment, the applicable ASCO HER2 Testing Guideline is the current (i.e., most recently published and updated) ASCO HER2 Testing Guideline as of the date of using the ASCO HER2 Testing Guideline to determine that the cancer is not indicated for treatment with trastuzumab. In an alternative, preferred embodiment, the applicable ASCO HER2 Testing Guideline is the current (e.g., most recently published and updated) ASCO/CAP guideline recommendations for HER2 testing in breast cancer ("ASCO HER2 Breast Cancer Testing Guideline") (see, e.g., Wolff et al., Journal of Clinical Oncology, 2013, 31(31):3997-4013) as of the date of determining that the cancer is not indicated for treatment with trastuzumab, regardless of the type of cancer that is determined not to be indicated for treatment with trastuzumab (e.g., the type of cancer may be breast cancer or any other HER2-positive cancer). In another embodiment, the applicable ASCO HER2 Testing Guideline is the current (e.g., most recently published and updated) ASCO HER2 Testing Guideline as of the date of determining that the cancer is not indicated for treatment with trastuzumab and the applicable ASCO HER2 Testing Guideline is for the same type of cancer (e.g., same tissue type, for example, both being breast cancers, or both being gastric cancers) as the cancer that is determined not to be indicated for treatment with trastuzumab.

In a specific embodiment, the HER2-positive cancer is determined not to be indicated for treatment with trastuzumab based on the following characterization of the cancer (see, e.g., the 2013 ASCO HER2 Breast Cancer Testing Guideline (e.g., as set forth in Wolff et al., Journal of Clinical Oncology, 2013, 31(31):3997-4013)): (a) a first determination of a level of HER2 in a test specimen comprising cells of the cancer is reported as negative, or (b) a first determination of a level of HER2 in a test specimen comprising cells of the cancer is reported as equivocal, and a second determination of a level of HER2 in a test specimen comprising cells of the cancer is reported as equivocal or negative. In a specific embodiment, the HER2-positive cancer is determined not to be indicated for treatment with trastuzumab when a first determination of a level of HER2 in a test specimen comprising cells of the cancer is reported as negative according to the applicable ASCO HER2 Testing Guideline (e.g., the 2013 ASCO HER2 Breast Cancer Testing Guideline (e.g., as set forth in Wolff et al., Journal of Clinical Oncology, 2013, 31(31):3997-4013)). In a specific embodiment, the HER2-positive cancer is determined not to be indicated for treatment with trastuzumab when a first determination of a level of HER2 in a test specimen comprising cells of the cancer is reported as equivocal according to the applicable ASCO HER2 Testing Guideline (e.g., the 2013 ASCO HER2 Breast Cancer Testing Guideline (e.g., as set forth in Wolff et al., Journal of Clinical Oncology, 2013, 31(31):3997-4013)) and a second determination of a level of HER2 in a test specimen comprising cells of the cancer is reported as equivocal or negative according to the applicable ASCO HER2 Testing Guideline (e.g., the 2013 ASCO HER2 Breast Cancer Testing Guideline (e.g., as set forth in Wolff et al., Journal of Clinical Oncology, 2013, 31(31):3997-4013)). The test specimen can be from a primary tumor or a metastatic tumor.

In a specific embodiment, the determination of the level of HER2 in the test specimen is reported as negative when the level of HER2 in the test specimen is characterized as (see, e.g., the 2013 ASCO HER2 Breast Cancer Testing Guideline (e.g., as set forth in Wolff et al., Journal of Clinical Oncology, 2013, 31(31):3997-4013)): (i) (1) IHC 1+, wherein the level of HER2 in the test specimen is characterized as IHC 1+ when the test specimen exhibits an incomplete HER2 membrane staining that is faint/barely perceptible and within greater than 10% of the invasive tumor cells, wherein the staining is readily appreciated using a low-power objective; (2) IHC 0, wherein the level of HER2 in the test specimen is characterized as IHC 0 when the test specimen exhibits no staining observed, wherein the lack of staining is readily appreciated using a low-power objective, or a HER2 membrane staining that is incomplete and is faint/barely perceptible and within less than or equal to 10% of the invasive tumor cells, wherein the staining is readily appreciated using a low-power objective; or (ii) ISH negative, wherein the level of HER2 in the test specimen is characterized as ISH negative when the test specimen exhibits (1) a single-probe average HER2 copy number of less than 4.0 signals per cell; or (2) a dual-probe HER2/CEP17 ratio of less than 2.0 with an average HER2 copy number of less than 4.0 signals per cell.

In a specific embodiment, the determination of the level of HER2 in the test specimen is reported as equivocal when the level of HER2 in the test specimen is characterized as (see, e.g., the 2013 ASCO HER2 Breast Cancer Testing Guideline (e.g., as set forth in Wolff et al., Journal of Clinical Oncology, 2013, 31(31):3997-4013)): (i) IHC 2+, wherein the level of HER2 in the test specimen is characterized as IHC 2+ when the test specimen exhibits(1) a circumferential HER2 membrane staining that is incomplete and/or weak/moderate and within greater than 10% of invasive tumor cells, wherein the staining is observed in a homogenous and contiguous population, and wherein the staining is readily appreciated using a low-power objective; or (2) a complete and circumferential HER2 membrane staining that is intense and within less than or equal to 10% of invasive tumor cells, wherein the staining is readily appreciated using a low-power objective; or (ii) ISH equivocal, wherein the level of HER2 in the test specimen is characterized as ISH equivocal when the test specimen exhibits which comprises: (1) a single-probe ISH average HER2 copy number of greater than or equal to 4.0 and less than 6.0 signals/cell, wherein the copy number is determined by counting at least 20 cells within the area and is observed in a homogenous and contiguous population; or (2) a dual-probe HER2/CEP17 ratio of less than 2.0 with an average HER2 copy number of greater than or equal to 4.0 and less than 6.0 signals per cell, wherein the copy number is determined by counting at least 20 cells within the area and is observed in a homogenous and contiguous population. In a specific embodiment, when two determinations of the level of HER2 in a subject are made to determine that a cancer is not indicated for treatment with trastuzumab (e.g., a first determination is reported as equivalent and a second determination is reported as equivalent or negative), the two determinations are either: (1) based on the same test specimen using different assays; or (2) based on different test specimens using the same assay. For example, if the first determination is based on a first test specimen using ISH, the second determination is based on the first test specimen using IHC. In an alternative example, if the first determination is made based on a first test specimen using ISH, the second determination is based on a second test specimen using ISH.

In a specific embodiment, the level of HER2 in the test specimen is determined according to one or more assays approved by the U.S. Food and Drug Administration ("FDA") for determining the level of HER2. Nonlimiting examples of U.S. Food and Drug Administration-approved assays for determining a level of HER2 include HercepTest™ (manufactured by DAKO), PATHWAY® (manufactured by Ventana Medical Systems Inc.), InSite® (manufactured by Biogenex Laboratories Inc.), Bond Oracle™ (manufactured by Leica Biosystems), PathVysion® (manufactured by Abbott Molecular Inc.), PharmDx™ Kit (manufactured by DAKO), SPoT-Light® (manufactured by Life Technologies Inc.), INFORM HER2 dual IDS DNA probe cocktail (manufactured by Ventana Medical Systems Inc.), and PharmDx™ (manufactured by DAKO). In another specific embodiment, the level of HER2 in the test specimen is determined according to a laboratory-developed test performed in a Clinical Laboratory Improvement Amendments-certified laboratory.

Also provided herein is a method of treating a HER2-positive cancer in a subject in need thereof, comprising administering to the subject a therapeutically effective amount of a bispecific binding molecule as described in Section 5.1 or in Section 5.2, a therapeutically effective amount of a cell, polynucleotide, or vector encoding such a bispecific binding molecule as described in Section 5.3, or a therapeutically effective amount of a pharmaceutical composition as described in Section 5.5, or a therapeutically effective amount of T cells bound to a bispecific binding molecule as described in Section 5.4, wherein the cancer expresses a low level of HER2, and wherein the cancer is not a head and neck cancer. In a specific embodiment, the cancer is breast cancer. In another specific embodiment, the cancer is gastric cancer. In a specific embodiment, the cancer is gastroesophageal junction adenocarcinoma.

In a preferred embodiment, the HER2-positive cancer is deemed to express a low level of HER2 when a level of HER2 in a test specimen comprising cells of the cancer is characterized as IHC 2+ or less (e.g., IHC 1+ or IHC 0) according to the applicable ASCO HER2 Testing Guideline. In a specific embodiment, the HER2-positive cancer is deemed to express a low level of HER2 when a level of HER2 in a test specimen comprising cells of the cancer is characterized as IHC 2+ according to the applicable ASCO HER2 Testing Guideline. In a specific embodiment, the HER2-positive cancer is deemed to express a low level of HER2 when a level of HER2 in a test specimen comprising cells of the cancer is characterized as IHC 1+ according to the applicable ASCO HER2 Testing Guideline. In a specific embodiment, the HER2-positive cancer is deemed to express a low level of HER2 when a level of HER2 in a test specimen comprising cells of the cancer is characterized as IHC 0 according to the applicable ASCO HER2 Testing Guideline. The applicable ASCO HER2 Testing Guideline will be known to one of skill in the art. In a specific embodiment, the applicable ASCO HER2 Testing Guideline is the current (e.g., most recently published and updated) ASCO HER2 Testing Guideline as of the date of characterizing the level of HER2 in the test specimen comprising cells of the cancer as IHC 2+ or less (e.g., IHC 1+ or IHC 0). In a preferred embodiment, the applicable ASCO HER2 Testing Guideline is the current (e.g., most recently published and updated) ASCO HER2 Breast Cancer Testing Guideline (see, e.g., Wolff et al., Journal of Clinical Oncology, 2013, 31(31):3997-4013) as of the date of characterizing the level of HER2 in the test specimen, regardless of the type of cancer of the test specimen (e.g., the test specimen may be of breast cancer or any other HER2-positive cancer). In another embodiment, the applicable ASCO HER2 Testing Guideline is for the same type of cancer (e.g., same tissue type, for example, both being breast cancers, or both being gastric cancers) as the cancer of the test specimen. In another embodiment, the applicable ASCO HER2 Testing Guideline is the current (e.g., most recently published and updated) ASCO HER2 Testing Guideline as of the date of characterizing the level of HER2 in the test specimen and the applicable ASCO HER2 Testing Guideline is for the same type of cancer (e.g., same tissue type, for example, both being breast cancers, or both being gastric cancers) as the test specimen. In a specific embodiment, the level of HER2 in the test specimen comprising cells of the cancer is characterized as IHC 2+ when the test specimen exhibits (see, e.g., Wolff et al., Journal of Clinical Oncology, 2013, 31(31):3997-4013) (1) a circumferential HER2 membrane staining that is incomplete and/or weak/moderate and within greater than 10% of invasive tumor cells, wherein the staining is observed in a homogenous and contiguous population, and wherein the staining is readily appreciated using a low-power objective; or (2) a complete and circumferential HER2 membrane staining that is intense and within less than or equal to 10% of invasive tumor cells, wherein the staining is readily appreciated using a low-power objective. In a specific embodiment, the level of HER2 in a test specimen comprising cells of the cancer is characterized as IHC 1+ when the test specimen exhibits (see, e.g., Wolff et al., Journal of Clinical Oncology, 2013, 31(31):3997-4013) an incomplete HER2 membrane staining that is faint/barely perceptible and within greater than 10% of the invasive tumor cells, wherein the staining is readily appreciated using a low-power objective. In a specific embodiment, the level of HER2 in the test specimen comprising cells of the cancer is characterized as IHC when the test specimen exhibits (see, e.g., Wolff et al., Journal of Clinical Oncology, 2013, 31(31): 3997-4013) no HER2 staining observed, wherein the lack of staining is readily appreciated using a low-power objective, or a HER2 membrane staining that is incomplete and is faint/barely perceptible and within less than or equal to 10% of the invasive tumor cells, wherein the staining is readily appreciated using a low-power objective.

In another embodiment, the HER2-positive cancer is deemed to express a low level of HER2 when the cancer expresses a lower level of HER2 than the level of HER2 expressed by cancers that are indicated for treatment with trastuzumab and are of the same type (e.g., same tissue type, for example, both being breast cancers, or both being gastric cancers) as the HER2-positive cancer. In a specific embodiment, the HER2 positive cancer is deemed to express a low level of HER2 when the HER2-positive cancer expresses a level of HER2 that is at least 10%, 20%, 30%, 40%, 50%, 60%, 70%, 80%, 90%, or 100% lower than the level of HER2 expressed by cancers that are indicated for treatment with trastuzumab and are of the same type (e.g., same tissue type, for example, both being breast cancers, or both being gastric cancers) as the HER2-positive cancer. In a specific embodiment, HER2 expression is measured by measuring HER2 protein levels. In a specific embodiment, HER2 expression is measured by measuring HER2 nucleic acid levels (e.g, genomic DNA, cDNA, or RNA encoding HER2). In a specific embodiment, HER2 protein level is measured according to any assay known in the art, such as, e.g., IHC, western blot, enzyme-linked immunosorbent assay, or fluorescence-activated cell sorting. In a preferred embodiment, HER2 protein level is measured according to IHC. In a specific embodiment, HER2 nucleic acid level is measured according to any assay known in the art, such as, e.g., ISH, southern blot, northern blot, quantitative reverse transcriptase polymerase chain reaction, or deep sequencing. In a preferred embodiment, HER2 nucleic acid level is measured according to ISH.

In a specific embodiment, the level of HER2 in the test specimen is determined according to one or more assays approved by the U.S. Food and Drug Administration ("FDA") for determining the level of HER2. Nonlimiting examples of U.S. Food and Drug Administration-approved assays for determining a level of HER2 include HercepTest™ (manufactured by DAKO), PATHWAY® (manufactured by Ventana Medical Systems Inc.), InSite® (manufactured by Biogenex Laboratories Inc.), Bond Oracle™ (manufactured by Leica Biosystems), PathVysion® (manufactured by Abbott Molecular Inc.), PharmDx™ Kit (manufactured by DAKO), SPoT-Light® (manufactured by Life Technologies Inc.), INFORM HER2 dual IDS DNA probe cocktail (manufactured by Ventana Medical Systems Inc.), and PharmDx™ (manufactured by DAKO). In another specific embodiment, the level of HER2 in the test specimen is determined according to a laboratory-developed test performed in a Clinical Laboratory Improvement Amendments-certified laboratory.

In a specific embodiment, the HER2-positive cancer that expresses a low level of HER2 is a breast cancer, a gastric cancer, an osteosarcoma, desmoplastic small round cell cancer, an ovarian cancer, a prostate cancer, a pancreatic cancer, glioblastoma multiforme, gastric junction adenocarcinoma, gastroesophageal junction adenocarcinoma, a cervical cancer, a salivary gland cancer, a soft tissue sarcoma, a leukemia, a melanoma, a Ewing's sarcoma, a rhabdomyosarcoma, a brain tumor, or neuroblastoma. In a preferred embodiment, the HER2-positive cancer that expresses a low level of HER2 is breast cancer. In a specific embodiment, the HER2-positive cancer that expresses a low level of HER2 is gastric cancer. In a specific embodiment, the HER2-positive cancer that expresses a low level of HER2 is ovarian cancer, pancreatic cancer, a desmoplastic small round cell tumor, an osteosarcoma, a melanoma, a brain tumor, a cervical cancer, a prostate cancer, or a salivary gland cancer. In a specific embodiment, the HER2-positive cancer that expresses a low level of HER2 is not a head and neck cancer.

In a specific embodiment, the HER2-positive cancer that expresses a low level of HER2 is resistant to treatment with trastuzumab, cetuximab, lapatinib, erlotinib, or any other small molecule or antibody that targets the HER family of receptors, and is responsive to treatment with a bispecific binding molecule of the invention. In a specific embodiment, the HER2-positive cancer that expresses a low level of HER2 is resistant to treatment with necitumumab, pantitumumab, pertuzumab, or ado-trastuzumab emtansine, and is responsive to treatment with a bispecific binding molecule of the invention.

In a specific embodiment, a cancer is considered resistant to a therapy (e.g., an anti-PDL1 therapy, an anti-PD1 therapy, trastuzumab, cetuximab, necitumumab, panitumumab, pertuzumab, ado-trastuzumab emtansine, lapatinib, erlotinib, or any small molecule that targets the HER family of receptors) if it has no response, or has an incomplete response (a response that is less than a complete remission), or progresses, or relapses after the therapy.

In specific embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total), whether detectable or undetectable. In a specific embodiment, "treatment" can also be to prolong survival as compared to expected survival if not receiving treatment.

5.6.2 Diagnostic Uses

In certain embodiments, bispecific binding molecules described herein can be used for diagnostic purposes to detect, diagnose, or monitor a condition described herein (e.g., a condition involving HER2-positive cancer cells). In certain embodiments, bispecific binding molecules for use in diagnostic purposes are labeled as described in Section 5.2.

In certain embodiments, provided herein are methods for the detection of a condition described herein comprising (a) assaying the expression of HER2 in cells or a tissue sample of a subject using one or more bispecific binding molecules described herein; and (b) comparing the level of HER2 expression with a control level, for example, levels in normal tissue samples (e.g., from a subject not having a condition described herein, or from the same patient before onset of the condition), whereby an increase or decrease in the assayed level of HER2 expression compared to the control level of HER2 expression is indicative of a condition described herein.

Antibodies described herein can be used to assay HER2 levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (MA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

In certain embodiments, monitoring of a condition described herein (e.g., a HER2-positive cancer), is carried out by repeating the method for diagnosing for a period of time after initial diagnosis.

Presence of the labeled molecule can be detected in the subject using methods known in the art for in vivo scanning. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MM), and sonography.

5.7 Patient Population

A subject treated in accordance with the methods provided herein can be any mammal, such as a rodent, a cat, a canine, a horse, a cow, a pig, a monkey, a primate, or a human, etc. In a preferred embodiment, the subject is a human. In another preferred embodiment, the subject is a canine.

In certain embodiments, a subject treated in accordance with the methods provided herein has been diagnosed with a HER2-positive cancer, including but not limited to, breast cancer, gastric cancer, an osteosarcoma, desmoplastic small round cell cancer, squamous cell carcinoma of head and neck cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, neuroblastoma, or any other neoplastic tissue that expresses the HER2 receptor.

In a specific embodiment, a subject treated in accordance with the methods provided herein has not been diagnosed with HER2-positive squamous cell carcinoma of head and neck cancer.

In certain embodiments, the subject is resistant to treatment with trastuzumab, cetuximab, lapatinib, erlotinib, or any other small molecule or antibody that targets the HER family of receptors. In a specific embodiment, the tumor that is resistant to treatment with trastuzumab, cetuximab, lapatinib, erlotinib, or any other small molecule or antibody that targets the HER family of receptors is responsive to treatment with a bispecific binding molecule to the invention.

In certain embodiments, a subject treated in accordance with the methods provided herein has a HER2-positive cancer that is resistant to treatment with trastuzumab, cetuximab, lapatinib, erlotinib, or any other small molecule or antibody that targets the HER family of receptors. In certain embodiments, a subject treated in accordance with the methods provided herein has a HER2-positive cancer that is responsive to treatment with a bispecific binding molecule to the invention.

In certain embodiments, the subject treated in accordance with the methods provided herein has previously received one or more chemotherapy regimens for metastatic disease, e.g., brain or peritoneal metastases. In certain embodiments, the subject has not previously received treatment for metastatic disease.

5.8 Doses and Regimens

In certain embodiments, the dose of a bispecific binding molecule as described in Section 5.1 administered to a subject according to the methods provided herein is a dose determined by the needs of the subject. In certain embodiments, the dose is determined by a physician according to the needs of the subject.

In a specific embodiment, the dose of a bispecific binding molecule provided herein is less than the dose of trastuzumab. See, for example, Trastuzumab [Highlights of Prescribing Information]. South San Francisco, Calif.: Genentech, Inc.; 2014. In a specific embodiment, the dose of a bispecific binding molecule provided herein is approximately between 20 and 40 fold less than an FDA-approved dose of trastuzumab.

In certain embodiments, the dose of a bispecific binding molecule as described in Section 5.1 administered to a subject according to the methods provided herein is between 0.01 mg/kg and 0.025 mg/kg, is between 0.025 mg/kg and 0.05 mg/kg, is between 0.05 mg/kg and 0.1 mg/kg, is between 0.1 mg/kg and 0.5 mg/kg, between 0.1 mg/kg and 0.6 mg/kg, between 0.2 mg/kg and 0.7 mg/kg, between 0.3 mg/kg and 0.8 mg/kg, between 0.4 mg/kg and 0.8 mg/kg, between 0.5 mg/kg and 0.9 mg/kg, or between 0.6 mg/kg and 1.

In certain embodiments, the dose of a bispecific binding molecule as described in Section 5.1 administered to a subject according to the methods provided herein is an initial dose followed by an adjusted dose that is the maintenance dose. In certain embodiments, the initial dose is administered once. In certain embodiments, the initial dose is between 0.01 mg/kg and 0.025 mg/kg, is between 0.025 mg/kg and 0.05 mg/kg, is between 0.05 mg/kg and 0.1 mg/kg, is between 0.1 mg/kg and 0.5 mg/kg, between 0.1 mg/kg and 0.6 mg/kg, between 0.2 mg/kg and 0.7 mg/kg, between 0.3 mg/kg and 0.8 mg/kg, between 0.4 mg/kg and 0.8 mg/kg, between 0.5 mg/kg and 0.9 mg/kg, or between 0.6 mg/kg and 1. In certain embodiments, the initial dose is administered via intravenous infusion over 90 minutes. In certain embodiments, the adjusted dose is administered once every about 4 weeks. In certain embodiments, the adjusted dose is administered for at least 13, at least 26, or at most 52 weeks. In certain embodiments, the adjusted dose is administered for 52 weeks. In certain embodiments, the adjusted dose is between 0.01 mg/kg and 0.025 mg/kg, is between 0.025 mg/kg and 0.05 mg/kg, is between 0.05 mg/kg and 0.1 mg/kg, is between 0.1 mg/kg and 0.5 mg/kg, between 0.1 mg/kg and 0.6 mg/kg, between 0.2 mg/kg and 0.7 mg/kg, between 0.3 mg/kg and 0.8 mg/kg, between 0.4 mg/kg and 0.8 mg/kg, between 0.5 mg/kg and 0.9 mg/kg, or between 0.6 mg/kg and 1. In certain embodiments, the adjusted dose is administered via intravenous infusion over 30 minutes. In certain embodiments, the adjusted dose is administered via intravenous infusion over 30 to 90 minutes.

In another specific embodiment, a bispecific binding molecule as described in Section 5.1 for use with the methods provided herein is administered 1, 2, or 3 times a week, every 1, 2, 3, or 4 weeks. In certain embodiments, the bispecific binding molecule is administered according to the following regimen: (i) 1, 2, or 3 administrations in a first week; (ii) 1, 2, 3, or 4 administrations a week after the first week; followed by (iii) 1, 2, or 3 administrations in one week each month for a total of 1, 2, 3, 4, 5, 6, 7, 8, 9, 10, 11, or 12 months. In certain embodiments, the bispecific binding molecule is administered according to the following regimen: (i) 3 administrations in a first week; (ii) 3 administrations a week after the first week; followed by (iii) 3 administrations in one week each month for a total of 1, 2, 3, 4, 5, 6, 7, 8, 9, 10, 11, or 12 months. In certain embodiments, the bispecific binding molecule is administered according to the following regimen: (i) 3 administrations in a first week; (ii) 2 administrations a week after the first week; followed by (iii) 2 administrations in one week each month for a total of 1, 2, 3, 4, 5, 6, 7, 8, 9, 10, 11, or 12 months. In certain embodiments, the bispecific binding molecule is administered according to the following regimen: (i) 3 administrations in a first week; (ii) 1 administration a week after the first week; followed by (iii) 1 administrations in one week each month for a total of 1, 2, 3, 4, 5, 6, 7, 8, 9, 10, 11, or 12 months. In certain embodiments, the bispecific binding molecule is administered according to the following regimen: (i) 2 administrations in a first week; (ii) 2 administrations a week after the first week; followed by (iii) 2 administrations in one week each month for a total of 1, 2, 3, 4, 5, 6, 7, 8, 9, 10, 11, or 12 months. In certain embodiments, the bispecific binding molecule is administered according to the following regimen: (i) 2 administrations in a first week; (ii) 1 administration a week after the first week; followed by (iii) 1 administrations in one week each month for a total of 1, 2, 3, 4, 5, 6, 7, 8, 9, 10, 11, or 12 months. In certain embodiments, the bispecific binding molecule is administered according to the following regimen: (i) 1 administrations in a first week; (ii) 1 administrations a week after the first week; followed by (iii) 1 administrations in one week each month for a total of 1, 2, 3, 4, 5, 6, 7, 8, 9, 10, 11, or 12 months.

In certain embodiments, a bispecific binding molecule as described in Section 5.1 is administered to a subject according to the methods provided herein in combination with a second pharmaceutically active agent as described in Section 5.9.

In another preferred embodiment, the bispecific binding molecule is administered intrathecally, intraventricularly in the brain, intraparenchymally in the brain, or intraperitoneally.

5.9 Combination Therapy

In certain embodiments, a bispecific binding molecule provided herein, or polynucleotide, vector, or cell encoding the bispecific binding molecule, may be administered in combination with one or more additional pharmaceutically active agents, e.g., a cancer chemotherapeutic agent. In certain embodiments, such combination therapy may be achieved by way of simultaneous, sequential, or separate dosing of the individual components of the treatment. In certain embodiments, the bispecific binding molecule or polynucleotide, vector, or cell encoding the bispecific binding molecule, and one or more additional pharmaceutically active agents may be synergistic, such that the dose of either or of both of the components may be reduced as compared to the dose of either component that would be given as a monotherapy. Alternatively, In certain embodiments, the bispecific binding molecule or polynucleotide, vector, or cell encoding the bispecific binding molecule and the one or more additional pharmaceutically active agents may be additive, such that the dose of the bispecific binding molecule and of the one or more additional pharmaceutically active agents is similar or the same as the dose of either component that would be given as a monotherapy.

In certain embodiments, a bispecific binding molecule provided herein, or polynucleotide, vector, or cell encoding the bispecific binding molecule is administered on the same day as one or more additional pharmaceutically active agents. In certain embodiments, the bispecific binding molecule or polynucleotide, vector, or cell encoding the bispecific binding molecule is administered 1, 2, 3, 4, 5, 6, 7, 8, 9, 10, 11, or 12 hours before the one or more additional pharmaceutically active agents. In certain embodiments, the bispecific binding molecule or polynucleotide, vector, or cell encoding the bispecific binding molecule is administered 1, 2, 3, 4, 5, 6, 7, 8, 9, 10, 11, or 12 hours after the one or more additional pharmaceutically active agents. In certain embodiments, the bispecific binding molecule or polynucleotide, vector, or cell encoding the bispecific binding molecule is administered 1, 2, 3, or more days before the one or more additional pharmaceutically active agents. In certain embodiments, the bispecific binding molecule or polynucleotide, vector, or cell encoding the bispecific binding molecule is administered 1, 2, 3 or more days after the one or more additional pharmaceutically active agents. In certain embodiments, the bispecific binding molecule or polynucleotide, vector, or cell encoding the bispecific binding molecule is administered 1, 2, 3, 4, 5, or 6 weeks before the one or more additional pharmaceutically active agents. In certain embodiments, the bispecific binding molecule or polynucleotide, vector, or cell encoding the bispecific binding molecule is administered 1, 2, 3, 4, 5, or 6 weeks after the one or more additional pharmaceutically active agents.

In certain embodiments, the additional pharmaceutically active agent is doxorubicin. In certain embodiments, the additional pharmaceutically active agent is cyclophosphamide. In certain embodiments, the additional pharmaceutically active agent is paclitaxel. In certain embodiments, the additional pharmaceutically active agent is docetaxel. In certain embodiments, the one or more additional pharmaceutically active agents is carboplatin.

In certain embodiments, the additional pharmaceutically active agent is a cytokine, such as, for example, IL15, IL15R/IL15 complex, IL2, or GMCSF.

In certain embodiments, the additional pharmaceutically active agent is an agent that increases cellular HER2 expression, such as, for example, external beam or radioimmunotherapy. See, for example, Wattenberg et al., 2014, British Journal of Cancer, 110: 1472.

In certain embodiments, the additional pharmaceutically active agent is a radiotherapeutic agent.

In certain embodiments, the additional pharmaceutically active agent is an agent that directly controls the HER2 signaling pathway, e.g., lapatinib. See, for example, Scaltiri et al., 2012, 28(6): 803-814.

In certain embodiments, the additional pharmaceutically active agent is an agent that increases cell death, apoptosis, autophagy, or necrosis of tumor cells.

In certain embodiments, a bispecific binding molecule provided herein, or polynucleotide, vector, or cell encoding the bispecific binding molecule is administered in combination with two additional pharmaceutically active agents, e.g., those used in combination with trastuzumab (see, Trastuzumab [Highlights of Prescribing Information]. South San Francisco, Calif.: Genentech, Inc.; 2014). In certain embodiments, the two additional pharmaceutically active agents are doxorubicin and paclitaxel. In certain embodiments, the two additional pharmaceutically active agents are doxorubicin and docetaxel. In certain embodiments, the two additional pharmaceutically active agents are cyclophosphamid and paclitaxel. In certain embodiments, the two additional pharmaceutically active agents are cyclophosphamide and docetaxel. In certain embodiments, the two additional pharmaceutically active agents are docetaxel and carboplatin. In certain embodiments, the two additional pharmaceutically active agents are cisplatin and capecitabine. In certain embodiments, the two additional pharmaceutically active agents are cisplatin and 5-fluorouracil.

In certain embodiments, a bispecific binding molecule provided herein, or polynucleotide, vector, or cell encoding the bispecific binding molecule is administered as a single agent following multi-modality anthracycline based therapy.

In certain embodiments, a bispecific binding molecule provided herein, or polynucleotide, vector, or cell encoding the bispecific binding molecule is administered after one or more chemotherapy regimens for metastatic disease, e.g., brain or peritoneal metastases. In specific embodiments, a bispecific binding molecule provided herein, or polynucleotide, vector, or cell encoding the bispecific binding molecule is administered in combination with cytoreductive chemotherapy. In a specific embodiment, the administering is performed after treating the subject with cytoreductive chemotherapy.

In specific embodiments, a bispecific binding molecule provided herein, polynucleotide, vector, or cell encoding the bispecific binding molecule, or a pharmaceutical composition comprising the bispecific binding molecule, is administered in combination with T cell infusion. In specific embodiments, the bispecific binding molecule is not bound to a T cell. In specific embodiments, the bispecific binding molecule is bound to a T cell. In specific embodiments, the binding of the bispecific binding molecule to the T cell is noncovalently. In a specific embodiment, the administering of a bispecific binding molecule provided herein, polynucleotide, vector, or cell encoding the bispecific binding molecule, or a pharmaceutical composition comprising the bispecific binding molecule is performed after treating the patient with T cell infusion. In specific embodiments the T cell infusion is performed with T cells that are autologous to the subject to whom the T cells are administered. In specific embodiments, the T cell infusion is performed with T cells that are allogeneic to the subject to whom the T cells are administered. In specific embodiments, the T cells can be bound to molecules identical to a bispecific binding molecule as described herein. In specific embodiments, the binding of the T cells to molecules identical to the bispecific binding molecule is noncovalently. In specific embodiments, the T cells are human T cells. Methods that can be used to bind bispecific binding molecules to T cells are known in the art. See, e.g., Lum et al., 2013, Biol Blood Marrow Transplant, 19:925-33, Janeway et al., Immunobiology: The Immune System in Health and Disease, $5^{th}$ edition, New York: Garland Science; Vaishampayan et al., 2015, Prostate Cancer, 2015:285193, and Stromnes et al., 2014, Immunol Rev. 257(1):145-164. See, also, Vaishampayan et al., 2015, Prostate Cancer, 2015:285193, which describes the following exemplary, non-limiting method for binding bispecific binding molecules to T cells:

Peripheral blood mononuclear cells (PBMCs) can be collected to obtain lymphocytes for activated T cell expansion from 1 or 2 leukopheresis. PBMCs can be activated with, for example, 20 ng/mL of OKT3 and expanded in 100 IU/mL of IL-2 to generate 40-320 billion activated T cells during a maximum of 14 days of culture under cGMP conditions as described in Ueda et al., 1993, Transplantation, 56(2):351-356 and Uberti et al., 1994, Clinical Immunology and Immunopathology, 70(3):234-240. Cells are grown in breathable flasks (FEP Bag Type 750-C1, American Fluoroseal Corporation, Gaithersburg, Md.) in RPMI 1640 medium (Lonza) supplemented with 2% pooled heat inactivated human serum. Activated T cells are split approximately every 2-3 days based on cell counts. After 14 days, activated T cells are cultured with 50 ng of a bispecific binding molecule described herein per $10^6$ activated T cells. The mixture is then washed and cryopreserved.

6. EXAMPLES

6.1 Example 1

6.1.1 Introduction

This example describes a HER2/CD3 bi-specific binding molecule (herein referred to as "HER2-BsAb") based on an IgG1 platform. This platform was utilized to allow for: (1) an optimal size to maximize tumor uptake, (2) bivalency towards the tumor target to maintain avidity, (3) a scaffold that is naturally assembled like any IgG (heavy chain and light chain) in CHO cells, purifiable by standard protein A affinity chromatography, (4) structural arrangement to render the anti-CD3 component functionally monovalent, hence reducing spontaneous activation of T cells, and (5) a platform with proven tumor targeting efficiency in animal models. This bispecific binding molecule has the same specificity as trastuzumab; but also recruits and activates CD3(+) T cells redirecting them against HER2 expressing tumor cells, generating robust anti-tumor responses. Without being bound by any theory, the effectiveness of this BsAb centers on the exploitation of the cytotoxic potential of polyclonal T cells, and its unique capacity to target tumor cells that express even low levels of HER2, independent of the activation status of the HER2 pathway.

6.1.2 Materials and Methods

6.1.2.1 HER2-BsAb Design, Production, and Purification Analyses

The HER2-BsAb format was designed as a huOKT3 scFv fusion to the C-terminus of the light chain of a human IgG1. The $V_H$ was identical to that of Trastuzumab IgG1, except N297A mutation in a standard human IgG1 Fc region for aglycosylated form (SEQ ID NO: 62), while the light chain is constructed as VL-Cκ-$(G_4S)_3$-scFv (SEQ ID NO: 60). Nucleotide sequences encoding VH and VL domains from Trastuzumab, and the huOKT3 scFv were synthesized by GenScript with appropriate flanking restriction enzyme sites, and were subcloned into a standard mammalian expression vector. HER2-C825 control BsAb (C825 is a murine scFv antibody with high affinity for 1,4,7,10-tetraazacyclododecane-1,4,7,10-tetraacetic acid (DOTA)-metal complexes with lanthanides including lutetium and yttrium) was constructed in a similar way.

Linearized plasmid DNA was used to transfect CHO-S cells (Invitrogen) for stable production of BsAb. 2×$10^6$ cells were transfected with 5 μg of plasmid DNA by Nucleofection (Lonza) and then recovered in CD OptiCHO medium supplemented with 8 mM L-glutamine (Invitrogen) for 2 d at 37° C. in 6-well culture plates. Stable pools were selected with 500 μg/mL hygromycin for approximately two weeks and single clones were then selected out with limited dilution. HER2-BsAb titer was determined by HER2(+) AU565 cell and CD3(+) Jurket cell ELISA, respectively, and stable clones with highest expression were selected.

The BsAb producer line was cultured in OptiCHO medium and the mature supernatant harvested. A protein A affinity column (GE Healthcare) was pre-equilibrated with 25 mM sodium citrate buffer with 0.15 M NaCl, pH 8.2. Bound BsAb was eluted with 0.1 M citric acid/sodium citrate buffer, pH 3.9 and neutralized with 25 mM sodium citrate, pH 8.5 (1:10 v/v ratio). For storage, BsAb was dialyzed into 25 mM sodium citrate, 0.15 M NaCl, pH 8.2 and frozen in aliquots at −80° C. Two micrograms of the protein was analyzed by SDS-PAGE under reducing conditions using 4-15% Tris-Glycine Ready Gel System (Bio-Rad). Invitrogen SeeBlue Plus2 Pre-Stained Standard was used as the protein MW marker. After electrophoresis, the gel was stained using Coomassie G-250 (GelCode Blue Stain Reagent; Pierce). The purity of HER2-BsAb was also evaluated by size-exclusion high-performance liquid chromatography (SE-HPLC). Approximately 20 μg of protein was injected into a TSK-GEL G3000SWXL 7.8 mm×30 cm, 5 μm column (TOSOH Bioscience) with 0.4 M $NaClO_4$, 0.05 M $NaH_2PO_4$, pH 6.0 buffer at flow rate of 0.5 mL/min, and UV detection at 280 nm. Ten microliters of gel-filtration standard (Bio-Rad) was analyzed in parallel for MW markers.

6.1.2.2 FACS Analyses

Cells were incubated with 5 μg/mL of primary antibody (trastuzumab, HER2-BsAb, or cetuximab) for thirty minutes at 4° C. in PBS, and a secondary phycoerythrin-labeled antibody specific for human Fc was used after wash of excess primary antibody. Cells were fixed with 1% paraformaldehyde (PFA) prior to analysis on FACSCalibur cytometer (BD biosciences). Controls were cells with secondary antibody only, for which the mean fluorescent intensity (MFI) was set to 5. FACS data display the MFI in the upper right panel of each plot.

6.1.2.3 $^{51}Cr$ Release Assay

The $^{51}Cr$ release assay was performed with effector T cells cultured in vitro in the presence of anti-CD3 and anti-CD28 for about 14 days. All target tumor cells were harvested with 2 mM EDTA in PBS, labeled with $^{51}Cr$ (Amersham, Arlington Height, Ill.) at 100 μCi/106 cells at 37° C. for 1 h. 5000 target cells/well were mixed with 50,000 effector cells (E:T=10:1) and BsAb antibodies in 96-well polystyrene round-bottom plates (BD Biosciences) to a final volume of 250 μl/well. The plates were incubated at 37° C. for 4 h. The released $^{51}Cr$ in supernatant was counted in a γ-counter (Packed Instrument, Downers Grove, Ill.). Percentage of specific release was calculated using the formula: (experimental cpm−background cpm)/(total cpm−background cpm)×100%, where cpm represented counts per minute of $^{51}Cr$ released. Total release was assessed by lysis with 10% SDS (Sigma, St Louis, Mo.), and background release was measured in the absence of effector cells. EC50 was calculated using SigmaPlot software.

6.1.2.4 Competition Assay

To assess the ability of trastuzumab and/or huOKT3 to interfere with HER2-BsAb binding, the HER2-positive SKOV3 cell line was incubated for thirty minutes a 4° C. with PBS or with 10 μg/mL of trastuzumab or huOKT3. Cells were subsequently stained with 10 μg/mL of Alexa-Fluor 488-conjugated HER2-BsAb and analyzed by flow cytometry. Alexa-Fluor 488-conjugated HER2-BsAb was generated with the Zenon® Alexa Fluor® 488 Human IgG Labeling Kit (Life Technologies) according to the manufacturer's instructions.

6.1.2.5 Binding Assay

Binding assays were performed by Surface Plasmon Resonance using Biacore T100 similar as described in Okazaki et al., 2004, J Mol Biol; 336(5): 1239-1249.

6.1.2.6 Avidity Assay

To compare the avidity of HER2-BsAb and trastuzumab, HER2-positive SKOV3 cells were incubated with 10 fold dilutions (from 10 to $1 \times 10^{-5}$ µg/mL) of trastuzumab or HER2-BsAb and analyzed by flow cytometry with FITC-labeled human Fc-specific antibody as the secondary antibody. MFI was plotted against the antibody concentration and the curves were compared.

6.1.2.7 Proliferation Assay

To determine anti-proliferative effects, cells were treated with isotype control monoclonal antibody, 10 nM lapatinib (as a positive control), 10 µg/mL HER2-BsAb, 10 µg/mL Trastuzumab, 10 nM lapatinib, 10 nM erlotinib, 10 nM neratinib, or 10 µg/mL cetuximab for 72 hours and cell proliferation assayed. Cell proliferation was determined using an ELISA plate reader and the WST-8 kit (Dojindo technologies) following the manufacturer's instructions and using the formula: % survival rate=(Sample-Background)/ (Negative control-Background). Lapatinib (MSKCC pharmacy) was ground using a mortar and pestle and suspended in DMSO as previously described. To determine statistical significance, the results were analyzed using one-way ANOVA using Prism 6.0.

6.1.2.8 qRT-PCR

RNA was extracted when cells were at 70% confluence and cDNA was analyzed in a prism 7700 sequence detection system using the HER2 specific, commercially available kit Hs01001580_m1 from Applied Biosciences.

6.1.2.9 Animals and In Vivo Assays

For in vivo studies, BALB-Rag2-KO-IL-2R-γc-KO (DKO) mice (derived from colony of Dr. Mamoru Ito, CIEA, Kawasaki, Japan). See, for example, Koo et al., 2009, Expert Rev Vaccines, 8: 113-120 and Andrade et al., 2011, Arthritis Rheum, 2011, 63: 2764-2773. MCF7 cells or HCC1954 were mixed at a 1:1 ratio with PMBCs (unactivated, from buffy coat) and implanted in DKO mice subcutaneously. Four days post implantation, mice were treated with PBS, 10 µg of trastuzumab, or 10 µg of HER2-BsAb twice a week for two weeks. Tumor size was measured at the indicated days post implantation. Tumor size was determined by either calipers with the formula V=0.5 (length× width×width), or by using the Peira TM900 optical system.

For the metastatic model, MCF7 cells expressing luciferase were administered to DKO mice intravenously. Four days post administration, mice were treated with 100 ug of HER2-BsAb, 20 ug or HER2-BsAb, or 20 ug of a HER2-BsAb lacking CD3 targeting (HER2-C825) twice a week for three weeks, with or without intravenous administration of $5 \times 10^6$ PBMC. Tumor size was quantified at the indicated timepoints using IVIS 200 (Xenogen) to quantify luciferin bioluminescence.

6.1.3 Results

6.1.3.1 HER2-BsAb Binds to Both Tumor Cells and T Cells.

The HER2-BsAb was generated utilizing a trastuzumab variant comprising a N297A mutation in the human IgG1 Fc region to remove glycosylation (SEQ ID NO: 62). The BsAb light chain fusion polypeptide was generated by attaching the anti-CD3 humanized OKT3 (huOKT3) single chain Fv fragment (ScFv) to the carboxyl end of the trastuzumab IgG1 light chain via a C-terminal $(G_4S)_3$ linker (FIG. 1A and SEQ ID NO: 60). To avoid aggregation, a cysteine at position 105 of the variable heavy chain of huOKT3 was substituted with serine. A N297A mutation was also introduced into the HER2-BsAb Fc region to eliminate binding of HER2-BsAb to Fc receptors. This mutation has previously been shown to eliminate the capacity of human IgG1-Fc binding to CD16A (FIG. 1D) and CD32A Fc receptors (FIG. 1E).

To produce the HER2-BsAb, a mammalian expression vector encoding both the heavy chain and the light chain fusion polypeptide was transfected into CHO-S cells, stable clones were selected, supernatants collected, and the HER2-BsAb was purified by protein A affinity chromatography. Biochemical purity analysis of the BsAb is depicted in FIG. 1B and FIG. 1C. Under reducing SDS-PAGE conditions, HER2-BsAb gave rise to two bands at around 50 KDa, since the huOKT3 scFv fusion to trastuzumab light chain increased the MW to ~50 KDa. SEC-HPLC showed a major peak (97% by UV analysis) with an approximate MW of 210 KDa, as well as a minor peak of multimers removable by gel filtration. The HER2-BsAb was stable by SDS-PAGE and SEC-HPLC after multiple freeze and thaw cycles.

FACS and immunostaining were performed to assess the binding of HER2-BsAb to both target cells and effector cells. Trastuzumab and HER2-BsAb displayed comparable binding to the HER2-positive breast carcinoma cell line, AU565 (FIG. 2A). In contrast, HER2-BsAb demonstrated more than 20-fold less binding to CD3+ T cells than huOKT3 (FIG. 2B). This is consistent with the observation that light chain-anchored scFv had lower avidity for T cells than regular huOKT3 IgG1, purposely designed to minimize cytokine release in the absence of target tumor cells.

The lower avidity of HER2-BsAb for T cells was further confirmed by the binding affinity analysis by Biacore as described in Cheung et al. 2012, OncoImmunology, 1:477-486. For antigen CD3, HER2-BsAb had a $k_{on}$ at $4.53 \times 10^5 M^{-1}s^{-1}$, a $k_{off}$ at $8.68 \times 10^{-2}$ $s^{-1}$, and overall $K_D$ at 192 nM; comparable to parental huOKT3 IgG1-aGlyco at $k_{off}$ ($1.09 \times 10^{-1}$ $s^{-1}$), but less at $k_{on}$ ($1.68 \times 10^6$ $M^{-1}s^{-1}$) and overall $K_D$ (64.6 nM). In summary, HER2-BsAb had much lower $k_{on}$ than its parental huOKT3-aGlyco, suggesting less chance of BsAb binding to and activating T cells under the same condition, hence less cytokine release.

6.1.3.2 HER2-BsAb Redirected T Cell Killing of Human Tumor Cell Lines.

To evaluate whether HER2-BsAb could redirect T cells to kill tumor cells, T cell cytotoxicity on HER2(+) breast cancer AU565 cells was tested in a standard 4-hour $^{51}$Cr release assay. Substantial killing of tumor cells was observed n the presence of HER2-BsAb, with an EC50 at 300 fM (FIG. 3). Moreover, the killing was effective for an extensive panel of human tumor cell lines including breast carcinoma, ovarian carcinoma, melanoma, osteosarcoma, Ewing's sarcoma, rhabdomyosarcoma, and neuroblastoma, wherein the killing potency correlated with the HER2 expression level in the cells by FACS (FIG. 4).

6.1.3.3 HER2-BsAb Mediates Tumor Antigen Specific T Cell Cytotoxicity.

To investigate the tumor antigen specificity of HER2-BsAb in T cell cytotoxicity, a cytotoxicity assay was performed in the HER2-positive UM SCC 47 cells (a model for head and neck cancer) and in the HER2-negative HTB-132 cells (a model for breast cancer). HER2-BsAb mediated T cell cytotoxicity against the HER2-positive UM-SCC47 cells (EC50 of 14.5 pM), but not against the HER2-negative HTB-132 cells (FIG. 5A).

To investigate the specificity of HER2-BsAb in the T cell cytotoxicity, HER2-positive cells were first blocked with huOKT3 or with trastuzumab. In the absence of HER2-BsAb, the T cells displayed minimal cytotoxicity, reassuring that T cells on their own have minimum non-specific cytotoxicity. Both huOKT3 and trastuzumab blocked the ability of HER2-BsAb to induce T cell cytotoxicity.

6.1.3.4 HER2-BsAb Mediates T Cell Cytotoxicity Against HER2-Positive Cells Below the HER2 Threshold of Detection by Flow Cytometry.

The HER2+ ovarian carcinoma cell line SKOV3 was used in a $^{51}$Cr cytotoxicity assay with 10 fold dilutions of HER2-BsAb in the presence of T cells. These same cells were stained using HER2-BsAb at the same concentrations and analyzed by flow cytometry, MFI was plotted over the same x-axis as cytotoxicity, and EC50 was calculated for both curves. HER2-BsAb mediated T cell cytotoxicity against HER2-positive cells even when HER2-BsAb binding was not detected by flow cytometry (FIG. 6). Comparing the EC50 for the cytotoxicity assay (2 pM) vs EC50 for flow cytometry curve (3.5 nM) suggests that T cells in the presence of HER2-BsAb were 2500× more effective in detecting HER2-positive cells than flow cytometry.

6.1.3.5 HER2-BsAb has the Same Specificity, Affinity and Antiproliferative Effects as Trastuzumab.

Prior to treatment with HER2-BsAb, HER2-positive cells were pre-incubated with trastuzumab to determine if HER2-BsAb shares the same antigen specificity as trastuzumab. Pre-incubation with trastuzumab blocked HER2-BsAb binding to the cells, demonstrating a shared specificity (FIG. 7A). To compare the affinity of HER2-BsAb to trastuzumab, HER2-positive cells were incubated with dilutions of trastuzumab or HER2-BsAb and analyzed by flow cytometry for cellular binding. Plotting of MFI against the antibody concentration revealed similar curves for trastuzumab and HER2-BsAb, demonstrating a similar binding affinity (FIG. 7B). Further, trastuzumab and HER2-BsAb demonstrated similar anti-proliferative effects against HER2-positive cells (FIG. 7C).

6.1.3.6 HER2-BsAb Mediated T Cell Cytotoxicity Against SCCHN with an EC50 in the Picomolar Range.

The level and frequency of HER2 in the previously characterized head and neck cancer cell lines 93-VU-147T, PCI-30, UD-SCC2, SCC90, UMSCC47 and PCI-15B were assessed via flow cytometry with trastuzumab. The cells were also tested for HER2 expression by qRT-PCR (FIG. 8). HER2 was comparably expressed in the panel of head and neck cancer cell lines. Finally, the level of cytotoxicity in the presence of T cells and HER2-BsAb was correlated with the level of HER2 in the cells, revealing HER2-BsAb displays an EC50 in the picomolar range for these head and neck cell lines (FIG. 8).

6.1.3.7 HER2-BsAb Mediates T Cell Cytotoxicity Against SCCHN Resistant to Other HER Targeted Therapies.

To determine the EGFR and HER2 status of the SCCHN cell line PCI-30, cells were stained with trastuzumab or cetuximab and analyzed by flow cytometry as previously described (FIG. 9A). A proliferation assay demonstrated that these cells are resistant to the HER-specific targeted therapies, trastuzumab, cetuximab, lapatinib, erlotinib and pan-HER inhibitor neratinib (FIG. 9B). However, PCI-30 cells were sensitive to treatment with HER2-BsAb utilizing three different cytotoxicity assays (FIG. 9C). HER2-BsAb generated potent cytotoxic responses against PCI-30 independent of their sensitivity to other HER targeted therapies, even when these drugs target more than one of these receptors. These assays suggest that HER2-BsAb was able to generate powerful cytotoxic responses, regardless of target cell sensitivity to EGFR or HER2 targeted therapies.

6.1.3.8 HER2-BsAb Mediated T Cell Cytotoxicity Against Osteosarcoma Cell Lines with an EC50 in the Picomolar Range.

The previously characterized osteosarcoma cell lines, RG-160, CRL 1427 and U2OS, were assessed for their HER2 expression by flow cytometry with trastuzumab (FIG. 10) and by qRT-PCR, and the levels of HER2 were correlated with cytotoxicity in the presence of T cells and HER2-BsAb (FIG. 10). All tested cell lines were positive for HER2, although the expression level varied. Further, all HER2-positive cells were sensitive to T cell cytotoxicity mediated by HER2 BsAb, with an EC50 ranging from 11-25 pM.

6.1.3.9 HER2-BsAb Mediates T Cell Cytotoxicity Against HER-Therapy Resistant Osteosarcoma Cell Lines.

U2OS cells are a HER2-positive, EGFR-positive osteosarcoma cell line (FIG. 11A). U2OS cells were analyzed for their sensitivity to trastuzumab, cetuximab, lapatinib and the pan-HER inhibitor Neratinib by proliferation assay in the presence of each of the inhibitors. These cells were resistant to cetuximab and trastuzumab with minimal sensitivity to Lapatinib, erlotinib and neratinib (FIG. 11B). These same cells were tested for sensitivity for T cell cytotoxic responses mediated by HER2-BsAb. HER2-BsAb generated potent cytotoxic responses against U2OS cells using three different cytotoxicity assays, independent of its sensitivity to other HER targeted therapies (FIG. 11C).

6.1.3.10 HER2-BsAb Mediates T Cell Cytotoxicity Against HER-Therapy Resistant Cervical Cancer HeLa Cells.

HeLa cells are a HER2-positive, EGFR-positive cervical carcinoma cell line (FIG. 12A). HeLa cells were analyzed for their sensitivity to HER family tyrosine kinase inhibitors, Erlotinib, Lapatinib or Neratinib, or to the HER specific antibodies, Cetuximab or trastuzumab. These results demonstrated that HeLa cells are pan-resistant to these therapies (FIG. 12B). However, these same cells were tested for sensitivity for T cell cytotoxic responses mediated by HER2-BsAb. HER2-BsAb generated potent cytotoxic responses against HeLa cells using three different cytotoxicity assays, independent of its sensitivity to other HER targeted therapies (FIG. 12C). Interestingly, pretreatment with lapatinib increased sensitivity to HER2-BsAb mediated cytotoxicity, even when lapatinib alone had no effect on cell proliferation.

6.1.3.11 HER2-BsAb is Effective Against Human Breast Cancer in Humanized Mice.

For in vivo therapy studies, BALB-Rag2-KO-IL-2R-γc-KO (DKO) mice (derived from colony of Dr. Mamoru Ito, CIEA, Kawasaki, Japan) were used. See, for example, Koo et al. 2009, Expert Rev Vaccines 8: 113-120 and Andrade et al. 2011, Arthritis Rhem 63: 2764-2773. MCF7-Luciferase breast cancer cells were mixed with peripheral blood mononuclear cells (PBMC) and planted subcutaneously. Four days post cell implantation, the mice were treated with HER2-BsAb or with trastuzumab and the tumor size was analyzed over time (FIG. 13). HER2-BsAb demonstrated a significant suppression of tumor progression. HER2-BsAb was also effective against tumor progression when the trastuzumab resistant HCC1954 breast cancer cells (See, for example, Huang et al., 2011, Breast Cancer Research, 13: R84) were planted subcutaneously with PBMCs (FIG. 14).

To assess a metastatic tumor model, MCF7-Luciferace cells were inoculated intravenously. HER2-BsAb was administered and subsequently in combination with PBMC. Tumor luciferin bioluminescence signal demonstrated HER2-BsAb plus PBMC showed complete suppression of tumor progression (FIG. 15, FIG. 16A, FIG. 16B, FIG. 16C, and FIG. 16D).

6.1.4 Conclusions

The aglycosylated HER2-BsAb allowed for minimized Fc functions and avoidance of a cytokine storm and elimination of all complement activation, complement mediated and complement receptor mediated immune adherence. In addition, despite bivalency of huOKT3 in the IgG-scFv platform, binding to CD3 was functionally monovalent; hence there was no spontaneous activation of T cells in the absence of tumor target. HER2-BsAb displayed potent cytotoxicity against HER2-positive tumor cells in vitro, even against cells with low antigen expression, or cells that are resistant to trastuzumab, cetuximab, lapatinib, erlotinib or the pan-HER inhibitor neratinib. HER2-BsAb also displayed potent cytotoxicity against breast cancer, ovarian cancer, SCCHN, osteosarcomas, and sarcomas. Finally, HER2-BsAb displayed strong in vivo efficacy against tumor xenografts, substantially better than the trastuzumab hIgG1 counterpart.

6.2 Example 2

This example provides (a) a more detailed description of certain of the experiments described in Example 1 (Section 6.1); and (b) additional experiments as compared to Example 1 (Section 6.1).

6.2.1 Introduction

Trastuzumab has significantly improved patient outcomes in breast cancer and has also been key in the design and implementation of other targeted therapies (Singh et al., 2014, Br J Cancer 111:1888-98). However, HER2 expression does not guarantee a clinical response to trastuzumab or other HER2 targeted therapies (Gajria et al., 2011, Expert Review of Anticancer Therapy, 11(2):263-75; Lipton et al., 2013, Breast Cancer Research and Treatment, 141(1):43-53). Less than 35% of patients with HER2 positive breast cancer initially respond to trastuzumab and 70% of the initial responders will ultimately progress with metastatic disease within a year (Vu and Claret., 2011, Frontiers in Oncology 2:62). In osteosarcoma and Ewing's sarcoma, where high levels of HER2 expression are associated with decreased survival (Gorlick et al., 1999, Journal of Clinical Oncology: Official Journal of The American Society of Clinical Oncology 17:2781-2788), trastuzumab has not shown any benefit even when used in conjunction with cytotoxic chemotherapy (Ebb et al., 2012, Journal of Clinical Oncology: Official Journal of the American Society of Clinical Oncology 30:2545-2551). Furthermore, trastuzumab, like other HER targeted therapies, has shown modest or no benefit against HER2-positive head and neck cancer (Pollock et al., 2014, Clinical Cancer Research, 21(3):526-33).

The reasons for these failures are complex and only partially understood. The genomic diversity and constant evolution of malignancies make them less prone to oncogene addiction, a requirement for the success of targeted therapy. Furthermore, even when oncogene addiction is present, resistance can emerge from selection pressure induced by the use of targeted therapies (Lipton et al., 2013, Breast Cancer Research and Treatment, 141(1):43-53). In fact, despite the initial enthusiasm received, the majority of targeted therapies have not produced a significant benefit in the overall cure of patients receiving it (Nathanson et al., 2014, Science, 343:72-76). A different approach, one that selectively targets malignant cells that overexpress HER family receptors, and that can generate cytotoxic anti-tumor responses independently of the receptor activation status can be beneficial.

Blinatumomab—a CD19/CD3 BsAb was approved in 2014 for treating Acute Lymphoplastic Leukemia (Sanford, 2015, Drugs 75:321-7). However, despite its promising results, the unfavorable PK of these small size molecules necessitates prolonged infusions, complicating their administration (Shalaby et al., 1995, Clin Immunol Immunopathol 74:185-92, 1995; Portell et al., 2013, Clin Pharmacol 5:5-11). Furthermore, the resulting cytokine release syndrome (CRS) still poses costly and often life-threatening complications. Importantly, despite the ability of bispecific antibodies to activate T cells, the same inhibitory pathways that regulate classic T cell function might still limit their effectiveness. For example, the heterodimeric design of a monovalent binding HER2/CD3 bispecific antibody was inhibited by the PD-1/PD-L1 inhibitory axis (Junttila et al., 2014, Cancer Res 74:5561-71).

The present example provides a bispecific binding molecule (herein referred to as "HER2-BsAb") that offers two distinct advantages over the existing technologies: (1) it is based on the fully humanized HER2 specific IgG1 mAb Trastuzumab, preserving its pharmacologic advantages (Wittrup et al., 2012, Methods Enzymol 503:255-68) and bivalent binding to HER2; maximizing tumor avidity; and (2) its binding to CD3 is functionally monovalent through the scFv derived from the humanized huOKT3 mAb sequence. Thus, HER2-BsAb is built on two mAbs with extensive records of clinical safety. Furthermore, this is a platform with its Fc function deleted to eliminate all antibody-dependent cell-mediated cytotoxicity (ADCC) and CMC activities in order to reduce the cytokine release syndrome.

The data presented in this example demonstrate the ability of HER2-BsAb to produce potent anti-tumor responses, both in vitro and in vivo, against tumor cells that are resistant to HER2 targeted therapy or trastuzumab.

6.2.2 Materials and Methods

6.2.2.1 Cell Lines

All cell lines were purchased from ATCC (Manassas Va.) except: UM-SCC47, obtained from Dr. Carey at the University of Michigan; SCC-90, PCI-30 and PCI-15B, obtained from Dr. Robert Ferris at the University of Pittsburgh; HCC1954, obtained from Dr. Sarat Chandarlapaty at Memorial Sloan Kettering Cancer Center; 93-VU-147T and HeLa, obtained from Dr. Luc Morris; and UD-SCC2, obtained from Henning Bier at Hals-Nasen-Ohrenklinik and Poliklinik. All cells were authenticated by short tandem repeat profiling using PowerPlex 1.2 System (Promega), and periodically tested for mycoplasma using a commercial kit (Lonza). The luciferase-labeled tumor cell lines MCF7-Luc were generated by retroviral infection with a SFG-GFLuc vector.

6.2.2.2 HER2-BsAb Design and Expression in CHO-S Cells

In the HER2-BsAb IgG-scFv format (FIG. 17A, "HER2-BsAb"), the $V_H$ was identical to that of the trastuzumab IgG1 $V_H$, except that an N297A mutation in the Fc region was introduced into the HER2-BsAb to remove glycosylation, thereby depleting Fc function (SEQ ID NO: 62). The light chain fusion polypeptide was constructed by extending the trastuzumab IgG1 light chain with a C-terminal $(G_4S)_3$ linker followed by huOKT3 scFv (SEQ ID NO: 60). The DNA encoding both the heavy chain and the light chain was inserted into a mammalian expression vector, transfected into CHO-S cells, and stable clones of the highest expression were selected. Supernatants were collected from shaker flasks and the HER2-BsAb was purified by protein A affinity chromatography. The control BsAb, HER2-C825 (composed of SEQ ID NOS: 71 and 72), was generated as previously described (Xu et al., 2015, Cancer Immunol Res 3:266-77; Cheal et al., 2014, Mol Cancer Ther 13:1803-12).

6.2.2.3 Other Antibodies and Small Molecules

Fluorophore-labeled HER2-BsAb was generated with the Zenon® Alexa Fluor® 488 Human IgG Labeling Kit from Life Technologies following the manufacturer's instructions. Pembrolizumab, cetuximab, trastuzumab, Erlotinib, Lapatinib and Neratinib were purchased from the Memorial Sloan Kettering Cancer Center pharmacy. Small molecules were re-suspended in DMSO. The CD4, CD8, CD16 and CD56 antibodies were purchased from BD Biosciences (San Jose Calif.). The commercially available PE labeled PD-L1 specific mAb 10F.9G2 was purchased from BioLegend.

6.2.2.4 Cell Proliferation Assays

For cell proliferation assays, 5,000 tumor cells were plated using RPMI-1640 supplemented with 10% FBS in a 96 well plate for 36 hours before being treated with lapatinib or the antibodies at the specified concentrations. Cell proliferation was determined using an ELISA plate reader and the WST-8 kit (Dojindo technologies) following the manufacturer's instructions and using the formula: % survival rate=(Sample-Background)/(Negative control-Background). Lapatinib (Memorial Sloan Kettering Cancer Center pharmacy) was ground using a mortar and pestle and suspended in DMSO as previously described (Chen et al., 2012, Molecular cancer therapeutics 11:660-669). To determine statistical significance, the results were analyzed using one-way ANOVA using Prism 6.0.

6.2.2.5 Cytotoxicity Assays ($^{51}$Chromium Release Assay)

Cell cytotoxicity was assayed by $^{51}$Cr release as previously described (Xu et al., 2015, Cancer Immunol Res 3:266-77), and EC50 was calculated using SigmaPlot software. Effector T cells were purified from human PBMC using Pan T cell isolation kit (Miltenyi Biotec), and then activated and expanded with CD3/CD28 Dynabeads (Invitrogen) according to the manufacturer's protocol.

6.2.2.6 PD-1/PD-L1 Expression

To overexpress PD-L1 in HEK293 cells, cells were cultured in DMEM (Cellgro) supplemented with 10% heat-inactivated FBS and Penicillin (100 IU/ml) and streptomycin (100 µg/ml). On Day(−1), HEK293 cells were trypsinized, counted and plated into 6 well plates at 0.5 M cells/well and kept in 2 mL of fresh media. On the day of transfection, Day(0), the media was exchanged with 2 mL of fresh media. Transfection reagents were prepared as follows for both hPD-L1 and control plasmids: 2.5 µg of DNA was diluted into 250 µl of unsupplemented DMEM (no serum). 5 µl of Lipofectamine 2000 (Invitrogen) was diluted into a separate 250 µl of DMEM (no serum), and incubated for 5 minutes at room temperature. After 5 minutes, the diluted DNA was combined with the diluted Lipofectamine 2000 (Invitrogen) and incubated for another 30 minutes at room temperature. After 30 minutes, the entire 500 µl reaction was added, dropwise, onto a single well of HEK293 cells. The plate was rocked back and forth briefly to help mix the reagents. For the untransfected control, 500 µl of unsupplemented DMEM without DNA or Lipofectamine 2000 was added to one well. Cells were incubated at 37° C. for 24-48 hours before harvesting. On Day(1) or Day(2), cells were lifted from the plate using 2 mM EDTA in PBS, and counted. 100,000-200,000 cells were used for FACS analysis and the rest were used for the killing assays.

To induce PD-1 expression of activated T cells (ATCs), effector cells were incubated in a 3:1 ratio for 24 hours with the HER2-high Breast Carcinoma Cell line HCC1954 after these target cells were incubated with HER2-BsAb at a concentration of 10 µg/mL for 30 minutes and antibody excess was removed. Cells were harvested and used in cytotoxicity assays as previously described against the HEK293 cells transfected with PD-L1.

6.2.2.7 In Vivo Experiments

For in vivo therapy studies, BALB-Rag2-/−IL-2R-γc-KO ("DKO") mice (derived from colony of Dr. Mamoru Ito, CIEA, Kawasaki, Japan; see, e.g., Koo et al., 2009, Expert Rev Vaccines 8:113-20 and Andrade et al., 2011, Arthritis Rheum 63:2764-73) were used. Three humanized mouse xenograft models were used: (1) intravenous tumor plus intravenous effector cells; (2) subcutaneous tumor plus subcutaneous effector cells; and (3) subcutaneous tumor plus intravenous effector cells. Subcutaneous xenografts were created with 5×10$^6$ cells suspended in Matrigel (Corning Corp, Tewksbury Mass.) and implanted in the flank of DKO mice. Effector peripheral blood mononuclear cell (PBMC) cells were purified from buffy coats purchased from the New York Blood Center. Prior to every experimental procedure, PBMCs were analyzed for their percentage of CD3, CD4, CD8 and CD56 cells to ensure consistency. HER2-BsAb was injected intravenously twice a week at 100 µg/injection, beginning two days before effectors cells for three weeks, given as 5-10×10$^6$ PBMC per injection, once a week for 2 weeks. Tumor size was measured using (1) hand-held TM900 scanner (Pieira, Brussels, BE); (2) Calipers; or (3) bioluminescence. Bioluminescence imaging was conducted using the Xenogen In Vivo Imaging System (IVIS) 200 (Caliper LifeSciences). Briefly, mice were injected intravenously with 0.1 mL solution of D-luciferin (Gold Biotechnology; 30 mg/mL stock in PBS). Images were collected 1 to 2 minutes after injection using the following parameters: a 10- to 60-second exposure time, medium binning, and an 8 f/stop. Bioluminescence image analysis was performed using Living Image 2.6 (Caliper LifeSciences).

6.2.3 Results 6.2.3.1 HER2-BsAb

HER2-BsAb was designed using an IgG-scFv format (FIG. 17A). The VH was identical to that of trastuzumab IgG1, except for the N297A mutation in the Fc region of HER2-BsAb to remove glycosylation (SEQ ID NO: 62). The light chain fusion polypeptide was constructed by extending the trastuzumab IgG1 light chain with a C-terminal $(G_4S)_3$ linker followed by huOKT3 scFv (Xu et al., 2015, Cancer Immunol Res 3:266-77) (SEQ ID NO: 60). The DNAs encoding both heavy chain and light chain were inserted into a mammalian expression vector, transfected into CHO-S cells, and stable clones of highest expression were selected. Supernatants were collected from shaker flasks and purified on protein A affinity chromatography.

SEC-HPLC and SDS-PAGE of the HER2-BsAb is shown in FIG. 17B and FIG. 17C, respectively. Under reducing SDS-PAGE conditions, HER2-BsAb gave rise to two bands at around 50 kDa, since the huOKT3 scFv fusion to trastuzumab light chain increased the molecular weight to approximately 50 kDa. SEC-HPLC showed a major peak (97% by UV analysis) with an approximate molecular weight of 200 KDa, as well as a minor peak of multimers removable by gel filtration. The BsAb remained stable by SDS-PAGE and SEC-HPLC after multiple freeze and thaw cycles.

6.2.3.2 HER2-BsAb Retained Specificity, Affinity and Anti-Proliferative Effects of Trastuzumab To determine if HER2-BsAb retained the specificity and anti-proliferative effects of trastuzumab, the HER2-positive-high SKOV3 ovarian carcinoma cell line was pre-incubated with 10 µg/mL of trastuzumab for 30 minutes and then immunostained using HER2-BsAb labeled with Alexa 488

(FIG. 18A). Incubation with trastuzumab prevented HER2-BsAb binding to SKOV3 cells, demonstrating that these antibodies shared the same specificity. To compare the avidity of HER2-BsAb to trastuzumab, the same cell line was incubated with 10-fold downward dilutions (from 10 µg/ml to 1×10$^{-5}$ µg/mL) of trastuzumab or HER2-BsAb and analyzed by flow cytometry. The mean fluorescence intensity (MFI) was plotted against the antibody concentration in µM. The similarity in the binding curves confirmed that trastuzumab and HER2-BsAb had similar binding avidities for their common HER2 target (FIG. 18B).

Finally, the trastuzumab-sensitive breast carcinoma cell line SKBR3 was treated with isotype control mAb, 10 mM Lapatinib (as a positive control), 10 µg/mL HER2-BsAb, or 10 µg/mL trastuzumab for 72 hours and cell proliferation was assayed. As shown in FIG. 18C, trastuzumab and HER2-BsAb had similar anti-proliferative effects that were significant as compared to the negative control. As expected, lapatinib showed the strongest inhibition of cell proliferation.

6.2.3.3 HER2-BsAb Redirected T Cell Cytotoxicity was HER2-Specific and Dependent on CD3

To establish the specificity of cytotoxic responses by T cells in the presence of HER2-BsAb; HER2-negative and HER2-positive cell lines were assayed in a cytotoxicity assays using ATCs (effector:T cell ("E:T") ratio of 10:1) and HER2-BsAb at decreasing concentrations (FIG. 19A and FIG. 20). Cytotoxicity was absent for HER2-negative cell lines. To demonstrate the dependency of cytotoxicity on CD3, HER2-BsAb cytotoxicity was tested in the presence of the CD3 specific blocking mAb OKT3 (FIG. 19B). Pre-incubation with either trastuzumab or OKT3 prevented HER2-BsAb T cell mediated cytotoxicity.

6.2.3.4 HER2-BsAb Mediated Cytotoxicity Against HER2-Positive Cell Lines that were Resistant to Other HER2 Targeted Therapies.

Several cell lines from different tumor systems (e.g., head and neck, breast, and sarcoma) were characterized for their HER2 level of expression by flow cytometry (FIG. 20). In this panel, 75% of these cells tested positive for HER2 expression by flow cytometry. Representative cell lines were assayed for their sensitivity to tyrosine kinase inhibitors (e.g., erlotinib, lapatinib, and neratinib), or HER antibodies (e.g., trastuzumab and cetuximab), as well as HER2-BsAb mediated T cell cytotoxicity. FIG. 21 shows representative examples of these experiments from three different lines from three different tumor systems. As shown, HER2 expression—even in low quantities—was sufficient to mediate T cell cytotoxicity in the presence of ATC and HER2-BsAb in cell lines otherwise resistant in vitro to HER-targeted therapies. When these cell lines were tested for cytotoxicity in the presence of ATC and HER2-BsAb, sensitivity to HER2-BsAb, expressed as EC50, strongly correlated with surface HER2 expression (FIG. 22)

6.2.3.5 HER2-BsAb Mediated T Cell Cytotoxicity was Relatively Insensitive to PD-L1 Expression on the Tumor Target or PD-1 Expression on T Cells.

Activation of tumor-specific CTL in the tumor microenvironment is known to promote expression of PD-1/PD-L1, leading to T cell exhaustion or suppression, a phenomenon termed "adaptive immune resistance" (Tumeh et al., 2014, Nature 515:568-71). The presence of the PD-1/PD-L1 pathway has also been reported to limit the anti-tumor effects of T cell engaging bispecific antibodies (Junttila et al., 2014, Cancer Res 74:5561-71). To determine if HER2-BsAb had the same limitations, PD-1-positive ATCs were used against the HER2-positive, PD-L1-positive breast carcinoma cell line HCC1954, with or without the PD-1-specific mAb pembrolizumab. As shown in FIG. 23A, FIG. 23B, and FIG. 23C, PD-1-positive T cells generated similar cytotoxic responses in the presence of HER2-BsAb, independently of the presence of pembrolizumab. When HER2-positive human embryonic kidney cells (HEK-293) were transfected with the full sequence of PD-L1 and used as targets, cytotoxicity against cells expressing PD-L1 was not significantly different to the cytotoxicity observed in non-transfected HEK-293 cells (although maximal cytotoxicity was slightly less with PD-L1-positive HEK-293 versus PD-L1-negative HEK-293) (FIG. 24A and FIG. 24B shows the average of six experiments, and error bars represent standard error).

6.2.3.6 HER2-BsAb was Effective Against HER2-Positive Xenografts

Figure 25A:
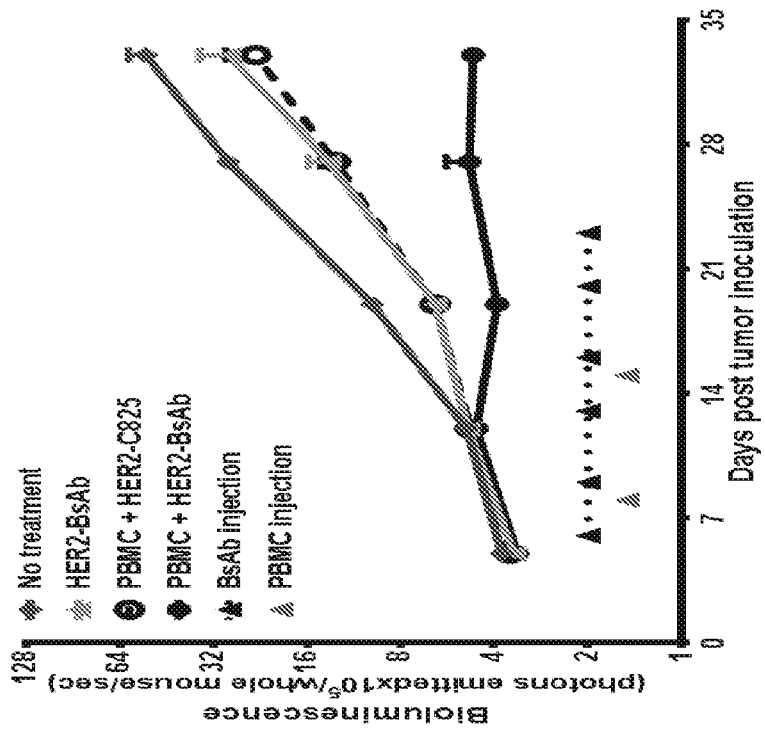
Figure 25B:
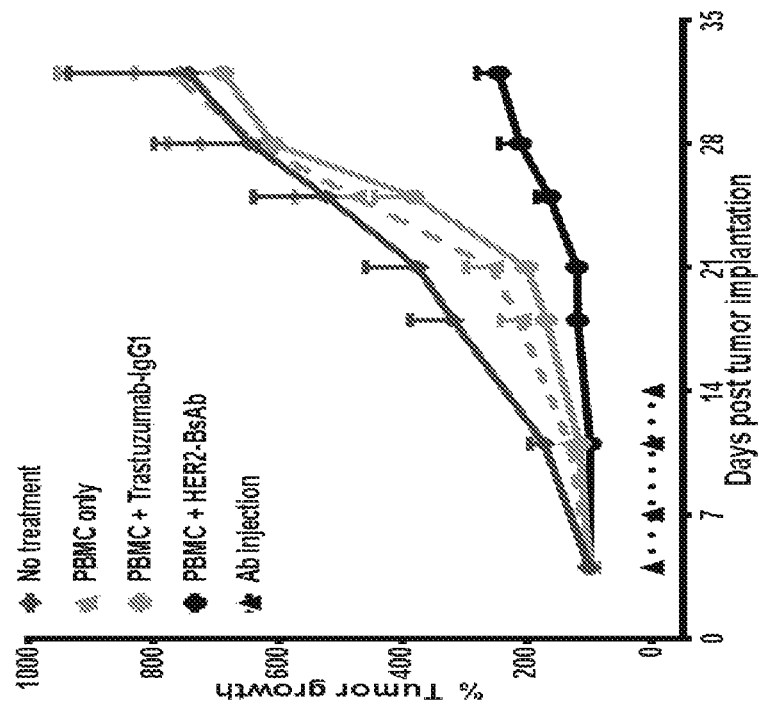
Figure 25D:
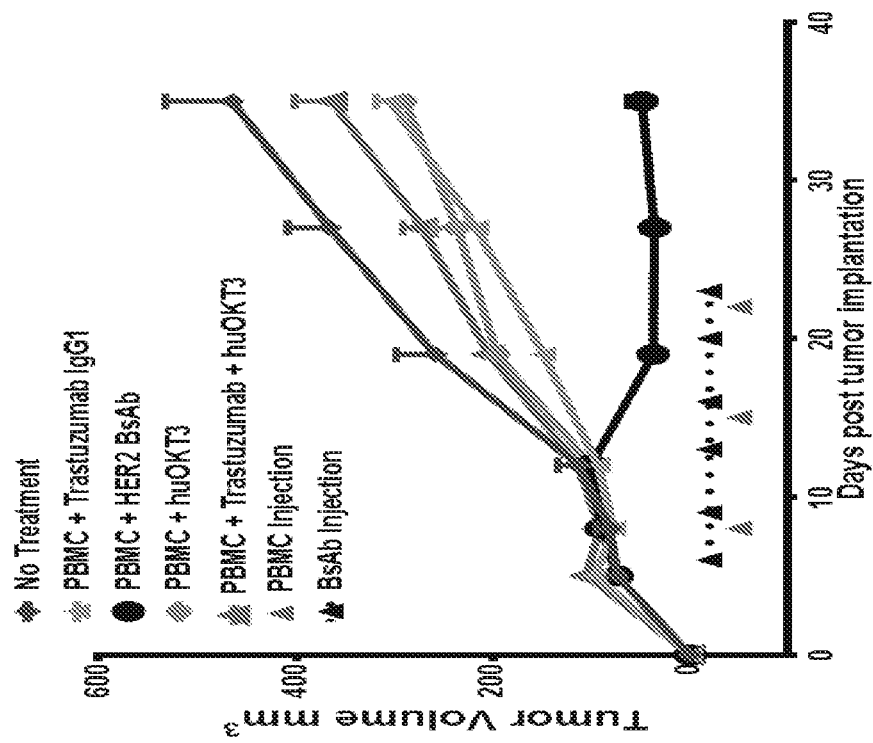
Figure 25C:
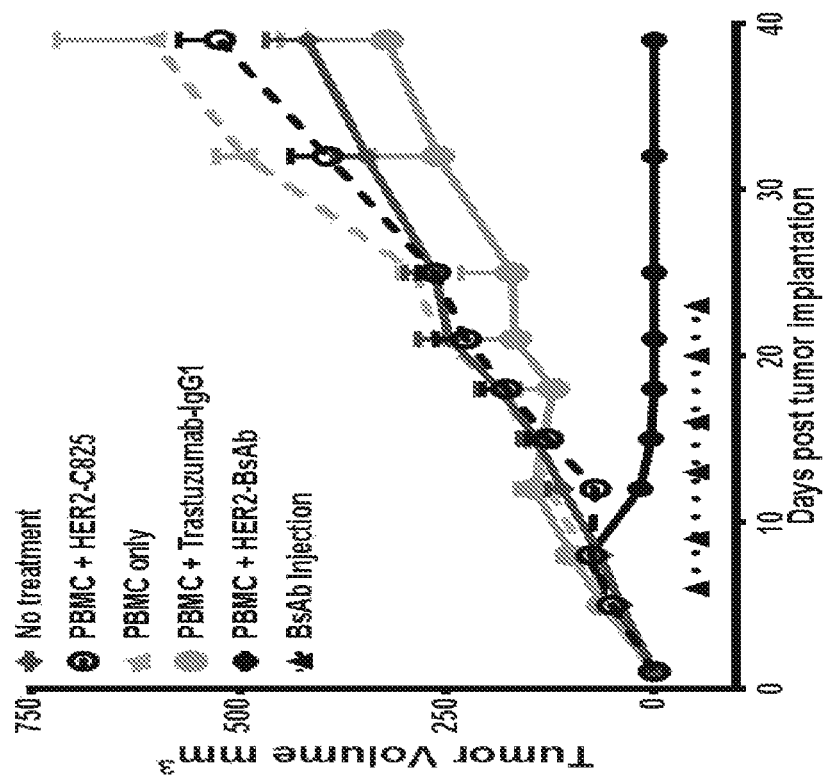

To determine the in vivo efficacy of HER2-BsAb, the breast carcinoma cell lines HCC1954 (HER2-high) and MCF-7 (HER2-low) were used in xenograft models in DKO mice. Three tumor models differing in tumor locations and effector routes were used: (1) intravenous tumor cells and intravenous effector PBMCs; (2) subcutaneous tumor cells and SC PBMCs; and (3) subcutaneous tumor cells and intravenous PBMCs. FIG. 25 summarizes the results of these experiments. The HER2-low MCF-7-luc (carrying luciferase reporter) cells were inoculated via tail vein injection into DKO. When tumor presence was confirmed by bioluminescence, mice were treated with six doses of intravenous HER2-BsAb or control BsAb twice a week for 3 weeks. Intravenous effector PBMCs were administered 48 hours after the first dose of HER2-BsAb, and again (one week later). Mice were evaluated for tumor burden using luciferin bioluminescence every week. In this hematogenous disease model, MCF-7 cells were completely eradicated without disease progression (FIG. 25B). This same cell line was implanted subcutaneously mixed with effector PBMCs subcutaneously and treated with four injections of HER2-BsAb twice a week for 2 weeks (totaling 4 injections in the first experiment) or twice a week for 3 weeks (totaling 6 injections in 2nd experiment). In both experiments, HER2-BsAb caused a significant delay in tumor progression while PBMC+trastuzumab or PBMC alone were ineffective (FIG. 25A). In two other separate experiments, subcutaneous HER2-positive breast carcinoma cell line HCC1954 was mixed with subcutaneous PBMCs. Again, both 4 or 6 injections of HER2-BsAb resulted in a complete suppression of tumor growth, while trastuzumab or control BsAb HER2-C825 had no effect (FIG. 25C). In the third model, where subcutaneous HCC1954 xenografts were treated with intravenous PBMC (once a week for 3 weeks), and intravenous HER2-BsAb twice a week for 3 weeks, tumor growth was substantially delayed (in 2 separate experiments), in contrast to only modest effects for trastuzumab+huOKT3+PBMC, control antibody (HER2-C825)+PBMC, huOKT3+PBMC, or HER2-BsAb alone without PBMC (FIG. 25D). The following observation were made: when effector PBMCs were mixed with tumor cells subcutaneously, complete tumor regression without recurrence was seen for mice over 90 days post-tumor implantation. When effector PBMCs were administered intravenously, there was significant reduction in the size of the tumors, but complete regression was only observed in a subset of animals.

6.2.4 Conclusions

This example describes a HER2-specific BsAb that has been shown to have potent T cell-mediated anti-tumor activity in vitro and in vivo, ablating tumors or delaying tumor growth in 3 separate tumor models in the presence of human PBMCs. Unlike monovalent bispecific antibodies, this HER2-BsAb had identical anti-proliferative capacity as trastuzumab. In addition, the serum half-life and area under the curve of HER2-BsAb were similar to IgG. Unlike other bispecific antibodies, which tended to aggregate, HER2-BsAb was stable at −20° C. and at 37° C., despite long term storage. Most importantly, the T cell-mediated cytotoxicity it induced was relatively insensitive to inhibition by the PD-1/PD-L1 pathway.

When compared to the existing platforms that target HER2, HER2-BsAb offers advantages. The F(ab)×F(ab) format, though effective in vitro, was similar in size to Blinatumomab (Sanford, 2015, Drugs, 75:321-7) and was expected to share similar pharmacokinetic and toxicity profiles (Shalaby et al., 1995, Clin Immunol Immunopathol 74:185-92, 1995), having a short half-life, thus requiring daily infusions, potential leakage into the central nervous system (CNS), potential CNS toxicity, and potential significant cytokine release syndrome. In addition, the anti-proliferative capacity of this F(ab)×F(ab) univalent system was 10-fold lower than trastuzumab. The IgG×IgG chemical conjugate between trastuzumab and OKT3 was useful for arming T cells ex vivo, but was not useful as an injectable, likely due to impurities associated with chemical conjugates (Lum and Thakur, 2011, BioDrugs 25:365-79; Lum et al., Clin Cancer Res 21:2305, 2015); in contrast, the HER2-BsAb provided herein is tolerated as an injectable. A heterodimer format was recently described using a monovalent system (Junttila et al., 2014, Cancer Res 74:5561-71) that does not preserve trastuzumab's anti-proliferative effects retained in HER2-BsAb.

There are other design features that distinguish HER2-BsAb from other known candidates of this class. Unlike most bispecific antibodies, HER2-BsAb's bivalent binding to the HER2 target was preserved, providing anti-proliferative activity similar to that of trastuzumab IgG1. Unlike F(ab)×F(ab) (Shalaby et al., 1995, Clin Immunol Immunopathol 74:185-92) or tandem scFv constructs (Sanford, 2015, Drugs, 75:321-7), HER2-BsAb had a molecular weight high enough to behave in pharmacokinetic analyses like a wild-type IgG. Unlike other bivalent bispecifics (Reusch et al., MAbs, 7:584, 2015), HER2-BsAb's reaction with CD3 was functionally monovalent. HER2-BsAb also differed from man heterodimeric bispecifics in its modified Fc, where aglycosylation removed both ADCC and CMC functions, thereby reducing cytokine release syndrome without affecting serum pharmacokinetics or compromising T cell activation. The other advantage is manufacturability; HER2-BsAb was produced in CHO cells and purified using procedures standard for IgG, without significant aggregation despite prolonged incubation at 37° C. HER2-BsAb is an important salvage option for patients who progress on standard HER2-based therapies, or a replacement for trastuzumab given its dual anti-proliferative and T cell retargeting properties.

6.3 Example 3

This example provides (a) a more detailed description of certain of the experiments described in Example 1 (Section 6.1); and (b) additional experiments as compared to Example 1 (Section 6.1).

T-cell based therapies have emerged as one of the most clinically effective ways to target solid and non-solid tumors. HER2 is responsible for the oncogenesis and treatment resistance of several human solid tumors. As a member of the HER family of tyrosine kinase receptors, its overactivity confers unfavorable clinical outcome. Targeted therapies directed at this receptor have achieved responses, although development of resistance is common. This example explores a novel HER2/CD3 bispecific antibody (HER2-BsAb) platform that, while preserving the anti-proliferative effects of trastuzumab, recruits and activates non-specific circulating T-cells, promoting T cell tumor infiltration and ablating HER2-positive ("HER2(+)") tumors, even when these are resistant to standard HER2 targeted therapies. Its in vitro tumor cytotoxicity, when expressed as EC50, correlated with the surface HER2 expression in a large panel of human tumor cell lines, irrespective of lineage or tumor type. HER2-BsAb-mediated cytotoxicity was relatively insensitive to PD-1/PD-L1 immune checkpoint inhibition. In four separate humanized mouse models of human breast cancer and ovarian cancer cell line xenografts, as well as in human breast cancer and gastric cancer patient-derived xenografts ("PDXs"), HER2-BsAb was highly effective in promoting T cell infiltration and suppressing tumor growth when used in the presence of human peripheral blood mononuclear cells ("PBMC") or activated T cells ("ATC"). The in vivo and in vitro antitumor properties of this BsAb support its further clinical development as a cancer immunotherapeutic.

6.3.1 Introduction

Trastuzumab has significantly improved patient outcomes in breast cancer, and has also been key in the design and implementation of other targeted therapies (Singh et al., Br J Cancer 2014; 111:1888-98). However, HER2 expression does not guarantee a clinical response to trastuzumab or other HER2 targeted therapies (Devika & Sarat, Expert Review Of Anticancer Therapy 2011; 11(2):263-75; Lipton et al., Breast Cancer Research and Treatment 2013; 141(1): 43-53). HER2-positive breast cancer patients with metastatic disease initially respond to trastuzumab and/or other HER2 targeted therapies, but almost all eventually will develop resistance and relapse (Montemurro & Scaltriti, J Pathol 2014; 232:219-29). In osteosarcoma and Ewing's sarcoma, where high levels of HER2 expression was associated with decreased survival (Gorlick et al., J Clin Oncol 1999; 17:2781-8), trastuzumab has not shown any benefit even when used in conjunction with cytotoxic chemotherapy (Ebb et al., J Clin Oncol 2012; 30:2545-51). Furthermore, trastuzumab, like other HER targeted therapies, has shown modest or no benefit against HER2(+) positive head and neck cancer (Pollock & Grandis, Clinical Cancer Research 2014; 21(3):526-33).

The reasons for these failures are complex and only partially understood. The genomic diversity and constant evolution of malignancies make them less prone to oncogene addiction, a requirement for the success of targeted therapy. Furthermore, even when oncogene addiction is present, resistance can emerge from selection pressure induced by the use of targeted therapies (Lipton et al., Breast Cancer Research and Treatment 2013; 141(1):43-53). In fact, despite the initial enthusiasm received, the majority of targeted therapies have not produced a significant benefit in the overall cure of patients receiving them (Nathanson et al., Science 2014; 343:72-6). A different approach, one that selectively targets malignant cells that overexpress HER family receptors, and that can generate cytotoxic anti-tumor responses independently of the receptor activation status could be beneficial.

Redirecting the immune system against tumor cells has gained acceptance as an effective strategy to overcome resistance to cytotoxic chemotherapy and targeted therapy. In the forefront of these treatments, T-cell based therapies constitute the most promising approach. Both T-cell engaging bispecific antibodies and immune checkpoint antibody blockade have received accelerated approval from the FDA based on their outstanding clinical performance (Asher, Nature Reviews Drug Discovery 2015). The clinical success of chimeric antigen receptor (CAR) gene modified T-cells against non-solid tumors has further added to the enthusiasm among scientists, clinicians and the pharmaceutical industry.

The outstanding clinical responses seen with these therapies have consolidated T-cells as the most powerful effector cells within the immune system to eradicate tumor cells (Kershew et al., Clinical & Translational Immunology 2014; 3(5):e16). Thus, a number of approaches that redirect them against tumor cells have been proposed and tested by many investigators. In this regard, Bispecific antibodies ("BsAb") with specificity for T-cells and for tumor antigens have attracted the attention of researchers and big pharma. BsAb, in opposition to other antibody based therapies, only requires expression of its target of interest to be effective. By recruiting polyclonal T-cells through the CD3 surface receptor, BsAb activate T-cells irrespective of their lineage, antigen specificity, maturation, HLA restriction or co-stimulatory receptors. The direct activation of T-cells, bypassing the classic T cell receptor ("TCR"), removes the limitations imposed by HLA restriction and its level of expression (Brischwein et al., Journal of Immunotherapy 2006; 30:798-807), a well-established immune resistance mechanism (Sabbatino et al., Clinical transplants 2013:453-63).

Blinatumomab—a CD19/CD3 BsAb was approved in 2014 for treating Acute Lymphoplastic Leukemia (Sanford, Drugs 2015; 75:321-7). However, despite its promising results, the unfavorable pharmacokinetics of these small size molecules necessitate prolonged infusions, complicating their administration (Shalaby et al., J Exp Med 1992; 175:217-25; Portell et al., Clinical Pharmacology: Advances And Applications 2013; 5:5-11). Furthermore, the resulting cytokine release syndrome ("CRS") still poses costly and often life-threatening complications. Importantly, despite the ability of bispecific antibodies to activate T-cells, the same inhibitory pathways that regulate classic T-cell function might still limit their effectiveness. For example, the heterodimeric design of a monovalent binding HER2/CD3 bispecific antibody was inhibited by the PD-1/PD-L1 inhibitory axis (Junttila et al., Cancer Research 2014; 74:5561-71).

This example reports a BsAb against the HER2 tumor antigen that offers two distinct advantages over the existing technologies: (1) it is based on the fully humanized HER2-specific IgG1 trastuzumab, preserving its pharmacologic advantages (Wittrup et al., Methods Enzymol 2012; 503: 255-68) and bivalent binding to HER2, maximizing tumor avidity; (2) its binding to CD3 is functionally monovalent through the scFv derived from the humanized huOKT3 IgG1 sequence. Thus, HER2-BsAb is built on two mAbs with an extensive record of clinical safety. Previous studies have also shown that scFv linked to the carboxyl end of the light chain did not affect the targeting ability of these IgG forms (Cheal et al., Mol Cancer Ther 2014; 13:1803-12; Orcutt et al., Protein Eng Des Sel 2010; 23:221-8). Furthermore, this is a platform with its Fc function silenced to reduce the cytokine release syndrome. This example presents data to show that this HER2-BsAb has potent anti-tumor properties both in vitro and in vivo, against tumor cells that are resistant to HER2 targeted therapy or to trastuzumab.

6.3.2 Materials and Methods 6.3.2.1 Cell Lines

All cell lines were purchased from ATCC (Manassas Va.) except: UM-SCC47 obtained from Dr. Carey at the University of Michigan, SCC-90, PCI-30 and PCI-15B from Dr. Robert Ferris at the University of Pittsburgh, SKOV3-luc from Dr. Dmitry Pankov at MSK, 93-VU-147T and HeLa from Dr. Luc Morris and UD-SCC2 from Henning Bier at Hals-Nasen-Ohrenklinik and Poliklinik. All cells were authenticated by short tandem repeat profiling using PowerPlex 1.2 System (Promega), and periodically tested for mycoplasma using a commercial kit (Lonza). The luciferase-labeled tumor cell lines MCF7-Luc were generated by retroviral infection with a SFG-GFLuc vector.

6.3.2.2 HER2-BsAb Design and Expression in CHO-S Cells

In the HER2-BsAb IgG-scFv format, VH was identical to that of trastuzumab IgG1, except N297A mutation in the Fc region was introduced to remove glycosylation, thereby depleting Fc function. The sequence of the heavy chain is set forth in SEQ ID NO: 62. The light chain fusion polypeptide (SEQ ID NO: 60) was constructed by extending the trastuzumab IgG1 light chain with a C-terminal (G4S)$_3$ linker followed by huOKT3 scFv. The DNA encoding both heavy chain and light chain was inserted into a mammalian expression vector, transfected into CHO-S cells, and stable clones of highest expression were selected. Supernatants were collected from shaker flasks and the HER2-BsAb was purified by protein A affinity chromatography. The other control BsAb, HER2-C825, was generated as previously described (Cheal et al., Mol Cancer Ther 2014; 13:1803-12). HuOKT3 IgG1 was made using the same variable sequences as in huOKT3 scFv, and huOKT3 Fab was prepared from huOKT3 IgG1 using the Pierce Fab Preparation Kit (Thermo Scientific).

6.3.2.3 Other Antibodies and Small Molecules

Fluorophore-labeled HER2-BsAb was generated with the Zenon® Alexa Fluor® 488 Human IgG Labeling Kit from Life Technologies following the manufacturer's instructions. Pembrolizumab, cetuximab, trastuzumab, Erlotinib, Lapatinib and Neratinib were purchased from the Memorial Sloan Kettering Cancer Center pharmacy. Small molecules were re-suspended in dimethylsulfoxide ("DMSO"). The CD3, CD4, CD8 and CD56 antibodies were purchased from BD Biosciences (San Jose Calif.). The commercially available PE labeled PD-L1 specific mAb 10F.9G2 was purchased from BioLegend.

6.3.2.4 Cell Proliferation Assays

For tumor cell proliferation, 5,000 tumor cells were plated using RPMI-1640 supplemented with 10% fetal bovine serum ("FBS") in a 96 well plate for 36 hours before being treated with—kinase inhibitors or the antibodies at the specified concentration. Cell proliferation was determined using the cell counting WST-8 kit (Dojindo technologies) following the manufacturer's instructions and using the formula: % survival rate=(Sample-Background)/(Negative control-Background). Lapatinib was ground using a mortar and pestle and suspended in DMSO as previously described (Chen et al., Molecular cancer therapeutics 2012; 11:660-9). To determine statistical significance, the results were analyzed using one-way ANOVA using Prism 6.0.

For T cell proliferation, naïve T cells were purified from human PBMC using Pan T cell isolation kit (Miltenyi Biotec). $2\times10^5$ purified T cells were mixed with different antibodies in 96-well cell culture plate to a final volume of 250 µl/well. T cells were cultured and maintained in RPMI-1640 supplemented with 10% FBS in 37° C. for 6 days. T cell proliferation was quantitated using the WST-8 kit as described above.

6.3.2.5 Cytotoxicity Assays ($^{51}$Chromium Release Assay)

Cell cytotoxicity was assayed by $^{51}$Cr release as previously described (Xu et al., Cancer immunology research 2015; 3:266-77), and EC50 was calculated using SigmaPlot software. Effector PBMC cells were purified from buffy coats purchased from the New York Blood Center. ATCs were first purified from human PBMC using Pan T cell isolation kit, and then activated and expanded for approximately 14 days with CD3/CD28 Dynabeads (Invitrogen) according to manufacturer's protocol. For pre-incubation experiment, HER2-BsAb was pre-incubated with either ATCs (T cells pre-armed) or chromium-labeled tumor target cells (AU565 pre-targeted) for 30 minutes at room temperature, and unbound BsAb was washed off for two times before adding the other cells.

6.3.2.6 Cytokine Release Assay

Cytokine release was assayed as previously described (Ahmed et al., OncoImmunology 2015; 4:e989776), using naïve T cells prepared as described above. T cells (200,000/well) were cultured with or without NCI-N87 tumor cells (10,000/well) for 24 hours before supernatants being harvested for ELISA-based cytokine assay.

6.3.2.7 PD-1/PD-L1 Expression

To overexpress PD-L1 in HEK293 cells, cells were cultured in DMEM (Cellgro) supplemented with 10% heat-inactivated FBS and Penicillin (100 IU/ml) and streptomycin (100 µg/ml). HEK293 cells were plated into 6 well plates at 0.5 million cells/well with 2 ml fresh media the day before transfection. Transfection was done with 2.5 µg hPD-L1 plasmid DNA using Lipofectamine 2000 (Invitrogen) according to manufacturer's protocol. Cells were incubated at 37° C. for 48 hours before harvesting with 2 mM EDTA in PBS. 100,000-200,000 cells were used for FACS analysis and the rest were used for the killing assays.

To induce PD-1 expression in ATCs, effector cells were incubated in a 3:1 ratio for 24 hours with the HER2(+) breast carcinoma cell line HCC1954, after these target cells were incubated with HER2-BsAb at a concentration of 10 µg/mL for 30 minutes and excessive antibody was removed. Cells were harvested and used in cytotoxicity assays as previously described against the HEK293 cells or HCC1954 cells. For PD-1 blockade, PD-1-induced ATCs were pre-incubated with 10 µg/mL pembrolizumab for 30 minutes before adding to the well.

6.3.2.8 In Vivo Experiments

All animal procedures were performed in compliance with Institutional Animal Care and Use Committee (IACUC) guidelines. For in vivo therapy studies, BALB-Rag2-/-IL-2R-γc-KO (DKO) mice (derived from colony of Dr. Mamoru Ito, CIEA, Kawasaki, Japan)(Koo et al., Expert Rev Vaccines 2009; 8:113-20; Andrade et al., Arthritis Rheum 2011; 63:2764-73) were used. Four humanized mouse xenograft models were used: (1) intravenous ("i.v.") tumor plus i.v. effector cells, (2) subcutaneous ("sc") tumor plus sc effector cells, (3) sc tumor plus i.v. effector cells, and (4) intraperitoneal ("i.p.") tumor plus i.p./i.v. effector cells. Patient derived xenografts ("PDXs") were established from fresh surgical specimens with Memorial Sloan Kettering Cancer Center Institutional Review Board approval. Effector PBMC cells and ATCs were prepared as described above. Prior to every experimental procedure, PBMCs and ATCs were analyzed by FACS for their percentage of CD3, CD4, CD8 and CD56 cells to ensure consistency. Antibodies were injected i.v. or i.p. twice a week started two days before effectors cells for 3-6 weeks, given as i.v. 5-10×106 PBMC/ATC per injection, once a week for 2-3 weeks. s.c. xenografts were created with tumor cells suspended in Matrigel (Corning Corp, Tewksbury Mass.) and implanted in the flank of DKO mice. Tumor size was measured using 1) hand-held TM900 scanner (Pieira, Brussels, BE), 2) Calipers, or 3) Bioluminescence. Bioluminescence imaging was conducted using the Xenogen In Vivo Imaging System (IVIS) 200 (Caliper LifeSciences). Briefly, mice were injected i.v. with 0.1 mL solution of D-luciferin (Gold Biotechnology; 30 mg/mL stock in PBS). Images were collected 1 to 2 minutes after injection using the following parameters: a 10- to 60-second exposure time, medium binning, and an 8 f/stop. Bioluminescence image analysis was performed using Living Image 2.6 (Caliper LifeSciences).

6.3.2.9 Immunohistochemistry Staining

The immunohistochemical detection was performed at Molecular Cytology Core Facility of Memorial Sloan Kettering using Discovery XT processor (Ventana Medical Systems). Paraffin-embedded tumor sections were deparaffinized with EZPrep buffer (Ventana Medical Systems), antigen retrieval was performed with CC1 buffer (Ventana Medical Systems) and sections were blocked for 30 minutes with Background Buster solution (Innovex). Anti-CD3 (DAKO, cat # A0452, 1.2 µg/ml), anti-HER2 (Enzo, cat # ALX-810-227, 5 µg/ml), and anti-PD-1 (Ventana, cat #760-4895, 3.1 ug/ml) antibodies were applied and sections were incubated for 5 hours, followed by 60 minutes incubation with biotinylated goat anti-rabbit IgG (Vector labs, cat # PK6101) for CD3 and HER2 antibodies, or biotinylated horse anti-mouse IgG (Vector Labs, cat # MKB-22258) for PD-1 antibodies at 1:200 dilution. The detection was performed with DAB detection kit (Ventana Medical Systems) according to manufacturer's instruction. Slides were counterstained with hematoxylin and coverslipped with Permount (Fisher Scientific). For PD-L1 staining, the sections were pre-treated with Leica Bond ER2 Buffer (Leica Biosystems) for 20 minutes at 100° C. The staining was done on Leica Bond RX (Leica Biosystems) with PD-L1 mouse monoclonal antibody (Cell Signaling, cat #29122, 2.5 µg/ml) for 1 hour on Leica Protocol F. All images were captured from tumor sections using Nikon ECLIPSE Ni-U microscope and NIS-Elements 4.0 imaging software.

6.3.2.10 Statistics

Differences between samples indicated in the figures were tested for significance by one-way ANOVA using Prism 6.0, and p<0.05 was considered statistically significant.

6.3.3 Results 6.3.3.1 HER2-BsAb

HER2-BsAb heavy chain was constructed using the standard human IgG1, except for the N297A mutation in the Fc region to remove glycosylation. The light chain was constructed by extending the trastuzumab IgG1 light chain with a C-terminal $(G4S)_3$ linker followed by huOKT3 scFv (Xu et al., Cancer Immunology Research 2015; 3:266-77). The DNAs encoding both heavy chain and light chain were inserted into a mammalian expression vector, transfected into CHO-S cells, and stable clones of highest expression were selected. Supernatants were collected from shaker flasks and purified on protein A affinity chromatography (Xu et al., Cancer Immunology Research 2015; 3:266-77).

The SEC-HPLC and SDS-PAGE of the HER2-BsAb was analyzed. Under reducing SDS-PAGE conditions, HER2-BsAb gave rise to two bands at around 50 KDa, since the huOKT3 scFv fusion to trastuzumab light chain increased the MW to ~50 KDa (data not shown). SEC-HPLC showed a major peak (97% by UV analysis) with an approximate MW of 210 KDa, as well as a minor peak of multimers (data not shown). The BsAb remained stable by SDS-PAGE and SEC-HPLC after multiple freeze and thaw cycles (data not shown).

6.3.3.2 HER2-BsAb Retained Specificity, Affinity and Anti-Proliferative Effects of Trastuzumab To determine if HER2-BsAb retained the specificity of trastuzumab, the HER2(+)high SKOV3 ovarian carcinoma cell line was pre-incubated with 10 µg/mL of trastuzumab for 30 minutes and then immunostained using 1 µg/mL HER2-BsAb labeled with Alexa 488 (FIG. 26A). Pre-incubation with trastuzumab prevented HER2-BsAb from binding to SKOV3 cells, demonstrating that these antibodies shared the same specificity. To compare the avidity of HER2-BsAb to trastuzumab, the same cell line was incubated with 10 fold downward dilutions (from 10 µg/ml to $1 \times 10^{-5}$ µg/mL) of trastuzumab or HER2-BsAb and analyzed by flow cytometry. The mean fluorescence intensity ("MFI") was plotted against the antibody concentration in µM. Again the similarity in the binding curves confirmed that trastuzumab and HER2-BsAb had similar binding avidities for their common HER2 target (FIG. 26B).

Finally, the trastuzumab-sensitive breast carcinoma cell line SKBR3 was treated with Isotype control mAb, 10 nM lapatinib (as a positive control), 10 µg/mL HER2-BsAb or 10 µg/mL trastuzumab for 72 hours and cell proliferation was assayed. As shown in FIG. 26C, trastuzumab and HER2-BsAb had similar anti-proliferative effects that were significant compared to the negative control. As expected, lapatinib showed the strongest inhibition of cell proliferation.

6.3.3.3 HER2-BsAb Redirected T Cell Cytotoxicity was HER2 Specific and Dependent on CD3

Prior to the cytotoxicity assay, HER2-BsAb was shown capable of binding different T cells at the similar level (MFI around 450 with the BsAb concentration of 1 ug/106 cells), no matter whether they were naïve T cells purified from fresh PBMC or activated T cells (ATCs) (FIG. 27A). To establish the specificity of cytotoxic responses by T cells in the presence of HER2-BsAb, HER2-negative ("HER2(−)") breast carcinoma HTB-132 cells and HER2(+) MCF-7 cells were tested in a cytotoxicity assays using ATCs (E:T ratio of 10:1) and HER2-BsAb at decreasing concentrations (FIG. 26D). Cytotoxicity was robust for HER2(+) cells but absent for HER2(−) cells. In fact, HER2-BsAb was able to redirect efficient T cell killing no matter whether BsAb was present throughout the 4 hour assay (mixing), or used to pre-arm T cells and then washed off, or to pre-target AU565 tumor cells and then washed off. Although pre-targeted AU565 cells were killed as well as mixing all three together, pre-armed T cells were less potent due to the low avidity of BsAb binding to CD3 on T cells (FIG. 27B). To demonstrate the dependency of cytotoxicity on both HER2 and CD3, HER2-BsAb cytotoxicity against HER2(+) SCCHN cell line PCI-13 was tested in the presence of trastuzumab, or the CD3 specific blocking huOKT3 IgG1 (FIG. 26E). Pre-incubation with either trastuzumab or huOKT3 prevented HER2-BsAb mediated T-cell cytotoxicity.

6.3.3.4 HER2-BsAb Mediated Cytotoxicity Against HER2(+) Cell Lines that were Resistant to Other HER2 Targeted Therapies.

A panel of a total of 39 cell lines from different tumor systems (breast, ovarian, gastric, head and neck, sarcoma, etc.) was characterized for their HER2 expression levels by flow cytometry and CTL activity (Table 9). In this panel, 75% of these cells were tested positive for HER2 expression. Representative cell lines were assayed for their sensitivity to tyrosine kinase inhibitors (10 nM each of Erlotinib, Lapatinib, Neratinib), or HER antibodies (10 µg/mL each of trastuzumab and cetuximab), as well as HER2-BsAb mediated T-cell cytotoxicity. FIG. 28A, FIG. 28B and FIG. 28C showed three representative lines from three different tumor systems. As shown, HER2 expression, even in low quantities, was sufficient to mediate T-cell cytotoxicity in the presence of ATC and HER2-BsAb in cell lines otherwise resistant in vitro to HER-targeted therapies. When these cell lines were tested for cytotoxicity in the presence of ATC and HER2-BsAb, sensitivity to HER2-BsAb expressed as EC50 inversely correlated with surface HER2 expression in general (FIG. 28D, Table 9).

TABLE 9

| Tumor Type | Cell Line | HER2 Expression (MFI)* | EC50 (pM)** |
|---|---|---|---|
| Breast carcinoma | AU565 | 1175 | 0.3 |
| Gastric Carcinoma | NCI-N87 | 4900 | 1.1 |
| Ovarian Carcinoma | OVCAR3 | 183 | 1.8 |
| Breast Carcinoma | MDA-MB-361 | 777 | 2.5 |
| Ovarian Carcinoma | SKOV3 | 1577 | 2.8 |
| Melanoma | SKMEL28 | 190 | 3 |
| Breast Carcinoma | SKBR3 | 2506 | 4.1 |
| Breast Carcinoma | HCC1954 | 1597 | 5.5 |
| Head and Neck Cancer | SCC90 | 274 | 5.7 |
| Ewings | SKEAW | 246 | 10 |
| Osteosarcoma | CRL1427 | 108 | 10 |
| Rhabdomyosarcoma | HTB82 | 204 | 10 |
| Osteosarcoma | RG 160 | 563 | 11 |
| Head and Neck Cancer | PCI-30 | 359 | 12.2 |
| Gastric Carcinoma | KATO III | 201 | 13.5 |
| Melanoma | HT-144 | 156 | 15 |
| Neuroblastoma | NB5 | 66 | 15.5 |
| Osteosarcoma | RG 164 | 439 | 17.7 |
| Head and Neck Cancer | UM SCC47 | 302 | 19.8 |
| Osteosarcoma | U2OS | 90 | 22.5 |
| Gastric Adenocarcinoma | AGS | 172 | 23 |
| Head and Neck Cancer | UDSCC2 | 178 | 26.9 |
| Gastric Carcinoma | SNU-16 | 29 | 30.5 |
| Head and Neck Cancer | 93VU147T | 127 | 32.4 |
| Ewings | SKES-1 | 146 | 50 |
| Breast Carcinoma | MDA-MB-231 | 76 | 50.2 |
| Head and Neck Cancer | 15B | 305 | 62.8 |
| Breast Carcinoma | MCF7 | 398 | 64.9 |
| Cervical Cancer | HeLa | 104 | 120.7 |
| Melanoma | M14 | 57 | 130 |
| Breast Carcinoma | MDA-MB-468 | 6 | >5000 |
| Neuroblastoma | NMB7 | 12 | >5000 |
| Neuroblastoma | SKNBE(2)C | 8 | >5000 |
| Neuroblastoma | IMR32 | 6 | >5000 |
| Neuroblastoma | SKNBE(2)S | 4 | >5000 |
| Neuroblastoma | SKNBE(1)N | 3 | >5000 |
| Small Cell lung Cancer | NCI-H524 | 14 | >5000 |
| Small Cell lung Cancer | NCI-H69 | 10 | >5000 |
| Small Cell lung Cancer | NCI-H345 | 6 | >5000 |

6.3.3.5 HER2-BsAb Mediated In Vitro T-Cell Cytotoxicity was Relatively Insensitive to PD-L1 Expression on the Tumor Targets or PD-1 Expression on T Cells.

Activation of tumor-specific CTL in the tumor microenvironment is known to promote expression of PD-1/PD-L1, leading to T-cell exhaustion or suppression, a phenomenon termed "adaptive immune resistance" (Tumeh et al., Nature 2014; 515:568-71). The presence of PD-1/PD-L1 pathway has also been reported to limit the anti-tumor effects of T-cell engaging bispecific antibodies (Junttila et al., Cancer Research 2014; 74:5561-71). To determine if HER2-BsAb had this same limitation, PD-1-positive ("PD-1(+)") ATCs were used against the HER2(+) PD-L1-positive ("PD-L1(+)") breast carcinoma cell line HCC1954 with or without the PD-1-specific antibody pembrolizumab. As shown in FIG. 29A, PD-1(+) T cells generated similar cytotoxic responses in the presence of HER2-BsAb no matter whether pembrolizumab was present or not. When HER2(+) human embryonic kidney cells (HEK-293) were transfected with the full sequence of PD-L1 and used as targets, cytotoxicity against cells expressing PD-L1 was not significantly different to the cytotoxicity observed in non-transfected HEK-293 cells, although maximal cytotoxicity was slightly less with PD-L1 (+) HEK-293 versus PD-L1-negative ("PD-L1(−)") parental HEK-293 (FIG. 29B).

6.3.3.6 HER2-BsAb was Effective Against HER2(+) Xenografts

To determine the in vivo efficacy of HER2-BsAb, the breast carcinoma cell lines HCC1954 (HER2high) and MCF-7 (HER2low), ovarian carcinoma cell line SKOV3, and HER2(+) patient-derived breast cancer and gastric cancer xenografts ("PDXs") were used in DKO mice xenograft models. Four tumor models differing in tumor locations and effector routes were used, with the first three described before (Xu et al., Cancer Immunology Research 2015; 3:266-77) to simulate different clinical situations: (1) intravenous ("i.v.") tumor cells/i.v. effector PBMC; (2) subcutaneous ("s.c." tumor cells/s.c. PBMC; (3) s.c. tumor cells/i.v. PBMC; and (4) intraperitoneal ("i.p." tumor cells plus i.p. or i.v. effector T cells to simulate ovarian cancer metastasizing to the peritoneal cavity. FIG. 30 and FIG. 31 summarize the results of these experiments using cell lines, and FIG. 32 summarizes the results of these experiments using PDXs (M37 breast cancer and EK gastric cancer).

$3 \times 10^6$ HER2low MCF-7-luc (carrying luciferase reporter) cells were inoculated via tail vein i.v. injection into DKO mice. When tumor presence was confirmed by bioluminescence, mice were treated with HER2-BsAb or control BsAb (20 μg i.v., 2 times per week for 3 weeks), in combination with PBMC ($5 \times 10^6$ i.v., once per week for 2 weeks). Mice were evaluated for tumor burden using luciferin bioluminescence every week. In this hematogenous disease model, MCF-7 cells were completely eradicated without disease progression (FIG. 30A). This same cell line was implanted s.c. mixed with effector PBMC (1:1, $7 \times 10^6$ each), and treated with HER2-BsAb (10 μg i.v., 2 times per week for 2 weeks in the 1st experiment; or 20 μg i.v. 2 times per week for 3 weeks in the 2nd experiment). In both experiments, HER2-BsAb caused a significant delay in tumor progression, while PBMC+trastuzumab or PBMC alone was ineffective (FIG. 30B). In two other separate experiments, $5 \times 10^6$ HER2(+) breast carcinoma HCC1954 cells were implanted s.c. mixed with $2.5 \times 10^6$ PBMC (2:1). Again, after either 4 or 6 injections of HER2-BsAb (20 μg i.v. per dose), there was complete suppression of tumor growth, while trastuzumab or control BsAb HER2-C825 almost had no effect (FIG. 30C). In the third model, where s.c. $5 \times 10^6$ HCC1954 xenografts were treated with i.v. PBMC ($5 \times 10^6$, once per week for 3 weeks) and i.v. HER2-BsAb (100 μg, twice per week for 3 weeks), tumor growth was substantially delayed (2 separate experiments), in contrast to only modest effects for PBMC+trastuzumab+huOKT3, PBMC+trastuzumab, or PBMC+huOKT3 (FIG. 30D). For HCC1954 xenografts, the following observations were made: (1) when effector PBMCs were mixed with tumor cells s.c., complete tumor regression without recurrence was seen past 90 days from tumor implantation; and (2) when effector PBMCs were administered i.v., there was significant reduction in the size of the tumors, but complete regression was only observed in a subset of animals (data not shown).

Since T cell homing into tumor is critical for anti-tumor response in cancer immunotherapy (Tang et al., Cancer Cell 2016; 29:285-96), T-cell tumor infiltration was studied using the s.c. tumor model described in FIG. 30D. Tumors were collected 5 days after i.v. PBMC and immunohistochemistry ("IHC") was performed (FIG. 30E). T-cell tumor infiltration by CD3(+) staining was detected only in PBMC+HER2-BsAb-treated group, but not in control group (PBMC+Trastuzumab+huOKT3). These infiltrated T cells also had PD-1 expression, although it was very weak. Interestingly, PD-L1 expression in the tumor cells was strongly upregulated in the HER2-BsAb-treated mice, presumably induced by the cytokines released by the infiltrated T cells in the vicinity. But still, HER2-BsAb treatment eradicated these tumors. This was consistent with the in vitro data (FIG. 29) showing HER2-BsAb-mediated T-cell cytotoxicity was relatively insensitive to or sufficient to overcome the PD-1/PD-L1 immune checkpoint inhibition.

To simulate ovarian cancer that metastasized into the peritoneal cavity, $1 \times 10^5$ ovarian cancer SKOV3-luc cells were injected peritoneally in DKO mice, and treatments were started after confirming tumor growth by bioluminescence. Besides i.v.ATC, i.p.ATC was also tested as a source of effectors. As shown in FIG. 31A and FIG. 31B, after treatment with ATC ($7.5 \times 10^6$ i.v. or i.p., once a week for 2 weeks), and i.p. HER2-BsAb (100 μg, twice per week for 3 weeks), tumors were completely eradicated without evidence of recurrence at followup. Both i.v.ATC and i.p.ATC were equally effective in this fourth model.

HER2-BsAb was next tested using PDXs, since they could approximate the tumor heterogeneity and microenvironment typically found in fresh human tumor specimens. To determine whether HER2-BsAb is effective against PDXs, two HER2(+) PDXs (gastric cancer PDX (EK) and breast cancer PDX (M37)) were tested using the s.c. tumor cells/i.v. PBMC model similar to the one described in FIG. 30D. The PDXs were recently characterized by IHC using the PATHWAY anti-HER2/neu (4B5) Rabbit Monoclonal Primiary Antibody (VENTANA) and scored (according to the 2013 ASCO HER2 Breast Cancer Testing Guidelines (see, e.g., Wolff et al., Journal of Clinical Oncology, 2013, 31(31):3997-4013)) as IHC 3+ for breast cancer PDX M37 and IHC 2+ for gastric cancer PDX EK. When the gastric PDX (EK) was passaged s.c. in DKO mice and treated with i.v. PBMC ($1 \times 10^7$, once a week for 3 weeks) and i.v. HER2-BsAb (100 μg, twice per week for 5 weeks), tumors were completely eradicated without disease progression, (FIG. 32A), accompanied by substantial amount of T cell tumor infiltration (FIG. 32B), even though the HER2 expression level was relatively low compared to the M37 breast cancer PDX (FIG. 32C). In this next experiment, M37 PDX was passaged s.c. in DKO mice, and treated with i.v. PBMC ($7.5 \times 10^6$, once a week for 3 weeks) and i.v. HER2-BsAb (100 μg, twice per week for 6 weeks). Tumor growth was completely suppressed in the group treated with HER2-BsAb and PBMC (FIG. 32D). Interestingly, despite characterization of the M37 PDX as IHC 3+, which is a HER2 level indicative of suitability for treatment with trastuzumab (see, e.g., Wolff et al., Journal of Clinical Oncology, 2013, 31(31): 3997-4013), tumor growth was not suppressed in the M37 PDX group treated with PBMC+trastuzumab+huOKT3 (FIG. 32E). Taken together, these experiments showed that HER2-BsAb was effective against early passaged HER2(+) human tumor specimens.

6.3.4 Conclusions

This example described a HER2-specific BsAb with potent T cell mediated anti-tumor activity in vitro and in vivo, ablating tumors or delaying tumor growth in four separate tumor-human PBMC compartment models. Unlike monovalent bispecifics, this HER2-BsAb had identical anti-proliferative capacity to its parental trastuzumab. Its serum half-life and area under the curve were similar to IgG (data not shown). Most importantly, the T cell-mediated cytotoxicity it induced was relatively insensitive to inhibition by the PD-1/PD-L1 pathway, not previously described for this IgG-scFv platform (Xu et al., Cancer Immunology Research 2015; 3:266-77). To date, other than the anti-GD2 hu3F8-BsAb (Xu et al., Cancer Immunology Research 2015; 3:266-77), no published T-cell redirecting bispecific antibodies have used this format. The ability of this IgG-scFv antibody platform to recruit circulating lymphocytes into the tumor stroma is critical, given the importance of tumor-infiltrating lymphocyte (TIL) cells for a successful anti-tumor effect in most checkpoint blockade studies to date (Tumeh et al., Nature 2014; 515:568-71), distinguishing responders from nonresponders (Gajewski et al., Semin Oncol 2015; 42:663-71).

Schreiber has proposed that tumor cells evolve to evade the immune system through a process termed "immuno-editing". Broadly speaking, this process occurs at two levels: by changes within the (1) tumor cells or (2) the tumor microenvironment. Tumor cells can evade T-cell responses by down-regulating MHC/peptide complexes or by decreasing tumor-antigen expression or through the loss of antigen presenting machinery components. On the other hand, suppression of the immune response in the tumor microenvironment is the result of T-regulatory cells, Myeloid-derived suppressor cells, M2 macrophages (Diaz-Montero et al., Semin Oncol 2014; 41:174-84; Laoui et al., Frontiers in immunology 2014; 5:489; Nishikawa & Sakaguchi, Curr Opin Immunol 2014; 27:1-7), immuno-suppressive cytokines (including IDO) (Munn & Mellor, Trends Immunol 2013; 34:137-43), immune checkpoint molecules (Callahan et al., Frontiers in Oncology 2014; 4:385; Postow et al., J Clin Oncol 2015; 33(17):1974-82) and the consumption of IL-2 (Schreiber et al., Science 2011; 331:1565-70).

Immune checkpoint antibodies that target the CTLA-4 and PD-1/PD-L1 inhibitory pathways are capable of reversing the inhibitory tumor-microenvironment and producing significant and long-lasting clinical responses (Farolfi et al., Melanoma research 2012; 22:263-70). However, these strategies are not effective against all tumor types and their success is limited to a subset of patients. Durable clinical responses to the CTLA-4 blockade were recently correlated with tumor mutational load and the expression of antigenic tetra-peptides that resembled those found in viral and bacterial pathogens (Snyder et al., N Engl J Med 2014; 371: 2189-99). Clonal neoantigens were shown to elicit T cell immunoreactivity and sensitivity to blockade of the PD-1/PD-L1 axis (McGranahan et al., Science 2016; 351(6280): 1463-9). Based on these data, the pre-existence of CD8(+) T-cells in the tumor (TILs) would be critical. More importantly, IHC evidence of negative regulation of tumor infiltrating lymphocytes (TIL) by the PD-1/PD-L1 axis, was correlated with clinical response to checkpoint blockade (Tumeh et al., Nature 2014; 515:568-71).

As data continues to accumulate, a consensus is emerging that these immune modulations would likely be ineffective against tumors with low immunogenicity because the presence of tumor specific lymphocytes is required for their clinical activity. Indeed, HER2 has been linked to immune resistance (Seliger & Kiessling, Trends in Molecular Medicine 2013; 19:677-84). This subset of patients, with "T-cell resistant" HER2(+) tumor cells and/or insufficient clonal frequency of tumor-specific T-cells, would likely not benefit from immune checkpoint blockade alone. The unique property of the HER2-BsAb described in this example to recruit T-cells of any specificity and direct them against established tumors with relative insensitivity to the PD-1 immune checkpoint pathway is of interest, as it directly addresses the known limitations of immune checkpoint blockade. In fact, preliminary in vivo data showed no additional benefit of PD-1 blockade to the HER2-BsAb therapeutic efficacy (data not shown), even though tumor PD-L1 expression was up-regulated substantially following T cell infiltration (FIG. 30E).

When compared to the existing platforms that target HER2, HER2-BsAb offers advantages. Shalaby and colleagues described the development of a bispecific (Fab')2 antibody (anti-HER2 Fab'×anti-CD3 Fab') through expressing each Fab' separately and ligating the two together by chemical conjugation (Shalaby et al., J Exp Med 1992; 175:217-25). More recently, Junttila and colleagues developed a heterodimeric bispecific IgG (anti-HER2×anti-CD3) using "knob-and-hole" format (Junttila et al., Cancer Research 2014; 74:5561-71). Both formats have monovalent binding to either HER2 or CD3, and are substantially different, both structurally and functionally, when compared to the HER2-BsAb described herein for the following reasons. First, the bivalent binding to HER2 is critical for the anti-proliferation capability, which is preserved in the HER2-BsAb construct described herein (FIG. 26C) but not in those two monovalent systems, as demonstrated by Junttila et al. Junttila et al. showed that the anti-proliferation capability of monovalent binding to HER2 (either heterodimeric bispecific IgG or trastuzumab-Fab) was 10-fold lower than bivalent trastuzumab (Junttila et al., Cancer Research 2014; 74:5561-71). Without being bound by any particular theory, it is hypothesized that the dual mechanism (anti-proliferation plus T cell cytotoxicity) may create synergism and partly explains the potent efficacy of the HER2-BsAb in vivo. This may provide a salvage option for patients who progress on standard HER2-based therapies, or a replacement for trastuzumab given its dual anti-proliferative and T cell retargeting properties. Second, the bivalent binding to HER2 in our BsAb maintains high avidity (FIG. 26B) so as to maximize tumor binding, while the monovalent binding to HER2 (either heterodimeric bispecific IgG or trastuzumab-Fab) is 10-fold lower than trastuzumab (Junttila et al., Cancer Research 2014; 74:5561-71). Higher avidity results in higher T cell dependent cell cytotoxicity, a phenomenon that has been demonstrated in T cell engaging bispecific antibodies (Ahmed et al., OncoImmunology 2015; 4:e989776). Additionally, without being bound by any particular theory, it is hypothesized that the high avidity of the HER2-BsAb contributes to overcoming PD-1/PD-L1 checkpoints (FIG. 29), whereas the monovalent system by Juntilla was shown to be inhibited by the PD-1/PD-L1 axis. Third, the BsAb described in this example has the trastuzumab IgG backbone, preserving its pharmacologic advantages, while Shalaby's construct doesn't have FcR(n) affinity, should have much shorter serum half-life, and probably needs to be administered as a continuous infusion (as for Blinatumomab) to be effective in vivo. Fourth, the other advantage is manufacturability: once a CHO stable line established, the HER2-BsAb can be produced in large scale and purified like normal IgG without significant aggregation despite prolonged incubation at 37° C., while chemical conjugates require more complicated syntheses and downstream processing—each Fab' expressed and purified separately, chemically modified, and then the two chemically conjugated and repurified. To ensure a final product that is pure and chemically stable for direct clinical infusion is technically challenging and costly. Such chemically crosslinked reagents have only been feasible for ex vivo arming of T cells, but not for direct parenteral injections in the clinic (Lum & Thakur A, BioDrugs 2011; 25:365-79).

A primary goal was to build a BsAb that has the bivalent binding to tumor targets (to preserve high avidity and/or anti-proliferation capability) and the monovalent binding to CD3 on effector T cells (to minimize spontaneous T cell activation in the absence of tumor targets). A number of uniquely different bivalent formats were surveyed, including chemical conjugation (Yankelevich et al., Pediatr Blood Cancer 2012; 59:1198-205), dual-variable-domain (DVD), or attaching huOKT3 scFv to different positions in the IgG backbone (C-terminal of heavy chain or C-terminal of light chain) (Kontermann, MAbs 2012; 4), and it was found that the last option gave the best functionality. Although the HER2-BsAb has anti-CD3 scFv attached to both light chains, its reaction with CD3 on T cells was considered as functionally monovalent primarily for the following reasons. First, although the HER2-BsAb format contains two anti-CD3 scFvs positioned at the end of the light chains, these scFvs are oriented in geometrically opposed directions which restrict their ability to cooperatively bind to neighboring CD3 on T cells. This restricts the BsAb from binding bivalently and hence results in functional monovalency to CD3. It has previously been shown in a different BsAb format that geometrical restriction of two anti-CD3 scFv can result in functionally monovalent binding to T cell and lower cytokine release (Ahmed et al., OncoImmunology 2015; 4:e989776). Second, the functional consequence of bivalent binding to CD3 on T cells is the triggering of spontaneous T cell activation, hence strong cytokine release in the absence of tumor targets. As shown in FIG. 33A, HER2-BsAb only stimulated background cytokine release similar to that of the monovalent huOKT3 Fab, while bivalent huOKT3 IgG induced substantially more cytokines in the absence of tumor targets (left panel). However, in the presence of HER2(+) NCI-N87 tumor target, anti-tumor TH1 cytokines (TNFα and IFNγ) were released but only in the presence of BsAb (right panel), a format previously shown to induce immunologic synapse formation between the T cells and tumor targets (Xu et al., Cancer Immunology Research 2015; 3:266-77). Furthermore, only bivalent huOKT3 IgG induced robust T cell proliferation, while HER2-BsAb and monovalent huOKT3 Fab had negligible effects comparable to the T cells only Control (FIG. 33B). In addition, the aglycosylation of the Fc removed both ADCC and most CMC functions, thereby further reducing cytokine release without affecting serum pharmacokinetics or compromising T cell activation.

Chimeric antigen receptor technology has rapidly accelerated investigations into HER2-directed gene modified T cells in several clinical trials: NCT00902044 (for sarcoma), NCT00889954 (all HER2(+) cancers), NCT01109095 (GBM), NCT00924287 (metastatic cancer), and NCT01935843 (HER2(+) solid tumors). Toxicities from off target effects were initially concerning (Morgan et al., Mol Ther 2010; 18:843-51), although subsequent patients have been safely managed pharmacologically. There, the ability of T cells to overcome low levels of antigen expression was again observed. Osteosarcoma was a good example where the expression level has been controversial (Thomas et al., Clin Cancer Res 2002; 8:788-93), and where CAR-modified T cells were highly efficient against locoregional and metastatic xenografts (Ahmed et al., Mol Ther 2009; 17:1779-87), and against osteosarcoma tumor initiating cells (Rainusso et al., Cancer Gene Ther 2012; 19:212-7). Although the successful clinical application of CAR T cells has reassured many skeptics, there remain obstacles, including the necessity of cytoreductive chemotherapy prior to T cell infusion for meaningful clinical responses, logistics of cell harvest, processing, storage, transport and product release, T cell exhaustion (Long et al., Nat Med 2015; 21:581-90) and inadequate T cell persistence after infusion.

In summary, this example demonstrates a successful IgG-scFv platform to engage T cells for HER2-directed immunotherapy. This BsAb for retargeting T cells was built with structural considerations for bivalency towards the target, and functionally monovalency towards CD3 on effector T cells, plus Fc aglycosylation for minimal spontaneous cytokine release. Its relative insensitivity to the PD-1/PD-L1 axis was novel. It has excellent anti-tumor activity both in vitro and in vivo, which is superior to trastuzumab.

6.4 Example 4

This example demonstrates that HER2-BsAb described in section 6.3.3.1 above (comprising a heavy chain consisting of the amino acid sequence set forth in SEQ ID NO: 62 and a light chain fusion polypeptide consisting of the amino acid sequence set forth in SEQ ID NO: 60) is effective against HER2(+) breast cancer cell line xenografts that express PDL1 but are resistant to PD1 or PDL1 treatment (FIG. 34). See Section 6.3.2.8 for materials and methods. In particular, $5 \times 10^6$ HCC1954 xenografts were implanted subcutaneously in mice and mice were treated intravenously with $7.5 \times 10^6$ PBMC once per week for two weeks and intravenously with HER2-BsAb, anti-PD1 antibody Pembrolizumab, or anti-PDL1 antibody Atezolizumab. HER2-BsAb, anti-PD1 antibody, and anti-PDL1 antibody treatments were performed with 100 µg each, twice per week for 4 weeks. HER2-BsAb-treated tumors were completely eradicated. In contrast, there was no effect on tumors treated with PD1/PDL1 blockade (i.e., treatment with anti-PD1 antibody Pembrolizumab or anti-PDL1 antibody Atezolizumab).

7. EQUIVALENTS

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A method of treating a cancer that expresses a low level of HER2 in a subject in need thereof comprising administering a therapeutically effective amount of a pharmaceutical composition to the subject,
wherein the cancer has been determined not to overexpress HER2 based on a determination of a level of HER2 in a test specimen comprising cells of the cancer reported as equivocal or negative, wherein the level of HER2 in a test specimen comprising cells of the cancer is characterized as IHC 2+ or IHC 1+,
wherein the pharmaceutical composition comprises T cells bound to a bispecific binding molecule comprising
a heavy chain-aglycosylated monoclonal antibody that is an immunoglobulin that binds to HER2, comprising two identical heavy chains and two identical light chains, said light chains being a first light chain and a second light chain, wherein the first light chain is fused to a first single chain variable fragment (scFv), via a peptide linker, to create a first light chain fusion polypeptide, and wherein the second light chain is fused to a second scFv, via a peptide linker, to create a second light chain fusion polypeptide, wherein the first and second scFv (i) are identical, and (ii) bind to CD3, and wherein the first and second light chain fusion polypeptides are identical,
wherein each heavy chain comprises a heavy chain variable domain (VH) present in any one of SEQ ID NOs: 23, 27, 62 or 63, and wherein each light chain comprises a light chain variable domain (VL) present in SEQ ID NO: 25; and
wherein each scFv comprises a VH sequence of any one of SEQ ID NOs: 15, 17 or 64, and a VL sequence of any one of SEQ ID NOs: 16 or 65.

2. The method of claim 1, wherein the cancer is breast cancer, gastric cancer, an osteosarcoma, desmoplastic small round cell cancer, ovarian cancer, prostate cancer, pancreatic cancer, glioblastoma multiforme, gastric junction adenocarcinoma, gastroesophageal junction adenocarcinoma, cervical cancer, salivary gland cancer, soft tissue sarcoma, leukemia, melanoma, Ewing's sarcoma, rhabdomyosarcoma, or neuroblastoma and/or wherein the cancer is resistant to treatment with trastuzumab, cetuximab, lapatinib, erlotinib, or any other small molecule or antibody that targets the HER family of receptors.

3. The method of claim 1, wherein the sequence of each heavy chain is any one of SEQ ID NOs: 23, 27, 62 or 63, and wherein the sequence of each light chain is SEQ ID NO: 25.

4. The method of claim 1, wherein the sequence of the peptide linker is any one of SEQ ID NOs: 14 or 35-41.

5. The method of claim 1, wherein the scFv comprises an intra-scFv peptide linker between the VH and the VL of the scFv, optionally wherein the sequence of the intra-scFv peptide linker is any one of SEQ ID NOs: 14 or 35-41.

6. The method of claim 1, wherein the sequence of the scFv is any one of SEQ ID NOs: 19 or 48-59, or wherein the scFv is disulfide stabilized.

7. The method of claim 1, wherein the sequence of the first light chain fusion polypeptide is any one of SEQ ID NOs: 29, 34, 42-47, or 60.

8. The method of claim 1, wherein the sequence of the heavy chain and the sequence of each light chain fusion polypeptide is SEQ ID NO: 62 and SEQ ID NO: 60; SEQ ID NO: 27 and SEQ ID NO: 47; SEQ ID NO: 27 and SEQ ID NO: 34, or SEQ ID NO: 27 and SEQ ID NO: 29, respectively.

9. The method of claim 1, wherein the bispecific binding molecule does not bind an Fc receptor in its soluble or cell-bound form and/or does not activate complement.

10. The method of claim 1, wherein the cancer is a metastatic tumor, optionally wherein the metastatic tumor is a peritoneal metastasis.

11. The method of claim 1, wherein the administering is intravenous, intraperitoneal, intrathecal, intraventricular in the brain, or intraparenchymal in the brain.

12. The method of claim 1, wherein the method further comprises administering to the subject
doxorubicin, cyclophosphamide, paclitaxel, docetaxel, and/or carboplatin;
radiotherapy;
multi-modality anthracycline-based therapy;
an agent that increases cellular HER2 expression; or
T cells, optionally wherein the T cells are bound to the bispecific binding molecule.

* * * * *

SEQUENCE LISTING

<160> NUMBER OF SEQ ID NOS: 72

<210> SEQ ID NO 1
<211> LENGTH: 4664
<212> TYPE: DNA

<213> ORGANISM: Homo sapiens
<300> PUBLICATION INFORMATION:
<308> DATABASE ACCESSION NUMBER: NM_004448.3
<309> DATABASE ENTRY DATE: 2014-05-26
<313> RELEVANT RESIDUES IN SEQ ID NO: (1)..(4664)

<400> SEQUENCE: 1

```
gcttgctccc aatcacagga gaaggaggag gtggaggagg agggctgctt gaggaagtat      60
aagaatgaag ttgtgaagct gagattcccc tccattggga ccggagaaac caggggagcc     120
ccccgggcag ccgcgcgccc cttcccacgg ggcccttta c tgcgccgcgc gcccggcccc    180
caccc ctcgc agcaccccgc gccccgcgcc ctcccagccg gtccagccg  agccatggg     240
gccggagccg cagtgagcac catggagctg gcggccttgt gccgctgggg gctcctcctc    300
gccctcttgc ccccggagc cgcgagcacc caagtgtgca ccggcacaga catgaagctg     360
cggctccctg ccagtcccga gacccacctg gacatgctcc gccacctcta ccagggctgc   420
caggtggtgc agggaaacct ggaactcacc tacctgccca ccaatgccag cctgtccttc    480
ctgcaggata tccaggaggt gcagggctac gtgctcatcg ctcacaacca agtgaggcag    540
gtcccactgc agaggctgcg gattgtgcga ggcacccagc tctttgagga caactatgcc    600
ctggccgtgc tagacaatgg agacccgctg aacaatacca cccctgtcac agggccctcc    660
ccaggaggcc tgcgggagct gcagcttcga agcctcacag agatcttgaa aggaggggtc    720
ttgatccagc gaaccccca gctctgctac caggacacga ttttgtggaa ggacatcttc    780
cacaagaaca accagctggc tctcacactg atagacacca accgctctcg ggcctgccac   840
ccctgttctc cgatgtgtaa gggctcccgc tgctggggag agagttctga ggattgtcag    900
agcctgacgc gcactgtctg tgccggtggc tgtgcccgct gcaaggggcc actgcccact    960
gactgctgcc atgagcagtg tgctgccggc tgcacgggcc ccaagcactc tgactgcctg   1020
gcctgcctcc acttcaacca cagtggcatc tgtgagctgc actgcccagc cctggtcacc   1080
tacaacacag acacgtttga gtccatgccc aatcccgagg ccggtatac attcggcgcc  1140
agctgtgtga ctgcctgtcc ctacaactac ctttctacgg acgtgggatc ctgcaccctc   1200
gtctgccccc tgcacaacca agaggtgaca gcagaggatg aaacagcgcg tgtgagaag   1260
tgcagcaagc cctgtgcccg agtgtgctat ggtctgggca tggagcactt gcgagaggtg   1320
agggcagtta ccagtgccaa tatccaggag tttgctggct gcaagaagat ctttgggagc   1380
ctggcatttc tgccggagag cttt gatggg gacccagcct ccaacactgc cccgctccag  1440
ccagagcagc tccaagtgtt tgagactctg gaagagatca caggttacct atacatctca  1500
gcatggccgg acagcctgcc tgacctcagc gtcttccaga acctgcaagt aatccgggga    1560
cgaattctgc acaatggcgc ctactcgctg accctgcaag gcctgggcat cagctggctg   1620
gggctgcgct cactgaggga actgggcagt ggactggccc tcatccacca taacacccac    1680
ctctgcttcg tgcacacggt gccctgggac cagctctttc ggaacccgca ccaagctctg   1740
ctccacactg ccaaccggcc agaggacgag tgtgtgggcg agggcctggc ctgccaccag   1800
ctgtgcgccc gagggcactg ctgggggcca gggcccaccc agtgtgtcaa ctgcagccag   1860
ttccttcggg gccaggagtg cgtggaggaa tgccgagtac tgcagggcct ccccaggag   1920
tatgtgaatg ccaggcactg tttgccgtgc caccctgagt gtcagcccca gaatggctca   1980
gtgacctgtt ttggaccgga ggctgaccag tgtgtggcct gtgcccacta taaggaccct   2040
cccttctgcg tggcccgctg ccccagcggt gtgaaacctg acctctccta catgcccatc   2100
tggaagtttc cagatgagga gggcgcatgc cagccttgcc ccatcaactg cacccactcc   2160
```

```
tgtgtggacc tggatgacaa gggctgcccc gccgagcaga gagccagccc tctgacgtcc    2220
atcatctctg cggtggttgg cattctgctg gtcgtggtct tgggggtggt ctttgggatc    2280
ctcatcaagc gacggcagca gaagatccgg aagtacacga tgcggagact gctgcaggaa    2340
acggagctgg tggagccgct gacacctagc ggagcgatgc ccaaccaggc gcagatgcgg    2400
atcctgaaag agacggagct gaggaaggtg aaggtgcttg gatctggcgc ttttggcaca    2460
gtctacaagg gcatctggat ccctgatggg gagaatgtga aaattccagt ggccatcaaa    2520
gtgttgaggg aaaacacatc ccccaaagcc aacaagaaaa tcttagacga agcatacgtg    2580
atggctggtg tgggctcccc atatgtctcc cgccttctgg gcatctgcct gacatccacg    2640
gtgcagctgg tgacacagct tatgcccctat ggctgcctct tagaccatgt ccgggaaaac   2700
cgcggacgcc tgggctccca ggacctgctg aactggtgta tgcagattgc caaggggatg    2760
agctacctgg aggatgtgcg gctcgtacac agggacttgg ccgctcggaa cgtgctggtc    2820
aagagtccca accatgtcaa aattacagac ttcgggctgg ctcggctgct ggacattgac    2880
gagacagagt accatgcaga tgggggcaag gtgcccatca gtggatggc gctggagtcc     2940 attctccgcc ggcggttcac ccaccagagt gatgtgtgga gttatggtgt gactgtgtgg    3000
gagctgatga cttttggggc caaaccttac gatgggatcc cagcccggga gatccctgac    3060
ctgctggaaa aggggagcg gctgcccag ccccccatct gcaccattga tgtctacatg       3120
atcatggtca aatgttggat gattgactct gaatgtcggc caagattccg ggagttggtg    3180
tctgaattct cccgcatggc cagggacccc cagcgctttg tggtcatcca gaatgaggac    3240
ttgggcccag ccagtccctt ggacagcacc ttctaccgct cactgctgga ggacgatgac    3300 atggggggacc tggtggatgc tgaggagtat ctggtacccc agcagggctt cttctgtcca   3360
gaccctgccc cgggcgctgg gggcatggtc caccacaggc accgcagctc atctaccagg    3420
agtggcggtg gggaccctgac actagggctg gagccctctg aagaggaggc ccccaggtct   3480
ccactggcac cctccgaagg ggctggctcc gatgtatttg atggtgacct gggaatgggg    3540
gcagccaagg ggctgcaaag cctccccaca catgacccca gccctctaca gcggtacagt    3600
gaggacccca cagtaccccct gccctctgag actgatggct acgttgcccc cctgacctgc   3660 agccccagc ctgaatatgt gaaccagcca gatgttcggc cccagccccc ttcgccccga     3720
gagggccctc tgcctgctgc ccgacctgct ggtgccactc tggaaaggcc caagactctc    3780
tccccaggga agaatggggt cgtcaaagac gttttttgcct ttgggggtgc cgtggagaac   3840
cccgagtact tgacacccca gggaggagct gccctcagc ccacccctcc tcctgccttc     3900
agcccagcct tcgacaacct ctattactgg gaccaggacc caccagagcg gggggctcca    3960
cccagcacct tcaaagggac acctacgcca gagaacccag agtacctggg tctggacgtg    4020
ccagtgtgaa ccagaaggcc aagtccgcag aagccctgat gtgtcctcag ggagcaggga    4080
aggcctgact tctgctggca tcaagaggtg ggagggccct ccgaccactt ccaggggaac    4140
ctgccatgcc aggaacctgt cctaaggaac cttccttcct gcttgagttc ccagatggct    4200 ggaagggggtc cagcctcgtt ggaagaggaa cagcactggg gagtctttgt ggattctgag   4260
gccctgccca atgagactct agggtccagt ggatgccaca gcccagcttg gccctttcct    4320
tccagatcct gggtactgaa agccttaggg aagctggcct gagagggaa gcggccctaa     4380 gggagtgtct aagaacaaaa gcgacccatt cagagactgt ccctgaaacc tagtactgcc    4440
ccccatgagg aaggaacagc aatggtgtca gtatccaggc tttgtacaga gtgctttttct  4500
```

```
gtttagtttt tactttttttt gttttgtttt tttaaagatg aaataaagac ccaggggggag   4560 aatgggtgtt gtatggggag gcaagtgtgg ggggtccttc tccacaccca ctttgtccat     4620
ttgcaaatat attttggaaa acagctaaaa aaaaaaaaaa aaaa                     4664
```

<210> SEQ ID NO 2
<211> LENGTH: 1255
<212> TYPE: PRT
<213> ORGANISM: Homo sapiens
<300> PUBLICATION INFORMATION:
<308> DATABASE ACCESSION NUMBER: NP_004439.2
<309> DATABASE ENTRY DATE: 2014-05-26
<313> RELEVANT RESIDUES IN SEQ ID NO: (1)..(1255)

<400> SEQUENCE: 2

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
```

-continued

```
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
            355                 360                 365
Lys Ile Phe Gly Ser Leu Ala Phe Leu Pro Glu Ser Phe Asp Gly Asp
        370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
            435                 440                 445
Gly Ile Ser Trp Leu Gly Leu Arg Ser Leu Arg Glu Leu Gly Ser Gly
        450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
            515                 520                 525
Val Asn Cys Ser Gln Phe Leu Arg Gly Gln Glu Cys Val Glu Glu Cys
        530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
        610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Leu Gly Val Val Phe Gly
            660                 665                 670
Ile Leu Ile Lys Arg Arg Gln Gln Lys Ile Arg Lys Tyr Thr Met Arg
            675                 680                 685
Arg Leu Leu Gln Glu Thr Glu Leu Val Glu Pro Leu Thr Pro Ser Gly
        690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
```

-continued

```
Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
    995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155
```

| Ala | Ala | Arg | Pro | Ala | Gly | Ala | Thr | Leu | Glu | Arg | Pro | Lys | Thr | Leu |
| | 1160 | | | | 1165 | | | | | 1170 | | | | |

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 3
<211> LENGTH: 3780
<212> TYPE: DNA
<213> ORGANISM: Canine
<300> PUBLICATION INFORMATION:
<308> DATABASE ACCESSION NUMBER: NM_001003217.1
<309> DATABASE ENTRY DATE: 2014-02-23
<313> RELEVANT RESIDUES IN SEQ ID NO: (1)..(3780)

<400> SEQUENCE: 3

```
atggagctgg cggcctggtg ccgctggggg ctccttctcg ccctcctgcc ctccggagcc      60
gcgggcaccc aagtgtgcac cggcacagac atgaagctcc ggctcccggc cagtcccgag     120
acccacctgg atatgctccg ccacctgtac cagggctgtc aagtggtaca ggggaacctg     180
gagctcactt acctgcctgc caatgccagc ctgtccttcc tgcaggatat ccaggaggtg     240
cagggctatg tgctcattgc tcacagccaa gtgaggcaga tcccactgca gaggctacga     300
attgtgcgag gcacccagct ctttgaggac aactacgccc tggccgtgct ggacaatgga     360
gacccgctgg agggtggcat ccctgcacca ggggcggccc aaggagggct gcgggagctg     420
cagcttcgaa gcctcacaga gatcctgaag ggagggtct tgattcagcg gagcccgcag     480
ctctgccacc aggacacgat tttatggaag gacgtcttcc ataagaacaa ccagctggcc     540
ctcacgctga tagacaccaa ccgctttttcg gcctgcccgc cctgttctcc agcttgtaaa     600
gacgcccact gctgggggc cagctccggg gactgtcaga gcttgacgcg gactgtctgt     660
gccgggggct gtgcccgctg caagggccca caacccaccg actgctgcca cgagcagtgt     720
gctgctggct gcacgggccc caagcactct gactgcctgg cctgccttca cttcaaccac     780
agtggcatct gtgagctgca ctgcccagcc ctggtcacct acaacacgga caccttcgaa     840
tccatgccca accctgaggg ccgatatacc ttcggggcca gctgtgtgac ctcctgtccc     900
tacaactacc tgtctacgga tgtgggatcc tgcacccctgg tctgtccct gaacaaccaa     960 gaggtgacgg ctgaggatgg gacacagcgg tgcgagaaat gcagcaagcc ctgtgcccga    1020
gtgtgctacg gtctgggcat ggagcacctg cgagaggtga gcggtcac cagtgcgaac    1080 atccaggagt ttgccggctg caagaagatc tttggaagcc tggcattttt gccagagagc    1140
tttgatgggg acccagcctc caacactgcc cccctacagc ctgagcagct cagagtgttt    1200
gaggctctgg aggagatcac aggttacctg tacatctcag cgtggccaga cagcctgcct    1260
aacctcagtg tcttccagaa cctgcgagta atccggggac gagttctgca tgatggtgcc    1320
tactcgctga ccctgcaagg gctgggcatc agctggctgg gctgcgctc gctgcgggaa    1380
```

```
ctgggcagtg ggctggccct catccaccgc aacgcccgcc tttgcttcgt gcacacggtg    1440
ccctgggacc agctcttccg gaaccccgac caggccctgc tccatagtgc caaccggcca    1500
gaggaggagt gcgtgggcga gggcctggcc tgctacccct gtgcccatgg gcactgctgg    1560
ggtccagggc ccacccagtg cgtcaactgc agccaattcc tccggggcca ggagtgcgtg    1620
gaggaatgcc gagtactgca ggggctgccc cgagagtatg tgaaggacag gtactgtcta    1680
ccgtgccact cagagtgtca gccccagaat ggctcagtga cctgtttcgg atcggaggct    1740
gaccagtgtg tggcctgcgc ccactacaag gaccctccct tctgtgtggc tcgctgcccc    1800
agtggtgtga aacctgacct gtccttcatg cccatctgga agttcgcaga tgaggagggc    1860
acttgccagc cgtgccccat caactgcacc cactcctgtg cggacctgga cgagaagggc    1920
tgtcccgccg agcagagagc cagccctgtg catccatca ttgccgctgt ggtgggcatt    1980
ctgctggctg tggtcgtggg gctggtcctc ggcatcctga tcaagcgaag gcggcagaag    2040
atccggaagt acactatgcg gaggctgctg caggaaaccg agctggtgga gccgctgacg    2100
cctagtggag cgatgcccaa ccaggctcag atgcggatcc tgaaagagac agagctgagg    2160
aaggtgaagg tgcttggatc cggagctttt ggcacagtct acaagggcat ctggatccct    2220 gatgggggaaa atgtgaaaat cccagtggcc atcaaagtgt tgagggaaaa cacatctccc    2280
aaagccaaca agaaatcttt ggacgaagca tatgtgatgg ctggagtggg ctccccgtat    2340
gtgtcccgcc tcctgggcat ctgcctgaca tccacggtgc agctggtgac acagcttatg    2400
ccctacggct gcctcttaga ccatgtccga gaacaccgtg gcgcctggg ctcccaggac    2460 ttgctgaact ggtgtgtgca gattgccaag gggatgagct acttggagga tgtccggctg    2520
gtgcacaggg acctggctgc ccggaatgtg ctggtcaaga gtcccaacca tgtcaagatt    2580
acagatttcg ggctggctcg gttgctggac atcgacgaga cagagtacca tgcggatggg    2640
ggcaaggtgc ccatcaagtg gatggcgctg gagtccattc ctccgcggcg gttcacccac    2700
cagagtgatg tgtggagcta tggtgtgact gtgtgggaac tgatgacttt tggggccaaa    2760
ccttatgatg ggatcccagc ccgggagatc cctgacctgc tggagaaggg ggaacggctg    2820
ccccagcccc ccatctgcac cattgatgtc tacatgatca tggtcaagtg ctggatgata    2880
gactctgaat gccgaccccg gttccgggag ttggtggccg aattctcacg tatggccagg    2940 gaccccagc gctttgtggt cattcagaat gaagacttgg gccccgccag ccccttggac    3000
agcaccttct accgttcact actggaagat gatgacatgg gggacctggt ggatgctgag    3060
gagtacctgg tacccagca gggttttctc tgcccagaac ctaccccagg ggctgggggc    3120
actgcccacc gacggcaccg cagctcatcc accaggaatg gcggtggtga gctgactcta    3180
ggactggagc cctccgagga ggagccccc aagtctccac tggcaccctc agagggcgct    3240
ggctctgacg tgtttgatgg tgacttggga atgggggcag ccaaggggct gcagagcctt    3300
ccctcacagg accccagccc tctccagcgg tacagtgagg accctacggt acccttgccc    3360
cctgagactg atggtaaggt tgccccccctg acctgcagcc cccagcctga atatgtgaac    3420
cagccagaag tttggccgca gcccccctt gccctagaag gccctttgcc tccttcccga    3480
ccggctggtg ccactctgga aaggcccaag actctgtccc caagactct ctcccctggc    3540 aagaatgggg ttgtcaaaga cgttttgcc tttgggagtg ctgtggagaa tccggagtac    3600
ctggcacccc ggggcagagc tgcccctcag cccaccctc ctccagcctt cagcccagcc    3660
tttgacaacc tgtattactg ggaccaggat ccatcagagc ggggctctcc acccagcacc    3720
tttgaaggga ccctacagc agagaacccg gagtacctgg ggctggacgt gccagtgtga    3780
```

-continued

<210> SEQ ID NO 4
<211> LENGTH: 1259
<212> TYPE: PRT
<213> ORGANISM: Canine
<300> PUBLICATION INFORMATION:
<308> DATABASE ACCESSION NUMBER: NP_001003217.1
<309> DATABASE ENTRY DATE: 2014-02-23
<313> RELEVANT RESIDUES IN SEQ ID NO: (1)..(1259)

<400> SEQUENCE: 4

```
Met Glu Leu Ala Ala Trp Cys Arg Trp Gly Leu Leu Ala Leu Leu
1               5                   10                  15

Pro Ser Gly Ala Ala Gly Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Ala Asn Ala Ser Leu Ser Phe Leu Gln Asp Ile Gln Glu Val
65                  70                  75                  80

Gln Gly Tyr Val Leu Ile Ala His Ser Gln Val Arg Gln Ile Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Glu Gly Gly Ile Pro
        115                 120                 125

Ala Pro Gly Ala Ala Gln Gly Gly Leu Arg Glu Leu Gln Leu Arg Ser
    130                 135                 140

Leu Thr Glu Ile Leu Lys Gly Gly Val Leu Ile Gln Arg Ser Pro Gln
145                 150                 155                 160

Leu Cys His Gln Asp Thr Ile Leu Trp Lys Asp Val Phe His Lys Asn
                165                 170                 175

Asn Gln Leu Ala Leu Thr Leu Ile Asp Thr Asn Arg Phe Ser Ala Cys
            180                 185                 190

Pro Pro Cys Ser Pro Ala Cys Lys Asp Ala His Cys Trp Gly Ala Ser
        195                 200                 205

Ser Gly Asp Cys Gln Ser Leu Thr Arg Thr Val Cys Ala Gly Gly Cys
    210                 215                 220

Ala Arg Cys Lys Gly Pro Gln Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ser Cys Pro Tyr Asn Tyr Leu
    290                 295                 300

Ser Thr Asp Val Gly Ser Cys Thr Leu Val Cys Pro Leu Asn Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350
```

```
Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Arg Val Phe
385                 390                 395                 400

Glu Ala Leu Glu Glu Ile Thr Gly Tyr Leu Tyr Ile Ser Ala Trp Pro
                405                 410                 415

Asp Ser Leu Pro Asn Leu Ser Val Phe Gln Asn Leu Arg Val Ile Arg
            420                 425                 430

Gly Arg Val Leu His Asp Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His Arg Asn Ala Arg Leu Cys Phe Val His Thr Val
465                 470                 475                 480

Pro Trp Asp Gln Leu Phe Arg Asn Pro His Gln Ala Leu Leu His Ser
                485                 490                 495

Ala Asn Arg Pro Glu Glu Glu Cys Val Gly Glu Gly Leu Ala Cys Tyr
            500                 505                 510

Pro Cys Ala His Gly His Cys Trp Gly Pro Gly Pro Thr Gln Cys Val
        515                 520                 525

Asn Cys Ser Gln Phe Leu Arg Gly Gln Glu Cys Val Glu Glu Cys Arg
    530                 535                 540

Val Leu Gln Gly Leu Pro Arg Glu Tyr Val Lys Asp Arg Tyr Cys Leu
545                 550                 555                 560

Pro Cys His Ser Glu Cys Gln Pro Gln Asn Gly Ser Val Thr Cys Phe
                565                 570                 575

Gly Ser Glu Ala Asp Gln Cys Val Ala Cys Ala His Tyr Lys Asp Pro
            580                 585                 590

Pro Phe Cys Val Ala Arg Cys Pro Ser Gly Val Lys Pro Asp Leu Ser
        595                 600                 605

Phe Met Pro Ile Trp Lys Phe Ala Asp Glu Glu Gly Thr Cys Gln Pro
    610                 615                 620

Cys Pro Ile Asn Cys Thr His Ser Cys Ala Asp Leu Asp Glu Lys Gly
625                 630                 635                 640

Cys Pro Ala Glu Gln Arg Ala Ser Pro Val Thr Ser Ile Ile Ala Ala
                645                 650                 655

Val Val Gly Ile Leu Leu Ala Val Val Val Gly Leu Val Leu Gly Ile
            660                 665                 670

Leu Ile Lys Arg Arg Gln Lys Ile Arg Lys Tyr Thr Met Arg Arg
        675                 680                 685

Leu Leu Gln Glu Thr Glu Leu Val Glu Pro Leu Thr Pro Ser Gly Ala
    690                 695                 700

Met Pro Asn Gln Ala Gln Met Arg Ile Leu Lys Glu Thr Glu Leu Arg
705                 710                 715                 720

Lys Val Lys Val Leu Gly Ser Gly Ala Phe Gly Thr Val Tyr Lys Gly
                725                 730                 735

Ile Trp Ile Pro Asp Gly Glu Asn Val Lys Ile Pro Val Ala Ile Lys
            740                 745                 750

Val Leu Arg Glu Asn Thr Ser Pro Lys Ala Asn Lys Glu Ile Leu Asp
        755                 760                 765

Glu Ala Tyr Val Met Ala Gly Val Gly Ser Pro Tyr Val Ser Arg Leu
```

```
            770             775             780
Leu Gly Ile Cys Leu Thr Ser Thr Val Gln Leu Val Thr Gln Leu Met
785             790             795             800

Pro Tyr Gly Cys Leu Leu Asp His Val Arg Glu His Arg Gly Arg Leu
            805             810             815

Gly Ser Gln Asp Leu Leu Asn Trp Cys Val Gln Ile Ala Lys Gly Met
            820             825             830

Ser Tyr Leu Glu Asp Val Arg Leu Val His Arg Asp Leu Ala Ala Arg
            835             840             845

Asn Val Leu Val Lys Ser Pro Asn His Val Lys Ile Thr Asp Phe Gly
850             855             860

Leu Ala Arg Leu Leu Asp Ile Asp Glu Thr Glu Tyr His Ala Asp Gly
865             870             875             880

Gly Lys Val Pro Ile Lys Trp Met Ala Leu Glu Ser Ile Pro Pro Arg
            885             890             895

Arg Phe Thr His Gln Ser Asp Val Trp Ser Tyr Gly Val Thr Val Trp
            900             905             910

Glu Leu Met Thr Phe Gly Ala Lys Pro Tyr Asp Gly Ile Pro Ala Arg
            915             920             925

Glu Ile Pro Asp Leu Leu Glu Lys Gly Glu Arg Leu Pro Gln Pro Pro
930             935             940

Ile Cys Thr Ile Asp Val Tyr Met Ile Met Val Lys Cys Trp Met Ile
945             950             955             960

Asp Ser Glu Cys Arg Pro Arg Phe Arg Glu Leu Val Ala Glu Phe Ser
            965             970             975

Arg Met Ala Arg Asp Pro Gln Arg Phe Val Val Ile Gln Asn Glu Asp
            980             985             990

Leu Gly Pro Ala Ser Pro Leu Asp Ser Thr Phe Tyr Arg Ser Leu Leu
            995             1000            1005

Glu Asp Asp Asp Met Gly Asp Leu Val Asp Ala Glu Glu Tyr Leu
    1010            1015            1020

Val Pro Gln Gln Gly Phe Phe Cys Pro Glu Pro Thr Pro Gly Ala
    1025            1030            1035

Gly Gly Thr Ala His Arg Arg His Arg Ser Ser Ser Thr Arg Asn
    1040            1045            1050

Gly Gly Gly Glu Leu Thr Leu Gly Leu Glu Pro Ser Glu Glu Glu
    1055            1060            1065

Pro Pro Lys Ser Pro Leu Ala Pro Ser Glu Gly Ala Gly Ser Asp
    1070            1075            1080

Val Phe Asp Gly Asp Leu Gly Met Gly Ala Ala Lys Gly Leu Gln
    1085            1090            1095

Ser Leu Pro Ser Gln Asp Pro Ser Pro Leu Gln Arg Tyr Ser Glu
    1100            1105            1110

Asp Pro Thr Val Pro Leu Pro Pro Glu Thr Asp Gly Lys Val Ala
    1115            1120            1125

Pro Leu Thr Cys Ser Pro Gln Pro Glu Tyr Val Asn Gln Pro Glu
    1130            1135            1140

Val Trp Pro Gln Pro Pro Leu Ala Leu Glu Gly Pro Leu Pro Pro
    1145            1150            1155

Ser Arg Pro Ala Gly Ala Thr Leu Glu Arg Pro Lys Thr Leu Ser
    1160            1165            1170

Pro Lys Thr Leu Ser Pro Gly Lys Asn Gly Val Val Lys Asp Val
    1175            1180            1185
```

| Phe | Ala | Phe | Gly | Ser | Ala | Val | Glu | Asn | Pro | Glu | Tyr | Leu | Ala | Pro |
| | 1190 | | | | 1195 | | | | 1200 | | | | | |

| Arg | Gly | Arg | Ala | Ala | Pro | Gln | Pro | His | Pro | Pro | Pro | Ala | Phe | Ser |
| 1205 | | | | | 1210 | | | | 1215 | | | | | |

| Pro | Ala | Phe | Asp | Asn | Leu | Tyr | Tyr | Trp | Asp | Gln | Asp | Pro | Ser | Glu |
| | 1220 | | | | 1225 | | | | 1230 | | | | | |

| Arg | Gly | Ser | Pro | Pro | Ser | Thr | Phe | Glu | Gly | Thr | Pro | Thr | Ala | Glu |
| 1235 | | | | | 1240 | | | | 1245 | | | | | |

| Asn | Pro | Glu | Tyr | Leu | Gly | Leu | Asp | Val | Pro | Val |
| | 1250 | | | | 1255 | | | | | |

```
<210> SEQ ID NO 5
<211> LENGTH: 1311
<212> TYPE: DNA
<213> ORGANISM: Homo sapiens
<300> PUBLICATION INFORMATION:
<308> DATABASE ACCESSION NUMBER: NM_000073.2
<309> DATABASE ENTRY DATE: 2014-05-03
<313> RELEVANT RESIDUES IN SEQ ID NO: (1)..(1311)

<400> SEQUENCE: 5
agtctagctg ctgcacaggc tggctggctg gctggctgct aagggctgct ccacgctttt     60
gccggaggac agagactgac atggaacagg ggaagggcct ggctgtcctc atcctggcta    120
tcattcttct tcaaggtact ttggcccagt caatcaaagg aaaccacttg gttaaggtgt    180
atgactatca agaagatggt tcggtacttc tgacttgtga tgcagaagcc aaaaatatca    240
catggtttaa agatgggaag atgatcggct tcctaactga agataaaaaa aaatggaatc    300
tgggaagtaa tgccaaggac cctcgaggga tgtatcagtg taaaggatca cagaacaagt    360
caaaaccact ccaagtgtat tacagaatgt gtcagaactg cattgaacta aatgcagcca    420
ccatatctgg ctttctcttt gctgaaatcg tcagcatttt cgtccttgct gttggggtct    480
acttcattgc tggacaggat ggagttcgcc agtcgagagc ttcagacaag cagactctgt    540
tgcccaatga ccagctctac cagcccctca aggatcgaga gatgaccag tacagccacc    600 ttcaaggaaa ccagttgagg aggaattgaa ctcaggactc agagtagtcc aggtgttctc    660
ctcctattca gttcccagaa tcaaagcaat gcattttgga agctcctag cagagagact    720 ttcagcccta aatctagact caaggttccc agagatgaca aatggagaag aaaggccatc    780
agagcaaatt tggggggtttc tcaaataaaa taaaaataaa aacaaatact gtgtttcaga    840
agcgccacct attggggaaa attgtaaaag aaaaatgaaa agatcaaata accccctgga    900
tttgaatata attttttgtg ttgtaatttt tatttcgttt ttgtataggt tataattcac    960
atggctcaaa tattcagtga aagctctccc tccaccgcca tccctgcta cccagtgacc   1020 ctgttgccct cttcagagac aaattagttt ctcttttttt ttttttttt ttttttttg   1080 agacagtctg gctctgtcac ccaggctgaa atgcagtggc accatctcgg ctcactgcaa   1140
cctctgcctc ctgggttcaa gcgattctcc tgcctcagcc tcccgggcag ctgggattac   1200
aggcacacac taccacacct ggctaatttt tgtattttta gtagagacag gttttgctc    1260 tgttggccaa gctggtctcg aactcctgac ctcaagtgat ccgcccgcct c             1311

<210> SEQ ID NO 6
<211> LENGTH: 182
<212> TYPE: PRT
<213> ORGANISM: Homo sapiens
<300> PUBLICATION INFORMATION:
<308> DATABASE ACCESSION NUMBER: NP_000064.1
```

<309> DATABASE ENTRY DATE: 2014-05-03
<313> RELEVANT RESIDUES IN SEQ ID NO: (1)..(182)

<400> SEQUENCE: 6

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 7
<211> LENGTH: 771
<212> TYPE: DNA
<213> ORGANISM: Homo sapiens
<300> PUBLICATION INFORMATION:
<308> DATABASE ACCESSION NUMBER: NM_000732.4
<309> DATABASE ENTRY DATE: 2014-05-03
<313> RELEVANT RESIDUES IN SEQ ID NO: (1)..(771)

<400> SEQUENCE: 7
agagaagcag acatcttcta gttcctcccc cactctcctc tttccggtac ctgtgagtca      60
gctaggggag ggcagctctc acccaggctg atagttcggt gacctggctt tatctactgg    120
atgagttccg ctgggagatg gaacatagca cgtttctctc tggcctggta ctggctaccc    180
ttctctcgca agtgagcccc ttcaagatac ctatagagga acttgaggac agagtgtttg    240
tgaattgcaa taccagcatc acatgggtag agggaacggt gggaacactg ctctcagaca    300
ttacaagact ggacctggga aaacgcatcc tggacccacg aggaatatat aggtgtaatg    360
ggacagatat atacaaggac aaagaatcta ccgtgcaagt tcattatcga atgtgccaga    420
gctgtgtgga gctggatcca gccaccgtgg ctggcatcat tgtcactgat gtcattgcca    480
ctctgctcct tgctttggga gtcttctgct tgctggaca tgagactgga aggctgtctg    540
gggctgccga cacacaagct ctgttgagga atgaccaggt ctatcagccc ctccgagatc    600
gagatgatgc tcagtacagc caccttggag gaaactgggc tcggaacaag tgaacctgag    660
actggtggct tctagaagca gccattacca actgtacctt cccttcttgc tcagccaata    720
aatatatcct ctttcactca gaaaaaaaaa aaaaaaaaa aaaaaaaaa a               771

<210> SEQ ID NO 8
<211> LENGTH: 171
<212> TYPE: PRT
<213> ORGANISM: Homo sapiens
<300> PUBLICATION INFORMATION:
<308> DATABASE ACCESSION NUMBER: NP_000723.1
<309> DATABASE ENTRY DATE: 2014-05-03
<313> RELEVANT RESIDUES IN SEQ ID NO: (1)..(171)

<400> SEQUENCE: 8

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 9
<211> LENGTH: 1534
<212> TYPE: DNA
<213> ORGANISM: Homo sapiens
<300> PUBLICATION INFORMATION:
<308> DATABASE ACCESSION NUMBER: NM_000733.3
<309> DATABASE ENTRY DATE: 2014-05-03
<313> RELEVANT RESIDUES IN SEQ ID NO: (1)..(1534)

<400> SEQUENCE: 9
tattgtcaga gtcctcttgt ttggccttct aggaaggctg tgggacccag ctttcttcaa      60
ccagtccagg tggaggcctc tgccttgaac gtttccaagt gaggtaaaac ccgcaggccc     120
agaggcctct ctacttcctg tgtggggttc agaaaccctc ctcccctccc agcctcaggt     180
gcctgcttca gaaatgaagt agtaagtct gctggcctcc gccatcttag taaagtaaca      240
gtcccatgaa acaaagatgc agtcgggcac tcactgagag ttctgggcc tctgcctctt      300 atcagttggc gtttggggc aagatggtaa tgaagaaatg ggtggtatta cacagacacc      360
atataaagtc tccatctctg gaaccacagt aatattgaca tgccctcagt atcctggatc     420
tgaaatacta tggcaacaca atgataaaaa cataggcggt gatgaggatg ataaaaacat     480
aggcagtgat gaggatcacc tgtcactgaa ggaatttttca gaattggagc aaagtggtta    540
ttatgtctgc taccccagag gaagcaaacc agaagatgcg aacttttatc tctacctgag     600
ggcaagagtg tgtgagaact gcatggagat ggatgtgatg tcggtggcca caattgtcat     660

-continued

```
agtggacatc tgcatcactg ggggcttgct gctgctggtt tactactgga gcaagaatag   720
aaaggccaag gccaagcctg tgacacgagg agcgggtgct ggcggcaggc aagggggaca   780
aaacaaggag aggccaccac ctgttcccaa cccagactat gagcccatcc ggaaaggcca   840
gcgggacctg tattctggcc tgaatcagag acgcatctga ccctctggag aacactgcct   900
cccgctggcc caggtctcct ctccagtccc cctgcgactc cctgtttcct gggctagtct   960
tggaccccac gagagagaat cgttcctcag cctcatggtg aactcgcgcc ctccagcctg  1020
atccccgct ccctcctccc tgccttctct gctggtaccc agtcctaaaa tattgctgct   1080
tcctcttcct ttgaagcatc atcagtagtc acaccctcac agctggcctg ccctcttgcc  1140
aggatattta tttgtgctat tcactccctt ccctttggat gtaacttctc cgttcagttc  1200
cctccttttc ttgcatgtaa gttgtccccc atcccaaagt attccatcta cttttctatc  1260
gccgtcccct tttgcagccc tctctgggga tggactgggt aaatgttgac agaggccctg  1320
ccccgttcac agatcctggc cctgagccag ccctgtgctc ctccctcccc caacactccc  1380
taccaacccc ctaatcccct actccctcca cccccctcc actgtaggcc actggatggt  1440
catttgcatc tccgtaaatg tgctctgctc ctcagctgag agagaaaaaa ataaactgta  1500
tttggctgca agaaaaaaaa aaaaaaaaa aaaa                              1534
```

<210> SEQ ID NO 10
<211> LENGTH: 207
<212> TYPE: PRT
<213> ORGANISM: Homo sapiens
<300> PUBLICATION INFORMATION:
<308> DATABASE ACCESSION NUMBER: NP_000724.1
<309> DATABASE ENTRY DATE: 2014-05-03
<313> RELEVANT RESIDUES IN SEQ ID NO: (1)..(207)

<400> SEQUENCE: 10

```
Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
```

<210> SEQ ID NO 11
<211> LENGTH: 1436
<212> TYPE: DNA
<213> ORGANISM: Canine
<300> PUBLICATION INFORMATION:
<308> DATABASE ACCESSION NUMBER: NM_001003379.1
<309> DATABASE ENTRY DATE: 2014-02-22
<313> RELEVANT RESIDUES IN SEQ ID NO: (1)..(1436)

<400> SEQUENCE: 11

```
ataaacgtta gttactattt ttatcaggac tcctgggacc cctatctcac taatttcctt    60
aaagacagta taatacagca gctcacacag actttcggat tcagaaaaac agttgtgtcg   120
ggccttgggt aaattatgta aggcaagcct cagtttgctc agcggtaaaa cgaggaaagt   180
aataagccac ccgcctccgc cattttgggt agaataaggg tgcatccagt gagagaagga   240
tgcagtcgag gaacctctgg agaattctgg gactctgtct cttatcagtt ggtgcttggg   300
ggcaggacga ggatttcaaa gcttctgatg acttgacaag tatatctcca gagaaacggt   360
ttaaggtctc catctctgga accgaggtag tggtgacatg ccctgatgtt tttggatatg   420
ataatataaa atgggaaaaa aatgataacc ttgtggaagg tgctagtaac agagagctat   480
ctcagaagga gttttcagaa gtggacgaca gtggttatta tgcctgctat gcagattcca   540
taaaggagaa gagctatctc tacctgagag caagagtgtg tgcaaactgc atagaggtga   600
atctgatggc agtggtcaca atcattgtag ctgacatctg ccttactctg gggttgctgc   660
tgatggtgta ttactggagc aagactagaa aggccaatgc caagcctgtg atgagaggaa   720
caggtgccgg cagcaggccc aggggacaaa acaaggagaa gccaccacct gttcccaatc   780
cagactacga gccatccgg aaaggccagc aggacctgta ttctggcctg aatcagagag   840
gcatctgacg gctcctgagg acacggcctc cccagggccc aggtcttggt gtctccaggt   900
cctgctactc ccagtaccct gggtaaatct tgaaccccag aagagaatta ttcctctgcc   960
ttctggagaa ctaactccca gcctgcagcc ttatccccag caccctccaa cccgccttct  1020
ctgctggcac ttggtcctgc aatatcacct cctcatcatg ccactcacc gccccccac   1080
cagccagact gccctctggt cggggtattt atttctgtta ccctgacgcc cccaccatca  1140
ccaattcctt cctaccctc agaggtatcc ttgctcccct tccgtacccct ctcccggaca  1200
gaacctgccc catcccctta ctatcccacc tacctttccg ttttccagc tctctctttg  1260
gtgaccctct gtggggatgg actaggtaac tctggtagag gtcctgcccc atccatgacc  1320
ttggcccaga gccaccctct gccagcaggc ccctggatga tcatttgcat tcttacaaat  1380
gtgctaggct ccttgacagc tagagagaaa ataataaagt gtatttggtt gaaaaa      1436
```

<210> SEQ ID NO 12
<211> LENGTH: 202
<212> TYPE: PRT
<213> ORGANISM: Canine
<300> PUBLICATION INFORMATION:
<308> DATABASE ACCESSION NUMBER: NP_001003379.1
<309> DATABASE ENTRY DATE: 2014-02-22
<313> RELEVANT RESIDUES IN SEQ ID NO: (1)..(202)

<400> SEQUENCE: 12

```
Met Gln Ser Arg Asn Leu Trp Arg Ile Leu Gly Leu Cys Leu Leu Ser
1               5                   10                  15

Val Gly Ala Trp Gly Gln Asp Glu Asp Phe Lys Ala Ser Asp Asp Leu
            20                  25                  30
```

```
Thr Ser Ile Ser Pro Glu Lys Arg Phe Lys Val Ser Ile Ser Gly Thr
        35                  40                  45

Glu Val Val Thr Cys Pro Asp Val Phe Gly Tyr Asp Asn Ile Lys
 50                  55                  60

Trp Glu Lys Asn Asp Asn Leu Val Glu Gly Ala Ser Asn Arg Glu Leu
 65                  70                  75                  80

Ser Gln Lys Glu Phe Ser Glu Val Asp Asp Ser Gly Tyr Tyr Ala Cys
                85                  90                  95

Tyr Ala Asp Ser Ile Lys Glu Lys Ser Tyr Leu Tyr Leu Arg Ala Arg
                100                 105                 110

Val Cys Ala Asn Cys Ile Glu Val Asn Leu Met Ala Val Val Thr Ile
            115                 120                 125

Ile Val Ala Asp Ile Cys Leu Thr Leu Gly Leu Leu Leu Met Val Tyr
        130                 135                 140

Tyr Trp Ser Lys Thr Arg Lys Ala Asn Ala Lys Pro Val Met Arg Gly
145                 150                 155                 160

Thr Gly Ala Gly Ser Arg Pro Arg Gly Gln Asn Lys Glu Lys Pro Pro
                165                 170                 175

Pro Val Pro Asn Pro Asp Tyr Glu Pro Ile Arg Lys Gly Gln Gln Asp
                180                 185                 190

Leu Tyr Ser Gly Leu Asn Gln Arg Gly Ile
                195                 200

<210> SEQ ID NO 13
<211> LENGTH: 45
<212> TYPE: DNA
<213> ORGANISM: Artificial Sequence
<220> FEATURE:
<223> OTHER INFORMATION: Peptide linker (G4S)3

<400> SEQUENCE: 13
ggcggcggag gatctggcgg aggtggaagt gggggaggcg gatct          45

<210> SEQ ID NO 14
<211> LENGTH: 15
<212> TYPE: PRT
<213> ORGANISM: Artificial Sequence
<220> FEATURE:
<223> OTHER INFORMATION: Peptide linker (G4S)3

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 119
<212> TYPE: PRT
<213> ORGANISM: Artificial Sequence
<220> FEATURE:
<223> OTHER INFORMATION: OKT3 VH

<400> SEQUENCE: 15

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
```

```
                 50                  55                  60
Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                     85                  90                  95

Ala Arg Tyr Tyr Asp Asp His Tyr Cys Leu Asp Tyr Trp Gly Gln Gly
                100                 105                 110

Thr Pro Val Thr Val Ser Ser
            115

<210> SEQ ID NO 16
<211> LENGTH: 107
<212> TYPE: PRT
<213> ORGANISM: Artificial Sequence
<220> FEATURE:
<223> OTHER INFORMATION: OKT3 VL

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Ser Ala Ser Ser Ser Val Ser Tyr Met
                20                  25                  30

Asn Trp Tyr Gln Gln Thr Pro Gly Lys Ala Pro Lys Arg Trp Ile Tyr
             35                  40                  45

Asp Thr Ser Lys Leu Ala Ser Gly Val Pro Ser Arg Phe Ser Gly Ser
         50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
                100                 105

<210> SEQ ID NO 17
<211> LENGTH: 119
<212> TYPE: PRT
<213> ORGANISM: Artificial Sequence
<220> FEATURE:
<223> OTHER INFORMATION: OKT3 VH C105S

<400> SEQUENCE: 17

Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Gly Leu Glu Trp Ile
             35                  40                  45

Gly Tyr Ile Asn Pro Ser Arg Gly Tyr Thr Asn Tyr Asn Gln Lys Phe
         50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
                100                 105                 110

Thr Pro Val Thr Val Ser Ser
            115
```

<210> SEQ ID NO 18
<211> LENGTH: 723
<212> TYPE: DNA
<213> ORGANISM: Artificial Sequence
<220> FEATURE:
<223> OTHER INFORMATION: OKT3 scFv C105S

<400> SEQUENCE: 18

```
caggtgcagc tggtgcagag tggtggcgga gtggtgcagc ctggcagatc cctgagactg      60
tcttgcaagg ccagcggcta caccttcacc cggtacacca tgcactgggt gcgacaggcc     120
cctggcaagg gcctggaatg gatcggctac atcaacccct cccggggcta caccaactac     180
aaccagaagt tcaaggaccg gttcaccatc agccgggaca actccaagaa caccgccttt     240
ctgcagatgg actccctgcg gcctgaggat accggcgtgt acttttgcgc ccggtactac     300
gacgaccact actctctgga ctactggggc caggaaccc tgtgacagt gtctagcgga       360
gggggaggtt caggtggcgg tggatcaggg ggcggaggct ctgatatcca gatgacccag     420
tcccctcca gcctgtctgc ctctgtggga cacagagtga caattacatg ctccgccagc      480
tccagcgtgt cctacatgaa ttggtatcag cagaccctg gcaaggctcc caagcggtgg      540
atctacgaca cctccaagct ggcctccggc gtgccctcca gattttctgg cagcggctcc     600
ggcacagact ataccttac aatcagctcc ctgcagcccg aagatatcgc cacctactac      660
tgccagcagt ggtcctccaa cccccttcacc tttggccagg ggacaaaact gcagatcacc    720
aga                                                                    723
```

<210> SEQ ID NO 19
<211> LENGTH: 241
<212> TYPE: PRT
<213> ORGANISM: Artificial Sequence
<220> FEATURE:
<223> OTHER INFORMATION: OKT3 scFv C105S

<400> SEQUENCE: 19

```
Gln Val Gln Leu Val Gln Ser Gly Gly Gly Val Val Gln Pro Gly Arg
 1               5                  10                  15

Ser Leu Arg Leu Ser Cys Lys Ala Ser Gly Tyr Thr Phe Thr Arg Tyr
             20                  25                  30

Thr Met His Trp Val Arg Gln Ala Pro Gly Lys Gly Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175
```

Pro Lys Arg Trp Ile Tyr Asp Thr Ser Lys Leu Ala Ser Gly Val Pro
            180                 185                 190

Ser Arg Phe Ser Gly Ser Gly Ser Gly Thr Asp Tyr Thr Phe Thr Ile
        195                 200                 205

Ser Ser Leu Gln Pro Glu Asp Ile Ala Thr Tyr Tyr Cys Gln Gln Trp
    210                 215                 220

Ser Ser Asn Pro Phe Thr Phe Gly Gln Gly Thr Lys Leu Gln Ile Thr
225                 230                 235                 240

Arg

<210> SEQ ID NO 20
<211> LENGTH: 1350
<212> TYPE: DNA
<213> ORGANISM: Artificial Sequence
<220> FEATURE:
<223> OTHER INFORMATION: exemplary heavy chain N297A

<400> SEQUENCE: 20

| | | | | | |
|---|---|---|---|---|---|
| gaggtgcagc | tggtggaatc | tggcggagga | ctggtgcagc | tggcggctc | tctgagactg | 60 |
| tcttgtgccg | cctccggctt | caacatcaag | gacacctaca | tccactgggt | gcgacaggcc | 120 |
| cctggcaagg | gactggaatg | ggtggccaga | atctacccca | ccaacggcta | caccagatac | 180 |
| gccgactctg | tgaagggccg | gttcaccatc | tccgccgaca | cctccaagaa | caccgcctac | 240 |
| ctgcagatga | actccctgcg | ggccgaggac | accgccgtgt | actactgtag | tagatgggga | 300 |
| ggcgacggct | tctacgccat | ggactattgg | ggccagggca | ccctcgtgac | cgtgtcctct | 360 |
| gcttctacca | agggccccts | tgtgtttcct | ctggcccct | ccagcaagtc | cacctctggt | 420 |
| ggaacagccg | ccctgggctg | cctcgtgaag | gactactttc | ccgagcccgt | gaccgtgtcc | 480 |
| tggaactctg | gcgctctgac | ctctggcgtg | cacaccttcc | ctgctgtgct | gcagtctagc | 540 |
| ggcctgtact | ccctgtcctc | cgtcgtgaca | gtgccctcca | gctctctggg | cacccagacc | 600 |
| tacatctgca | acgtgaacca | caagccctcc | aataccaagg | tggacaagcg | ggtggaaccc | 660 |
| aagtcctgcg | acaagaccca | cacctgtccc | ccttgtcctg | cccctgaact | gctgggcgga | 720 |
| ccttccgtgt | tcctgttccc | cccaaagccc | aaggacaccc | tgatgatctc | ccggaccccc | 780 |
| gaagtgacct | gcgtggtggt | ggatgtgtcc | cacgaggacc | ctgaagtgaa | gttcaattgg | 840 |
| tacgtggacg | gcgtggaagt | gcacaacgcc | aagaccaagc | ctagagagga | acagtacgcc | 900 |
| tccacctacc | gggtggtgtc | cgtgctgaca | gtgctgcacc | aggactggct | gaacggcaaa | 960 |
| gagtacaagt | gcaaagtgtc | caacaaggcc | ctgcctgccc | ccatcgaaaa | gaccatctcc | 1020 |
| aaggccaagg | gccagccccg | ggaaccccag | gtgtacacac | tgcccctag | cagggacgag | 1080 |
| ctgaccaaga | accaggtgtc | cctgacctgt | ctcgtgaaag | gcttctaccc | ctccgatatc | 1140 |
| gccgtggaat | gggagtccaa | cggccagcct | gagaacaact | acaagaccac | ccccctgtg | 1200 |
| ctggactccg | acggctcatt | cttcctgtac | agcaagctga | ccgtggacaa | gtcccggtgg | 1260 |
| cagcagggca | acgtgttctc | ctgctccgtg | atgcacgagg | ccctgcacaa | ccactacacc | 1320 |
| cagaagtccc | tgtccctgag | ccccggcaaa | | | | 1350 |

<210> SEQ ID NO 21
<211> LENGTH: 1350
<212> TYPE: DNA
<213> ORGANISM: Artificial Sequence
<220> FEATURE:
<223> OTHER INFORMATION: exemplary heavy chain K322A

<400> SEQUENCE: 21

```
gaggtgcagc tggtggaatc tggcggagga ctggtgcagc ctggcggctc tctgagactg      60
tcttgtgccg cctccggctt caacatcaag gacacctaca tccactgggt gcgacaggcc     120
cctggcaagg gactggaatg ggtggccaga atctacccca ccaacggcta caccagatac     180
gccgactctg tgaagggccg gttcaccatc tccgccgaca cctccaagaa caccgcctac     240
ctgcagatga actccctgcg ggccgaggac accgccgtgt actactgtag tagatgggga     300
ggcgacggct tctacgccat ggactattgg ggccagggca cctcgtgac cgtgtcctct     360 gcttctacca agggcccctc tgtgtttcct ctggccccct ccagcaagtc cacctctggt     420
ggaacagccg ccctgggctg cctcgtgaag gactactttc ccgagcccgt gaccgtgtcc     480
tggaactctg gcgctctgac ctctggcgtg cacaccttcc ctgctgtgct gcagtctagc     540
ggcctgtact ccctgtcctc cgtcgtgaca gtgccctcca gctctctggg cacccagacc     600
tacatctgca acgtgaacca caagccctcc aataccaagg tggacaagcg ggtggaaccc     660
aagtcctgcg acaagaccca cacctgtccc ccttgtcctg ccctgaact gctgggcgga     720 ccttccgtgt tcctgttccc cccaaagccc aaggacaccc tgatgatctc ccggaccccc     780
gaagtgacct gcgtggtggt ggatgtgtcc cacgaggacc ctgaagtgaa gttcaattgg     840
tacgtggacg gcgtggaagt gcacaacgcc aagaccaagc ctagagagga acagtacaac     900
tccacctacc gggtggtgtc cgtgctgaca gtgctgcacc aggactggct gaacggcaaa     960
gagtacaagt gcgccgtgtc caacaaggcc ctgcctgccc ccatcgaaaa gaccatctcc    1020
aaggccaagg gccagccccg ggaacccag gtgtacacac tgcccccctag cagggacgag    1080 ctgaccaaga accaggtgtc cctgacctgt ctcgtgaaag gcttctaccc ctccgatatc    1140
gccgtggaat gggagtccaa cggccagcct gagaacaact acaagaccac ccccctgtg    1200 ctggactccg acggctcatt cttcctgtac agcaagctga ccgtggacaa gtcccggtgg    1260
cagcagggca acgtgttctc ctgctccgtg atgcacgagg ccctgcacaa ccactacacc    1320
cagaagtccc tgtccctgag ccccggcaaa                                    1350
```

<210> SEQ ID NO 22
<211> LENGTH: 1350
<212> TYPE: DNA
<213> ORGANISM: Artificial Sequence
<220> FEATURE:
<223> OTHER INFORMATION: exemplary heavy chain

<400> SEQUENCE: 22

```
gaggtgcagc tggtggaatc tggcggagga ctggtgcagc ctggcggctc tctgagactg      60
tcttgtgccg cctccggctt caacatcaag gacacctaca tccactgggt gcgacaggcc     120
cctggcaagg gactggaatg ggtggccaga atctacccca ccaacggcta caccagatac     180
gccgactctg tgaagggccg gttcaccatc tccgccgaca cctccaagaa caccgcctac     240
ctgcagatga actccctgcg ggccgaggac accgccgtgt actactgtag tagatgggga     300
ggcgacggct tctacgccat ggactattgg ggccagggca cctcgtgac cgtgtcctct     360 gcttctacca agggcccctc tgtgtttcct ctggccccct ccagcaagtc cacctctggt     420
ggaacagccg ccctgggctg cctcgtgaag gactactttc ccgagcccgt gaccgtgtcc     480
tggaactctg gcgctctgac ctctggcgtg cacaccttcc ctgctgtgct gcagtctagc     540
ggcctgtact ccctgtcctc cgtcgtgaca gtgccctcca gctctctggg cacccagacc     600
tacatctgca acgtgaacca caagccctcc aataccaagg tggacaagcg ggtggaaccc     660
```

```
aagtcctgcg acaagaccca cacctgtccc ccttgtcctg cccctgaact gctgggcgga    720
ccttccgtgt tcctgttccc cccaaagccc aaggacaccc tgatgatctc ccggacccc    780 gaagtgacct gcgtggtggt ggatgtgtcc cacgaggacc ctgaagtgaa gttcaattgg    840
tacgtggacg gcgtggaagt gcacaacgcc aagaccaagc ctagagagga acagtacaac    900
tccacctacc gggtggtgtc cgtgctgaca gtgctgcacc aggactggct gaacggcaaa    960
gagtacaagt gcaaagtgtc caacaaggcc ctgcctgccc ccatcgaaaa gaccatctcc   1020
aaggccaagg gccagccccg ggaaccccag gtgtacacac tgcccctag cagggacgag    1080 ctgaccaaga accaggtgtc cctgacctgt ctcgtgaaag cttctaccc ctccgatatc    1140 gccgtggaat gggagtccaa cggccagcct gagaacaact acaagaccac ccccctgtg    1200 ctggactccg acggctcatt cttcctgtac agcaagctga ccgtggacaa gtcccggtgg    1260
cagcagggca acgtgttctc ctgctccgtg atgcacgagg ccctgcacaa ccactacacc    1320
cagaagtccc tgtccctgag ccccggcaaa                                    1350
```

<210> SEQ ID NO 23
<211> LENGTH: 450
<212> TYPE: PRT
<213> ORGANISM: Artificial Sequence
<220> FEATURE:
<223> OTHER INFORMATION: exemplary heavy chain

<400> SEQUENCE: 23

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 24
<211> LENGTH: 642
<212> TYPE: DNA
<213> ORGANISM: Artificial Sequence
<220> FEATURE:
<223> OTHER INFORMATION: HER2-BsAb light chain

<400> SEQUENCE: 24
gacatccaga tgacccagag cccttccagc ctgtccgcct ctgtgggcga cagagtgacc      60
atcacctgtc gggcctccca ggacgtgaac accgccgtgg cttggtatca gcagaagccc    120
ggcaaggccc ccaagctgct gatctactcc gcctccttcc tgtactccgg cgtgccctcc    180
agattctccg gcagcagatc tggcaccgac tttaccctga ccatctccag cctgcagccc    240
gaggacttcg ccacctacta ctgccagcag cactacacca ccccccccac ctttggccag    300
ggcaccaagg tggaaatcaa gcggaccgtg gccgctccct ccgtgttcat cttcccacct    360
tccgacgagc agctgaagtc cggcaccgct tctgtcgtgt gcctgctgaa caacttctac    420
ccccgcgagg ccaaggtgca gtggaaggtg acaacgccc tgcagtccgg caactcccag    480
gaatccgtga ccgagcagga ctccaaggac agcacctact ccctgtcctc caccctgacc    540
ctgtccaagg ccgactacga gaagcacaag gtgtacgcct gcgaagtgac ccaccagggc    600
ctgtctagcc ccgtgaccaa gtctttcaac cggggcgagt gc                        642

<210> SEQ ID NO 25
<211> LENGTH: 216
<212> TYPE: PRT
<213> ORGANISM: Artificial Sequence
```

<220> FEATURE:
<223> OTHER INFORMATION: HER2-BsAb light chain

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser
    210                 215

<210> SEQ ID NO 26
<211> LENGTH: 1350
<212> TYPE: DNA
<213> ORGANISM: Artificial Sequence
<220> FEATURE:
<223> OTHER INFORMATION: HER2-BsAb heavy chain

<400> SEQUENCE: 26
gaggtgcagc tggtggaatc tggcggagga ctggtgcagc ctggcggctc tctgagactg      60
tcttgtgccg cctccggctt caacatcaag gacacctaca tccactgggt gcgacaggcc     120
cctggcaagg gactggaatg ggtggccaga atctacccca ccaacggcta caccagatac     180
gccgactctg tgaagggccg gttcaccatc tccgccgaca cctccaagaa caccgcctac     240
ctgcagatga actccctgcg ggccgaggac accgccgtgt actactgtag tagatgggga     300
ggcgacggct ctacgccat ggactattgg ggccagggca cctcgtgac cgtgtcctct      360 gcttctacca agggcccctc tgtgtttcct ctggccccct ccagcaagtc cacctctggt     420
ggaacagccg ccctgggctg cctcgtgaag gactactttc ccgagcccgt gaccgtgtcc     480
tggaactctg gcgctctgac ctctggcgtg cacaccttcc ctgctgtgct gcagtctagc     540
ggcctgtact ccctgtcctc cgtcgtgaca gtgccctcca gctctctggg cacccagacc     600
tacatctgca acgtgaacca caagccctcc aataccaagg tggacaagcg ggtggaaccc     660

```
aagtcctgcg acaagaccca cacctgtccc ccttgtcctg cccctgaact gctgggcgga    720
ccttccgtgt tcctgttccc cccaaagccc aaggacaccc tgatgatctc ccggaccccc    780
gaagtgacct gcgtggtggt ggatgtgtcc cacgaggacc ctgaagtgaa gttcaattgg    840
tacgtggacg gcgtggaagt gcacaacgcc aagaccaagc ctagagagga acagtacgcc    900
tccacctacc gggtggtgtc cgtgctgaca gtgctgcacc aggactggct gaacggcaaa    960
gagtacaagt gcgccgtgtc caacaaggcc ctgcctgccc catcgaaaaa gaccatctcc   1020
aaggccaagg gccagccccg ggaaccccag gtgtacacac tgcccctag cagggacgag    1080 ctgaccaaga accaggtgtc cctgacctgt ctcgtgaaag gcttctaccc ctccgatatc   1140
gccgtggaat gggagtccaa cggccagcct gagaacaact acaagaccac ccccctgtg    1200 ctggactccg acggctcatt cttcctgtac agcaagctga ccgtggacaa gtcccggtgg   1260
cagcagggca acgtgttctc ctgctccgtg atgcacgagg ccctgcacaa ccactacacc   1320
cagaagtccc tgtccctgag ccccggcaaa                                    1350

<210> SEQ ID NO 27
<211> LENGTH: 450
<212> TYPE: PRT
<213> ORGANISM: Artificial Sequence
<220> FEATURE:
<223> OTHER INFORMATION: HER2-BsAb heavy chain

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Ala Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 28
<211> LENGTH: 1416
<212> TYPE: DNA
<213> ORGANISM: Artificial Sequence
<220> FEATURE:
<223> OTHER INFORMATION: HER2-BsAb light chain fusion polypeptide

<400> SEQUENCE: 28
gacatccaga tgacccagag cccttccagc ctgtccgcct ctgtgggcga cagagtgacc      60
atcacctgtc gggcctccca ggacgtgaac accgccgtgg cttggtatca gcagaagccc     120
ggcaaggccc ccaagctgct gatctactcc gcctccttcc tgtactccgg cgtgccctcc     180
agattctccg gcagcagatc tggcaccgac tttaccctga ccatctccag cctgcagccc     240
gaggacttcg ccacctacta ctgccagcag cactacacca ccccccccac ctttggccag     300
ggcaccaagg tggaaatcaa gcggaccgtg gccgctccct ccgtgttcat cttcccacct     360
tccgacgagc agctgaagtc cggcaccgct ctgtcgtgt gctgctgaa caacttctac      420
cccgcgagg ccaaggtgca gtggaaggtg gacaacgccc tgcagtccgg caactcccag     480
gaatccgtga ccgagcagga ctccaaggac agcacctact ccctgtcctc caccctgacc     540
ctgtccaagg ccgactacga aagcacaag gtgtacgcct gcgaagtgac ccaccagggc     600
ctgtctagcc ccgtgaccaa gtctttcaac cggggcgagt gcactagtgg cggcggagga     660
tctggcggag gtggaagtgg gggaggcgga tctcaggtgc agctggtgca gagtggtggc     720
ggagtggtgc agcctggcag atccctgaga ctgtcttgca aggccagcgg ctacaccttc     780
acccggtaca ccatgcactg ggtgcgacag gcccctggca agggcctgga atggatcggc     840

```
tacatcaacc cctcccgggg ctacaccaac tacaaccaga agttcaagga ccggttcacc     900
atcagccggg acaactccaa gaacaccgcc tttctgcaga tggactccct gcggcctgag     960
gataccggcg tgtacttttg cgcccggtac tacgacgacc actactctct ggactactgg    1020
ggccagggaa cccctgtgac agtgtctagc ggaggggggag gttcaggtgg cggtggatca    1080
gggggcggag gctctgatat ccagatgacc cagtccccct ccagcctgtc tgcctctgtg    1140
ggagacagag tgacaattac atgctccgcc agctccagcg tgtcctacat gaattggtat    1200
cagcagaccc ctggcaaggc tcccaagcgg tggatctacg acacctccaa gctggcctcc    1260
ggcgtgccct ccagattttc tggcagcggc tccggcacag actatacctt tacaatcagc    1320
tccctgcagc ccgaagatat cgccacctac tactgccagc agtggtcctc caacccttc    1380 acctttggcc aggggacaaa actgcagatc accaga                              1416
```

<210> SEQ ID NO 29
<211> LENGTH: 472
<212> TYPE: PRT
<213> ORGANISM: Artificial Sequence
<220> FEATURE:
<223> OTHER INFORMATION: HER2-BsAb light chain fusion polypeptide

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255
```

```
Gly Tyr Thr Phe Thr Arg Tyr Thr Met His Trp Val Arg Gln Ala Pro
            260                 265                 270

Gly Lys Gly Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Asp Ile Gln
        355                 360                 365

Met Thr Gln Ser Pro Ser Ser Leu Ser Ala Ser Val Gly Asp Arg Val
    370                 375                 380

Thr Ile Thr Cys Ser Ala Ser Ser Val Ser Tyr Met Asn Trp Tyr
385                 390                 395                 400

Gln Gln Thr Pro Gly Lys Ala Pro Lys Arg Trp Ile Tyr Asp Thr Ser
                405                 410                 415

Lys Leu Ala Ser Gly Val Pro Ser Arg Phe Ser Gly Ser Gly Ser Gly
            420                 425                 430

Thr Asp Tyr Thr Phe Thr Ile Ser Ser Leu Gln Pro Glu Asp Ile Ala
        435                 440                 445

Thr Tyr Tyr Cys Gln Gln Trp Ser Ser Asn Pro Phe Thr Phe Gly Gln
    450                 455                 460

Gly Thr Lys Leu Gln Ile Thr Arg
465                 470

<210> SEQ ID NO 30
<211> LENGTH: 462
<212> TYPE: PRT
<213> ORGANISM: Artificial Sequence
<220> FEATURE:
<223> OTHER INFORMATION: HER2-BsAb light chain fusion polypeptide (5aa
      scFv linker)

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Gly Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Gly Gly
            340                 345                 350

Gly Gly Ser Asp Ile Gln Met Thr Gln Ser Pro Ser Ser Leu Ser Ala
        355                 360                 365

Ser Val Gly Asp Arg Val Thr Ile Thr Cys Ser Ala Ser Ser Ser Val
370                 375                 380

Ser Tyr Met Asn Trp Tyr Gln Gln Thr Pro Gly Lys Ala Pro Lys Arg
385                 390                 395                 400

Trp Ile Tyr Asp Thr Ser Lys Leu Ala Ser Gly Val Pro Ser Arg Phe
                405                 410                 415

Ser Gly Ser Gly Ser Gly Thr Asp Tyr Thr Phe Thr Ile Ser Ser Leu
            420                 425                 430

Gln Pro Glu Asp Ile Ala Thr Tyr Tyr Cys Gln Gln Trp Ser Ser Asn
        435                 440                 445

Pro Phe Thr Phe Gly Gln Gly Thr Lys Leu Gln Ile Thr Arg
    450                 455                 460

<210> SEQ ID NO 31
<211> LENGTH: 467
<212> TYPE: PRT
<213> ORGANISM: Artificial Sequence
<220> FEATURE:
<223> OTHER INFORMATION: HER2-BsAb light chain fusion polypeptide (10aa
      scFv linker)

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
```

```
            35                  40                  45
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Thr Ser Gly Gly Gly Ser Gly Gly Gly Gly
210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
                260                 265                 270

Gly Lys Gly Leu Glu Trp Ile Gly Tyr Ile Asn Pro Ser Arg Gly Tyr
                275                 280                 285

Thr Asn Tyr Asn Gln Lys Phe Lys Asp Arg Phe Thr Ile Ser Arg Asp
290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
                340                 345                 350

Gly Gly Ser Gly Gly Gly Ser Asp Ile Gln Met Thr Gln Ser Pro
                355                 360                 365

Ser Ser Leu Ser Ala Ser Val Gly Asp Arg Val Thr Ile Thr Cys Ser
                370                 375                 380

Ala Ser Ser Ser Val Ser Tyr Met Asn Trp Tyr Gln Gln Thr Pro Gly
385                 390                 395                 400

Lys Ala Pro Lys Arg Trp Ile Tyr Asp Thr Ser Lys Leu Ala Ser Gly
                405                 410                 415

Val Pro Ser Arg Phe Ser Gly Ser Gly Ser Gly Thr Asp Tyr Thr Phe
                420                 425                 430

Thr Ile Ser Ser Leu Gln Pro Glu Asp Ile Ala Thr Tyr Tyr Cys Gln
                435                 440                 445

Gln Trp Ser Ser Asn Pro Phe Thr Phe Gly Gln Gly Thr Lys Leu Gln
450                 455                 460
```

Ile Thr Arg
465

<210> SEQ ID NO 32
<211> LENGTH: 477
<212> TYPE: PRT
<213> ORGANISM: Artificial Sequence
<220> FEATURE:
<223> OTHER INFORMATION: HER2-BsAb light chain fusion polypeptide (20aa scFv linker)

<400> SEQUENCE: 32

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Gly Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
```

```
                340             345             350
Gly Gly Ser Gly Gly Gly Ser Gly Gly Gly Ser Gly Gly
            355             360             365
Gly Ser Asp Ile Gln Met Thr Gln Ser Pro Ser Ser Leu Ser Ala Ser
        370                 375                 380
Val Gly Asp Arg Val Thr Ile Thr Cys Ser Ala Ser Ser Ser Val Ser
385                 390                 395                 400
Tyr Met Asn Trp Tyr Gln Gln Thr Pro Gly Lys Ala Pro Lys Arg Trp
                405                 410                 415
Ile Tyr Asp Thr Ser Lys Leu Ala Ser Gly Val Pro Ser Arg Phe Ser
            420                 425                 430
Gly Ser Gly Ser Gly Thr Asp Tyr Thr Phe Thr Ile Ser Ser Leu Gln
        435                 440                 445
Pro Glu Asp Ile Ala Thr Tyr Tyr Cys Gln Gln Trp Ser Ser Asn Pro
    450                 455                 460
Phe Thr Phe Gly Gln Gly Thr Lys Leu Gln Ile Thr Arg
465                 470                 475

<210> SEQ ID NO 33
<211> LENGTH: 482
<212> TYPE: PRT
<213> ORGANISM: Artificial Sequence
<220> FEATURE:
<223> OTHER INFORMATION: HER2-BsAb light chain fusion polypeptide (25aa
      scFv linker)

<400> SEQUENCE: 33

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
    50                  55                  60
Ser Arg Ser Gly Thr Asp Phe Thr Leu Thr Ile Ser Ser Leu Gln Pro
65                  70                  75                  80
Glu Asp Phe Ala Thr Tyr Tyr Cys Gln Gln His Tyr Thr Thr Pro Pro
                85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Thr Ser Gly Gly Gly Ser Gly Gly Gly
    210                 215                 220
```

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
            245                 250                 255

Gly Tyr Thr Phe Thr Arg Tyr Thr Met His Trp Val Arg Gln Ala Pro
        260                 265                 270

Gly Lys Gly Leu Glu Trp Ile Gly Tyr Ile Asn Pro Ser Arg Gly Tyr
    275                 280                 285

Thr Asn Tyr Asn Gln Lys Phe Lys Asp Arg Phe Thr Ile Ser Arg Asp
290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
            325                 330                 335

Leu Asp Tyr Trp Gly Gln Gly Thr Pro Val Thr Val Ser Ser Gly Gly
        340                 345                 350

Gly Gly Ser Gly Gly Gly Ser Gly Gly Gly Ser Gly Gly Gly Gly
    355                 360                 365

Gly Ser Gly Gly Gly Ser Asp Ile Gln Met Thr Gln Ser Pro Ser
370                 375                 380

Ser Leu Ser Ala Ser Val Gly Asp Arg Val Thr Ile Thr Cys Ser Ala
385                 390                 395                 400

Ser Ser Ser Val Ser Tyr Met Asn Trp Tyr Gln Gln Thr Pro Gly Lys
            405                 410                 415

Ala Pro Lys Arg Trp Ile Tyr Asp Thr Ser Lys Leu Ala Ser Gly Val
        420                 425                 430

Pro Ser Arg Phe Ser Gly Ser Gly Ser Gly Thr Asp Tyr Thr Phe Thr
    435                 440                 445

Ile Ser Ser Leu Gln Pro Glu Asp Ile Ala Thr Tyr Tyr Cys Gln Gln
450                 455                 460

Trp Ser Ser Asn Pro Phe Thr Phe Gly Gln Gly Thr Lys Leu Gln Ile
465                 470                 475                 480

Thr Arg

<210> SEQ ID NO 34
<211> LENGTH: 487
<212> TYPE: PRT
<213> ORGANISM: Artificial Sequence
<220> FEATURE:
<223> OTHER INFORMATION: HER2-BsAb light chain fusion polypeptide (30aa
      scFv linker)

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Gly Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Gly Gly Gly Gly Ser Gly Gly Gly
        355                 360                 365

Gly Ser Gly Gly Gly Gly Ser Gly Gly Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Ser Ala Ser Ser Ser Val Ser Tyr Met Asn Trp Tyr Gln
                405                 410                 415

Gln Thr Pro Gly Lys Ala Pro Lys Arg Trp Ile Tyr Asp Thr Ser Lys
            420                 425                 430

Leu Ala Ser Gly Val Pro Ser Arg Phe Ser Gly Ser Gly Ser Gly Thr
        435                 440                 445

Asp Tyr Thr Phe Thr Ile Ser Ser Leu Gln Pro Glu Asp Ile Ala Thr
    450                 455                 460

Tyr Tyr Cys Gln Gln Trp Ser Ser Asn Pro Phe Thr Phe Gly Gln Gly
465                 470                 475                 480

Thr Lys Leu Gln Ile Thr Arg
                485

<210> SEQ ID NO 35
<211> LENGTH: 17
<212> TYPE: PRT

```
<213> ORGANISM: Artificial Sequence
<220> FEATURE:
<223> OTHER INFORMATION: T(G4S)3 Linker

<400> SEQUENCE: 35

Thr Ser Gly Gly Gly Gly Ser Gly Gly Gly Gly Ser Gly Gly Gly Gly
1               5                   10                  15

Ser

<210> SEQ ID NO 36
<211> LENGTH: 5
<212> TYPE: PRT
<213> ORGANISM: Artificial Sequence
<220> FEATURE:
<223> OTHER INFORMATION: G4S Linker

<400> SEQUENCE: 36

Gly Gly Gly Gly Ser
1               5

<210> SEQ ID NO 37
<211> LENGTH: 10
<212> TYPE: PRT
<213> ORGANISM: Artificial Sequence
<220> FEATURE:
<223> OTHER INFORMATION: (G4S)2 Linker

<400> SEQUENCE: 37

Gly Gly Gly Gly Ser Gly Gly Gly Gly Ser
1               5                   10

<210> SEQ ID NO 38
<211> LENGTH: 15
<212> TYPE: PRT
<213> ORGANISM: Artificial Sequence
<220> FEATURE:
<223> OTHER INFORMATION: (G4S)3 Linker

<400> SEQUENCE: 38

Gly Gly Gly Gly Ser Gly Gly Gly Gly Ser Gly Gly Gly Gly Ser
1               5                   10                  15

<210> SEQ ID NO 39
<211> LENGTH: 20
<212> TYPE: PRT
<213> ORGANISM: Artificial Sequence
<220> FEATURE:
<223> OTHER INFORMATION: (G4S)4 Linker

<400> SEQUENCE: 39

Gly Gly Gly Gly Ser Gly Gly Gly Gly Ser Gly Gly Gly Gly Ser Gly
1               5                   10                  15

Gly Gly Gly Ser
            20

<210> SEQ ID NO 40
<211> LENGTH: 25
<212> TYPE: PRT
<213> ORGANISM: Artificial Sequence
<220> FEATURE:
<223> OTHER INFORMATION: (G4S)5 Linker

<400> SEQUENCE: 40

Gly Gly Gly Gly Ser Gly Gly Gly Gly Ser Gly Gly Gly Gly Ser Gly
1               5                   10                  15
```

```
Gly Gly Gly Ser Gly Gly Gly Gly Ser
            20                  25

<210> SEQ ID NO 41
<211> LENGTH: 30
<212> TYPE: PRT
<213> ORGANISM: Artificial Sequence
<220> FEATURE:
<223> OTHER INFORMATION: (G4S)6 Linker

<400> SEQUENCE: 41

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 42
<211> LENGTH: 462
<212> TYPE: PRT
<213> ORGANISM: Artificial Sequence
<220> FEATURE:
<223> OTHER INFORMATION: HER2-BsAb light chain fusion polypeptide
      (5aa scFv linker) + disulfide mut

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
```

```
              260                 265                 270
Gly Lys Cys Leu Glu Trp Ile Gly Tyr Ile Asn Pro Ser Arg Gly Tyr
            275                 280                 285

Thr Asn Tyr Asn Gln Lys Phe Lys Asp Arg Phe Thr Ile Ser Arg Asp
290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
                340                 345                 350

Gly Gly Ser Asp Ile Gln Met Thr Gln Ser Pro Ser Ser Leu Ser Ala
            355                 360                 365

Ser Val Gly Asp Arg Val Thr Ile Thr Cys Ser Ala Ser Ser Ser Val
370                 375                 380

Ser Tyr Met Asn Trp Tyr Gln Gln Thr Pro Gly Lys Ala Pro Lys Arg
385                 390                 395                 400

Trp Ile Tyr Asp Thr Ser Lys Leu Ala Ser Gly Val Pro Ser Arg Phe
                405                 410                 415

Ser Gly Ser Gly Ser Gly Thr Asp Tyr Thr Phe Thr Ile Ser Ser Leu
                420                 425                 430

Gln Pro Glu Asp Ile Ala Thr Tyr Tyr Cys Gln Gln Trp Ser Ser Asn
            435                 440                 445

Pro Phe Thr Phe Gly Cys Gly Thr Lys Leu Gln Ile Thr Arg
    450                 455                 460

<210> SEQ ID NO 43
<211> LENGTH: 467
<212> TYPE: PRT
<213> ORGANISM: Artificial Sequence
<220> FEATURE:
<223> OTHER INFORMATION: HER2-BsAb light chain fusion polypeptide (10aa
      scFv linker) + disulfide mut

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
            245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
            275                 280                 285

Thr Asn Tyr Asn Gln Lys Phe Lys Asp Arg Phe Thr Ile Ser Arg Asp
            290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
            325                 330                 335

Leu Asp Tyr Trp Gly Gln Gly Thr Pro Val Thr Val Ser Ser Gly Gly
            340                 345                 350

Gly Gly Ser Gly Gly Gly Gly Ser Asp Ile Gln Met Thr Gln Ser Pro
            355                 360                 365

Ser Ser Leu Ser Ala Ser Val Gly Asp Arg Val Thr Ile Thr Cys Ser
            370                 375                 380

Ala Ser Ser Ser Val Ser Tyr Met Asn Trp Tyr Gln Gln Thr Pro Gly
385                 390                 395                 400

Lys Ala Pro Lys Arg Trp Ile Tyr Asp Thr Ser Lys Leu Ala Ser Gly
            405                 410                 415

Val Pro Ser Arg Phe Ser Gly Ser Gly Ser Gly Thr Asp Tyr Thr Phe
            420                 425                 430

Thr Ile Ser Ser Leu Gln Pro Glu Asp Ile Ala Thr Tyr Tyr Cys Gln
            435                 440                 445

Gln Trp Ser Ser Asn Pro Phe Thr Phe Gly Cys Gly Thr Lys Leu Gln
            450                 455                 460

Ile Thr Arg
465

<210> SEQ ID NO 44
<211> LENGTH: 472
<212> TYPE: PRT
<213> ORGANISM: Artificial Sequence
<220> FEATURE:
<223> OTHER INFORMATION: HER2-BsAb light chain fusion polypeptide (15aa
      scFv linker) + disulfide mut

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

-continued

```
Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Thr Ser Gly Gly Gly Ser Gly Gly Gly
    210                 215                 220

Gly Ser Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
                260                 265                 270

Gly Lys Cys Leu Glu Trp Ile Gly Tyr Ile Asn Pro Ser Arg Gly Tyr
            275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
                340                 345                 350

Gly Gly Ser Gly Gly Gly Gly Ser Gly Gly Gly Gly Ser Asp Ile Gln
            355                 360                 365

Met Thr Gln Ser Pro Ser Ser Leu Ser Ala Ser Val Gly Asp Arg Val
    370                 375                 380

Thr Ile Thr Cys Ser Ala Ser Ser Ser Val Ser Tyr Met Asn Trp Tyr
385                 390                 395                 400

Gln Gln Thr Pro Gly Lys Ala Pro Lys Arg Trp Ile Tyr Asp Thr Ser
                405                 410                 415

Lys Leu Ala Ser Gly Val Pro Ser Arg Phe Ser Gly Ser Gly Ser Gly
            420                 425                 430

Thr Asp Tyr Thr Phe Thr Ile Ser Ser Leu Gln Pro Glu Asp Ile Ala
    435                 440                 445

Thr Tyr Tyr Cys Gln Gln Trp Ser Ser Asn Pro Phe Thr Phe Gly Cys
450                 455                 460
```

```
Gly Thr Lys Leu Gln Ile Thr Arg
465                 470
```

<210> SEQ ID NO 45
<211> LENGTH: 477
<212> TYPE: PRT
<213> ORGANISM: Artificial Sequence
<220> FEATURE:
<223> OTHER INFORMATION: HER2-BsAb light chain fusion polypeptide (20aa
      scFv linker) + disulfide mut

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
            260                 265                 270

Gly Lys Cys Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Ser
                325                 330                 335

Leu Asp Tyr Trp Gly Gln Gly Thr Pro Val Thr Val Ser Ser Gly Gly
            340                 345                 350
```

```
Gly Gly Ser Gly Gly Gly Ser Gly Gly Gly Ser Gly Gly
        355                 360                 365

Gly Ser Asp Ile Gln Met Thr Gln Ser Pro Ser Leu Ser Ala Ser
        370                 375                 380

Val Gly Asp Arg Val Thr Ile Thr Cys Ser Ala Ser Ser Val Ser
385                 390                 395                 400

Tyr Met Asn Trp Tyr Gln Gln Thr Pro Gly Lys Ala Pro Lys Arg Trp
            405                 410                 415

Ile Tyr Asp Thr Ser Lys Leu Ala Ser Gly Val Pro Ser Arg Phe Ser
            420                 425                 430

Gly Ser Gly Ser Gly Thr Asp Tyr Thr Phe Thr Ile Ser Ser Leu Gln
            435                 440                 445

Pro Glu Asp Ile Ala Thr Tyr Tyr Cys Gln Gln Trp Ser Ser Asn Pro
450                 455                 460

Phe Thr Phe Gly Cys Gly Thr Lys Leu Gln Ile Thr Arg
465                 470                 475
```

<210> SEQ ID NO 46
<211> LENGTH: 483
<212> TYPE: PRT
<213> ORGANISM: Artificial Sequence
<220> FEATURE:
<223> OTHER INFORMATION: HER2-BsAb light chain fusion polypeptide (25aa scFv linker) + disulfide mut

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Thr Ser Gly Gly Gly Ser Gly Gly Gly
    210                 215                 220

Gly Ser Gly Gly Gly Gly Ser Gln Val Gln Leu Val Gln Ser Gly Gly
```

-continued

```
                225                 230                 235                 240
        Gly Val Val Gln Pro Gly Arg Ser Leu Arg Leu Ser Cys Lys Ala Ser
                        245                 250                 255
        Gly Tyr Thr Phe Thr Arg Tyr Thr Met His Trp Val Arg Gln Ala Pro
                        260                 265                 270
        Gly Lys Cys Leu Glu Trp Ile Gly Tyr Ile Asn Pro Ser Arg Gly Tyr
                        275                 280                 285
        Thr Asn Tyr Asn Gln Lys Phe Lys Asp Arg Phe Thr Ile Ser Arg Asp
                        290                 295                 300
        Asn Ser Lys Asn Thr Ala Phe Leu Gln Met Asp Ser Leu Arg Pro Glu
        305                 310                 315                 320
        Asp Thr Gly Val Tyr Phe Cys Ala Arg Tyr Tyr Asp His Tyr Ser
                        325                 330                 335
        Leu Asp Tyr Trp Gly Gln Gly Thr Pro Val Thr Val Ser Gly Gly
                        340                 345                 350
        Gly Gly Ser Gly Gly Gly Ser Gly Gly Gly Ser Gly Gly Gly
                        355                 360                 365
        Gly Ser Gly Gly Gly Gly Ser Asp Ile Gln Met Thr Gln Ser Pro Ser
                        370                 375                 380
        Ser Leu Ser Ala Ser Val Gly Asp Arg Val Thr Ile Thr Cys Ser Ala
        385                 390                 395                 400
        Ser Ser Ser Val Ser Tyr Met Asn Trp Tyr Gln Gln Thr Pro Gly Lys
                        405                 410                 415
        Ala Pro Lys Arg Trp Ile Tyr Asp Thr Ser Lys Leu Ala Ser Gly Val
                        420                 425                 430
        Pro Ser Arg Phe Ser Gly Ser Gly Ser Gly Thr Asp Tyr Thr Phe Thr
                        435                 440                 445
        Ile Ser Ser Leu Gln Pro Glu Asp Ile Ala Thr Tyr Tyr Cys Gln Gln
                        450                 455                 460
        Trp Ser Ser Asn Pro Phe Thr Phe Gly Gln Cys Gly Thr Lys Leu Gln
        465                 470                 475                 480

Ile Thr Arg

<210> SEQ ID NO 47
<211> LENGTH: 487
<212> TYPE: PRT
<213> ORGANISM: Artificial Sequence
<220> FEATURE:
<223> OTHER INFORMATION: HER2-BsAb light chain fusion polypeptide (30aa
      scFv linker) + disulfide mut

<400> SEQUENCE: 47

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Val Asn Thr Ala
                        20                  25                  30

Val Ala Trp Tyr Gln Gln Lys Pro Gly Lys Ala Pro Lys Leu Leu Ile
                        35                  40                  45

Tyr Ser Ala Ser Phe Leu Tyr Ser Gly Val Pro Ser Arg Phe Ser Gly
                        50                  55                  60

Ser Arg Ser Gly Thr Asp Phe Thr Leu Thr Ile Ser Ser Leu Gln Pro
        65                  70                  75                  80

Glu Asp Phe Ala Thr Tyr Tyr Cys Gln Gln His Tyr Thr Thr Pro Pro
                        85                  90                  95

Thr Phe Gly Gln Gly Thr Lys Val Glu Ile Lys Arg Thr Val Ala Ala
```

```
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
            195                 200                 205
Phe Asn Arg Gly Glu Cys Thr Ser Gly Gly Gly Ser Gly Gly Gly
        210                 215                 220
Gly Ser Gly Gly Gly Ser Gln Val Gln Leu Val Gln Ser Gly Gly
225                 230                 235                 240
Gly Val Val Gln Pro Gly Arg Ser Leu Arg Leu Ser Cys Lys Ala Ser
                245                 250                 255
Gly Tyr Thr Phe Thr Arg Tyr Thr Met His Trp Val Arg Gln Ala Pro
                260                 265                 270
Gly Lys Cys Leu Glu Trp Ile Gly Tyr Ile Asn Pro Ser Arg Gly Tyr
            275                 280                 285
Thr Asn Tyr Asn Gln Lys Phe Lys Asp Arg Phe Thr Ile Ser Arg Asp
        290                 295                 300
Asn Ser Lys Asn Thr Ala Phe Leu Gln Met Asp Ser Leu Arg Pro Glu
305                 310                 315                 320
Asp Thr Gly Val Tyr Phe Cys Ala Arg Tyr Tyr Asp Asp His Tyr Ser
                325                 330                 335
Leu Asp Tyr Trp Gly Gln Gly Thr Pro Val Thr Val Ser Ser Gly Gly
                340                 345                 350
Gly Gly Ser Gly Gly Gly Gly Ser Gly Gly Gly Gly Ser Gly Gly Gly
            355                 360                 365
Gly Ser Gly Gly Gly Ser Gly Gly Gly Ser Asp Ile Gln Met
        370                 375                 380
Thr Gln Ser Pro Ser Ser Leu Ser Ala Ser Val Gly Asp Arg Val Thr
385                 390                 395                 400
Ile Thr Cys Ser Ala Ser Ser Val Ser Tyr Met Asn Trp Tyr Gln
                405                 410                 415
Gln Thr Pro Gly Lys Ala Pro Lys Arg Trp Ile Tyr Asp Thr Ser Lys
            420                 425                 430
Leu Ala Ser Gly Val Pro Ser Arg Phe Ser Gly Ser Gly Ser Gly Thr
        435                 440                 445
Asp Tyr Thr Phe Thr Ile Ser Ser Leu Gln Pro Glu Asp Ile Ala Thr
        450                 455                 460
Tyr Tyr Cys Gln Gln Trp Ser Ser Asn Pro Phe Thr Phe Gly Cys Gly
465                 470                 475                 480
Thr Lys Leu Gln Ile Thr Arg
                485

<210> SEQ ID NO 48
<211> LENGTH: 231
<212> TYPE: PRT
<213> ORGANISM: Artificial Sequence
```

```
<220> FEATURE:
<223> OTHER INFORMATION: huOKT3scFv(C105S) (5 aa scFv linker)

<400> SEQUENCE: 48
```

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Asp Ile Gln Met
        115                 120                 125

Thr Gln Ser Pro Ser Ser Leu Ser Ala Ser Val Gly Asp Arg Val Thr
    130                 135                 140

Ile Thr Cys Ser Ala Ser Ser Ser Val Ser Tyr Met Asn Trp Tyr Gln
145                 150                 155                 160

Gln Thr Pro Gly Lys Ala Pro Lys Arg Trp Ile Tyr Asp Thr Ser Lys
                165                 170                 175

Leu Ala Ser Gly Val Pro Ser Arg Phe Ser Gly Ser Gly Ser Gly Thr
            180                 185                 190

Asp Tyr Thr Phe Thr Ile Ser Ser Leu Gln Pro Glu Asp Ile Ala Thr
        195                 200                 205

Tyr Tyr Cys Gln Gln Trp Ser Ser Asn Pro Phe Thr Phe Gly Gln Gly
    210                 215                 220

Thr Lys Leu Gln Ile Thr Arg
225                 230

```
<210> SEQ ID NO 49
<211> LENGTH: 236
<212> TYPE: PRT
<213> ORGANISM: Artificial Sequence
<220> FEATURE:
<223> OTHER INFORMATION: huOKT3scFv(C105S) (10 aa scFv linker)

<400> SEQUENCE: 49
```

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly

```
            100                 105                 110
Thr Pro Val Thr Val Ser Ser Gly Gly Gly Ser Gly Gly Gly
            115                 120                 125

Ser Asp Ile Gln Met Thr Gln Ser Pro Ser Ser Leu Ser Ala Ser Val
            130                 135                 140

Gly Asp Arg Val Thr Ile Thr Cys Ser Ala Ser Ser Ser Val Ser Tyr
145                 150                 155                 160

Met Asn Trp Tyr Gln Gln Thr Pro Gly Lys Ala Pro Lys Arg Trp Ile
                165                 170                 175

Tyr Asp Thr Ser Lys Leu Ala Ser Gly Val Pro Ser Arg Phe Ser Gly
            180                 185                 190

Ser Gly Ser Gly Thr Asp Tyr Thr Phe Thr Ile Ser Ser Leu Gln Pro
            195                 200                 205

Glu Asp Ile Ala Thr Tyr Tyr Cys Gln Gln Trp Ser Ser Asn Pro Phe
            210                 215                 220

Thr Phe Gly Gln Gly Thr Lys Leu Gln Ile Thr Arg
225                 230                 235

<210> SEQ ID NO 50
<211> LENGTH: 246
<212> TYPE: PRT
<213> ORGANISM: Artificial Sequence
<220> FEATURE:
<223> OTHER INFORMATION: huOKT3scFv(C105S) (20 aa scFv linker)

<400> SEQUENCE: 50

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Gly Ser Gly Gly Gly Gly
            115                 120                 125

Ser Gly Gly Gly Gly Ser Gly Gly Gly Gly Ser Asp Ile Gln Met Thr
            130                 135                 140

Gln Ser Pro Ser Ser Leu Ser Ala Ser Val Gly Asp Arg Val Thr Ile
145                 150                 155                 160

Thr Cys Ser Ala Ser Ser Ser Val Ser Tyr Met Asn Trp Tyr Gln Gln
                165                 170                 175

Thr Pro Gly Lys Ala Pro Lys Arg Trp Ile Tyr Asp Thr Ser Lys Leu
            180                 185                 190

Ala Ser Gly Val Pro Ser Arg Phe Ser Gly Ser Gly Ser Gly Thr Asp
            195                 200                 205

Tyr Thr Phe Thr Ile Ser Ser Leu Gln Pro Glu Asp Ile Ala Thr Tyr
            210                 215                 220

Tyr Cys Gln Gln Trp Ser Ser Asn Pro Phe Thr Phe Gly Gln Gly Thr
```

Lys Leu Gln Ile Thr Arg
                245

<210> SEQ ID NO 51
<211> LENGTH: 251
<212> TYPE: PRT
<213> ORGANISM: Artificial Sequence
<220> FEATURE:
<223> OTHER INFORMATION: huOKT3scFv(C105S) (25 aa scFv linker)

<400> SEQUENCE: 51

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Gly Ser Gly Gly Gly Gly
        115                 120                 125

Ser Gly Gly Gly Gly Ser Gly Gly Gly Gly Ser Gly Gly Gly Gly Ser
    130                 135                 140

Asp Ile Gln Met Thr Gln Ser Pro Ser Ser Leu Ser Ala Ser Val Gly
145                 150                 155                 160

Asp Arg Val Thr Ile Thr Cys Ser Ala Ser Ser Val Ser Tyr Met
                165                 170                 175

Asn Trp Tyr Gln Gln Thr Pro Gly Lys Ala Pro Lys Arg Trp Ile Tyr
            180                 185                 190

Asp Thr Ser Lys Leu Ala Ser Gly Val Pro Ser Arg Phe Ser Gly Ser
        195                 200                 205

Gly Ser Gly Thr Asp Tyr Thr Phe Thr Ile Ser Ser Leu Gln Pro Glu
    210                 215                 220

Asp Ile Ala Thr Tyr Tyr Cys Gln Gln Trp Ser Ser Asn Pro Phe Thr
225                 230                 235                 240

Phe Gly Gln Gly Thr Lys Leu Gln Ile Thr Arg
                245                 250

<210> SEQ ID NO 52
<211> LENGTH: 256
<212> TYPE: PRT
<213> ORGANISM: Artificial Sequence
<220> FEATURE:
<223> OTHER INFORMATION: huOKT3scFv(C105S)  (30 aa scFv linker)

<400> SEQUENCE: 52

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

```
Thr Met His Trp Val Arg Gln Ala Pro Gly Lys Gly Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
                100                 105                 110

Thr Pro Val Thr Val Ser Ser Gly Gly Gly Ser Gly Gly Gly Gly
             115                 120                 125

Ser Gly Gly Gly Gly Ser Gly Gly Gly Ser Gly Gly Gly Gly Ser
         130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Gln Thr Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Gln Gly Thr Lys Leu Gln Ile Thr Arg
                245                 250                 255

<210> SEQ ID NO 53
<211> LENGTH: 231
<212> TYPE: PRT
<213> ORGANISM: Artificial Sequence
<220> FEATURE:
<223> OTHER INFORMATION: huOKT3scFv(C105S) + disulfide mut (5 aa scFv
      linker)

<400> SEQUENCE: 53

Gln Val Gln Leu Val Gln Ser Gly Gly Gly Val Val Gln Pro Gly Arg
  1               5                  10                  15

Ser Leu Arg Leu Ser Cys Lys Ala Ser Gly Tyr Thr Phe Thr Arg Tyr
             20                  25                  30

Thr Met His Trp Val Arg Gln Ala Pro Gly Lys Cys Leu Glu Trp Ile
         35                  40                  45

Gly Tyr Ile Asn Pro Ser Arg Gly Tyr Thr Asn Tyr Asn Gln Lys Phe
     50                  55                  60

Lys Asp Arg Phe Thr Ile Ser Arg Asp Asn Ser Lys Asn Thr Ala Phe
 65                  70                  75                  80

Leu Gln Met Asp Ser Leu Arg Pro Glu Asp Thr Gly Val Tyr Phe Cys
                 85                  90                  95

Ala Arg Tyr Tyr Asp Asp His Tyr Ser Leu Asp Tyr Trp Gly Gln Gly
                100                 105                 110

Thr Pro Val Thr Val Ser Ser Gly Gly Gly Ser Asp Ile Gln Met
             115                 120                 125

Thr Gln Ser Pro Ser Ser Leu Ser Ala Ser Val Gly Asp Arg Val Thr
         130                 135                 140
```

```
Ile Thr Cys Ser Ala Ser Ser Val Ser Tyr Met Asn Trp Tyr Gln
145                 150                 155                 160

Gln Thr Pro Gly Lys Ala Pro Lys Arg Trp Ile Tyr Asp Thr Ser Lys
            165                 170                 175

Leu Ala Ser Gly Val Pro Ser Arg Phe Ser Gly Ser Gly Ser Gly Thr
            180                 185                 190

Asp Tyr Thr Phe Thr Ile Ser Ser Leu Gln Pro Glu Asp Ile Ala Thr
            195                 200                 205

Tyr Tyr Cys Gln Gln Trp Ser Ser Asn Pro Phe Thr Phe Gly Cys Gly
            210                 215                 220

Thr Lys Leu Gln Ile Thr Arg
225                 230
```

<210> SEQ ID NO 54
<211> LENGTH: 236
<212> TYPE: PRT
<213> ORGANISM: Artificial Sequence
<220> FEATURE:
<223> OTHER INFORMATION: huOKT3scFv(C105S) + disulfide mut (10 aa scFv linker)

<400> SEQUENCE: 54

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Cys Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Asp Ile Gln Met Thr Gln Ser Pro Ser Ser Leu Ser Ala Ser Val
130                 135                 140

Gly Asp Arg Val Thr Ile Thr Cys Ser Ala Ser Ser Val Ser Tyr
145                 150                 155                 160

Met Asn Trp Tyr Gln Gln Thr Pro Gly Lys Ala Pro Lys Arg Trp Ile
            165                 170                 175

Tyr Asp Thr Ser Lys Leu Ala Ser Gly Val Pro Ser Arg Phe Ser Gly
            180                 185                 190

Ser Gly Ser Gly Thr Asp Tyr Thr Phe Thr Ile Ser Ser Leu Gln Pro
            195                 200                 205

Glu Asp Ile Ala Thr Tyr Tyr Cys Gln Gln Trp Ser Ser Asn Pro Phe
            210                 215                 220

Thr Phe Gly Cys Gly Thr Lys Leu Gln Ile Thr Arg
225                 230                 235
```

<210> SEQ ID NO 55
<211> LENGTH: 241
<212> TYPE: PRT

<213> ORGANISM: Artificial Sequence
<220> FEATURE:
<223> OTHER INFORMATION: huOKT3scFv(C105S) + disulfide mut (15 aa scFv linker)

<400> SEQUENCE: 55

| Gln | Val | Gln | Leu | Val | Gln | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Lys | Ala | Ser | Gly | Tyr | Thr | Phe | Thr | Arg | Tyr |
| | | | 20 | | | | | 25 | | | | | 30 | | |

| Thr | Met | His | Trp | Val | Arg | Gln | Ala | Pro | Gly | Lys | Cys | Leu | Glu | Trp | Ile |
| | | 35 | | | | | 40 | | | | | 45 | | | |

| Gly | Tyr | Ile | Asn | Pro | Ser | Arg | Gly | Tyr | Thr | Asn | Tyr | Asn | Gln | Lys | Phe |
| | 50 | | | | | 55 | | | | | 60 | | | | |

| Lys | Asp | Arg | Phe | Thr | Ile | Ser | Arg | Asp | Asn | Ser | Lys | Asn | Thr | Ala | Phe |
| 65 | | | | | 70 | | | | | 75 | | | | | 80 |

| Leu | Gln | Met | Asp | Ser | Leu | Arg | Pro | Glu | Asp | Thr | Gly | Val | Tyr | Phe | Cys |
| | | | | 85 | | | | | 90 | | | | | 95 | |

| Ala | Arg | Tyr | Tyr | Asp | Asp | His | Tyr | Ser | Leu | Asp | Tyr | Trp | Gly | Gln | Gly |
| | | | 100 | | | | | 105 | | | | | 110 | | |

| Thr | Pro | Val | Thr | Val | Ser | Ser | Gly | Gly | Gly | Gly | Ser | Gly | Gly | Gly | Gly |
| | | 115 | | | | | 120 | | | | | 125 | | | |

| Ser | Gly | Gly | Gly | Gly | Ser | Asp | Ile | Gln | Met | Thr | Gln | Ser | Pro | Ser | Ser |
| | 130 | | | | | 135 | | | | | 140 | | | | |

| Leu | Ser | Ala | Ser | Val | Gly | Asp | Arg | Val | Thr | Ile | Thr | Cys | Ser | Ala | Ser |
| 145 | | | | | 150 | | | | | 155 | | | | | 160 |

| Ser | Ser | Val | Ser | Tyr | Met | Asn | Trp | Tyr | Gln | Gln | Thr | Pro | Gly | Lys | Ala |
| | | | | 165 | | | | | 170 | | | | | 175 | |

| Pro | Lys | Arg | Trp | Ile | Tyr | Asp | Thr | Ser | Lys | Leu | Ala | Ser | Gly | Val | Pro |
| | | | 180 | | | | | 185 | | | | | 190 | | |

| Ser | Arg | Phe | Ser | Gly | Ser | Gly | Ser | Gly | Thr | Asp | Tyr | Thr | Phe | Thr | Ile |
| | | | 195 | | | | | 200 | | | | | 205 | | |

| Ser | Ser | Leu | Gln | Pro | Glu | Asp | Ile | Ala | Thr | Tyr | Tyr | Cys | Gln | Gln | Trp |
| | 210 | | | | | 215 | | | | | 220 | | | | |

| Ser | Ser | Asn | Pro | Phe | Thr | Phe | Gly | Cys | Gly | Thr | Lys | Leu | Gln | Ile | Thr |
| 225 | | | | | 230 | | | | | 235 | | | | | 240 |

Arg

<210> SEQ ID NO 56
<211> LENGTH: 246
<212> TYPE: PRT
<213> ORGANISM: Artificial Sequence
<220> FEATURE:
<223> OTHER INFORMATION: huOKT3scFv(C105S) + disulfide mut (20 aa scFv linker)

<400> SEQUENCE: 56

| Gln | Val | Gln | Leu | Val | Gln | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Lys | Ala | Ser | Gly | Tyr | Thr | Phe | Thr | Arg | Tyr |
| | | | 20 | | | | | 25 | | | | | 30 | | |

| Thr | Met | His | Trp | Val | Arg | Gln | Ala | Pro | Gly | Lys | Cys | Leu | Glu | Trp | Ile |
| | | 35 | | | | | 40 | | | | | 45 | | | |

| Gly | Tyr | Ile | Asn | Pro | Ser | Arg | Gly | Tyr | Thr | Asn | Tyr | Asn | Gln | Lys | Phe |
| | 50 | | | | | 55 | | | | | 60 | | | | |

| Lys | Asp | Arg | Phe | Thr | Ile | Ser | Arg | Asp | Asn | Ser | Lys | Asn | Thr | Ala | Phe |
| 65 | | | | | 70 | | | | | 75 | | | | | 80 |

```
Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly
        115                 120                 125

Ser Gly Gly Gly Ser Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Ser Ala Ser Ser Val Ser Tyr Met Asn Trp Tyr Gln Gln
            165                 170                 175

Thr Pro Gly Lys Ala Pro Lys Arg Trp Ile Tyr Asp Thr Ser Lys Leu
            180                 185                 190

Ala Ser Gly Val Pro Ser Arg Phe Ser Gly Ser Gly Ser Gly Thr Asp
            195                 200                 205

Tyr Thr Phe Thr Ile Ser Ser Leu Gln Pro Glu Asp Ile Ala Thr Tyr
        210                 215                 220

Tyr Cys Gln Gln Trp Ser Ser Asn Pro Phe Thr Phe Gly Cys Gly Thr
225                 230                 235                 240

Lys Leu Gln Ile Thr Arg
                245

<210> SEQ ID NO 57
<211> LENGTH: 252
<212> TYPE: PRT
<213> ORGANISM: Artificial Sequence
<220> FEATURE:
<223> OTHER INFORMATION: huOKT3scFv(C105S) + disulfide mut (25 aa scFv
      linker)

<400> SEQUENCE: 57

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Gly Ser Gly Gly Gly Ser Gly Gly Gly Ser
    130                 135                 140

Asp Ile Gln Met Thr Gln Ser Pro Ser Ser Leu Ser Ala Ser Val Gly
145                 150                 155                 160

Asp Arg Val Thr Ile Thr Cys Ser Ala Ser Ser Val Ser Tyr Met
            165                 170                 175

Asn Trp Tyr Gln Gln Thr Pro Gly Lys Ala Pro Lys Arg Trp Ile Tyr
```

Asp Thr Ser Lys Leu Ala Ser Gly Val Pro Ser Arg Phe Ser Gly Ser
          180                 185                 190

Gly Ser Gly Thr Asp Tyr Thr Phe Thr Ile Ser Ser Leu Gln Pro Glu
          195                 200                 205

Asp Ile Ala Thr Tyr Tyr Cys Gln Gln Trp Ser Ser Asn Pro Phe Thr
225                 230                 235                 240

Phe Gly Gln Cys Gly Thr Lys Leu Gln Ile Thr Arg
                    245                 250

<210> SEQ ID NO 58
<211> LENGTH: 256
<212> TYPE: PRT
<213> ORGANISM: Artificial Sequence
<220> FEATURE:
<223> OTHER INFORMATION: huOKT3scFv(C105S) + disulfide mut (30 aa scFv
      linker)

<400> SEQUENCE: 58

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Cys Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser Gly Gly Gly Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Asp Ile Gln Met Thr Gln Ser Pro Ser Ser Leu
145                 150                 155                 160

Ser Ala Ser Val Gly Asp Arg Val Thr Ile Thr Cys Ser Ala Ser Ser
                165                 170                 175

Ser Val Ser Tyr Met Asn Trp Tyr Gln Thr Pro Gly Lys Ala Pro
            180                 185                 190

Lys Arg Trp Ile Tyr Asp Thr Ser Lys Leu Ala Ser Gly Val Pro Ser
        195                 200                 205

Arg Phe Ser Gly Ser Gly Ser Gly Thr Asp Tyr Thr Phe Thr Ile Ser
    210                 215                 220

Ser Leu Gln Pro Glu Asp Ile Ala Thr Tyr Tyr Cys Gln Gln Trp Ser
225                 230                 235                 240

Ser Asn Pro Phe Thr Phe Gly Cys Gly Thr Lys Leu Gln Ile Thr Arg
                245                 250                 255

<210> SEQ ID NO 59
<211> LENGTH: 241
<212> TYPE: PRT
<213> ORGANISM: Artificial Sequence
<220> FEATURE:

<223> OTHER INFORMATION: huOKT3scFv + disulfide mut (15 aa scFv linker)

<400> SEQUENCE: 59

```
Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175

Pro Lys Arg Trp Ile Tyr Asp Thr Ser Lys Leu Ala Ser Gly Val Pro
            180                 185                 190

Ser Arg Phe Ser Gly Ser Gly Ser Gly Thr Asp Tyr Thr Phe Thr Ile
        195                 200                 205

Ser Ser Leu Gln Pro Glu Asp Ile Ala Thr Tyr Tyr Cys Gln Gln Trp
    210                 215                 220

Ser Ser Asn Pro Phe Thr Phe Gly Gln Gly Thr Lys Leu Gln Ile Thr
225                 230                 235                 240

Arg
```

<210> SEQ ID NO 60
<211> LENGTH: 472
<212> TYPE: PRT
<213> ORGANISM: Artificial Sequence
<220> FEATURE:
<223> OTHER INFORMATION: Her2-BsAb light chain fusion polypeptide

<400> SEQUENCE: 60

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95
```

-continued

```
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
        180                 185                 190
Ala Cys Glu Val Thr His Gln Gly Leu Ser Ser Pro Val Thr Lys Ser
195                 200                 205
Phe Asn Arg Gly Glu Cys Thr Ser Gly Gly Gly Ser Gly Gly Gly
        210                 215                 220
Gly Ser Gly Gly Gly Gly Ser Gln Val Gln Leu Val Gln Ser Gly Gly
225                 230                 235                 240
Gly Val Val Gln Pro Gly Arg Ser Leu Arg Leu Ser Cys Lys Ala Ser
                245                 250                 255
Gly Tyr Thr Phe Thr Arg Tyr Thr Met His Trp Val Arg Gln Ala Pro
        260                 265                 270
Gly Lys Gly Leu Glu Trp Ile Gly Tyr Ile Asn Pro Ser Arg Gly Tyr
275                 280                 285
Thr Asn Tyr Asn Gln Lys Phe Lys Asp Arg Phe Thr Ile Ser Arg Asp
290                 295                 300
Asn Ser Lys Asn Thr Ala Phe Leu Gln Met Asp Ser Leu Arg Pro Glu
305                 310                 315                 320
Asp Thr Gly Val Tyr Phe Cys Ala Arg Tyr Tyr Asp Asp His Tyr Cys
                325                 330                 335
Leu Asp Tyr Trp Gly Gln Gly Thr Pro Val Thr Val Ser Ser Gly Gly
        340                 345                 350
Gly Gly Ser Gly Gly Gly Gly Ser Gly Gly Gly Gly Ser Asp Ile Gln
355                 360                 365
Met Thr Gln Ser Pro Ser Ser Leu Ser Ala Ser Val Gly Asp Arg Val
370                 375                 380
Thr Ile Thr Cys Ser Ala Ser Ser Ser Val Ser Tyr Met Asn Trp Tyr
385                 390                 395                 400
Gln Gln Thr Pro Gly Lys Ala Pro Lys Arg Trp Ile Tyr Asp Thr Ser
                405                 410                 415
Lys Leu Ala Ser Gly Val Pro Ser Arg Phe Ser Gly Ser Gly Ser Gly
        420                 425                 430
Thr Asp Tyr Thr Phe Thr Ile Ser Ser Leu Gln Pro Glu Asp Ile Ala
435                 440                 445
Thr Tyr Tyr Cys Gln Gln Trp Ser Ser Asn Pro Phe Thr Phe Gly Gln
450                 455                 460
Gly Thr Lys Leu Gln Ile Thr Arg
465                 470
```

<210> SEQ ID NO 61
<211> LENGTH: 214
<212> TYPE: PRT
<213> ORGANISM: Artificial Sequence
<220> FEATURE:
<223> OTHER INFORMATION: Her2-bsab light chain sequence

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 450
<212> TYPE: PRT
<213> ORGANISM: Artificial Sequence
<220> FEATURE:
<223> OTHER INFORMATION: her2 bsab heavy chain sequence

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 63
<211> LENGTH: 450
<212> TYPE: PRT
<213> ORGANISM: Artificial Sequence
<220> FEATURE:
<223> OTHER INFORMATION: Trastuzumab heavy chain K322A

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

-continued

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
             100                 105                 110
Gly Thr Leu Val Thr Val Ser Ser Ala Ser Thr Lys Gly Pro Ser Val
         115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
         195                 200                 205
Pro Ser Asn Thr Lys Val Asp Lys Arg Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
         275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Ala Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Asp Glu Leu Thr Lys Asn Gln Val Ser Leu
         355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
Gly Lys
```

<210> SEQ ID NO 64
<211> LENGTH: 119
<212> TYPE: PRT
<213> ORGANISM: Artificial Sequence
<220> FEATURE:
<223> OTHER INFORMATION: huOKT3 VH C105S + VH44

<400> SEQUENCE: 64

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
                20                  25                  30

Thr Met His Trp Val Arg Gln Ala Pro Gly Lys Cys Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115

<210> SEQ ID NO 65
<211> LENGTH: 107
<212> TYPE: PRT
<213> ORGANISM: Artificial Sequence
<220> FEATURE:
<223> OTHER INFORMATION: huOKT3 VL + VL100

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
                20                  25                  30

Asn Trp Tyr Gln Gln Thr Pro Gly Lys Ala Pro Lys Arg Trp Ile Tyr
            35                  40                  45

Asp Thr Ser Lys Leu Ala Ser Gly Val Pro Ser Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Cys Gly Thr Lys Leu Gln Ile Thr Arg
            100                 105

<210> SEQ ID NO 66
<211> LENGTH: 241
<212> TYPE: PRT
<213> ORGANISM: Artificial Sequence
<220> FEATURE:
<223> OTHER INFORMATION: huOKT3 scFv; 15 aa linker

<400> SEQUENCE: 66

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
            35                  40                  45

Gly Tyr Ile Asn Pro Ser Arg Gly Tyr Thr Asn Tyr Asn Gln Lys Phe
50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser Gly Gly Gly Gly Ser Gly Gly Gly Gly
            115                 120                 125

Ser Gly Gly Gly Gly Ser Asp Ile Gln Met Thr Gln Ser Pro Ser Ser
130                 135                 140

Leu Ser Ala Ser Val Gly Asp Arg Val Thr Ile Thr Cys Ser Ala Ser
145                 150                 155                 160

Ser Ser Val Ser Tyr Met Asn Trp Tyr Gln Gln Thr Pro Gly Lys Ala
                165                 170                 175

Pro Lys Arg Trp Ile Tyr Asp Thr Ser Lys Leu Ala Ser Gly Val Pro
            180                 185                 190

Ser Arg Phe Ser Gly Ser Gly Ser Gly Thr Asp Tyr Thr Phe Thr Ile
            195                 200                 205

Ser Ser Leu Gln Pro Glu Asp Ile Ala Thr Tyr Tyr Cys Gln Gln Trp
        210                 215                 220

Ser Ser Asn Pro Phe Thr Phe Gly Gln Gly Thr Lys Leu Gln Ile Thr
225                 230                 235                 240

Arg

<210> SEQ ID NO 67
<211> LENGTH: 1416
<212> TYPE: DNA
<213> ORGANISM: Artififial Sequence
<220> FEATURE:
<223> OTHER INFORMATION: DNA encoding sequence of SEQ ID NO:60

<400> SEQUENCE: 67
gatattcaga tgactcagtc tccctcttcc ctgtccgctt cagtcggcga tcgggtcact      60
attacttgtc gggcttcaca ggatgtcaac acagccgtgg cttggtacca gcagaagccc     120
gggaaagcac ctaagctgct gatctactct gccagtttcc tgtattctgg cgtcccaagt     180
aggttttcag gctcccggag cggaactgac ttcaccctga caatttccag cctgcagccc     240
gaggattttg ctacctacta ttgccagcag cattatacta ccccccccaa cattcggcca g    300 ggcacaaaag tcgaaatcaa gcggaccgtg gccgcccct ccgtgttcat cttcccccc c     360 tccgacgagc agctgaagtc cggcaccgcc tccgtggtgt gcctgctgaa caacttctac     420
ccccgggagg ccaaggtgca gtggaaggtg gacaacgccc tgcagtccgg caactcccag     480
gagtccgtga ccgagcagga ctccaaggac tccacctact ccctgtcctc cacc ctgacc    540 ctgtccaagg ccgactacga gaagcacaag gtgtacgcct gcgaggtgac ccaccagggc    600
ctgtcctccc ccgtgaccaa gtccttcaac cggggcgagt gcactagtgg aggaggaggt    660
agcggaggag gaggttctgg cggaggggg t tcccaggtgc agctggtgca gagcggagga    720

| | |
|---|---:|
| ggagtggtgc agccaggaag gagcctgcga ctgtcttgca aggctagtgg ctacaccttc | 780 |
| acacgatata ctatgcactg ggtgaggcag gcacctggta aaggcctgga gtggatcggc | 840 |
| tacattaacc cctctagggg atacaccaac tataatcaga agttcaaaga caggttcacc | 900 |
| atctcacgcg ataactccaa gaataccgcc ttcctgcaga tggactccct gcggcccgaa | 960 |
| gatacaggcg tgtattttg cgctagatac tatgacgatc attactgtct ggactattgg | 1020 |
| ggacagggga cccctgtgac agtgtccagc ggtggaggag ggtcaggtgg aggagggagc | 1080 |
| ggtggcggag ggtctgacat ccagatgacc cagtccccat ctagtctgag cgcctctgtg | 1140 |
| ggcgatagag tgactattac ctgcagtgct tcatccagcg tgagctacat gaactggtat | 1200 |
| cagcagacac ccggaaaggc acctaaacgc tggatctacg atactagcaa gctggcctct | 1260 |
| ggcgtgccca gtcgattcag tggttcaggc tccggaaccg actataccct taccatctct | 1320 |
| agtctgcagc ctgaggatat tgccacatac tattgtcagc agtggtcatc caatccattc | 1380 |
| acttttgggc agggtaccaa actgcagatt acaagg | 1416 |

<210> SEQ ID NO 68
<211> LENGTH: 1350
<212> TYPE: DNA
<213> ORGANISM: Artificial Sequence
<220> FEATURE:
<223> OTHER INFORMATION: DNA encoding sequence of SEQ ID NO:62

<400> SEQUENCE: 68

| | |
|---|---:|
| gaagtgcagc tggtcgagag cggaggaggt ctggtgcagc ccggaggttc cctgagactg | 60 |
| tcctgtgccg catctgggtt taatatcaag gacacataca tccactgggt gagacaggca | 120 |
| cccggcaaag gactggagtg ggtcgccagg atctacccta ccaacgggta cacaagatat | 180 |
| gctgactctg tgaagggccg gttcaccatc tccgccgata ctagcaaaaa caccgcttac | 240 |
| ctgcagatga attccctgag ggcagaagat accgctgtct actactgttc aagatggggg | 300 |
| ggggatggtt tttacgctat ggattattgg ggccagggca ccctggtgac cgtgtcctcc | 360 |
| gcctccacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggccgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagag agttgagccc | 660 |
| aaatcttgtg acaaaactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacgcc | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggtaaa | 1350 |

<210> SEQ ID NO 69
<211> LENGTH: 1410
<212> TYPE: DNA
<213> ORGANISM: Artificial Sequence
<220> FEATURE:
<223> OTHER INFORMATION: HER2-C825 Light Chain

<400> SEQUENCE: 69

```
gatattcaga tgactcagtc tccctcttcc ctgtccgctt cagtcggcga tcgggtcact      60
attacttgtc gggcttcaca ggatgtcaac acagccgtgg cttggtacca gcagaagccc     120
gggaaagcac ctaagctgct gatctactct gccagtttcc tgtattctgg cgtcccaagt     180
aggttttcag gctcccggag cggaactgac ttcaccctga caatttccag cctgcagccc     240
gaggattttg ctacctacta ttgccagcag cattatacta ccccccccaa cattcggcca     300
ggcacaaaag tcgaaatcaa gcggaccgtg gccgccccct ccgtgttcat cttcccccc     360
tccgacgagc agctgaagtc cggcaccgcc tccgtggtgt gcctgctgaa caacttctac     420
ccccgggagg ccaaggtgca gtggaaggtg gacaacgccc tgcagtccgg caactcccag     480
gagtccgtga ccgagcagga ctccaaggac tccaccctact ccctgtcctc cacccctgacc     540
ctgtccaagg ccgactacga aagcacaag gtgtacgcct gcgaggtgac ccaccagggc     600
ctgtcctccc ccgtgaccaa gtccttcaac cggggcgagt gcgtggtggt ggtagcggc     660
ggcggtggaa gcgcatccca tgtgaaactg caggaaagcg gcccaggtct ggtccagcca     720
tcccagtctc tgagcctgac atgcactgtg agcggattct ctctgacaga ctatggggtg     780
cactgggtca gacagagtcc aggaaagggg ctggagtggc tgggcgtcat ctggtcaggc     840
ggagggactg cttataacac cgcactgatc agcagactga atatctaccg cgacaactct     900
aaaaatcagg tgttcctgga gatgaacagt ctgcaggccg aagataccgc tatgtactat     960
tgcgccaggc gggcagcta cccttataat tactttgacg cttggggttg tggcaccaca    1020
gtgacagtct ccagcggtgg aggagggagt ggtggaggag ggtcaggtgg aggagggtcc    1080
caggcagtgg tcattcagga gtctgccctg actaccccc ctggagaaac cgtgacactg    1140
acttgcggat ctagtacagg ggcagtgact gcctccaact atgcaaattg ggtccaggaa    1200
aagcctgatc actgtttcac tggcctgatc ggtggccata caatcgacc acccggagtg    1260
ccagctaggt tttcaggttc cctgatcggc gacaaagccg ctctgaccat tgctggcacc    1320
cagacagagg atgaagcaat ctacttttgt gccctgtggt attccgatca ctgggtcatt    1380
ggggggggga cacgtctgac tgtgctgggg                                    1410
```

<210> SEQ ID NO 70
<211> LENGTH: 1350
<212> TYPE: DNA
<213> ORGANISM: Artificial Sequence
<220> FEATURE:
<223> OTHER INFORMATION: HER2-C825 Heavy Chain

<400> SEQUENCE: 70

```
gaagtgcagc tggtcgagag cggaggaggt ctggtgcagc ccggaggttc cctgagactg      60
tcctgtgccg catctgggtt taatatcaag gacacataca tccactgggt gagacaggca     120
cccggcaaag gactggagtg ggtcgccagg atctacccta ccaacgggta cacaagatat     180
gctgactctg tgaagggccg gttcaccatc tccgccgata ctagcaaaaa caccgcttac     240
ctgcagatga attccctgag ggcagaagat accgctgtct actactgttc aagatggggg     300
```

```
ggggatggtt tttacgctat ggattattgg ggccagggca ccctggtgac cgtgtcctcc    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggccgtcct acagtcctca    540
ggactctact ccctcagcag cgtggtgacc gtgccctcca gcagcttggg cacccagacc    600
tacatctgca acgtgaatca caagcccagc aacaccaagg tggacaagag agttgagccc    660
aaatcttgtg acaaaactca cacatgccca ccgtgcccag cacctgaact cctggggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcggaggga gcagtacgcc    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag ggcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 71
<211> LENGTH: 470
<212> TYPE: PRT
<213> ORGANISM: Artificial Sequence
<220> FEATURE:
<223> OTHER INFORMATION: HER2-C825 Light Chain sequence

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
              180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Ala Ser His Val Lys Leu Gln Glu Ser Gly Pro Gly Leu Val Gln Pro
225                 230                 235                 240

Ser Gln Ser Leu Ser Leu Thr Cys Thr Val Ser Gly Phe Ser Leu Thr
                245                 250                 255

Asp Tyr Gly Val His Trp Val Arg Gln Ser Pro Gly Lys Gly Leu Glu
        260                 265                 270

Trp Leu Gly Val Ile Trp Ser Gly Gly Thr Ala Tyr Asn Thr Ala
        275                 280                 285

Leu Ile Ser Arg Leu Asn Ile Tyr Arg Asp Asn Ser Lys Asn Gln Val
        290                 295                 300

Phe Leu Glu Met Asn Ser Leu Gln Ala Glu Asp Thr Ala Met Tyr Tyr
305                 310                 315                 320

Cys Ala Arg Arg Gly Ser Tyr Pro Tyr Asn Tyr Phe Asp Ala Trp Gly
                325                 330                 335

Cys Gly Thr Thr Val Thr Val Ser Ser Gly Gly Gly Ser Gly Gly
        340                 345                 350

Gly Gly Ser Gly Gly Gly Gly Ser Gln Ala Val Val Ile Gln Glu Ser
        355                 360                 365

Ala Leu Thr Thr Pro Pro Gly Glu Thr Val Thr Leu Thr Cys Gly Ser
370                 375                 380

Ser Thr Gly Ala Val Thr Ala Ser Asn Tyr Ala Asn Trp Val Gln Glu
385                 390                 395                 400

Lys Pro Asp His Cys Phe Thr Gly Leu Ile Gly Gly His Asn Asn Arg
                405                 410                 415

Pro Pro Gly Val Pro Ala Arg Phe Ser Gly Ser Leu Ile Gly Asp Lys
            420                 425                 430

Ala Ala Leu Thr Ile Ala Gly Thr Gln Thr Glu Asp Glu Ala Ile Tyr
            435                 440                 445

Phe Cys Ala Leu Trp Tyr Ser Asp His Trp Val Ile Gly Gly Gly Thr
450                 455                 460

Arg Leu Thr Val Leu Gly
465                 470

<210> SEQ ID NO 72
<211> LENGTH: 450
<212> TYPE: PRT
<213> ORGANISM: Artificial Sequence
<220> FEATURE:
<223> OTHER INFORMATION: HER2-C825 Heavy Chain sequence

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450
```